US012788807B2

(12) United States Patent
Adamo et al.

(10) Patent No.: US 12,788,807 B2
(45) **Date of Patent: *Nov. 10, 2026**

(54) **PENTAVALENT VACCINE AGAINST *Neisseria meningitidis* COMPRISING A SYNTHETIC MEN A ANTIGEN**

(71) Applicant: GlaxoSmithKline Biologicals SA, Rixensart (BE)

(72) Inventors: Roberto Adamo, Siena (IT); Maria Rosaria Romano, Siena (IT); Marta Tontini, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/042,355

(22) PCT Filed: Aug. 23, 2021

(86) PCT No.: PCT/EP2021/073217

§ 371 (c)(1),
(2) Date: Feb. 21, 2023

(87) PCT Pub. No.: WO2022/043238

PCT Pub. Date: Mar. 3, 2022

(65) Prior Publication Data

US 2023/0346905 A1 Nov. 2, 2023

(30) Foreign Application Priority Data

Aug. 25, 2020 (GB) ..................................... 2013262

(51) Int. Cl.

| | |
|---|---|
| ***A61K 39/095*** | (2006.01) |
| ***A61K 39/00*** | (2006.01) |
| ***A61P 31/04*** | (2006.01) |

(52) U.S. Cl.

CPC ............ *A61K 39/095* (2013.01); *A61P 31/04* (2018.01); *A61K 2039/55583* (2013.01); *A61K 2039/6037* (2013.01); *A61K 2039/6087* (2013.01); *A61K 2039/62* (2013.01); *A61K 2039/70* (2013.01)

(58) Field of Classification Search

CPC .......................... C08B 37/0009; A61K 31/716

See application file for complete search history.

(56) References Cited

U.S. PATENT DOCUMENTS

| | | | | |
|---|---|---|---|---|
| 8,753,651 | B2 | 6/2014 | Costantino | |
| 8,889,152 | B2 | 11/2014 | Costantino | |
| 8,895,516 | B2 | 11/2014 | Giannozzi et al. | |
| 10,272,147 | B2 * | 4/2019 | Costantino | A61K 39/095 |
| 10,668,142 | B2 * | 6/2020 | Costantino | C07K 14/22 |

(Continued)

FOREIGN PATENT DOCUMENTS

| | | | |
|---|---|---|---|
| CN | 1976724 | A | 6/2007 |
| JP | 2007507487 | A | 3/2007 |
| WO | 2020030782 | A1 | 2/2020 |

OTHER PUBLICATIONS

U.S. Appl. No. 18/869,582, filed Nov. 26, 2024, Marcelli; Agnese.*

(Continued)

*Primary Examiner* — Andrea Olson

(57) ABSTRACT

The inventors have identified a combined vaccine for immunisation against bacterial meningitis caused by multiple pathogens.

19 Claims, 23 Drawing Sheets

Specification includes a Sequence Listing.

(56) References Cited

U.S. PATENT DOCUMENTS

| | | | | |
|---|---|---|---|---|
| 2008/0241180 | A1* | 10/2008 | Contorni | A61P 25/00 424/197.11 |
| 2015/0004191 | A1 | 1/2015 | Contorni | |
| 2018/0243395 | A1 | 8/2018 | Constantino | |
| 2022/0152183 | A1* | 5/2022 | Adamo | A61K 47/6415 |

OTHER PUBLICATIONS

Gao et al., "Immunoactivity of Protein Conjugates of Carba Analogues from Neisseria meningitidis A Capsular Polysaccharide" ACS Chemical Biology vol. 8 pp. 2561-2567, DOI: 10.1021/cb400463u (Year: 2013).*

Fiebig et al., "Structural and mechanistic basis of capsule O-acetylation in Neisseria meningitidis serogroup A" Nature Communications vol. 11:4723, pp. 1-12, DOI: 10.1038/s41467-020-18464-y (Year: 2020).*

Gudlavalleti et al., "In vivo determination of Neisseria meningitidis serogroup A capsular polysaccharide by whole cell high-resolution magic angle spinning NMR spectroscopy" Carbohydrate Research vol. 341 pp. 557-562, DOI;10.1016/j.carres.2005.11.036 (Year: 2006).*

Lemercinier et al., "Full 1H NMR assignment and detailed O-acetylation patterns of capuslar polysaccharides from Neisseria meningitidis used in vaccine production" Carbohydrate Research vol. 296 pp. 83-96 (Year: 1996).*

Qi Gao, et al.: "Immunoactivity of Protein Conjugates of Carba Analogues from Neisseria meningitidis A Capsular Polysaccharide", ACS Chemical Biology, vol. 8, No. 11, Sep. 19, 2013 (Sep. 19, 2013), pp. 2561-2567, XP055612646, ISSN: 1554-8929, DOI: 10.1021/cb400463u.

Berry D.S., et al., "Effect of O acetylation of Neisseria meningitidis serogroup A capsular polysaccharide on development of functional immune responses," Infection and Immunity, Jul. 2002, vol. 70, No. 7, pp. 3707-3713, ISSN: 0019-9567.

Berti F., et al., "Relative stability of meningococcal serogroup A and X polysaccharides," Vaccine, Aug. 22, 2012, vol. 30, No. 45, pp. 6409-6415.

Greene T.W., et al., "Protective Groups in Organic Synthesis," A Wiley-Interscience Publication John Wiley & Sons, Inc, New York, 1999, Chapter 9, pp. 660-674, Oligonucleotides and Analogues a Practical Approach, Ekstein, F. Ed., IRL Press.

Harale K.R., et al., "Synthesis of a Tetrasaccharide and its Glycoconjugate Corresponding to the Capsular Polysaccharide of Neisseria Meningitidis Serogroup X and its Immunochemical Studies," RSC Advances, 2015, vol. 5, pp. 41332-41340, DOI: 10.1039/c5ra02993g.

Hlozek J., et al., "Conformations of Neisseria Meningitidis Serogroup A and X Polysaccharides: The Effects of Chain Length and O-Acetylation," Carbohydrate Research, Jul. 30, 2018, vol. 465, pp. 44-51, EPublished on Jun. 22, 2018.

International Search Report and Written Opinion for International Application No. PCT/EP2020/055950, mailed Jun. 4, 2020, 13 Pages.

Berti F., et al., "Role of O-acetylation in the Immunogenicity of Bacterial Polysaccharide Vaccines," Molecules, 2018, vol. 23, 1340, pp. 1-10, Retrieved from [doi:10.3390/molecules23061340].

Hlozek J., et al., "Modeling the Conformations of Neisseria Meningitidis Serogroup A CPS and a Carba-Analogue: Implications for Vaccine Development", Carbohydrate Research, 2019, vol. 486, Article 107838, pp. 1-7.

* cited by examiner

FIG. 6 A and FIG. 6 B
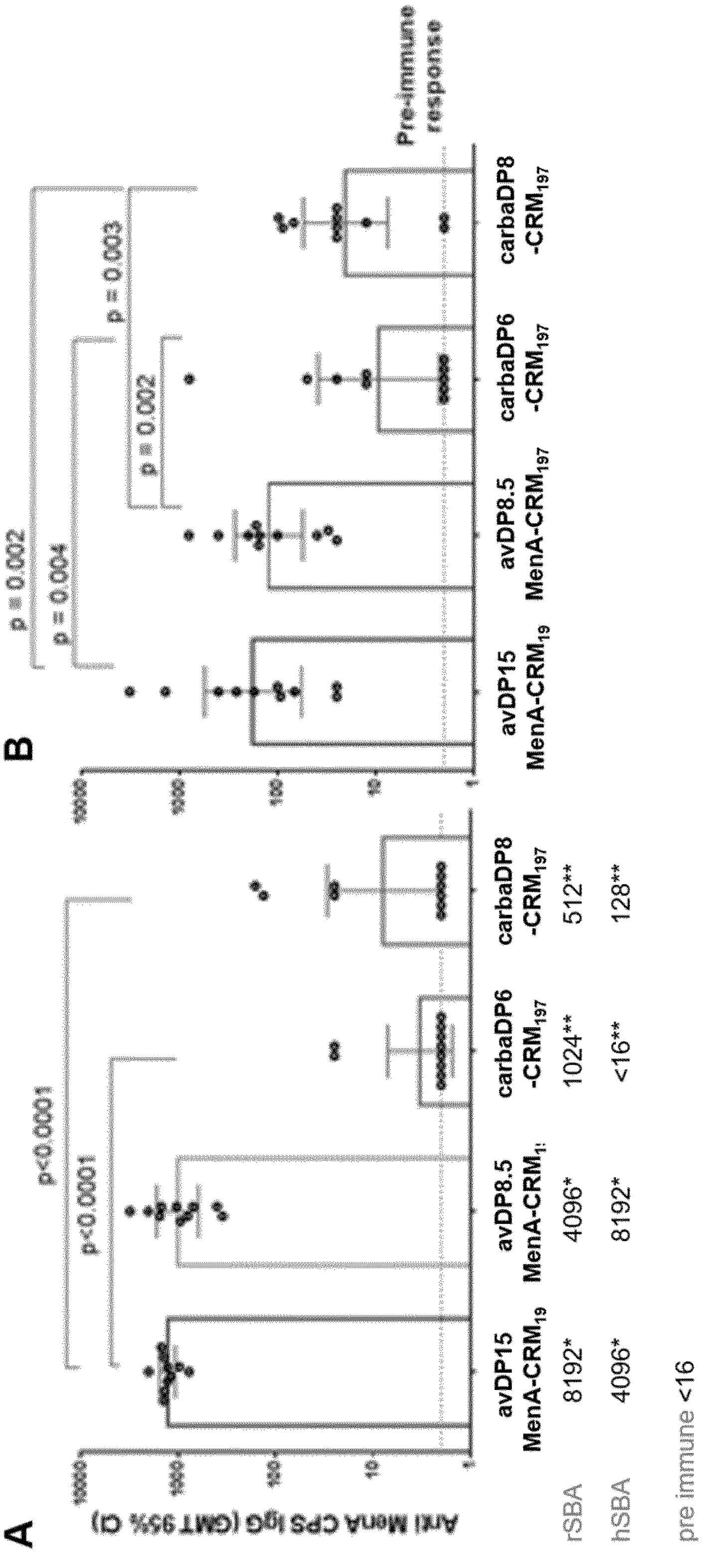

SEQUENCE LISTING

```
<160> NUMBER OF SEQ ID NOS: 42

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255


<210> SEQ ID NO 2
<211> LENGTH: 248
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15
```

```
Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Glu Lys Gly Ser Tyr Ser Leu Gly Ile Phe Gly Gly Gln Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln
                245


<210> SEQ ID NO 3
<211> LENGTH: 248
<212> TYPE: PRT
<213> ORGANISM: Artificial Sequence
<220> FEATURE:
<223> OTHER INFORMATION: MUTATED fhbp POLYPEPTIDE

<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125
```

```
Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Ala Lys Gly Ser Tyr Ser Leu Gly Ile Phe Gly Gly Gln Ala
    210                 215                 220

Gln Glu Val Ala Gly Ser Ala Ala Val Glu Thr Ala Asn Gly Ile His
225                 230                 235                 240

His Ile Gly Leu Ala Ala Lys Gln
                245


<210> SEQ ID NO 4
<211> LENGTH: 248
<212> TYPE: PRT
<213> ORGANISM: Artificial Sequence
<220> FEATURE:
<223> OTHER INFORMATION: MUTATED fhbp POLYPEPTIDE

<400> SEQUENCE: 4

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Ala Lys Gly Ser Tyr Arg Leu Gly Ile Phe Gly Gly Gln Ala
    210                 215                 220

Gln Glu Val Ala Gly Ser Ala Glu Val Glu Thr Ala Asn Gly Ile His
225                 230                 235                 240
```

```
His Ile Gly Leu Ala Ala Lys Gln
                245


<210> SEQ ID NO 5
<211> LENGTH: 263
<212> TYPE: PRT
<213> ORGANISM: Neisseria meningitidis

<400> SEQUENCE: 5

Cys Ser Ser Gly Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260


<210> SEQ ID NO 6
<211> LENGTH: 251
<212> TYPE: PRT
<213> ORGANISM: Neisseria meningitidis

<400> SEQUENCE: 6

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45
```

```
Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Glu Lys Gly Ser Tyr Ser Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln
                245                 250
```

<210> SEQ ID NO 7
<211> LENGTH: 251
<212> TYPE: PRT
<213> ORGANISM: Artificial Sequence
<220> FEATURE:
<223> OTHER INFORMATION: MUTATED fhbp POLYPEPTIDE

<400> SEQUENCE: 7

```
Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160
```

```
Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Glu Lys Gly Ser Tyr Arg Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln
                245                 250


<210> SEQ ID NO 8
<211> LENGTH: 251
<212> TYPE: PRT
<213> ORGANISM: Artificial Sequence
<220> FEATURE:
<223> OTHER INFORMATION: MUTATED fhbp POLYPEPTIDE

<400> SEQUENCE: 8

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Ala Lys Gly Ser Tyr Arg Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln
                245                 250


<210> SEQ ID NO 9
```

<211> LENGTH: 251
<212> TYPE: PRT
<213> ORGANISM: Artificial Sequence
<220> FEATURE:
<223> OTHER INFORMATION: MUTATED fhbp POLYPEPTIDE

<400> SEQUENCE: 9

Val Ala Ala Asp Ile Gly Ala Gly Leu Ala Asp Ala Leu Thr Ala Pro
1 5 10 15

Leu Asp His Lys Asp Lys Gly Leu Lys Ser Leu Thr Leu Glu Asp Ser
20 25 30

Ile Ser Gln Asn Gly Thr Leu Thr Leu Ser Ala Gln Gly Ala Glu Arg
35 40 45

Thr Phe Lys Ala Gly Asp Lys Asp Asn Ser Leu Asn Thr Gly Lys Leu
50 55 60

Lys Asn Asp Lys Ile Ser Arg Phe Asp Phe Ile Arg Gln Ile Glu Val
65 70 75 80

Asp Gly Gln Leu Ile Thr Leu Glu Ser Gly Glu Phe Gln Val Tyr Lys
85 90 95

Gln Ser His Ser Ala Leu Thr Ala Leu Gln Thr Glu Gln Val Gln Asp
100 105 110

Ser Glu His Ser Gly Lys Met Val Ala Lys Arg Gln Phe Arg Ile Gly
115 120 125

Asp Ile Val Gly Glu His Thr Ser Phe Gly Lys Leu Pro Lys Asp Val
130 135 140

Met Ala Thr Tyr Arg Gly Thr Ala Phe Gly Ser Asp Asp Ala Gly Gly
145 150 155 160

Lys Leu Thr Tyr Thr Ile Asp Phe Ala Ala Lys Gln Gly His Gly Lys
165 170 175

Ile Glu His Leu Lys Ser Pro Glu Leu Asn Val Asp Leu Ala Ala Ala
180 185 190

Asp Ile Lys Pro Asp Glu Lys His His Ala Val Ile Ser Gly Ser Val
195 200 205

Leu Tyr Asn Gln Ala Ala Lys Gly Ser Tyr Ser Leu Gly Ile Phe Gly
210 215 220

Gly Gln Ala Gln Glu Val Ala Gly Ser Ala Ala Val Glu Thr Ala Asn
225 230 235 240

Gly Ile Arg His Ile Gly Leu Ala Ala Lys Gln
245 250

<210> SEQ ID NO 10
<211> LENGTH: 273
<212> TYPE: PRT
<213> ORGANISM: Neisseria meningitidis

<400> SEQUENCE: 10

Met Asn Arg Thr Ala Phe Cys Cys Leu Ser Leu Thr Ala Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

Ser Leu Gln Ser Leu Thr Leu Asp Gln Ser Val Arg Lys Asn Glu Lys
50 55 60

Leu Lys Leu Ala Ala Gln Gly Ala Glu Lys Thr Tyr Gly Asn Gly Asp
65 70 75 80

-continued

```
Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln


<210> SEQ ID NO 11
<211> LENGTH: 254
<212> TYPE: PRT
<213> ORGANISM: Neisseria meningitidis

<400> SEQUENCE: 11

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175
```

-continued

```
His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250


<210> SEQ ID NO 12
<211> LENGTH: 247
<212> TYPE: PRT
<213> ORGANISM: Neisseria meningitidis

<400> SEQUENCE: 12

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245


<210> SEQ ID NO 13
<211> LENGTH: 281
<212> TYPE: PRT
<213> ORGANISM: Neisseria meningitidis

<400> SEQUENCE: 13
```

-continued

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280
```

<210> SEQ ID NO 14
<211> LENGTH: 262
<212> TYPE: PRT
<213> ORGANISM: Neisseria meningitidis

<400> SEQUENCE: 14

```
Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95
```

```
Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260


<210> SEQ ID NO 15
<211> LENGTH: 250
<212> TYPE: PRT
<213> ORGANISM: Neisseria meningitidis

<400> SEQUENCE: 15

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
```

```
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250


<210> SEQ ID NO 16
<211> LENGTH: 247
<212> TYPE: PRT
<213> ORGANISM: Artificial Sequence
<220> FEATURE:
<223> OTHER INFORMATION: MUTATED fhbp POLYPEPTIDE

<400> SEQUENCE: 16

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245


<210> SEQ ID NO 17
<211> LENGTH: 250
<212> TYPE: PRT
<213> ORGANISM: Artificial Sequence
<220> FEATURE:
<223> OTHER INFORMATION: MUTATED fhbp POLYPEPTIDE

<400> SEQUENCE: 17
```

-continued

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250


<210> SEQ ID NO 18
<211> LENGTH: 757
<212> TYPE: PRT
<213> ORGANISM: Artificial Sequence
<220> FEATURE:
<223> OTHER INFORMATION: MUTATED fhbp POLYPEPTIDE

<400> SEQUENCE: 18

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110
```

-continued

```
Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
```

-continued

```
    530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Lys Leu Ile Thr
            580                 585                 590

Leu Glu Ser Gly Glu Phe Gln Val Tyr Lys Gln Ser His Ser Ala Leu
        595                 600                 605

Thr Ala Leu Gln Thr Glu Gln Val Gln Asp Ser Glu Asp Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Lys Gly Gly Ser Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly His Gly Lys Ile Glu His Leu Lys Ser
        675                 680                 685

Pro Glu Leu Asn Val Glu Leu Ala Thr Ala Tyr Ile Lys Pro Asp Glu
    690                 695                 700

Lys Arg His Ala Val Ile Ser Gly Ser Val Leu Tyr Asn Gln Asp Ala
705                 710                 715                 720

Lys Gly Ser Tyr Ser Leu Gly Ile Phe Gly Gly Gln Ala Gln Glu Val
                725                 730                 735

Ala Gly Ser Ala Ala Val Glu Thr Ala Asn Gly Ile His His Ile Gly
            740                 745                 750

Leu Ala Ala Lys Gln
        755


<210> SEQ ID NO 19
<211> LENGTH: 757
<212> TYPE: PRT
<213> ORGANISM: Artificial Sequence
<220> FEATURE:
<223> OTHER INFORMATION: MUTATED fhbp POLYPETIDE

<400> SEQUENCE: 19

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
```

-continued

```
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Gln Ser Leu Thr Leu Asp Gln Ser Val Arg Lys
    530                 535                 540

Asn Glu Lys Leu Lys Leu Ala Ala Gln Gly Ala Glu Lys Thr Tyr Gly
545                 550                 555                 560
```

```
Asn Gly Asp Ser Leu Asn Thr Gly Lys Leu Lys Asn Asp Lys Val Ser
                565                 570                 575

Arg Phe Asp Phe Ile Arg Gln Ile Glu Val Asp Gly Lys Leu Ile Thr
            580                 585                 590

Leu Glu Ser Gly Glu Phe Gln Val Tyr Lys Gln Ser His Ser Ala Leu
        595                 600                 605

Thr Ala Leu Gln Thr Glu Gln Val Gln Asp Ser Glu Asp Ser Gly Lys
    610                 615                 620

Met Val Ala Lys Arg Gln Phe Arg Ile Gly Asp Ile Ala Gly Glu His
625                 630                 635                 640

Thr Ser Phe Asp Lys Leu Pro Lys Gly Gly Ser Ala Thr Tyr Arg Gly
                645                 650                 655

Thr Ala Phe Gly Ser Asp Asp Ala Gly Gly Lys Leu Thr Tyr Thr Ile
            660                 665                 670

Asp Phe Ala Ala Lys Gln Gly His Gly Lys Ile Glu His Leu Lys Ser
        675                 680                 685

Pro Glu Leu Asn Val Glu Leu Ala Thr Ala Tyr Ile Lys Pro Asp Glu
    690                 695                 700

Lys Arg His Ala Val Ile Ser Gly Ser Val Leu Tyr Asn Gln Asp Ala
705                 710                 715                 720

Lys Gly Ser Tyr Arg Leu Gly Ile Phe Gly Gly Gln Ala Gln Glu Val
                725                 730                 735

Ala Gly Ser Ala Glu Val Glu Thr Ala Asn Gly Ile His His Ile Gly
            740                 745                 750

Leu Ala Ala Lys Gln
        755


<210> SEQ ID NO 20
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 20

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160
```

-continued

```
Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Lys Ser Leu Thr Leu Glu Asp Ser Ile Ser Gln
    530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575
```

-continued

```
Lys Ile Ser Arg Phe Asp Phe Ile Arg Gln Ile Glu Val Asp Gly Gln
            580                 585                 590

Leu Ile Thr Leu Glu Ser Gly Glu Phe Gln Val Tyr Lys Gln Ser His
        595                 600                 605

Ser Ala Leu Thr Ala Leu Gln Thr Glu Gln Val Gln Asp Ser Glu His
    610                 615                 620

Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
                645                 650                 655

Tyr Arg Gly Thr Ala Phe Gly Ser Asp Asp Ala Gly Gly Lys Leu Thr
            660                 665                 670

Tyr Thr Ile Asp Phe Ala Ala Lys Gln Gly His Gly Lys Ile Glu His
        675                 680                 685

Leu Lys Ser Pro Glu Leu Asn Val Asp Leu Ala Ala Ala Asp Ile Lys
    690                 695                 700

Pro Asp Glu Lys His His Ala Val Ile Ser Gly Ser Val Leu Tyr Asn
705                 710                 715                 720

Gln Ala Glu Lys Gly Ser Tyr Arg Leu Gly Ile Phe Gly Gly Gln Ala
                725                 730                 735

Gln Glu Val Ala Gly Ser Ala Glu Val Glu Thr Ala Asn Gly Ile Arg
            740                 745                 750

His Ile Gly Leu Ala Ala Lys Gln
        755                 760


<210> SEQ ID NO 21
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 21

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175
```

-continued

```
Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Lys Ser Leu Thr Leu Glu Asp Ser Ile Ser Gln
    530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575

Lys Ile Ser Arg Phe Asp Phe Ile Arg Gln Ile Glu Val Asp Gly Gln
            580                 585                 590

Leu Ile Thr Leu Glu Ser Gly Glu Phe Gln Val Tyr Lys Gln Ser His
```

```
        595                 600                 605

Ser Ala Leu Thr Ala Leu Gln Thr Glu Gln Val Gln Asp Ser Glu His
    610                 615                 620

Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
                645                 650                 655

Tyr Arg Gly Thr Ala Phe Gly Ser Asp Asp Ala Gly Gly Lys Leu Thr
            660                 665                 670

Tyr Thr Ile Asp Phe Ala Ala Lys Gln Gly His Gly Lys Ile Glu His
        675                 680                 685

Leu Lys Ser Pro Glu Leu Asn Val Asp Leu Ala Ala Ala Asp Ile Lys
    690                 695                 700

Pro Asp Glu Lys His His Ala Val Ile Ser Gly Ser Val Leu Tyr Asn
705                 710                 715                 720

Gln Ala Ala Lys Gly Ser Tyr Arg Leu Gly Ile Phe Gly Gly Gln Ala
                725                 730                 735

Gln Glu Val Ala Gly Ser Ala Glu Val Glu Thr Ala Asn Gly Ile Arg
            740                 745                 750

His Ile Gly Leu Ala Ala Lys Gln
        755                 760


<210> SEQ ID NO 22
<211> LENGTH: 760
<212> TYPE: PRT
<213> ORGANISM: Artificial Sequence
<220> FEATURE:
<223> OTHER INFORMATION: MUTATED fhbp POLYPEPTIDE

<400> SEQUENCE: 22

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
```

-continued

```
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
            420                 425                 430

Lys Thr Leu Glu Gln Asn Val Glu Leu Ala Ala Ala Glu Leu Lys Ala
        435                 440                 445

Asp Glu Lys Ser His Ala Val Ile Leu Gly Asp Thr Arg Tyr Gly Ser
    450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Glu Lys Val His Glu
                485                 490                 495

Ile Gly Ile Ala Gly Lys Gln Gly Ser Gly Gly Gly Gly Val Ala Ala
            500                 505                 510

Asp Ile Gly Ala Gly Leu Ala Asp Ala Leu Thr Ala Pro Leu Asp His
        515                 520                 525

Lys Asp Lys Gly Leu Lys Ser Leu Thr Leu Glu Asp Ser Ile Ser Gln
    530                 535                 540

Asn Gly Thr Leu Thr Leu Ser Ala Gln Gly Ala Glu Arg Thr Phe Lys
545                 550                 555                 560

Ala Gly Asp Lys Asp Asn Ser Leu Asn Thr Gly Lys Leu Lys Asn Asp
                565                 570                 575

Lys Ile Ser Arg Phe Asp Phe Ile Arg Gln Ile Glu Val Asp Gly Gln
            580                 585                 590

Leu Ile Thr Leu Glu Ser Gly Glu Phe Gln Val Tyr Lys Gln Ser His
        595                 600                 605

Ser Ala Leu Thr Ala Leu Gln Thr Glu Gln Val Gln Asp Ser Glu His
    610                 615                 620
```

```
Ser Gly Lys Met Val Ala Lys Arg Gln Phe Arg Ile Gly Asp Ile Val
625                 630                 635                 640

Gly Glu His Thr Ser Phe Gly Lys Leu Pro Lys Asp Val Met Ala Thr
            645                 650                 655

Tyr Arg Gly Thr Ala Phe Gly Ser Asp Asp Ala Gly Gly Lys Leu Thr
            660                 665                 670

Tyr Thr Ile Asp Phe Ala Ala Lys Gln Gly His Gly Lys Ile Glu His
        675                 680                 685

Leu Lys Ser Pro Glu Leu Asn Val Asp Leu Ala Ala Ala Asp Ile Lys
    690                 695                 700

Pro Asp Glu Lys His His Ala Val Ile Ser Gly Ser Val Leu Tyr Asn
705                 710                 715                 720

Gln Ala Ala Lys Gly Ser Tyr Ser Leu Gly Ile Phe Gly Gly Gln Ala
            725                 730                 735

Gln Glu Val Ala Gly Ser Ala Ala Val Glu Thr Ala Asn Gly Ile Arg
            740                 745                 750

His Ile Gly Leu Ala Ala Lys Gln
        755                 760


<210> SEQ ID NO 23
<211> LENGTH: 256
<212> TYPE: PRT
<213> ORGANISM: Artificial Sequence
<220> FEATURE:
<223> OTHER INFORMATION: fHbp polypeptide with His6 tag

<400> SEQUENCE: 23

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Gly Leu Ala Ala Lys Gln Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220
```

Gly Ile Phe Gly Gly Lys Ala Gln Glu Val Ala Gly Ser Ala Glu Val
225 230 235 240

Lys Thr Val Asn Gly Ile Arg His Leu Glu His His His His His His
245 250 255

<210> SEQ ID NO 24
<211> LENGTH: 256
<212> TYPE: PRT
<213> ORGANISM: Artificial Sequence
<220> FEATURE:
<223> OTHER INFORMATION: fHbp polypeptide with His6 tag

<400> SEQUENCE: 24

Val Ala Ala Asp Ile Gly Ala Gly Leu Ala Asp Ala Leu Thr Ala Pro
1 5 10 15

Leu Asp His Lys Asp Lys Gly Leu Gln Ser Leu Thr Leu Asp Gln Ser
20 25 30

Val Arg Lys Asn Glu Lys Leu Lys Leu Ala Ala Gln Gly Ala Glu Lys
35 40 45

Thr Tyr Gly Asn Gly Asp Ser Leu Asn Thr Gly Lys Leu Lys Asn Asp
50 55 60

Lys Val Ser Arg Phe Asp Phe Ile Arg Gln Ile Glu Val Asp Gly Lys
65 70 75 80

Leu Ile Thr Leu Glu Ser Gly Glu Phe Gln Val Tyr Lys Gln Ser His
85 90 95

Ser Ala Leu Thr Ala Leu Gln Thr Glu Gln Val Gln Asp Ser Glu Asp
100 105 110

Ser Gly Lys Met Val Ala Lys Arg Gln Phe Arg Ile Gly Asp Ile Ala
115 120 125

Gly Glu His Thr Ser Phe Asp Lys Leu Pro Lys Gly Gly Ser Ala Thr
130 135 140

Tyr Arg Gly Thr Ala Phe Gly Ser Asp Asp Ala Gly Gly Lys Leu Thr
145 150 155 160

Tyr Thr Ile Asp Phe Ala Ala Lys Gln Gly His Gly Lys Ile Glu His
165 170 175

Leu Lys Ser Pro Glu Leu Asn Val Glu Leu Ala Thr Ala Tyr Ile Lys
180 185 190

Pro Asp Glu Lys Arg His Ala Val Ile Ser Gly Ser Val Leu Tyr Asn
195 200 205

Gln Asp Glu Lys Gly Ser Tyr Ser Leu Gly Ile Phe Gly Gly Gln Ala
210 215 220

Gln Glu Val Ala Gly Ser Ala Glu Val Glu Thr Ala Asn Gly Ile His
225 230 235 240

His Ile Gly Leu Ala Ala Lys Gln Leu Glu His His His His His His
245 250 255

<210> SEQ ID NO 25
<211> LENGTH: 256
<212> TYPE: PRT
<213> ORGANISM: Artificial Sequence
<220> FEATURE:
<223> OTHER INFORMATION: Mutated fHbp polypeptide

<400> SEQUENCE: 25

Val Ala Ala Asp Ile Gly Ala Gly Leu Ala Asp Ala Leu Thr Ala Pro
1 5 10 15

Leu Asp His Lys Asp Lys Gly Leu Gln Ser Leu Thr Leu Asp Gln Ser

```
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Ala Lys Gly Ser Tyr Ser Leu Gly Ile Phe Gly Gly Gln Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln Leu Glu His His His His His His
                245                 250                 255


<210> SEQ ID NO 26
<211> LENGTH: 256
<212> TYPE: PRT
<213> ORGANISM: Artificial Sequence
<220> FEATURE:
<223> OTHER INFORMATION: Mutated fHbp polypeptide

<400> SEQUENCE: 26

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
65                  70                  75                  80

Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Lys Gly Gly Ser Ala Thr
```

```
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Tyr Ile Lys
            180                 185                 190

Pro Asp Glu Lys Arg His Ala Val Ile Ser Gly Ser Val Leu Tyr Asn
        195                 200                 205

Gln Asp Glu Lys Gly Ser Tyr Arg Leu Gly Ile Phe Gly Gly Gln Ala
    210                 215                 220

Gln Glu Val Ala Gly Ser Ala Glu Val Glu Thr Ala Asn Gly Ile His
225                 230                 235                 240

His Ile Gly Leu Ala Ala Lys Gln Leu Glu His His His His His His
                245                 250                 255


<210> SEQ ID NO 27
<211> LENGTH: 259
<212> TYPE: PRT
<213> ORGANISM: Artificial Sequence
<220> FEATURE:
<223> OTHER INFORMATION: fHbp polypeptide with His6 tag

<400> SEQUENCE: 27

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Glu Lys Gly Ser Tyr Ser Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln Leu Glu His His His
```

```
                245                 250                 255

His His His


<210> SEQ ID NO 28
<211> LENGTH: 259
<212> TYPE: PRT
<213> ORGANISM: Artificial Sequence
<220> FEATURE:
<223> OTHER INFORMATION: Mutated fHbp polypeptide with His6 tag

<400> SEQUENCE: 28

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Ala Lys Gly Ser Tyr Ser Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln Leu Glu His His His
                245                 250                 255

His His His


<210> SEQ ID NO 29
<211> LENGTH: 753
<212> TYPE: PRT
<213> ORGANISM: Artificial Sequence
<220> FEATURE:
<223> OTHER INFORMATION: fHbp fusion polypeptide

<400> SEQUENCE: 29

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30
```

-continued

```
Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Phe Asp Phe Ile Arg Gln Ile Glu Val Asp Gly Gln Leu
65                  70                  75                  80

Ile Thr Leu Glu Ser Gly Glu Phe Gln Ile Tyr Lys Gln Asp His Ser
                85                  90                  95

Ala Val Val Ala Leu Gln Ile Glu Lys Ile Asn Asn Pro Asp Lys Ile
            100                 105                 110

Asp Ser Leu Ile Asn Gln Arg Ser Phe Leu Val Ser Gly Leu Gly Gly
        115                 120                 125

Glu His Thr Ala Phe Asn Gln Leu Pro Asp Gly Lys Ala Glu Tyr His
    130                 135                 140

Gly Lys Ala Phe Ser Ser Asp Asp Ala Gly Gly Lys Leu Thr Tyr Thr
145                 150                 155                 160

Ile Asp Phe Ala Ala Lys Gln Gly His Gly Lys Ile Glu His Leu Lys
                165                 170                 175

Thr Pro Glu Gln Asn Val Glu Leu Ala Ala Ala Glu Leu Lys Ala Asp
            180                 185                 190

Glu Lys Ser His Ala Val Ile Leu Gly Asp Thr Arg Tyr Gly Ser Glu
        195                 200                 205

Glu Lys Gly Thr Tyr His Leu Ala Leu Phe Gly Asp Arg Ala Gln Glu
    210                 215                 220

Ile Ala Gly Ser Ala Thr Val Lys Ile Gly Glu Lys Val His Glu Ile
225                 230                 235                 240

Gly Ile Ala Gly Lys Gln Gly Ser Gly Gly Gly Gly Val Ala Ala Asp
                245                 250                 255

Ile Gly Thr Gly Leu Ala Asp Ala Leu Thr Ala Pro Leu Asp His Lys
            260                 265                 270

Asp Lys Gly Leu Lys Ser Leu Thr Leu Glu Asp Ser Ile Pro Gln Asn
        275                 280                 285

Gly Thr Leu Thr Leu Ser Ala Gln Gly Ala Glu Lys Thr Phe Lys Ala
    290                 295                 300

Gly Asp Lys Asp Asn Ser Leu Asn Thr Gly Lys Leu Lys Asn Asp Lys
305                 310                 315                 320

Ile Ser Arg Phe Asp Phe Val Gln Lys Ile Glu Val Asp Gly Gln Thr
                325                 330                 335

Ile Thr Leu Ala Ser Gly Glu Phe Gln Ile Tyr Lys Gln Asn His Ser
            340                 345                 350

Ala Val Val Ala Leu Gln Ile Glu Lys Ile Asn Asn Pro Asp Lys Thr
        355                 360                 365

Asp Ser Leu Ile Asn Gln Arg Ser Phe Leu Val Ser Gly Leu Gly Gly
    370                 375                 380

Glu His Thr Ala Phe Asn Gln Leu Pro Gly Gly Lys Ala Glu Tyr His
385                 390                 395                 400

Gly Lys Ala Phe Ser Ser Asp Asp Pro Asn Gly Arg Leu His Tyr Ser
                405                 410                 415

Ile Asp Phe Thr Lys Lys Gln Gly Tyr Gly Arg Ile Glu His Leu Lys
            420                 425                 430

Thr Leu Glu Gln Asn Val Glu Leu Ala Ala Ala Glu Leu Lys Ala Asp
        435                 440                 445
```

Glu Lys Ser His Ala Val Ile Leu Gly Asp Thr Arg Tyr Gly Ser Glu
450 455 460

Glu Lys Gly Thr Tyr His Leu Ala Leu Phe Gly Asp Arg Ala Gln Glu
465 470 475 480

Ile Ala Gly Ser Ala Thr Val Lys Ile Gly Glu Lys Val His Glu Ile
485 490 495

Gly Ile Ala Gly Lys Gln Gly Ser Gly Gly Gly Gly Val Ala Ala Asp
500 505 510

Ile Gly Ala Gly Leu Ala Asp Ala Leu Thr Ala Pro Leu Asp His Lys
515 520 525

Asp Lys Gly Leu Gln Ser Leu Thr Leu Asp Gln Ser Val Arg Lys Asn
530 535 540

Glu Lys Leu Lys Leu Ala Ala Gln Gly Ala Glu Lys Thr Tyr Gly Asn
545 550 555 560

Gly Ser Leu Asn Thr Gly Lys Leu Lys Asn Asp Lys Val Ser Arg Phe
565 570 575

Asp Phe Ile Arg Gln Ile Glu Val Asp Gly Gln Leu Ile Thr Leu Glu
580 585 590

Ser Gly Glu Phe Gln Val Tyr Lys Gln Ser His Ser Ala Leu Thr Ala
595 600 605

Phe Gln Thr Glu Gln Ile Gln Asp Ser Glu His Ser Gly Lys Met Val
610 615 620

Ala Lys Arg Gln Phe Arg Ile Gly Asp Ile Ala Gly Glu His Thr Ser
625 630 635 640

Phe Asp Lys Leu Pro Glu Gly Gly Arg Ala Thr Tyr Arg Gly Thr Ala
645 650 655

Phe Gly Ser Asp Asp Ala Gly Gly Lys Leu Thr Tyr Thr Ile Asp Phe
660 665 670

Ala Ala Lys Gln Gly Asn Gly Lys Ile Glu His Leu Lys Ser Pro Glu
675 680 685

Leu Asn Val Asp Leu Ala Ala Ala Ile Lys Pro Asp Gly Lys Arg His
690 695 700

Ala Val Ile Ser Gly Ser Val Leu Tyr Asn Gln Ala Glu Lys Gly Ser
705 710 715 720

Tyr Ser Leu Gly Ile Phe Gly Lys Ala Gln Glu Val Ala Gly Ser Ala
725 730 735

Glu Val Lys Thr Val Asn Gly Ile Arg His Ile Gly Leu Ala Ala Lys
740 745 750

Gln

<210> SEQ ID NO 30
<211> LENGTH: 753
<212> TYPE: PRT
<213> ORGANISM: Artificial Sequence
<220> FEATURE:
<223> OTHER INFORMATION: fHbp fusion polypeptide

<400> SEQUENCE: 30

Val Ala Ala Asp Ile Gly Ala Gly Leu Ala Asp Ala Leu Thr Ala Pro
1 5 10 15

Leu Asp His Lys Asp Lys Ser Leu Gln Ser Leu Thr Leu Asp Gln Val
20 25 30

Val Arg Lys Asn Glu Lys Leu Lys Leu Ala Ala Gln Gly Ala Glu Lys
35 40 45

Thr Tyr Gly Asn Gly Asp Ser Leu Asn Thr Gly Lys Leu Lys Asn Asp

-continued

```
    50                  55                  60

Lys Val Ser Phe Asp Phe Ile Arg Gln Ile Glu Val Asp Gly Gln Leu
65                  70                  75                  80

Ile Thr Leu Glu Ser Gly Glu Phe Gln Ile Tyr Lys Gln Asp His Ser
                85                  90                  95

Ala Val Val Ala Leu Gln Ile Glu Lys Ile Asn Asn Pro Asp Lys Ile
            100                 105                 110

Asp Ser Leu Ile Asn Gln Arg Ser Phe Arg Val Ser Gly Leu Gly Gly
        115                 120                 125

Glu His Thr Ala Phe Asn Gln Leu Pro Asp Gly Lys Ala Glu Tyr His
    130                 135                 140

Gly Lys Ala Phe Ser Ser Asp Asp Ala Gly Gly Lys Leu Thr Tyr Thr
145                 150                 155                 160

Ile Asp Phe Ala Ala Lys Gln Gly His Gly Lys Ile Glu His Leu Lys
                165                 170                 175

Thr Pro Glu Gln Asn Val Glu Leu Ala Ala Ala Glu Leu Lys Ala Asp
            180                 185                 190

Glu Lys Ser His Ala Val Ile Leu Gly Asp Thr Arg Tyr Gly Ser Glu
        195                 200                 205

Glu Lys Gly Thr Tyr His Leu Ala Leu Phe Gly Asp Arg Ala Gln Glu
    210                 215                 220

Ile Ala Gly Ser Ala Thr Val Lys Ile Gly Glu Lys Val His Glu Ile
225                 230                 235                 240

Gly Ile Ala Gly Lys Gln Gly Ser Gly Gly Gly Val Ala Ala Asp
                245                 250                 255

Ile Gly Thr Gly Leu Ala Asp Ala Leu Thr Ala Pro Leu Asp His Lys
            260                 265                 270

Asp Lys Gly Leu Lys Ser Leu Thr Leu Glu Asp Val Ile Pro Gln Asn
        275                 280                 285

Gly Thr Leu Thr Leu Ser Ala Gln Gly Ala Glu Lys Thr Phe Lys Ala
    290                 295                 300

Gly Asp Lys Asp Asn Ser Leu Asn Thr Gly Lys Leu Lys Asn Asp Lys
305                 310                 315                 320

Ile Ser Arg Phe Asp Phe Val Gln Lys Ile Glu Val Asp Gly Gln Thr
                325                 330                 335

Ile Thr Leu Ala Ser Gly Glu Phe Gln Ile Tyr Lys Gln Asn His Ser
            340                 345                 350

Ala Val Val Ala Leu Gln Ile Glu Lys Ile Asn Asn Pro Asp Lys Thr
        355                 360                 365

Asp Ser Leu Ile Asn Gln Arg Ser Phe Arg Val Ser Gly Leu Gly Gly
    370                 375                 380

Glu His Thr Ala Phe Asn Gln Leu Pro Gly Gly Lys Ala Glu Tyr His
385                 390                 395                 400

Gly Lys Ala Phe Ser Ser Asp Asp Pro Asn Gly Arg Leu His Tyr Ser
                405                 410                 415

Ile Asp Phe Thr Lys Lys Gln Gly Tyr Gly Arg Ile Glu His Leu Lys
            420                 425                 430

Thr Leu Glu Gln Asn Val Glu Leu Ala Ala Ala Glu Leu Lys Ala Asp
        435                 440                 445

Glu Lys Ser His Ala Val Ile Leu Gly Asp Thr Arg Tyr Gly Ser Glu
    450                 455                 460

Glu Lys Gly Thr Tyr His Leu Ala Leu Phe Gly Asp Arg Ala Gln Glu
465                 470                 475                 480
```

-continued

```
Ile Ala Gly Ser Ala Thr Val Lys Ile Gly Glu Lys Val His Glu Ile
                485                 490                 495

Gly Ile Ala Gly Lys Gln Gly Ser Gly Gly Gly Gly Val Ala Ala Asp
            500                 505                 510

Ile Gly Ala Gly Leu Ala Asp Ala Leu Thr Ala Pro Leu Asp His Lys
        515                 520                 525

Asp Lys Gly Leu Gln Ser Leu Thr Leu Asp Gln Ser Val Ser Lys Asn
    530                 535                 540

Glu Lys Leu Lys Leu Ala Ala Gln Gly Ala Glu Lys Thr Tyr Gly Asn
545                 550                 555                 560

Gly Ser Leu Asn Thr Gly Lys Leu Lys Asn Asp Lys Val Ser Arg Phe
                565                 570                 575

Asp Phe Ile Arg Gln Ile Glu Val Asp Gly Gln Leu Ile Thr Leu Glu
            580                 585                 590

Ser Gly Glu Phe Gln Val Tyr Lys Gln Ser His Ser Ala Leu Thr Ala
        595                 600                 605

Phe Gln Thr Glu Gln Ile Gln Asp Ser Glu His Ser Gly Lys Met Val
    610                 615                 620

Ala Lys Arg Gln Phe Arg Ile Gly Asp Ile Ala Gly Glu His Thr Ser
625                 630                 635                 640

Phe Asp Lys Leu Pro Glu Gly Gly Arg Ala Thr Tyr Arg Gly Thr Ala
                645                 650                 655

Phe Gly Ser Asp Asp Ala Gly Gly Lys Leu Thr Tyr Thr Ile Asp Phe
            660                 665                 670

Ala Ala Lys Gln Gly Asn Gly Lys Ile Glu His Leu Lys Ser Pro Glu
        675                 680                 685

Leu Asn Val Asp Leu Ala Ala Ala Ile Lys Pro Asp Gly Lys Arg His
    690                 695                 700

Ala Val Ile Ser Gly Ser Val Leu Tyr Asn Gln Ala Glu Lys Gly Ser
705                 710                 715                 720

Tyr Ser Leu Gly Ile Phe Gly Lys Ala Gln Glu Val Ala Gly Ser Ala
                725                 730                 735

Glu Val Lys Thr Val Asn Gly Ile Arg His Ile Gly Leu Ala Ala Lys
            740                 745                 750

Gln


<210> SEQ ID NO 31
<211> LENGTH: 274
<212> TYPE: PRT
<213> ORGANISM: Neisseria meningitidis

<400> SEQUENCE: 31

Met Asn Arg Thr Ala Phe Cys Cys Phe Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95
```

-continued

```
Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys Arg His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln


<210> SEQ ID NO 32
<211> LENGTH: 282
<212> TYPE: PRT
<213> ORGANISM: Neisseria meningitidis

<400> SEQUENCE: 32

Met Asn Arg Thr Thr Phe Cys Cys Leu Ser Leu Thr Ala Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Ala Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Ser Gln Asn Gly Thr Leu Thr Leu Ser Ala Gln Gly Ala Glu Arg Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Ile Arg Gln Ile Glu Val Asp
            100                 105                 110

Gly Gln Leu Ile Thr Leu Glu Ser Gly Glu Phe Gln Val Tyr Lys Gln
        115                 120                 125

Ser His Ser Ala Leu Thr Ala Leu Gln Thr Glu Gln Val Gln Asp Ser
    130                 135                 140

Glu His Ser Gly Lys Met Val Ala Lys Arg Gln Phe Arg Ile Gly Asp
145                 150                 155                 160

Ile Val Gly Glu His Thr Ser Phe Gly Lys Leu Pro Lys Asp Val Met
                165                 170                 175

Ala Thr Tyr Arg Gly Thr Ala Phe Gly Ser Asp Asp Ala Gly Gly Lys
            180                 185                 190
```

Leu Thr Tyr Thr Ile Asp Phe Ala Ala Lys Gln Gly His Gly Lys Ile
195 200 205

Glu His Leu Lys Ser Pro Glu Leu Asn Val Asp Leu Ala Ala Ala Asp
210 215 220

Ile Lys Pro Asp Glu Lys His His Ala Val Ile Ser Gly Ser Val Leu
225 230 235 240

Tyr Asn Gln Ala Glu Lys Gly Ser Tyr Ser Leu Gly Ile Phe Gly Gly
245 250 255

Gln Ala Gln Glu Val Ala Gly Ser Ala Glu Val Glu Thr Ala Asn Gly
260 265 270

Ile Arg His Ile Gly Leu Ala Ala Lys Gln
275 280

<210> SEQ ID NO 33
<211> LENGTH: 254
<212> TYPE: PRT
<213> ORGANISM: Neisseria meningitidis

<400> SEQUENCE: 33

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Gly Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Gln
65 70 75 80

Ile Glu Val Asp Gly Gln Leu Ile Thr Leu Glu Ser Gly Glu Phe Gln
85 90 95

Val Tyr Lys Gln Ser His Ser Ala Leu Thr Ala Phe Gln Thr Glu Gln
100 105 110

Ile Gln Asp Ser Glu His Ser Gly Lys Met Val Ala Lys Arg Gln Phe
115 120 125

Arg Ile Gly Asp Ile Ala Gly Glu His Thr Ser Phe Asp Lys Leu Pro
130 135 140

Glu Gly Gly Arg Ala Thr Tyr Arg Gly Thr Ala Phe Gly Ser Asp Asp
145 150 155 160

Ala Gly Gly Lys Leu Thr Tyr Thr Ile Asp Phe Ala Ala Lys Gln Gly
165 170 175

Asn Gly Lys Ile Glu His Leu Lys Ser Pro Glu Leu Asn Val Asp Leu
180 185 190

Ala Ala Ala Asp Ile Lys Pro Asp Gly Lys Arg His Ala Val Ile Ser
195 200 205

Gly Ser Val Leu Tyr Asn Gln Ala Glu Lys Gly Ser Tyr Ser Leu Gly
210 215 220

Ile Phe Gly Gly Lys Ala Gln Glu Val Ala Gly Ser Ala Glu Val Lys
225 230 235 240

Thr Val Asn Gly Ile Arg His Ile Gly Leu Ala Ala Lys Gln
245 250

<210> SEQ ID NO 34
<211> LENGTH: 12
<212> TYPE: PRT

```
<213> ORGANISM: Artificial Sequence
<220> FEATURE:
<223> OTHER INFORMATION: N-terminal sequence

<400> SEQUENCE: 34

Met Gly Pro Asp Ser Asp Arg Leu Gln Gln Arg Arg
1               5                   10


<210> SEQ ID NO 35
<211> LENGTH: 769
<212> TYPE: PRT
<213> ORGANISM: Artificial Sequence
<220> FEATURE:
<223> OTHER INFORMATION: MUTATED fhbp POLYPETIDE

<400> SEQUENCE: 35

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Val Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Arg Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Thr
            260                 265                 270

Gly Leu Ala Asp Ala Leu Thr Ala Pro Leu Asp His Lys Asp Lys Gly
        275                 280                 285

Leu Lys Ser Leu Thr Leu Glu Asp Val Ile Pro Gln Asn Gly Thr Leu
    290                 295                 300

Thr Leu Ser Ala Gln Gly Ala Glu Lys Thr Phe Lys Ala Gly Asp Lys
305                 310                 315                 320
```

-continued

```
Asp Asn Ser Leu Asn Thr Gly Lys Leu Lys Asn Asp Lys Ile Ser Arg
                325                 330                 335

Phe Asp Phe Val Gln Lys Ile Glu Val Asp Gly Gln Thr Ile Thr Leu
            340                 345                 350

Ala Ser Gly Glu Phe Gln Ile Tyr Lys Gln Asn His Ser Ala Val Val
        355                 360                 365

Ala Leu Gln Ile Glu Lys Ile Asn Asn Pro Asp Lys Thr Asp Ser Leu
    370                 375                 380

Ile Asn Gln Arg Ser Phe Arg Val Ser Gly Leu Gly Gly Glu His Thr
385                 390                 395                 400

Ala Phe Asn Gln Leu Pro Gly Gly Lys Ala Glu Tyr His Gly Lys Ala
                405                 410                 415

Phe Ser Ser Asp Asp Pro Asn Gly Arg Leu His Tyr Ser Ile Asp Phe
            420                 425                 430

Thr Lys Lys Gln Gly Tyr Gly Arg Ile Glu His Leu Lys Thr Leu Glu
        435                 440                 445

Gln Asn Val Glu Leu Ala Ala Ala Glu Leu Lys Ala Asp Glu Lys Ser
    450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
                485                 490                 495

Ser Ala Thr Val Lys Ile Gly Glu Lys Val His Glu Ile Gly Ile Ala
            500                 505                 510

Gly Lys Gln Gly Ser Gly Gly Gly Gly Val Ala Ala Asp Ile Gly Ala
        515                 520                 525

Gly Leu Ala Asp Ala Leu Thr Ala Pro Leu Asp His Lys Asp Lys Gly
    530                 535                 540

Leu Gln Ser Leu Thr Leu Asp Gln Ser Val Arg Lys Asn Glu Lys Leu
545                 550                 555                 560

Lys Leu Ala Ala Gln Gly Ala Glu Lys Thr Tyr Gly Asn Gly Asp Ser
                565                 570                 575

Leu Asn Thr Gly Lys Leu Lys Asn Asp Lys Val Ser Arg Phe Asp Phe
            580                 585                 590

Ile Arg Gln Ile Glu Val Asp Gly Lys Leu Ile Thr Leu Glu Ser Gly
        595                 600                 605

Glu Phe Gln Val Tyr Lys Gln Ser His Ser Ala Leu Thr Ala Leu Gln
    610                 615                 620

Thr Glu Gln Val Gln Asp Ser Glu Asp Ser Gly Lys Met Val Ala Lys
625                 630                 635                 640

Arg Gln Phe Arg Ile Gly Asp Ile Ala Gly Glu His Thr Ser Phe Asp
                645                 650                 655

Lys Leu Pro Lys Gly Gly Ser Ala Thr Tyr Arg Gly Thr Ala Phe Gly
            660                 665                 670

Ser Asp Asp Ala Gly Gly Lys Leu Thr Tyr Thr Ile Asp Phe Ala Ala
        675                 680                 685

Lys Gln Gly His Gly Lys Ile Glu His Leu Lys Ser Pro Glu Leu Asn
    690                 695                 700

Val Glu Leu Ala Thr Ala Tyr Ile Lys Pro Asp Glu Lys Arg His Ala
705                 710                 715                 720

Val Ile Ser Gly Ser Val Leu Tyr Asn Gln Asp Ala Lys Gly Ser Tyr
                725                 730                 735

Arg Leu Gly Ile Phe Gly Gly Gln Ala Gln Glu Val Ala Gly Ser Ala
```

740 745 750

Glu Val Glu Thr Ala Asn Gly Ile His His Ile Gly Leu Ala Ala Lys
755 760 765

Gln

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Gly Ser Gly
1

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Gly Ser Gly Gly
1 5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Ser Gly Ser Gly
1 5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Ser Gly Gly Gly
1 5

-continued

```
<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Ser Gly
1               5


<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Ser Ser Gly
1               5


<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Gly Gly Gly Gly
1               5
```

PENTAVALENT VACCINE AGAINST *Neisseria meningitidis* COMPRISING A SYNTHETIC MEN A ANTIGEN

CROSS-REFERENCE TO RELATED APPLICATIONS

This application is the § 371 U.S. National Phase entry of Int'l App No. PCT/EP2021/073217 filed Aug. 23, 2021, which claims priority to GB 2013262.7 filed Aug. 25, 2020, all of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 27, 2025, is named VB66961US01_SL.txt and is 113,791 bytes in size.

TECHNICAL FIELD

This invention relates to immunisation against bacterial meningitis, and particularly to a combined vaccine for immunisation against bacterial meningitis caused by multiple pathogens.

BACKGROUND

*Neisseria meningitidis* is a leading cause of bacterial meningitis and sepsis worldwide, capable of causing outbreaks and epidemics of invasive disease. Invasive meningococcal disease occurs worldwide. Although incidence varies in different regions of the world, infants, children, and adolescents are the most vulnerable to developing invasive disease. Symptoms of the disease progress rapidly and often result in devastating outcomes. Based on antigenic differences in their capsular polysaccharide, 12 serogroups of *N. meningitidis* have been identified. Virtually all disease-associated isolates are encapsulated, with serogroups A, B, C, W, X and Y being responsible for over 90% of invasive meningococcal infections worldwide. The distribution of these serogroups varies geographically and temporally.

Meningitis B is a serious and often deadly disease, affecting mainly infants and young adults. It is easily misdiagnosed, can kill within 24 hours of onset and can cause serious, life-long disabilities despite the administration of treatment.

There are currently two licensed vaccines that have been designed to immunize against serogroup B meningococcus: GSK's BEXSERO and Pfizer's TRUMENBA.

BEXSERO (also known as C4MenB) contains a preparation of outer membrane vesicles (OMVs) from the epidemic strain of group B Meningococcal NZ98/254 together with five meningococcal antigens: Neisserial Heparin Binding protein A (NHBA), factor H binding protein (fHbp) variant 1.1, Neisserial adhesion protein A (NadA), and accessory proteins GNA1030 and GNA2091. Four of these antigens are present as fusion proteins (an NHBA-GNA1030 fusion protein and a GNA2091-fHbp fusion protein). BEXSERO® is described in literature (for example, see Bai et al. (2011) *Expert Opin Biol Ther.* 11:969-85, Su & Snape (2011) *Expert Rev Vaccines* 10:575-88).

TRUMENBA® contains two lipidated MenB fHbp antigens (v1.55 and v3.45) adsorbed on aluminium phosphate.

fHbp (also known interchangeably in the art as genome-derived *Neisseria* antigen (GNA) 1870, LP2086 and protein '741') binds to human factor H (hfH), which is a large (180 kDa) multi-domain soluble glycoprotein, consisting of 20 complement control protein (CCP) modules connected by short linker sequences. hfH circulates in human plasma and regulates the Alternative Pathway of the complement system. Functional binding of fHbp to hfH relies predominantly on CCP modules (or domains) 6-7 of hfH, and enhances the ability of the bacterium to resist complement-mediated killing. Therefore, expression of fHbp enables survival in ex vivo human blood and serum.

As different fHbp classification schemes have been proposed, a dedicated database is available with a unified fHbp nomenclature for the assignment of new sub-variants: HyperText Transfer Protocol (http)://*neisseria*.org/nm/typing/fhbp (also as HyperText Transfer Protocol (https):// pubmlst.org/*neisseria*/fHbp/).

fHbp has been classified into three (main) variants 1, 2 and 3, which were further divided into sub/variants fHbp-1.x, fHbp-2.x and fHbp-3.x, where x denotes the specific peptide sub/variant. In a different nomenclature scheme, the sub/variants are grouped into subfamily A (corresponding to variants 2 and 3) and subfamily B (corresponding to variant 1) based on sequence diversity.

BEXSERO is predicted to provide broad coverage against MenB strains circulating worldwide (Medini D et al., *Vaccine* 2015; 33:2629-2636; Vogel U et al. *Lancet Infect Dis* 2013; 13:416-425; Křížová et al., *Epidemiol Mikrobiol Imunol* 2014; 63:103-106; Tzanakaki G et al. *BMC Microbiol* 2014; 14:111; Wasko I et al. *Vaccine* 2016; 34:510-515; 6. Simões M J et al. *PLoS ONE* 12(5): e0176177; and Parikh S R et al. *Lancet Infect Dis* 2017; 17:754-62). Furthermore, following the introduction of BEXSERO into the UK national infant immunization programme in September 2015, data at 10 months showed 83% vaccine efficacy on all MenB strains after two doses (Parikh S R et al., *Lancet* 2016; 388:2775-82).

However, bactericidal activity is variant specific; antibodies raised against one variant are not necessarily cross-protective against other variants, although some cross-reactivity has been described between fHbp v2 and v3 (Masignani V et al., *J Exp Med* 2003; 197:789-799). Antibodies raised against sub/variant fHbpv1.1, included in the BEXSERO vaccine, are highly cross-reactive with fHbp v1 and poorly cross-reactive with fHbp v2 and v3 (Brunelli B et al., *Vaccine* 2011; 29:1072-1081).

Therefore, despite the efficacy of licensed serogroup B meningococcus vaccines such as BEXSERO, there remains a need to develop vaccines with broadened MenB strain coverage and improved immunogenicity, without compromising on the strengths of, e.g., BEXSERO.

WO2020/030782 describes how strain coverage and immunogenicity of a MenB vaccine can be improved by including further fHbp variants in an immunogenic composition, together with the BEXSERO antigens. In particular, WO2020/030782 discloses an immunogenic composition comprising an fHbp fusion protein, comprising modified fHbp v2, v3 and v1.13 or v1.15 polypeptides.

Vaccine approaches for immunizing against serogroups A, C, W and Y have tended to focus on the *Neisseria meningitidis* capsular polysaccharides (CPSs). In general, CPSs are T-cell independent antigens, which means that they can give an immune response without the involvement of T-cells. This response lacks several important properties that characterize the T-cell dependent immune response, such as immunological memory, class switch from IgM to IgG, and affinity maturation. If the polysaccharide part is connected to a carrier protein, however, it triggers cellular immune response that creates memory effect, and also gives protection in young children. Such polysaccharide linked to a carrier protein are often referred to as glycoconjugates, and are especially valuable as vaccines. In this respect, especially efficient vaccines (glycoconjugate vaccines) can be made by covalently attaching the saccharide to a carrier protein through a linker moiety (or spacer) or even by direct coupling of the saccharide with the selected carrier protein. In any case, the glycoconjugates can induce a T-cell dependent immune response with memory and effect also in young children, while the non-conjugated CPS generally fails to provide either a memory effect in adults or any substantial immunogenic effect in infants.

Current serogroup C vaccines (MENJUGATE [Costantino et al. (1992) *Vaccine* 10:691-698, Jones (2001) *Curr Opin Investig Drugs* 2:47-49], MENINGITEC and NEISVAC-C) include conjugated saccharides. MENJUGATE and MENINGITEC have oligosaccharide antigens conjugated to a $CRM_{197}$ carrier, whereas NEISVAC-C uses the complete polysaccharide (de-O-acetylated) conjugated to a tetanus toxoid carrier.

The vaccine products marketed under the trade names MENVEO, MENACTRA, and NIMENRIX all contain conjugated capsular saccharide antigens from each of serogroups Y, W135, C and A.

In MENVEO (also known generically as Meningococcal (Groups A, C, Y, and W-135) Oligosaccharide Diphtheria CRM197 Conjugate Vaccine) each of the A, C, W135 and Y antigens is conjugated to a $CRM_{197}$ carrier.

In MENACTRA (also known generically as Meningococcal (Groups A, C, Y and W-135) Polysaccharide Diphtheria Toxoid Conjugate Vaccine) each of the A, C, W135 and Y antigens is conjugated to a diptheria toxoid carrier.

In NIMENRIX (also known generically as Meningococcal polysaccharide groups A, C, W-135 and Y conjugate vaccine) each of the A, C, W135 and Y antigens is conjugated to a tetanus toxoid carrier.

Among the *N. meningitidis* capsular polysaccharides, the *N. meningitidis* serogroup A capsular polysaccharide (MenA CPS) is known to suffer from inherent chemical instability in water (see e.g. Frasch et al. Adv. Biotechnol. Processes, 1990, 12, 123-145). As a result of this instability, serogroup A antigens are provided in a solid lyophilized form. Therefore, vaccines containing a serogroup A antigens, such as MENVEO, must currently be supplied in 2 vials that are combined (reconstituted) prior to administration. The MenCYW-135 component of the conjugate vaccine is provided as a liquid, which is used to reconstitute the MenA lyophilized conjugate vaccine component to form the complete vaccine product at the point of administration. However, this presentation of the vaccine product is inconvenient and a fully liquid single formulation would be most advantageous.

Furthermore, it would be advantageous to provide a fully liquid pentavalent vaccine composition, providing immune protection against infection by each of *N. meningitidis* serogroups A, B, C, W135 and Y.

The MenA CPS is composed of (1→6)-linked 2-acetamido-2-deoxy-α-D-mannopyranosyl phosphate repeating units and the hydrolysis instability of MenA polysaccharide is mainly due to the ring oxygen and N-acetamide promoted hydrolysis on the phosphodiester linkage. It has in fact been observed that both the oxygen in the ring and N-acetyl group (NHAc) destabilize the phosphodiester glycosidic linkage and the axial position of NHAc also contributes to this mechanism as indicated in the below reported Scheme A (Berti et al. Vaccine, 2012, 30, 6409-6415):

Scheme A

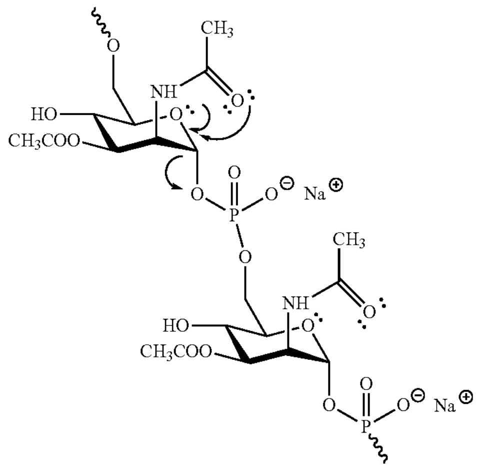

The availability of MenA polysaccharide mimics resistant to hydrolysis is very attractive for the development of more stable conjugate vaccines. Stabilization of the CPS can be achieved in different ways, and MenA CPS analogues in which the ring-oxygen is replaced by a methylene group, have been reported in the prior art. In particular in this respect, when the oxygen in the ring is replaced by a carbon, the destabilization described in Scheme A is prevented as provided in Scheme B:

Scheme B

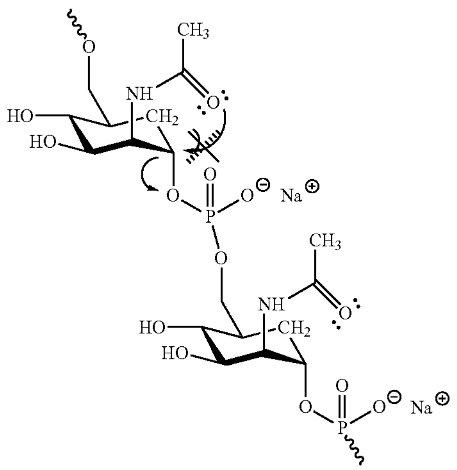

Toma et al. Org. Biomol. Chem., 2009, 7, 3734-3740 describe the preparation of the monomer O-(2-acetamido-2-deoxy-5a-carba-alpha-D-mannopyranosyl)phosphate, where a methylene group replaces the pyranose oxygen of the repeating unit of the MenA CPS. The publication refers to the chemical synthetic preparation of the monomer itself, only.

Gao et al. (Org. Biomol. Chem. 2012, 10(33), 6673, and ACS Chem. Biol. 2013, 8(11), 2561) and Ramella D. et al. (Eur J. Org. Chem, 2014, 5915-5924) describes the stabilization of the glycosyl 1-O-phosphates by using carbasugars, where a methylene group replaces the pyranose oxygen atom. They also report the conjugation of the synthetic carba-trimer to a protein carrier, without however further investigating the behaviour of carba-analogues having a higher degree of polymerization. There is also no mention of a carba-analogue, which has a specific level of acetylation and/or specific acetylation pattern. Even further, the trimer considered showed poor potential in inhibiting the binding of anti-MenA CPS antibodies, indicating the described derivatives to be relatively poor synthetic antigens. For native MenA polysaccharides it is suggested that the degree of acetylation recommended is 75-90% and that the WHO guidelines recommended that MenA vaccines have at least 61.5% O-acetylation. However, the authors further disclose that the acetylation make significant alterations to the hydrophobicity of the O-acetylated conjugated polysaccharide. Accordingly, considering structural conformational changes and conformation differences with the natural polysaccharides, the level and pattern of acetylations optimal for the carba-analogues are not obvious to be predicted. This is also confirmed in recent in silico studies that have shown conformational differences between the carba-analogues and the natural polysaccharide at the increase of the oligomer length (Carbohydrate Research, 486 (2019) 107838).

Thus, there is a need to identify carbaMenA analogue polysaccharide derivatives that have good stability, exhibit a good immunogenic profile, and which are obtainable following a reliable and convenient synthetic approach, and suitable for inclusion in a fully liquid pentavalent vaccine composition, providing immune protection against infection by each of *N. meningitidis* serogroups A, B, C, W135 and Y.

SUMMARY OF THE INVENTION

A first aspect of the invention provides an aqueous immunogenic composition which, after administration to a subject, is able to induce an immune response that is bactericidal against serogroups A, B, C, W135 and Y of *Neisseria meningitidis*, wherein the composition comprises:

i. a conjugated serogroup A antigen;

ii. a conjugated serogroup C antigen;

iii. a conjugated serogroup W135 antigen;

iv. a conjugated serogroup Y antigen; and v. one or more polypeptide antigens from serogroup B, wherein (ii), (iii) and (iv) are capsular saccharide antigens, and wherein (i) is a synthetic analogue of a serogroup A capsular saccharide.

In a preferred embodiment of the first aspect, the conjugated serogroup A antigen is an oligomer conjugate and comprises an oligomer of Formula (Ia) or (Ib):

(Ia)

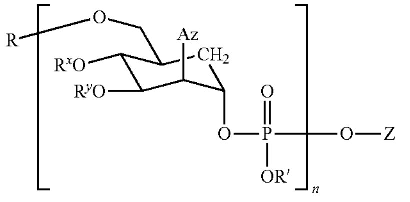

or

-continued (Ib)

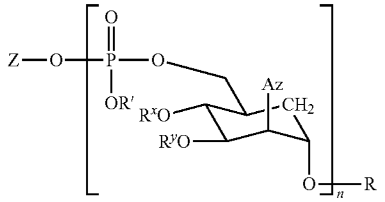

Wherein in the oligomer n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O)Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C—N.

In a preferred embodiment of the first aspect, the conjugated serogroup A antigen is an oligomer conjugate of Formula (IIa) or (IIb):

(IIa)

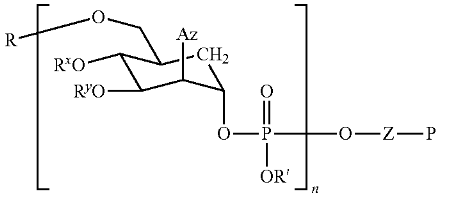

or (IIb)

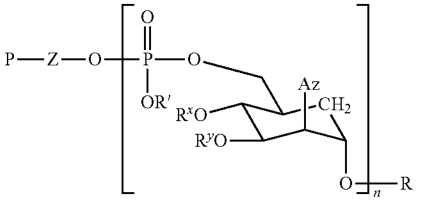

Wherein in the oligomer n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N$(R^1)_2$ and —$N_3$, wherein $R^1$ is independently selected from the group consisting of H, a linear or branched $C_1$-$C_6$-alkyl and a linear or branched $C_1$-$C_6$-haloalkyl;

Z is (i) a functional linker or a bond; and

P is a protein.

A second aspect of the invention provides a method for raising an immune response in a mammal, comprising administering an immunogenic composition according to the first aspect.

A third aspect of the invention provides an immunogenic composition according to the first aspect, for use in medicine.

A fourth aspect of the invention provides an immunogenic composition according to the first aspect, for use as a vaccine.

A fifth aspect of the invention provides an immunogenic composition according to the first aspect, for use in a method of raising an immune response in a mammal.

A sixth aspect of the invention provides an immunogenic composition according to the first aspect, for use in immunizing a mammal against *N. meningitidis* infection.

DESCRIPTION OF THE FIGURES

FIGS. 6A, 6B, 6C and 6D. Immune response elicited by the neo-glycoconjugates. FIGS. 6A, 6B and 6C panels show antibody titers reported as Geometric Mean (horizontal bar) with the 95% of CI (vertical bar). FIG. 6D panel shows rSBA titers reported as Geometric Mean (horizontal bar) with the 95% of CI (vertical bar). Two-tailed Mann-Whitney test was used to compare ranks; n=10. Pre-immune was the negative control in both types of analysis. FIG. 6A) Anti-MenA IgG titers estimated in individual murine sera after the second boost against the natural MenA CPS. $p<0.0001$ between avDP~15 MenA and carbaDP6/DP8 conjugates. FIG. 6B) Anti-deOAc MenA IgG titers determined against the de-O-acetylated MenA CPS conjugated to HSA. $p=0.002$ between avDP~15 and carbaDP8 conjugates, and between avDP8.5 and carbaDP6 conjugates; $p=0.003$ between avDP8.5 and carbaDP8 conjugates; and $p=0.004$ between avDP~15 and carbaDP6 conjugates comparison. FIG. 6C) Anti-MenA IgG titers estimated in individual sera after the second boost using MenA CPS for coating. $p=0.0011$ comparing avDP15 and Ac-carbaDP8 conjugates. FIG. 6D) Human and rabbit serum bactericidal titers measured after the third injection on pooled and individual mice sera, respectively. No significant differences were found comparing the ranks. Immunizations were conducted in duplicates and data from a representative experiment are here shown. *Human and rabbit SBA titers measured after the third injection on pooled sera; **Human and rabbit SBA titers measured after the third injection on pooled sera from responder mice. On the y-axes the "Anti Men A CPS IgG (GMT 95% Cl)" are indicated.

FIG. 15 shows SBA titers post three doses of vaccine.

DETAILED DESCRIPTION OF THE INVENTION

Figure 1:
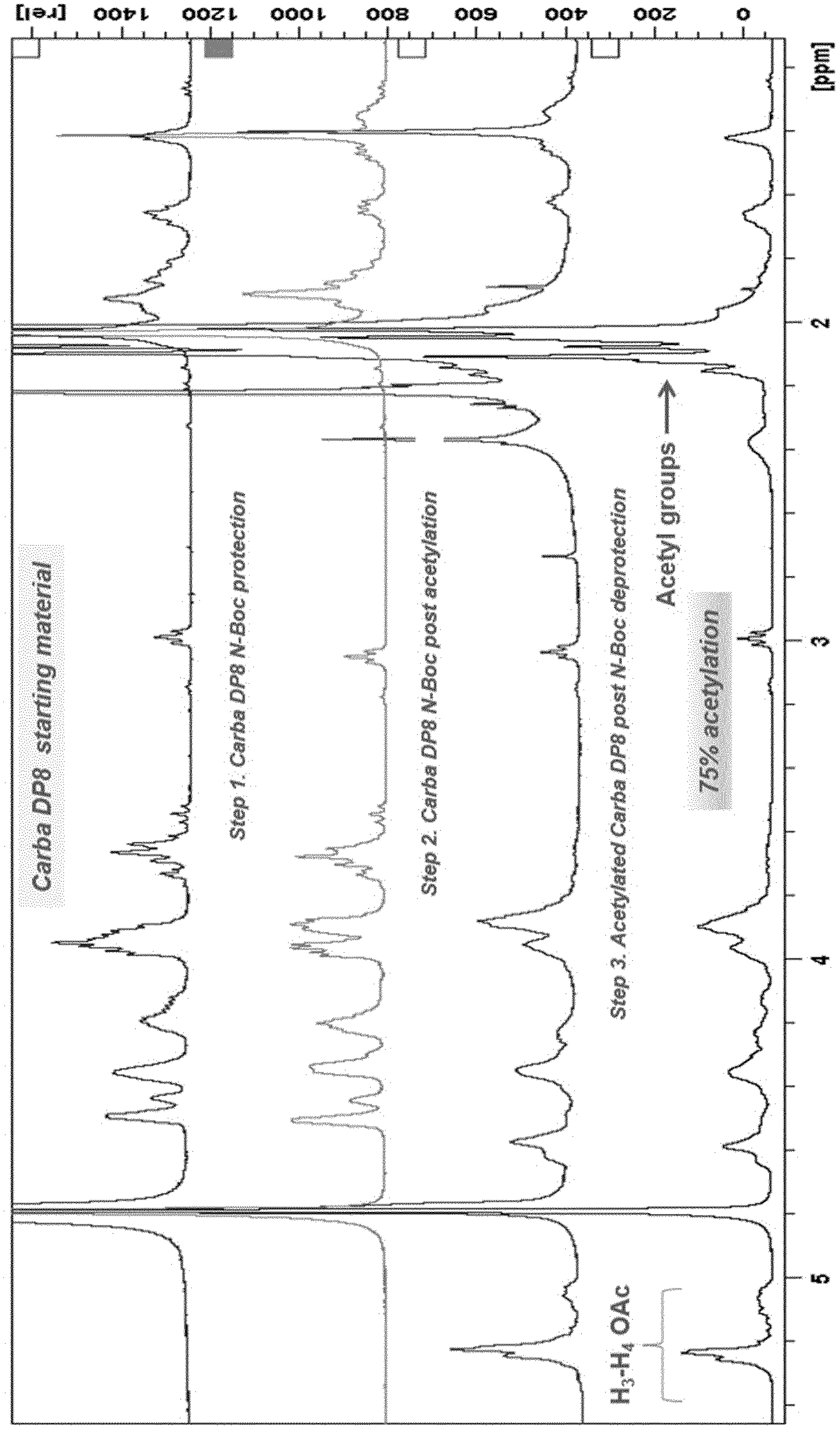
FIG. 1 is a $^1$H-NMR monitoring of the three reaction steps for random O-acetylation (i.e. where the oligomer is acetylated at one or more $R^x$ and/or $R^y$, in other words wherein at least one of $R^x$ and/or $R^y$ is —C(O)Me) of carba-analogue DP8, i.e. Formula (Ia) where n=8.

The present invention provides an aqueous immunogenic composition which, after administration to a subject, is able to induce an immune response that is bactericidal against serogroups A, B, C, W135 and Y of *Neisseria meningitidis*. Advantageously, the composition is provided as a fully liquid formulation, meaning that each of the antigenic components can be stably combined in a single aqueous dose without the need for lyophilisation. The immunogenic composition comprises:

i. a conjugated serogroup A antigen;
ii. a conjugated serogroup C antigen;
iii. a conjugated serogroup W135 antigen;
iv. a conjugated serogroup Y antigen; and
v. one or more polypeptide antigens from serogroup B, wherein (ii), (iii) and (iv) are capsular saccharide antigens, and wherein (i) is a synthetic analogue of a serogroup A capsular saccharide. Preferably the saccharide antigens are oligosaccharides.

The Conjugated Serogroup A Antigenic Component

The serogroup A antigenic component of the immunogenic composition of the invention is a synthetic polysaccharide carba-analogue (i.e. where the ring oxygen of the mannosamine unit is replaced with a methylene). In a preferred embodiment, the polysaccharide carba-analogue has a degree of polymerization of at least 6, and preferably having the first analogue monomer connected to the second analogue monomer through a 1,6 linkage which connects C-1 of the first unit to C-6 of the second unit, and wherein the 1,6-linkage comprises a phosphonate moiety.

Of note, such derivatives are not only able to mimic the native polysaccharide from MenA serogroup, but they are also expected to have improved stability versus the native CPS.

The term "oligosaccharide" comprises in its meaning polysaccharides having from 3 to 10 monosaccharide units, as generally known in the art (see e.g. https://en.wikipedia.org/wiki/Oligosaccharide).

The term "oligomer" refers to carba-analogue polysaccharides, where the endocyclic oxygen has been replaced by a methylene (—CH2-) group, thus providing a cyclohexane backbone.

"Degree of Polymerization" (DP) indicates the number of monomers connected together to provide the final oligomer. In the present invention, unless otherwise provided, the DP is represented by "n" in the formulae (I) and (II).

"Average Degree of Polymerization" (avDP) indicates the average number of repeating units composing the oligomer.

Unless otherwise provided, the term "conjugation" indicates the connection or linkage of the subjected entities, particularly the oligomers of the invention having n (i.e. DP) ≥6 and the selected protein.

As used herein, the term "alkyl" represents a saturated, straight, or branched hydrocarbon moiety. The term "$C_1$-$C_6$-alkyl" refers to an alkyl moiety containing from 1 to 6 carbon atoms.

As used herein, the term "haloalkyl" represents a saturated, straight, or branched hydrocarbon moiety where one or more of the hydrogen atoms has been replaced with a halogen atom. In particular, reference to "haloalkyl" is a reference to "fluoroalkyl", i.e. wherein the halogen is fluoro. The term "$C_1$-$C_6$-haloalkyl" refers to an alkyl moiety containing from 1 to 6 carbon atoms wherein one or more of the hydrogen atoms has been replaced with a halogen atom. Examples include $-CF_3$, $-CH_2F$, $-CH_2CF_3$ and so on.

As used herein, particularly according to the definition of Z, phenyl may be optionally substituted. The phenyl group may be optionally substituted with one or more reactive functional groups to enable conjugation, such as $N_3$, $NH_2$, SH. Other suitable groups are well known by a person skilled in the art.

As used herein, the term "protecting group" is any suitable protecting group for the intended purpose. Selection and usage of such protecting groups and details of their usage are available in, for example, Greene, T. W. and Wuts, P. G. M., "Protective Groups in Organic Synthesis". Suitable protecting groups are well known by a person skilled in the art.

As used herein, the term "pharmaceutically acceptable phosphate counterion" is any counterion suitable for a phosphate group, i.e., a metal cation which is within the scope of sound medical judgment, suitable for use in contact with the tissues of human beings and animals without excessive toxicity, irritation, or other problem or complication, commensurate with a reasonable benefit/risk ratio. The pharmaceutically acceptable phosphate counterion may be a Group 1 or Group 2 metal. Particular examples of such a pharmaceutically acceptable phosphate counterion are sodium ($Na^+$) and potassium ($K^+$). It is preferred that the counterion is sodium, for example when the oligomer or conjugate of the invention is in buffer.

In one embodiment, the invention relates to a conjugated serogroup A antigen, which is an oligomer conjugate and comprises an oligomer of Formula (Ia) or (Ib):

(Ia)

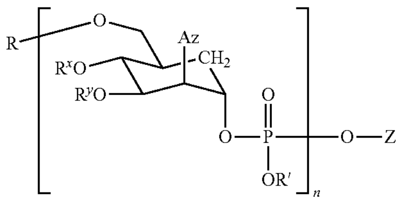

or

-continued (Ib)

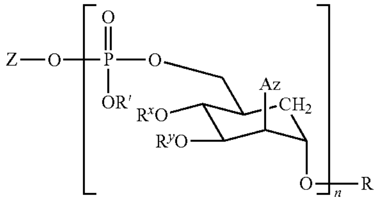

Wherein in the oligomer n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N($R^1$)2 and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O)Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C≡N.

In another embodiment, the conjugated serogroup A antigen is an oligomer conjugate of Formula (IIa) or (IIb):

(IIa)

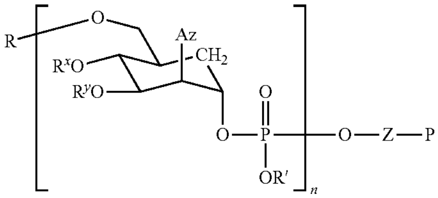

or (IIb)

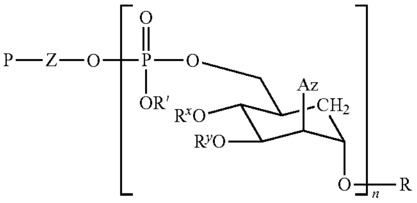

Wherein in the oligomer n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N($R^1$)2 and —$N_3$, wherein $R^1$ is independently selected from the group consisting of H, a linear or branched $C_1$-$C_6$-alkyl and a linear or branched $C_1$-$C_6$-haloalkyl;

Z is (i) a functional linker or a bond; and

P is a protein.

In a preferred embodiment, the oligomer is defined by Formula (Ia).

As defined above, n is 6, preferably 8. In one embodiment, n is from 8 to 30. In another embodiment, n is from 8 to 20. In a particular embodiment, n is from 8 to 15. In particular, n is 8 or 10. In one embodiment, n is 8. In one embodiment, n is 10.

In one embodiment, R is H or —P(O)(OR")$_2$, wherein at least one R" is $Na^+$. In one embodiment, R is H.

In one embodiment, R is NHC(O)$CH_3$.

In one embodiment, R' is $Na^+$, such that an oligomer of the invention is defined according to Formula (Ia') or (Ib'), preferably Formula (Ia'):

(Ia')

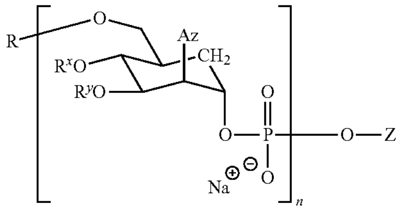

or (Ib')

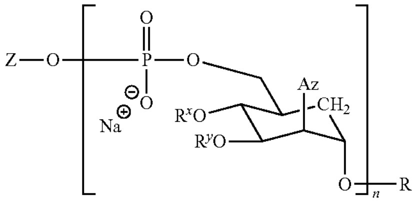

Therefore, it follows that in one embodiment, an oligomer conjugate antigen of the invention is defined according to Formula (IIa') or Formula (IIb'), preferably Formula (IIa'):

(IIa')

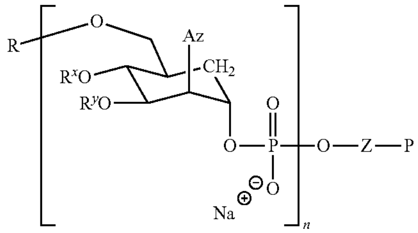

or

-continued (IIb')

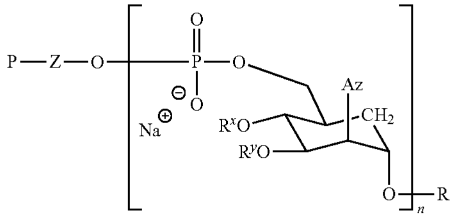

As defined above, $R^x$ is H or —C(O)$CH_3$ and may be the same or different in each repeat unit and $R^y$ is H or —C(O)$CH_3$ and may be the same or different in each repeat unit, wherein at least one of $R^x$ or $R^y$ is —C(O)$CH_3$ in at least one repeat unit. Thus, it should be understood that the formulae as defined inside the square brackets according to Formula (Ia), (IIa), (Ib) and (IIb), means that each unit of the oligomer has this backbone, but the monomer unit defined by the square brackets is not necessarily the same given that different options for $R^x$ and $R^y$ may be chosen for each repeat unit defined by the square brackets. It will therefore be appreciated that different % acetylation may be achieved, depending on n and the choice of H or —C(O)$CH_3$ for $R^x$ and $R^y$. For example, each repeat unit of the oligomer, defined by the square brackets, may be the same or different depending on the level of acetylation, i.e., depending on the choice of H or —C(O)$CH_3$ for each of $R^x$ and $R^y$.

In one embodiment, in the oligomer $R^x$ is —C(O)$CH_3$ in at least one repeat unit. In one embodiment, in the oligomer $R^x$ is H and $R^y$ is —C(O)$CH_3$ in at least one same repeat unit.

In one embodiment, in the oligomer $R^x$ is —C(O)$CH_3$ and $R^y$ is H in at least one same repeat unit.

In one embodiment, in the oligomer $R^x$ and $R^y$ are both —C(O)$CH_3$ in at least one same repeat unit.

In one embodiment, in the oligomer $R^x$ is H and $R^y$ is —C(O)$CH_3$ in at least one same repeat unit and $R^x$ is —C(O)$CH_3$ and $R^y$ is H in at least one another same repeat unit.

In one embodiment, in the oligomer $R^x$ is H and $R^y$ is —C(O)$CH_3$, within the same repeat unit, in at least four repeat units. In one embodiment, in the oligomer $R^x$ is H and $R^y$ is —C(O)$CH_3$, within the same repeat unit, in at least six repeat units. In one embodiment, in the oligomer $R^x$ is H and $R^y$ is —C(O)$CH_3$, within the same repeat unit, in at least eight repeat units. In one embodiment, in the oligomer $R^x$ is H and $R^y$ is —C(O)$CH_3$, within the same repeat unit, in at least ten repeat units.

In one embodiment, in the oligomer $R^x$ is —C(O)$CH_3$ and $R^y$ is H, within the same repeat unit, in at least four repeat units.

In one embodiment, in the oligomer $R^x$ is H and $R^y$ is —C(O)$CH_3$, within the same repeat unit, in four repeat units and $R^x$ is —C(O)$CH_3$ and $R^y$ is H, within the same repeat unit, in four repeat units.

In one embodiment, the oligomer may have $R^x$ or $R^y$ is —C(O)$CH_3$ in all repeat units, in other words the repeating units 3 or 4 acetylation on each repeating unit are selectively acetylated units.

In one embodiment, in the oligomer $R^x$ is H and $R^y$ is —C(O)$CH_3$ in at least one same repeat unit, $R^x$ is —C(O)$CH_3$ and $R^y$ is H in at least one same repeat unit and $R^x$ and $R^y$ are both —C(O)$CH_3$ in at least one same repeat unit.

In one embodiment, taken together, about 50 to 90% of $R^x$ and $R^y$ in the oligomer is —C(O)$CH_3$. In other words, the total amount of acetylation of the oligomer is about 50 to 90%. In other words, in the oligomer of the invention at least one of $R^x$ and one of $R^y$ is —C(O)$CH_3$ in a same or different repeat unit with the total of acetylation degree at 3 ($R^y$ is —C(O)$CH_3$) and 4 ($R^x$ is —C(O)$CH_3$) positions of about 50 to 90%. For the avoidance of doubt, as noted above, $R^x$ and $R^y$ may be the same or different in each repeat unit of the oligomer.

In another embodiment, taken together, about 60 to 80% of $R^x$ and $R^y$ in the oligomer is —C(O)$CH_3$. In other words, the total amount of acetylation of the oligomer is about 60 to 80%. For the avoidance of doubt, as noted above, $R^x$ and $R^y$ may be the same or different in each repeat unit of the oligomer.

In one embodiment, both of $R^x$ and $R^y$ are —C(O)$CH_3$ in at least one same repeat unit of the present oligomers, and preferably in about 40 to 50% of the repeat units of the oligomer; from about 10 to 30% of the remaining repeat units may have one of $R^x$ or $R^y$ that is —C(O)$CH_3$, the rest of the repeat units in the oligomer having $R^x$=$R^y$=H.

As defined above, Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl. The nitrogen atom is directly attached to the carba-analogue repeat unit.

Examples of such Az substituents include —$N_3$, —$NH_2$, —NH—$C_1$-$C_6$ alkyl, —N—($C_1$-$C_6$ alkyl)$_2$ and —NH(CO)—$C_1$-$C_6$ alkyl. In one embodiment, the —$C_1$-$C_6$ alkyl is a —$C_1$-$C_4$ alkyl, in particular a —$CH_3$. Thus, according to one embodiment, Az is —NH(CO)—$C_1$-$C_6$ Alkyl, in particular-NH(CO)—$CH_3$, also indicated as —NHAc (where Ac denotes an acetate, i.e. —C(O)$CH_3$).

Z may have different meanings depending on whether or not the oligomers of the invention are conjugated or not to a protein.

According to Formula (Ia) or (Ib), an oligomer of the invention is not conjugated to a protein. Therefore, as defined above, according to Formula (Ia) or (Ib) Z is one of the following:

(i) a protecting group, (ii) a linear or branched $C_1$-$C_6$ alkyl, optionally substituted aryl, —C(O)Y, or a linear or branched $C_1$-$C_6$-alkyl-X, or (iii) a functional linker for conjugation to a protein.

Thus, according to one embodiment, Z is a means for capping the terminal saccharide unit, such that it may be unreactive or reactive, for example to further chain elongation or for subsequent modification.

When Z is intended to be a means for capping the terminal carba-analogue unit, it can comprise protecting groups or capping groups, such as a linear or branched $C_1$-$C_6$ alkyl, optionally substituted phenyl, —C(O)—Y, or a linear or branched —$C_1$-$C_6$ alkyl-X, wherein X is —$NH_2$, —$N_3$, —C≡CH, —CH═$CH_2$, —SH or —S—C≡N, and wherein Y is H, a linear or branched $C_1$-$C_6$-alkyl or a protecting group.

As defined herein, Z may be a functional linker for conjugation to a protein. In this case, "functional linker" refers to any linker known in the art to be used for conjugation of a saccharide to a protein.

In one embodiment, X is —$NH_2$.

In one embodiment, Z according to Formula (Ia) or (Ib) is selected from: —($CH_2$)$_6$—$NH_2$, —($CH_2$)$_4$—$NH_2$, —($CH_2$)$_3$—$NH_2$ and —($CH_2$)$_2$—$NH_2$, where the amino group is optionally protected by a suitable protecting group, e.g. —C(O)$CH_3$ (selection and usage of such protecting groups and details of their usage are available in, for example, Greene, T. W. and Wuts, P. G. M., "protective groups in organic synthesis").

The oligomers of the invention can be prepared following synthetic approaches known in organic synthesis for the preparation of polysaccharide carba-analogues. Generally, the preparation of the oligomers of the invention can be achieved by linking at least 6 mannosamine carba-analogue building blocks in a desired way by forming a 1,6-alpha linkage between the repeating units, thus providing an oligomer having a degree of polymerization of at least 6. As indicated in Formula (I), the monomers are linked through an alpha-(1→6) phosphate linkage, and such a connection can be performed using standard polymerization techniques, such as among others the one described in Gao et al., Org. Biomol. Chem., 2012, 10, 6673.

The mannosamine carba-analogue building blocks could bear an acetate at position 3 or a protective group that can be replaced with an acetate at any stage of the synthesis.

Alternatively, and according to one embodiment, the invention relates to a process for the preparation of the oligomers of Formula (I) comprising the steps of:

a. Preparation of the monomer having phosphodiester linkage;
b. Elongation reaction of the thus obtained monomer using, for example, phosphoramidite.
c. O-acetylation of the oligomer.

In one embodiment, when $R^y$ is $C(O)CH_3$, steps (b) and (c) may be the other way around such that O-acetylation is performed prior to the elongation reaction.

In more detail, the process may comprise the steps illustrated in Scheme 1:

Scheme 1: Process for the preparation of an oligosaccharide of the invention

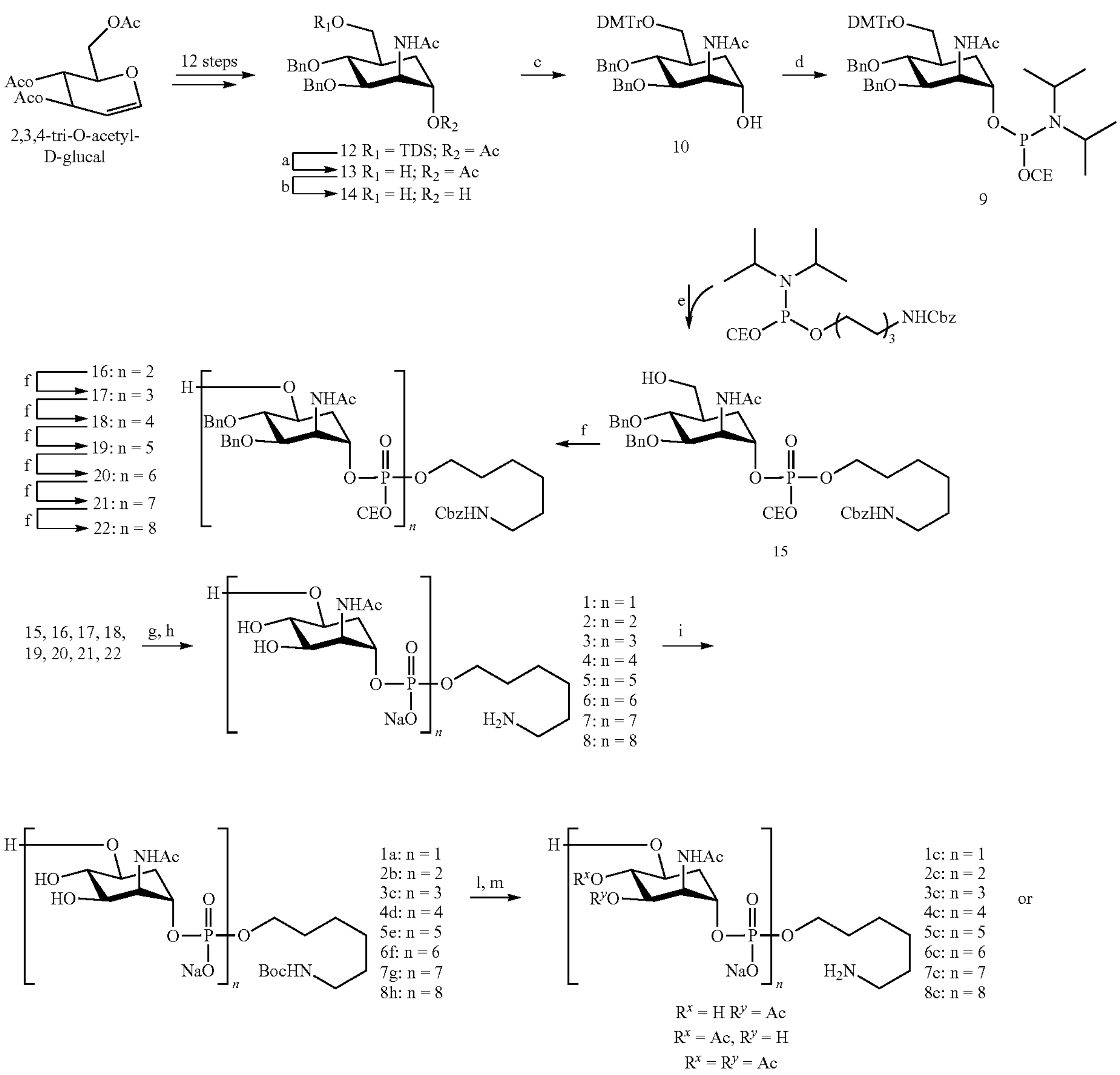

-continued

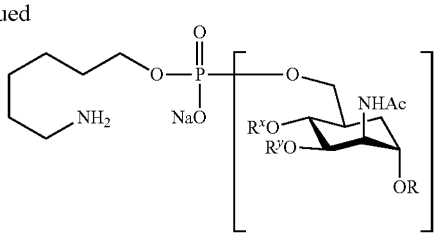

1d: n = 1
2d: n = 2
3d: n = 3
4d: n = 4
5d: n = 5
6d: n = 6
7d: n = 7
8d: n = 8

$R^x$ = H $R^y$ = Ac
$R^x$ = Ac, $R^y$ = H
$R^x$ = $R^y$ = Ac (a) TBAF, THF, 0 °C→rt, 92%.
(b) MeONa, MeOH, rt, 85%.
(c) DMTrCl, $Et_3N$, DCM, rt, 91%.
(d) 2-cyanoethyl N,N-diisopropyl-chlorophosphoramidite, N,N-diispropylethylamine, DCM, rt, 9 (94%).
(e) I. 11, DCl, MeCN, II. CSO, MeCN, III. TCA, DCM, $H_2O$, 94%.
(f) I. 9, DCl, MeCN, II. CSO, MeCN, III. TCA, DCM, $H_2O$, 16 (82%). 17 (95%), 18 (90%). 19 (92%), 20 (88%), 21 (86%), 22 (87%).
(g) $NH_4OH$, $H_2O$, dioxane.
(h) $H_2$, Pd black, $H_2O$, AcOH, 1 (99%), 2 (76%), 3 (69%), 4 (39%), 5 (88%), 6 (83%), 7 (77%), 8 (44%).
(i): $(Boc)_2O$, $NaHCO_3$, rt 16 h;
(l): $Ac_2O$/imidazole, 40 °C, ~9 d;
(m); TFA, rt, 1 h.

For the avoidance of doubt, Ac is intended to refer to an acetyl group, i.e. —$C(O)CH_3$.

In particular, the use of phosphoramidite building blocks is more effective for the formation of the phosphodiester linkages. We opted for the use of the dimethoxytrityl (DMTr) ether to temporarily mask the primary alcohol functions to be elongated. Each elongation step is based on the iteration of a three-step sequence, comprising the coupling of the phosphoramidite with the growing chain alcohol, oxidation of the intermediate phosphite to the corresponding phosphodiester and unmasking of the primary hydroxyl on the (n+1) oligomer. As illustrated in Scheme 1 the key building block 9 is obtained from intermediate 10, which in turn is derived in three steps from known carbasugar 12 (see e.g. Q. Gao et al. Org. Biomol. Chem., 2012, 10, 6673-6681). The latter carba mannose building block can be prepared from the commercially available 3,4,6-tri-O-acetyl-D-glucal according to prior art methodologies. Thus, the primary silyl ether and acetyl ester were removed from compound 12 by the consecutive action of tetrabutylammonium fluoride (TBAF) and NaOMe, to give diol 14 in 85% yield. Next the DMTr group regioselectively introduced providing alcohol 10 in 91% yield. This compound was converted into the elongation block phosphoramidite 9 by reaction with 2-cyanoethyl-N,N-diisopropyl-chlorophosphoramidite. With the building blocks in hand the target oligomers were assembled. The synthesis started with the installation of the aminohexanol spacer on alcohol 10 using known phosphoramidite 11. The building blocks were coupled in a two-step one pot reaction using dicyanoimidazole (DCI) as activator for activation of the phosphoramidite. Oxidation of the in situ formed phosphite was carried out with (1S)-(+)-(10-camphorsulfonyl)-oxaziridine (CSO). DCI ($pK_a$ 5.2) was preferred over the conventionally used tetrazole ($pK_a$ 4.9) because it is less acidic and suitable to be used in combination with the acid labile DMTr group. CSO was used instead of iodine because of its higher solubility in non-aqueous solvents such as acetonitrile. The crude phophodiester product was treated with TCA to cleave the DMTr group. The product was purified by size-exclusion chromatography (Sephadex LH-20) giving spacer-equipped monomer 15 in 94% yield. The subsequent couplings were all performed following the procedure described above until reaching the desired degree of polymerization of 8 or higher. For elongation of the longer oligomers, a larger amount of the phosphoramidite 9 was used and the coupling reaction time was increased to ensure complete conversion of the alcohol. The yield for each elongation cycle was good to excellent, ranging between 82% and 95%. Octamer 22 was obtained in 40% overall yield starting from 10. Fragments 16-22 were deprotected using a two-steps sequence. First the cyanoethyl groups (CE) were removed using an aqueous ammonia solution (33%). Next, all remaining protecting groups (the benzyl ethers and carboxybenzyl carbamate) on the so-formed phosphodiesters were cleaved off by hydrogenolysis over palladium black, to give the target non-acetylated oligomers 1-8.

The non-acetylated oligomers 1-8 may be O-acetylated in a random fashion at the 3- and/or 4-position, i.e. such that, taken together, about 50 to 90% of $R^x$ and $R^y$ in the oligomer is —$C(O)CH_3$. This may be achieved by (i) BOC-protecting the free amine group; (ii) O-acetylation using, for example $Ac_2O$/imidazole; and (iii) deprotection to afford acetylated oligomers 1c-8c or 1d to 8d. Such acetylated oligomers may then be activated with a linker group such as bis-succinimidyl adipate (also known as SIDEA) and conjugated to a protein such as $CRM_{197}$.

Scheme 2. Process leading to the preparation of the 3-O-acetylated monomer building block.

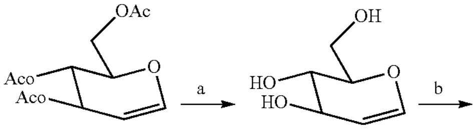

23

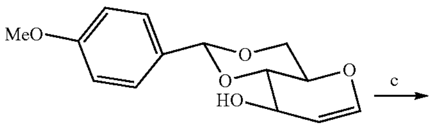

24

-continued

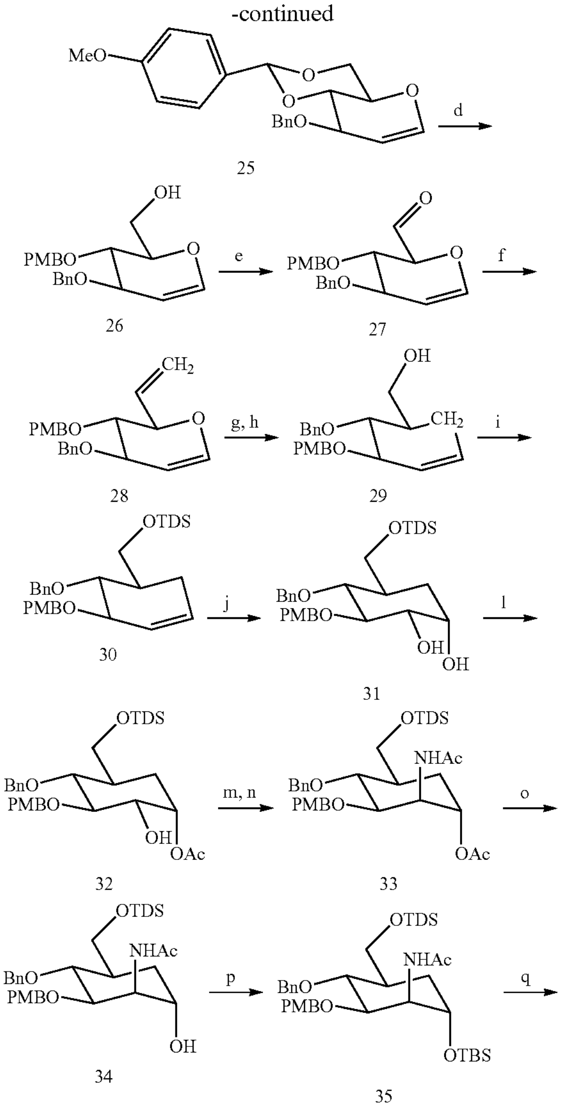

25, 26, 27, 28, 29, 30, 31, 32, 33, 34, 35

-continued

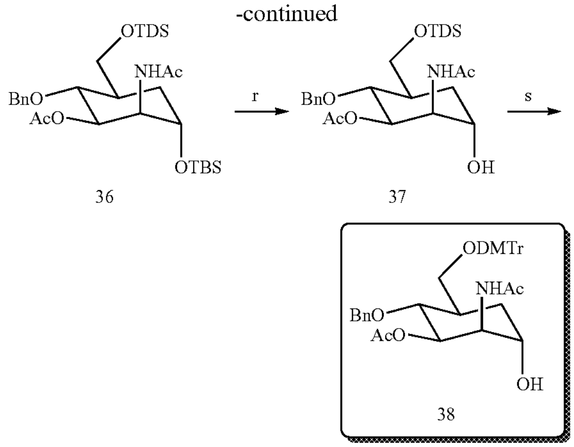

36, 37, 38

(a) $K_2CO_3$, MeOH;
(b) $PMBCH(OMe)_2$, PPTS;
(c) BnBr, NaH;
(d) DIBAL-H, DCM;
(e) DMP, DCM;
(f) $PPh_3CH_3I$, KHMDS, THF, -78 °C;
(g) m_dichlorobenzene, t, μ-waves;
(h) $NaBH_4$, EtOH/THF;
(i) TDSCl, Im, DCM;
(j) $OsO_4$, TMANO, 3:1 acetone-$H_2O$;
(l) $(MeO)_3CMe$, PTSA, CAN, then 80% AcOH;
(m) $Tf_2O$, DCM/py, -20 °C to rt; then $NaN_3$, 19:1 DMF-$H_2O$;
(n) $PPh^3$, THF, 60 °C, $H_2O$; then $Ac_2O$, MeOH
(o NaOMe/MeOH;
(p) TBSOTf, 2,6-lutidine, DCM;
(q) DDQ, then $Ac_2O$, py;
(r) HF/Pyridine, THF;
(s) DMTrCl, pyridine, DCM.

In the alternative, 3-O-acetylated monomer building blocks and 4-O-acetylated building blocks can be prepared by a process depicted in the following Scheme 3:

Scheme 3. Process leading to the preparation of 3-O-acetylated and of 4-O-acetylated monomer building block

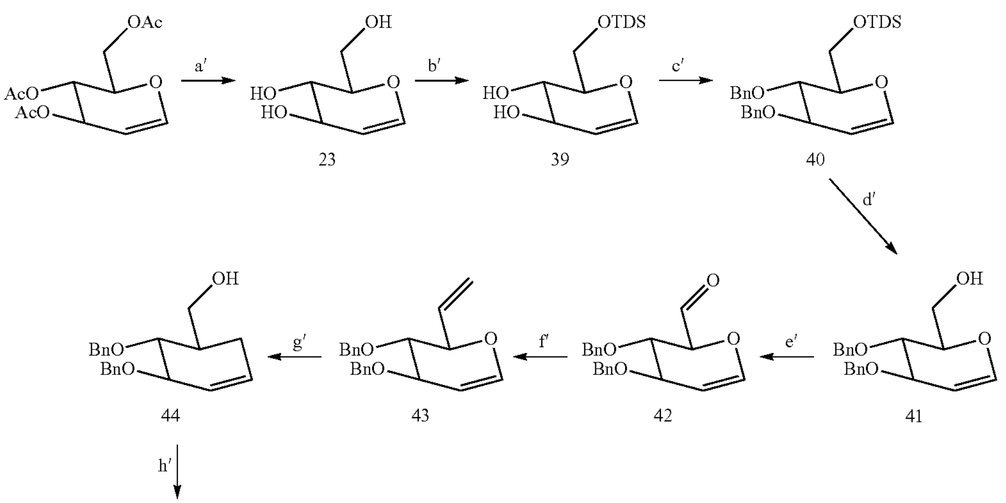

23, 39, 40, 41, 42, 43, 44

-continued

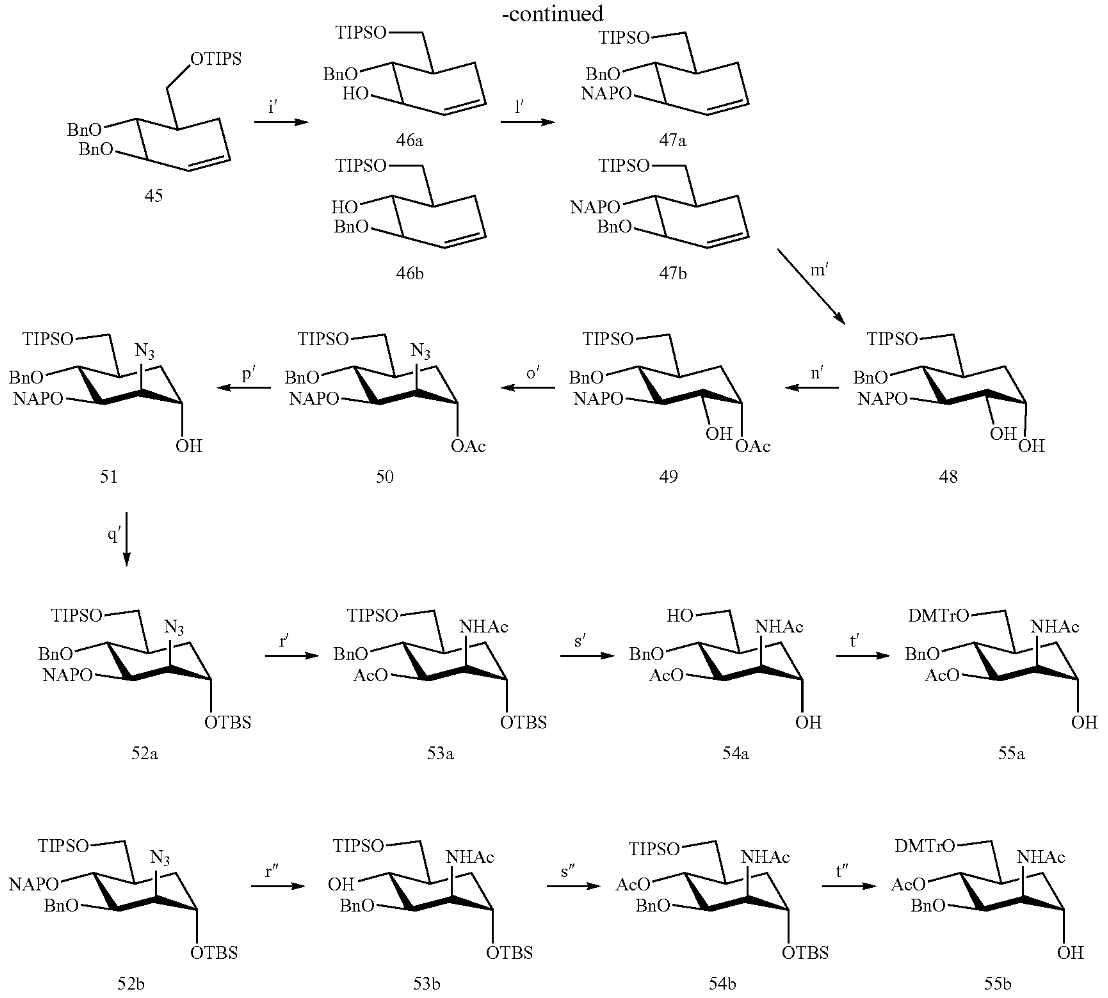

45, 46a, 46b, 47a, 47b, 48, 49, 50, 51, 52a, 53a, 54a, 55a, 52b, 53b, 54b, 55b (a') $K_2CO_3$, MeOH;
(b') TDSCl, imidazole, DMF, -30 °C;
(c') BnBr, NaH, DMF, 0 °C;
(d') TBAF, THF;
(e') IBX, AcOEt;
(f') $PPh_3CH_3I$, KHMDS, THF, -78° C. to rt;
(g') 1,3-dichlorobenzene, $NaBH_4$, EtOH/THF, 230 °C;
(h') TIPSCl, imidazole, DMF;
(i') $TiCl_4$, DCM/Toluene 2:8, -70° C.;
(l') NapBr, NaH, DMF, 0 °C;
(m') $Me_3NO\ 2H_2O$, acetone/$H_2O$ 3:1, $OsO_4$;
(n') $(MeO)_3CMe$, PTSA, ACN;
(o') $Tf_2O$, Ptr, DCM/Py, -20 °C to rt; then $NaN_3$, 19:1 DMF-$H_2O$;
(p') NaOMe, MeOH;
(q') TBSOTf, -10 °C to 70 °C, Pyr, DMAP;
(r') Pd/C, $H_2$, AcOH, then $Ac_2O$, Pyr;
(s') HR pyr, Pyr;
(t') DMTrCl, Pyr, 0 °C;
(r'') DDQ, DCM, $H_2O$;
(s'') $PPh_3$, $H_2O$, THF, then DMTrCl, Pyr.

Acetylated building blocks 38, 55a, 55b and fully acetylated building blocks (i.e. having O—Ac groups in both C3 and C4 positions of the same unit) may be converted to oligomeric versions by transformation to phosphorimidate and subsequent coupling as described above in relation to compound 9.

An important prerequisite for the immunogenicity of the carba-analogues of the invention is their ability to mimic the corresponding MenA capsular saccharide. To investigate this, competitive ELISA were performed using carba-analogues with different degrees of polymerization.

The oligomers of the invention can be introduced into a host, including a mammalian host and preferably a human host, either alone or linked to a carrier protein or as homopolymer or heteropolymer of mannose carba-analogue units. In a particular embodiment, oligomers of the invention are used as protein conjugates. Thus, in a further aspect, the invention comprises a conjugate derivative comprising the oligomers of the present invention of Formula (I), connected to a protein, according to general Formula (IIa) or (IIb):

(IIa)

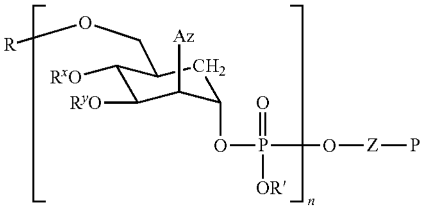

or (IIb)

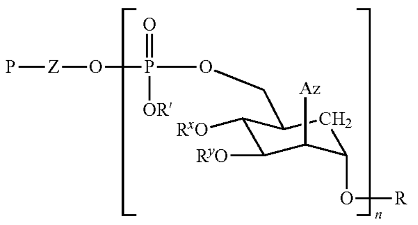

wherein n, Az, R, R', $R^x$ and $R^y$ are as defined above;

Z is a linker or a bond; and

P is a protein.

The oligomers of general Formula (Ia) or (Ib) are especially useful when conjugated to a protein, preferably through the Z moiety connected to the C-1 carbon of the first repeating unit through a phosphate moiety. The thus obtained oligomer-protein conjugated derivatives of Formula (IIa) or (IIb) are potentially useful for the preparation of compositions able to elicit immunogenic responses in infants, and also possibly able to elicit cellular responses that provide a memory effect to prolong the effectiveness of the vaccination.

In one embodiment, the oligomer conjugate is preferably defined by Formula (IIa), i.e. where the protein is conjugated at the 1-position rather than the 6-position of the carba-analogue.

The protein (or carrier protein) may influence the immunogenic response and even affect the precise nature of the antibodies that result from treatment of a mammal with one or more compounds of the invention when delivered as conjugates. Suitable proteins are those having functional groups able to react with the terminal portion of the Z moiety, thus forming the conjugate derivatives of the invention. Preferably, said functional groups are selected from —$NH_2$ and —SH, able to be connected to the Z moiety forming an amide bond or a thioether. More preferably, the protein has —$NH_2$ groups, suitable for the formation of an amide bond when reacted with Z.

Useful proteins are well known in the art. However, in one embodiment, P is an inactivated bacterial toxin selected from diphtheria toxoid (DT), tetanus toxoid (TT), $CRM_{197}$, *E. coli* ST and *Pseudomonas aeruginosa* exotoxin (rEPA), or P is a polyamino acid such as poly(lysine:glutamic acid) or P is hepatitis B virus core protein or SPR96-2021, or *N. meningitidis* serogroup B antigen fHbp-231 (i.e. the fusion protein of variant2, variant3, and variant1 of factor H binding protein (fHbp) as defined in WO 2015/128480, which is hereby incorporated by reference).

In one embodiment, P is TT, DT or $CRM_{197}$.

In a particular embodiment, P is $CRM_{197}$.

As defined above, according to Formula (IIa) or (IIb), Z is a linker or a bond. When Z is a linker, it can be derived from any suitable linker known in the art which is suitable for conjugation of an oligosaccharide to a protein.

In other words, Z in its unreacted form, i.e. when not linked to the oligomer and protein may have functional groups enabling it to act as a linker between the oligomers of the invention and the protein, such that Z is a functional linker (as defined according to Formula (Ia) and Formula (Ib)). Preferably, Z is derived from a compound comprising an amine, carboxylate, or hydroxyl group for coupling to a complementary group on a protein carrier, but other groups known in the art to provide a way to conjugate an oligosaccharide to a protein are also contemplated.

When oligomers of the invention are conjugated to a protein, a preferred Z moiety in Formula (IIa) or (IIb) is derived from a linker which is an amine-substituted alkoxy group, optionally in protected form. When in this form, the amine is acetylated or alkylated with a bi-functional reagent, the other end of which is similarly attached to a protein.

In one embodiment, according to Formula (IIa) or (IIb), Z is derived from a linker, either homobifunctional or heterobifunctional, able to connect an oligomer of the invention to a protein. In this respect, bifunctional linkers suitable for use in the conjugates of the invention include those known in the art, such as di-carboxylic acids, preferably malonic, succinic, adipic and suberic, or activated forms thereof. Alternatively, squarate esters can be used. These types of reagents are particularly convenient for linking a compound where the spacer moiety comprises an amine to a protein. Preferably, said bifunctional linkers are derived from adipic acid N-hydroxysuccinimide diester (SIDEA), and BS(PEG)5.

In some embodiments, Z is at least two or three atoms in length. Some non-limiting examples of linkers include: —$(CH_2)_m$-A, -Ph-A, —$(CH_2)_a$-Ph-$(CH_2)_a$-A and substituted forms thereof, wherein each Ph represents an optionally substituted phenyl group, and each a and m independently represents an integer from 1-10. "A" represents a functional group or a residue thereof that is capable of or links the protein, such as —$NH_2$, —OH or —SH, an ester, an amide, or other carboxyl-containing group, a diene, or a dienophile, a maleimide, an alkyne, a cycloalkyne. Z may comprise OR', SR' or $N(R')_2$, wherein each R' is independently H or $C_1$-$C_6$-alkyl, acyl, aryl, arylalkyl, heteroacyl, heteroaryl, or heteroarylalkyl group and may further comprise A.

In one embodiment, Z in Formula (IIa) or (IIb) is a heterobifunctional linker having the following formula:

$$*—(CH_2)_p—NH(CO)—(CH_2)_p—(X—(CH_2)_p)_p—C(O)—*$$

wherein * represents the point of attachment, and wherein p is independently selected from 1 to 10; and X is selected from —O—, —S— and —NH—.

In one embodiment, Z has the formula *—$(CH_2)_6$NHCO$(CH_2)_4$CO*.

In another embodiment, Z is a linker having the following formula:

$$*—(CH_2)_m—NHC(O)—(CH_2)_m—C(O)—*$$

wherein * represents the point of attachment, and wherein m is independently selected from 1 to 10.

In an alternative embodiment, Z has the following formula:

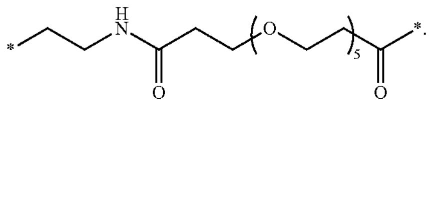

The Z linker is typically introduced into a monomer to be linked to the protein before elongating monomers are attached, and is optionally introduced in protected form, so to not impact or participate in the subsequent elongation reactions.

Therefore, in one embodiment, Z is a divalent linker having the general formula:

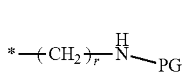

wherein r is an integer between 2 and 6, (*) represent the point of attachment to the oligomer and PG represents hydrogen or a protecting group, preferably selected from: alkoxycarbonyl, methoxycarbonyl, t-butyloxy carbonyl or benzyloxycarbonyl. The protein is attached through the amine.

When present, PG can be suitably removed to allow the reaction of the Z moiety with the protein to obtain the conjugate thereof. Alternatively, the PG can be removed and the free amino group thus obtained may be further functionalized, e.g. by introducing further spacer moieties, suitable for the connection to the protein.

In one embodiment, there is provided an oligomer conjugate according to the following formula:

The conjugation reaction may also be carried out using conjugation methods similar to those used for the conjugation of the MenA saccharide to a carrier protein, and e.g. described in WO2004/067030. In one embodiment, the oligomers of the invention can be coupled to $CRM_{197}$ using a conjugation procedure that takes advantage of the di-N-hydroxysuccinimidyl adipate linker, as e.g. reported in Berti et al., ACS Chem. Biol., 2012, 7, 1420-1428. After treatment with the selected linker in DMSO containing trimethylamine, the obtained activated oligomers can be purified by co-precipitation with acetone and used for conjugation. Thus, the desired neo-conjugate can be obtained by overnight incubation with $CRM_{197}$ at a 100:1 oligomer/protein molar ratio. The conjugation can contemplate the activation of an oligomer of Formula (Ia)/(Ib), followed by conjugation to the protein of choice, or the activation of the concerned protein functionality and subsequent conjugation with the oligosaccharides of the invention, typically through the Z moiety. Thus, according to one embodiment, the oligomers of the invention are first activated with an appropriate activating agent, followed by coupling with the $—NH_2$ residue of the selected protein, according to methods known in the art.

In one embodiment, the Z group is activated by reaction with a first terminal portion of a linker, whereby the other end of the linker can be connected to the protein of choice.

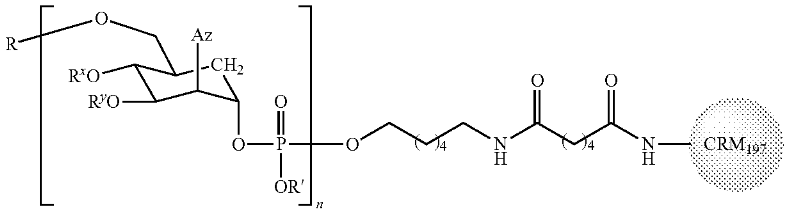

wherein n, Az, R, R', $R^x$ and $R^y$ are as defined above.

In one embodiment of the invention, there is provided an oligomer conjugate according to the following formula, i.e. where R' is $Na^+$:

For example, and according to one embodiment, the process may comprise the activation of the oligomers of the invention with SIDEA in the presence of triethylamine, to obtain an activated ester of the starting oligomer. Such activated

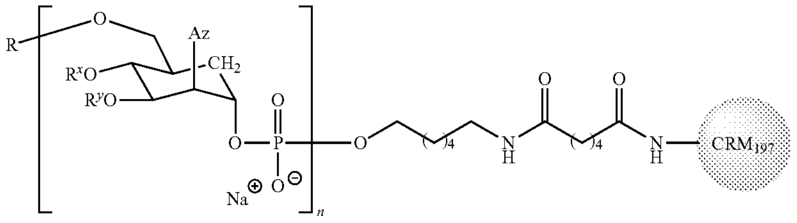

wherein n, Az, R, $R^x$ and $R^y$ are as defined above.

When the present randomly acetylated oligomer conjugate is incorporated into a vaccine composition it shows a higher stability of the acetylation percentage than a native MenA conjugate, with less than 5% of the acetylation that may be lost when the carba-analogue is formulated in the vaccine.

For the avoidance of doubt, it should be noted that the oligomers of the invention may be conjugated to a protein by any suitable method known in the art, for example, in accordance with those reported in "The design of semi-synthetic and synthetic glycoconjugate vaccines", P. Constantino et al., *Expert Opin. Drug. Discov.* ester may then be reacted with $CRM_{197}$ in the presence of a phosphonate buffer to give the desired conjugate.

After conjugation, the oligomer-protein conjugate may be purified by a variety of techniques known in the art. One goal of the purification step is to remove the unbound oligomers from the oligomer-protein conjugate. Typically, conjugates of the invention can be purified from unreacted protein and oligomers by any number of standard techniques including inter alia size exclusion chromatography, density gradient centrifugation, hydrophobic interaction chromatography or ammonium sulphate fractionation, as e.g. described in Anderson, P. W., et al. J. Immunol. (1986) 137:1181-1186, and in Jennings, H. J. et al., J. Immunol. (1981) 127:1011-1018.

In an additional embodiment, Z can be a monosaccharide, preferably a mannosamine as described below. Thus, in a further embodiment, the invention also relates to oligomers having the following formula (III), wherein:

(III)

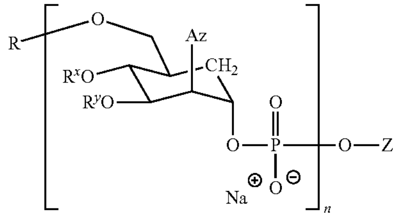

wherein R, Az and n are as defined above; and
Z is:

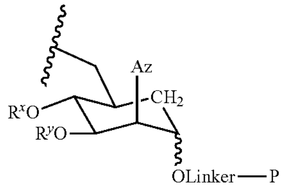

and P and the Linker are as above defined in connection with the definition of Z for Formulae (I) and (II).

For example, an example of a conjugate defined in this way is as follows:

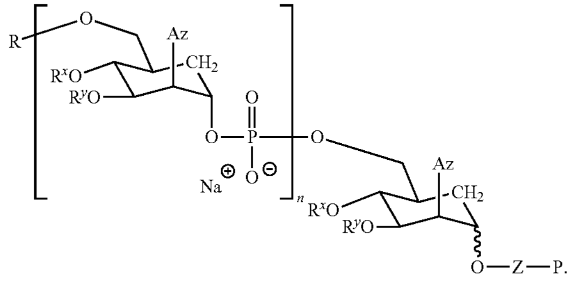

According to this embodiment, the derivatives of the invention can be linked to a selected protein directly through an —O-Linker Z moiety, thus leading to conjugate derivatives having the —OLinker-P moiety directly connected to the carbon atom of the terminal monomer. As far as the linker is concerned, this may be any suitable bivalent linker according to the above indicated linkers Z. Alternatively Z could be an amine for conjugation to a protein derivatized with linkers bearing a keto or aldehyde group.

The Conjugated Serogroup C, W135 and Y Antigenic Components

Immunogenic compositions of the present invention include capsular saccharide antigens from each of meningococcus serogroups C, W135 and Y, wherein the antigens are conjugated to carrier protein(s) and/or are oligosaccharides. Capsular saccharides may be used in the form of oligosaccharides. These are conveniently formed by fragmentation of purified capsular polysaccharide (e.g. by hydrolysis), which will usually be followed by purification of the fragments of the desired size.

For the avoidance of doubt, the term "capsular polysaccharides/saccharides" (CPSs) indicates those saccharides which can be found in the layer that lies outside the cell envelope of bacteria, thus being part of the outer envelope of the bacterial cell itself. CPSs are expressed on the outermost surface of a wide range of bacteria, and in some cases even in fungi.

The term "oligosaccharide" comprises in its meaning polysaccharides having from 3 to 10 monosaccharide units, as generally known in the art (see e.g. https://en.wikipedia.org/wiki/Oligosaccharide).

In general, conjugation enhances the immunogenicity of saccharides as it converts them from T-independent antigens to T-dependent antigens, thus allowing priming for immunological memory. Conjugation is particularly useful for paediatric vaccines and is a well-known technique.

Techniques for preparing capsular polysaccharides from meningococci have been known for many years (see for example WO2005/032583 and WO03/007985).

Typical carrier proteins are bacterial toxins, such as diphtheria or tetanus toxins, or toxoids or mutants thereof. The $CRM_{197}$ diphtheria toxin mutant [*Research Disclosure,* 453077 (January 2002)] is useful, and is the carrier in the *Streptococcus pneumoniae* vaccine sold under the trade name PREVNAR™. Other suitable carrier proteins include the *N. meningitidis* outer membrane protein complex [EP-A-0372501], synthetic peptides [EP-A-0378881, EP-A-0427347], heat shock proteins [WO93/17712, WO94/03208], pertussis proteins [WO98/58668, EP-A-0471177], cytokines [WO91/01146], lymphokines [WO91/01146], hormones [WO91/01146], growth factors [WO91/01146], artificial proteins comprising multiple human $CD4^+$ T cell epitopes from various pathogen-derived antigens [Falugi et al. (2001) *Eur J Immunol* 31:3816-3824] such as N19 [Baraldo et al. (2004) *Infect Immun* 72(8):4884-7], protein D from *H. influenzae* [EP-A-0594610, Ruan et al. (1990) *J Immunol* 145:3379-3384] pneumolysin [Kuo et al. (1995) *Infect Immun* 63:2706-13] or its non-toxic derivatives [Michon et al. (1998) *Vaccine.* 16:1732-41], pneumococcal surface protein PspA [WO02/091998], iron-uptake proteins [WO01/72337], toxin A or B from *C. difficile* [WO00/61761], recombinant *P. aeruginosa* exoprotein A (rEPA) [WO00/33882], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [Lees et al. (1996) *Vaccine* 14:190-198, WO95/08348 etc.]). Other suitable techniques use carbodiimides, hydrazides, active esters, norborane, p-nitrobenzoic acid, N-hydroxysuccinimide, S—NHS, EDC, TSTU, etc.

Linkages via a linker group may be made using any known procedure, for example, the procedures described in U.S. Pat. Nos. 4,882,317 and 4,695,624. One type of linkage involves reductive amination of the polysaccharide, coupling the resulting amino group with one end of an adipic acid linker group, and then coupling a protein to the other end of the adipic acid linker group [Porro et al. (1985) *Mol Immunol* 22:907-919, EP0208375]. Other linkers include B-propionamido [WO00/10599], nitrophenyl-ethylamine [Gever et al. Med. Microbiol. Immunol, 165: 171-288 (1979)], haloacyl halides [U.S. Pat. No. 4,057,685], glycosidic linkages [U.S. Pat. Nos. 4,673,574; 4,761,283; 4,808,700], 6-aminocaproic acid [U.S. Pat. No. 4,459,286], ADH [U.S. Pat. No. 4,965,338], $C_4$ to $C_{12}$ moieties [U.S. Pat. No. 4,663,160] etc. As an alternative to using a linker, direct linkage can be used. Direct linkages to the protein may comprise oxidation of the polysaccharide followed by reductive amination with the protein, as described in, for example, U.S. Pat. Nos. 4,761,283 and 4,356,170.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenC.

Current serogroup C vaccines (Menjugate™ [Costantino et al. (1992) *Vaccine* 10:691-698, Jones (2001) *Curr Opin Investig Drugs* 2:47-49], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier.

The vaccine products marketed under the trade names MENVEO, MENACTRA, and NIMENRIX all contain conjugated capsular saccharide antigens from each of serogroups Y, W135, C and A.

In MENVEO (also known generically as Meningococcal (Groups A, C, Y, and W-135) Oligosaccharide Diphtheria CRM197 Conjugate Vaccine) each of the A, C, W135 and Y antigens is conjugated to a $CRM_{197}$ carrier.

In a preferred embodiment of the invention, the serogroup C, W135 and Y oligosaccharide antigens are each conjugated to $CRM_{197}$. Preferably, each of the conjugated serogroup C, W135 and Y capsular saccharide antigens corresponds to the $CRM_{197}$-conjugated serogroup C., W135 and Y antigenic components of the licensed MENVEO vaccine.

In MENACTRA (also known generically as Meningococcal (Groups A, C, Y and W-135) Polysaccharide Diphtheria Toxoid Conjugate Vaccine) each of the A, C, W135 and Y antigens is conjugated to a diptheria toxoid carrier.

In a preferred embodiment of the invention, the serogroup C, W135 and Y oligosaccharide antigens are each conjugated to a diptheria toxoid carrier Preferably, each of the conjugated serogroup C, W135 and Y capsular saccharide antigens corresponds to the a diptheria toxoid carrier-conjugated serogroup C., W135 and Y antigenic components of the licensed MENACTRA vaccine.

In NIMENRIX (also known generically as Meningococcal polysaccharide groups A, C, W-135 and Y conjugate vaccine) each of the A, C, W135 and Y antigens is conjugated to a tetanus toxoid carrier.

In a preferred embodiment of the invention, the serogroup C, W135 and Y oligosaccharide antigens are each conjugated to a tetanus toxoid carrier Preferably, each of the conjugated serogroup C, W135 and Y capsular saccharide antigens corresponds to the tetanus toxoid carrier-conjugated serogroup C, W135 and Y antigenic components of the licensed NIMENRIX vaccine.

The Serogroup B Antigenic Component

The BEXSERO vaccine product (also known as C4MenB) contains a preparation of OMV from the epidemic strain of group B Meningococcal NZ98/254, B:4:P1.7b,4. The same OMVs are found in the MeNZB™ vaccine and are referred to herein as OMVnz. In addition, BEXSERO comprises five meningococcal antigens: NHBA (287; subvariant 1.2), fHbp (741; subvariant 1.1), NadA (961; subvariant 3.1), GNA1030 (953) and GNA2091 (936). Four of these antigens are present as fusion proteins (an NHBA-GNA1030 fusion protein (287-953) and a GNA2091-fHbp (936-741) fusion protein). A 0.5 ml dose of BEXSERO® includes 50 µg of each of NHBA, NadA and fHbp, adsorbed onto 1.5 mg aluminium hydroxide adjuvant, and with 25 µg OMVs from *N. meningitidis* strain NZ98/254. BEXSERO is described in literature (for example, see Bai et al. (2011) *Expert Opin Biol Ther.* 11:969-85, Su & Snape (2011) *Expert Rev Vaccines* 10:575-88).

In a preferred embodiment, the serogroup B antigenic component of the immunogenic composition of the invention comprises one or more of the protein antigen components of BEXSERO.

In a preferred embodiment, the immunogenic composition of the invention comprises all of the meningococcal antigenic components of BEXSERO described above (protein antigens and OMV).

In a further preferred embodiment, the immunogenic composition of the invention comprises the complete vaccine product marketed under the trade name BEXSERO.

In a further preferred embodiment, the immunogenic composition of the invention comprises one or more fHbp antigens, which are different to the fHbp v1.1 component of BEXSERO, Preferably the additional fHbp antigens are in the form of an fHbp 231 fusion polypeptide. Preferably the additional fHbp antigens are antigens disclosed in WO2020/030782. This fHbp antigenic component may in included in the immunogenic composition of the invention as the only MenB antigenic component of the composition, or, more preferably, in addition to one or more of the BEXSERO antigens or the complete BEXSERO vaccine product.

The lipoprotein factor H binding protein (fHbp) is expressed on the surface of all MenB strains. fHbp binds to the human complement regulatory protein factor H (hfH), forming a complex that protects the bacteria from complement-mediated killing and providing a survival mechanism for *N. meningitidis* in the human bloodstream. Antibodies against fHbp have a dual role: they are bactericidal per se, and by preventing binding to hfH they render strains more susceptible to bacterial killing. Reducing or abolishing the ability of fHbp to bind to hfH increases the immunogenicity of the fHbp antigen by preventing the formation of protective complexes between fHbp and hfH which have potential to mask fHbp epitopes and prevent antibody binding.

fHbp exists in three different genetic and immunogenic variants (v1, v2 and v3), with many subvariants. The majority of MenB strains that are not covered by BEXSERO express fHbp in v2, v3 or v1 subvariants distantly related to var1.1 (var1.1 being the fHbp antigen that is included in BEXSERO).

WO2020/030782 discloses mutated fHbp variant 1 (v1) polypeptides that are immunogenic and can be combined with existing meningococcal vaccines to provide improved *N. meningitidis* strain coverage. In particular, these v1 polypeptides are subvariants of fHbp variant 1 that are genetically diverse compared with the fHbp v1.1 antigen included in BEXSERO.

Furthermore, the v1 polypeptides disclosed in WO2020/030782 are mutated in order to reduce binding to hfH compared with the corresponding wildtype v1 polypeptide. In contrast, the fHbp v1.1 antigen included in BEXSERO, and the fHp v1.55 and v3.45 antigens included in TRUMENBA, do bind to hfH.

The v1 polypeptides disclosed in WO2020/030782 can be provided alone or as a component of a fusion protein, together with mutant forms of fHbp variants 2 and 3, which have been modified to improve stability and also to reduce fHbp binding. By providing a single fusion protein comprising these v2 and v3 antigens, together with a v1 antigen of the invention, the inventors improve strain coverage. For clarity, neither of the v2 and v3 antigens are present in, e.g., BEXSERO. The presence of v2 and v3 antigens within the fusion proteins of the present invention improves strain coverage as compared to, e.g., BEXSERO.

The v1 polypeptides and fusion proteins are preferably used in combination with a meningococcal NHBA antigen, a meningococcal NadA antigen, a meningococcal fHbp antigen, and a meningococcal outer membrane vesicle (e.g., in combination with the BEXSERO composition), to provide a combined immunogenic composition having increased immunogenicity (due to the addition/inclusion of non-binding forms of fHbp variants) and increased *N. meningitidis* serotype B strain coverage (due to the addition of new fHbp variants/subvariants), compared with BEXSERO alone.

Mutant v1.13 Meningococcal fHbp Polypeptides

The inventors of WO2020/030782 identified residues within the fHbp v1.13 sequence that can be modified to reduce binding to hfH. Such mutants are referred to herein as non-binding (NB) mutants. The inventors also identified combinations of mutations in the v1.13 sequence that are particularly useful to reduce binding to hfH. fHbp v1.13 is also known in the art as fHbp variant B09.

The mature wild-type fHbp v1.13 lipoprotein from strain M982 (GenBank Accession No. AAR84475.1) has the following amino acid sequence, with an N-terminal polyglycine signal sequence being underlined:

(SEQ ID NO: 1)

CSSGGGGVAADIGAGLADALTAPLDHKDKGLQSLTLDQSVRKNEKLKLA
AQGAEKTYGNGDSLNTGKLKNDKVSRFDFIRQIEVDGKLITLESGEFQV
YKQSHSALTALQTEQVQDSEDSGKMVAKRQFRIGDIAGEHTSFDKLPKG
GSATYRGTAFGSDDAGGKLTYTIDFAAKQGHGKIEHLKSPELNVELATA
YIKPDEKRHAVISGSVLYNQDEKGSYSLGIFGGQAQEVAGSAEVETANG
IHHIGLAAKQ

The mature v1.13 lipoprotein differs from the full-length wild-type sequence in that the full-length polypeptide has an additional 19 residue N-terminal leader sequence, which is cleaved from the mature polypeptide. Thus, full-length wild-type fHbp v1.13 has the following amino acid sequence (with the N-terminal leader sequence shown in bold font):

(SEQ ID NO: 31)

MNRTAFCCFSLTAALILTACSSGGGGVAADIGAGLADALTAPLDHKDKG
LQSLTLDQSVRKNEKLKLAAQGAEKTYGNGDSLNTGKLKNDKVSRFDFI
RQIEVDGKLITLESGEFQVYKQSHSALTALQTEQVQDSEDSGKMVAKRQ
FRIGDIAGEHTSFDKLPKGGSATYRGTAFGSDDAGGKLTYTIDFAAKQG
HGKIEHLKSPELNVELATAYIKPDEKRHAVISGSVLYNQDEKGSYSLGI
FGGQAQEVAGSAEVETANGIHHIGLAAKQ

The ΔG form of the mature v1.13 lipoprotein lacks the N-terminal poly-glycine sequence of the mature polypeptide, i.e. it lacks the first 7 amino acids of SEQ ID NO: 1, and it lacks the first 26 amino acids of SEQ ID NO: 31:

(SEQ ID NO: 2)

VAADIGAGLADALTAPLDHKDKGLQSLTLDQSVRKNEKLKLAAQGAEKT
YGNGDSLNTGKLKNDKVSRFDFIRQIEVDGKLITLESGEFQVYKQSHSA
LTALQTEQVQDSEDSGKMVAKRQFRIGDIAGEHTSFDKLPKGGSATYRG
TAFGSDDAGGKLTYTIDFAAKQGHGKIEHLKSPELNVELATAYIKPDEK
RHAVISGSVLYNQDEKGSYSLGIFGGQAQEVAGSAEVETANGIHHIGLA
AKQ

Therefore, in one embodiment, the serogroup B antigenic component of the immunogenic composition of the invention comprises a mutant v1.13 meningococcal fHbp polypeptide comprising an amino acid sequence having at least k % sequence identity to SEQ ID NO: 2, with the proviso that the amino acid sequence of said mutant v1.13 meningococcal fHbp polypeptide includes a substitution mutation at one or more of residues E211, S216 or E232 of SEQ ID NO: 2.

The value of k may be selected from 80, 85, 86, 87, 88, 89, 90, 91, 92, 93, 94, 95, 96, 97, 98, 99 or 100. It is preferably 80 (i.e. the mutant fHbp v1.13 amino acid sequence has at least 80% identity to SEQ ID NO: 2) and is more preferably 85, more preferably 90 and more preferably 95. Most preferably, the mutant fHbp v1.13 amino acid sequence has at least 97%, at least 98% or at least 99% identity to SEQ ID NO: 2.

Preferably, the amino acid sequence differs from SEQ ID NO: 2 by at least one or more of the substitutions E211A, S216R or E232A. More preferably, the amino acid sequence comprises substitutions at multiple residues selected from the following (i) E211A and E232A, or (ii) E211A and S216R. More preferably, the amino acid sequence comprises substitutions at residues E211A and S216R, relative to SEQ ID NO. 2.

Without wishing to be bound by theory, the substitution of glutamic acid (E) for alanine (A) at residue 211 of SEQ ID NO. 2 removes a negatively charged residue that is involved in hfH recruitment, thus contributing to the abrogation of fH binding. The substitution of arginine (R) for serine (S) at residue 216 of SEQ ID NO. 2 replaces the wildtype amino acid with a corresponding residue from *N. gonorrhoeae*, which does not bind hfH.

In preferred embodiments, a mutant v1.13 polypeptide has the amino acid sequence of SEQ ID NO: 3 (v1.13 ΔG E211A/E232A) or SEQ ID NO: 4 (v1.13 ΔG (E211A/S216R). More preferably, mutant v1.13 polypeptide has the amino acid sequence of SEQ ID NO: 4.

The mutant v1.13 polypeptide can, after administration to a host animal, preferably a mammal and more preferably a human, elicit antibodies which can recognise wild-type meningococcal fHbp polypeptides of SEQ ID NO: 1. These antibodies are ideally bactericidal (see below).

Mutant v1.15 Meningococcal fHbp Polypeptides

The inventors of WO2020/030782 also identified residues within the fHbp v1.15 sequence that can be modified to prevent binding to hfH. Such mutants are referred to herein as non-binding (NB) mutants. The inventors identified combinations of mutations in the v1.15 sequence that are particularly useful to prevent binding to hfH. fHbp v1.15 is also known in the art as fHbp variant B44.

The mature wild-type fHbp v1.15 lipoprotein from strain NM452 (GenBank Accession No. ABL14232.1) has the following amino acid sequence, with an N-terminal polyglycine signal sequence being underlined:

(SEQ ID NO: 5)
CSSGGGGSGGGGVAADIGAGLADALTAPLDHKDKGLKSLTLEDSISQNG
TLTLSAQGAERTFKAGDKDNSLNTGKLKNDKISRFDFIRQIEVDGQLIT
LESGEFQVYKQSHSALTALQTEQVQDSEHSGKMVAKRQFRIGDIVGEHT
SFGKLPKDVMATYRGTAFGSDDAGGKLTYTIDFAAKQGHGKIEHLKSPE
LNVDLAAADIKPDEKHHAVISGSVLYNQAEKGSYSLGIFGGQAQEVAGS
AEVETANGIRHIGLAAKQ

The mature v1.15 lipoprotein differs from the full-length wild-type sequence in that the full-length polypeptide has an additional 19 residue N-terminal leader sequence, which is cleaved from the mature polypeptide. Thus, full-length wild-type fHbp v1.15 has the following amino acid sequence (with the N-terminal leader sequence shown in bold font):

(SEQ ID NO: 32)
MNRTTFCCLSLTAALILTACSSGGGGSGGGGVAADIGAGLADALTAPLD
HKDKGLKSLTLEDSISQNGTLTLSAQGAERTFKAGDKDNSLNTGKLKND
KISRFDFIRQIEVDGQLITLESGEFQVYKQSHSALTALQTEQVQDSEHS
GKMVAKRQFRIGDIVGEHTSFGKLPKDVMATYRGTAFGSDDAGGKLTYT
IDFAAKQGHGKIEHLKSPELNVDLAAADIKPDEKHHAVISGSVLYNQAE
KGSYSLGIFGGQAQEVAGSAEVETANGIRHIGLAAKQ

The ΔG form of the mature v1.15 lipoprotein lacks the N-terminal poly-glycine sequence, i.e. it lacks the first 12 amino acids of SEQ ID NO: 5, and it lacks the first 31 amino acids of SEQ ID NO: 32:

(SEQ ID NO: 6)
VAADIGAGLADALTAPLDHKDKGLKSLTLEDSISQNGTLTLSAQGAERT
FKAGDKDNSLNTGKLKNDKISRFDFIRQIEVDGQLITLESGEFQVYKQS
HSALTALQTEQVQDSEHSGKMVAKRQFRIGDIVGEHTSFGKLPKDVMAT
YRGTAFGSDDAGGKLTYTIDFAAKQGHGKIEHLKSPELNVDLAAADIKP
DEKHHAVISGSVLYNQAEKGSYSLGIFGGQAQEVAGSAEVETANGIRHI
GLAAKQ

Therefore, in one embodiment, the serogroup B antigenic component of the immunogenic composition of the invention comprises an amino acid sequence having at least k % sequence identity to SEQ ID NO: 6, with the proviso that the amino acid sequence of said mutant v1.15 meningococcal fHbp polypeptide includes a substitution mutation at one or more of residues E214, S219 or E235 of SEQ ID NO: 6

The value of k may be selected from 80, 85, 86, 87, 88, 89, 90, 91, 92, 93, 94, 95, 96, 97, 98, 99 or 100. It is preferably 80 (i.e. the mutant fHbp v1.15 amino acid sequence has at least 80% identity to SEQ ID NO: 6) and is more preferably 85, more preferably 90 and more preferably 95. Most preferably, the mutant fHbp v1.15 amino acid sequence has at least 97%, at least 98% or at least 99% identity to SEQ ID NO: 6.

Preferably, the amino acid sequence differs from SEQ ID NO: 6 by at least one or more of the substitutions E214A, S219R or E235A. More preferably, the amino acid sequence comprises substitutions at residues selected from the following: (i) S219R, (ii) E214A and S219R, and (iii) E214A and E235A.

In preferred embodiments, a mutant v1.15 polypeptide has the amino acid sequence of SEQ ID NO: 7 (v.1.15_S219R), SEQ ID NO: 8 (v1.15_E214A/S219R) or SEQ ID NO: 9 (v1.15_E214A/E235A).

The mutant v1.15 polypeptide can, after administration to a host animal, preferably a mammal and more preferably a human, elicit antibodies which can recognise wild-type meningococcal fHbp polypeptides of SEQ ID NO: 5. These antibodies are ideally bactericidal (see below).

Fusion Polypeptide

The disclosure in WO2020/030782 also provides a fusion polypeptide comprising all three of v1, v2 and v3 meningococcal fHbp polypeptides, wherein the variant fHbp sequences are in the order v2-v3-v1 from N- to C-terminus. In a preferred embodiment, the serogroup B antigenic component of the immunogenic composition of the invention comprises such an fHbp fusion polypeptide.

Preferably, the fHbp fusion polypeptide has an amino acid sequence of formula $NH_2$-A-[-X-L]$_3$-B—COOH, wherein each X is a different variant fHbp sequence, L is an optional linker amino acid sequence, A is an optional N terminal amino acid sequence, and B is an optional C terminal amino acid sequence.

The v1 fHbp polypeptide component of the fusion is either a mutant v1.13 fHbp polypeptide or mutant v1.13 fHbp polypeptide as described above.

The v2 and v3 fHbp polypeptide components of the fusion are preferably mutant v2 and v3 polypeptides having enhanced stability and reduced ability to bind to hfH, compared to the wild-type v2 and v3 polypeptides. As explained above, reducing fHbp binding to hfH is advantageous because it prevents the formation of protective complexes between fHbp and hfH which can mask fHbp epitopes, and thereby increases the immunogenicity of the polypeptide antigen.

Residues within the v2 and v3 sequences, which can be modified to increase the stability of the polypeptide and also to reduce binding to hfH, have been identified and are described in detail in WO2015/128480.

Full-length wild-type fHbp v2 from strain 2996 has the following amino acid sequence (leader sequence shown in bold font and poly-glycine sequence being underlined):

(SEQ ID NO: 10)
MNRTAFCCLSLTAALILTACSSGGGGVAADIGAGLADALTAPLDHKDKS
LQSLTLDQSVRKNEKLKLAAQGAEKTYGNGDSLNTGKLKNDKVSRFDFI
RQIEVDGQLITLESGEFQIYKQDHSAVVALQIEKINNPDKIDSLINQRS
FLVSGLGGEHTAFNQLPDGKAEYHGKAFSSDDAGGKLTYTIDFAAKQGH
GKIEHLKTPEQNVELAAAELKADEKSHAVILGDTRYGSEEKGTYHLALF
GDRAQEIAGSATVKIGEKVHEIGIAGKQ

The mature lipoprotein lacks the first 19 amino acids of SEQ ID NO: 10:

(SEQ ID NO: 11)
CSSGGGGVAADIGAGLADALTAPLDHKDKSLQSLTLDQSVRKNEKLKLA
AQGAEKTYGNGDSLNTGKLKNDKVSRFDFIRQIEVDGQLITLESGEFQI
YKQDHSAVVALQIEKINNPDKIDSLINQRSFLVSGLGGEHTAFNQLPDG
KAEYHGKAFSSDDAGGKLTYTIDFAAKQGHGKIEHLKTPEQNVELAAAE

-continued
LKADEKSHAVILGDTRYGSEEKGTYHLALFGDRAQEIAGSATVKIGEKV

HEIGIAGKQ

The ΔG form of SEQ ID NO: 10 lacks the first 26 amino acids:

(SEQ ID NO: 12)
VAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSA

VVALQIEKINNPDKIDSLINQRSFLVSGLGGEHTAFNQLPDGKAEYHGK

AFSSDDAGGKLTYTIDFAAKQGHGKIEHLKTPEQNVELAAAELKADEKS

HAVILGDTRYGSEEKGTYHLALFGDRAQEIAGSATVKIGEKVHEIGIAG

KQ

In a preferred embodiment, the fusion polypeptide comprises a mutant v2 fHbp polypeptide comprising an amino acid sequence having at least k % sequence identity to SEQ ID NO: 12, with the proviso that the v2 fHbp amino acid sequence includes a substitution mutation at residues S32 and L123 of SEQ ID NO: 12. Preferably the substitutions are S32V and L123R.

The value of k may be selected from 80, 85, 86, 87, 88, 89, 90, 91, 92, 93, 94, 95, 96, 97, 98, 99 or 100. It is preferably 80 (i.e. the mutant fHbp v2 amino acid sequence has at least 80% identity to SEQ ID NO: 12) and is more preferably 85, more preferably 90 and more preferably 95.

In some embodiments, the fHbp v2 polypeptide included in the fusion protein is truncated relative to SEQ ID NO: 12. Compared to the wild-type mature sequence, SEQ ID NO: 12 is already truncated at the N-terminus up to and including the poly-glycine sequence (compare SEQ ID NOs: 11 and 12), but SEQ ID NO: 12 can be truncated at the C-terminus and/or further truncated at the N-terminus.

In a preferred embodiment, the v2 fHbp polypeptide included in the fusion protein comprises or consists of the amino acid sequence of SEQ ID NO: 16.

The v2 fHbp polypeptide included in the fusion protein has, under the same experimental conditions, a higher stability than the same polypeptide but without the sequence differences at residues S32 and L123 e.g. higher stability than a wild-type meningococcal polypeptide consisting of SEQ ID NO: 10. The S32V mutation stabilizes the structure by introducing favourable hydrophobic interactions. The L123R mutation abrogates fH binding by introducing clashes with fH and unfavorable charges.

The stability enhancement can be assessed using differential scanning calorimetry (DSC) e.g. as discussed in Johnson (2013) *Arch Biochem Biophys* 531:100-9 and Bruylants et al. *Current Medicinal Chemistry* 2005; 12:2011-20. DSC has previously been used to assess the stability of v2 fHbp (Johnson et al. *PLoS Pathogen* 2012; 8: e1002981). Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

The increase in stability is evidenced by an at least 5° C., e.g. at least 10° C., 15° C., 20° C., 25° C., 30° C., 35° C. or more, increase in thermal transition midpoint (Tm) of at least one peak as compared to wild-type when assessed by DSC. Wild-type fHbp shows two DSC peaks during unfolding (one for the N-terminal domain and one for the C-terminal domain) and, where a v2 polypeptide included in the fusion protein of the invention includes both such domains, an "increase in stability" refers to an at least 5° C. increase in the $T_m$ of the N-terminal domain. Tm of the N-terminal domain can occur at or even below 40° C. with wild-type v2 sequences (Johnson et al. (2012) *PLoS Pathogen* 8: e1002981), whereas C-terminal domains can have a Tm of 80° C. or more. Thus, the mutant fHbp v2 amino acid sequence included in the fusion protein of the invention preferably has a N-terminal domain with a Tm of at least 45° C. e.g. ≥50° C., ≥55° C., ≥60° C., ≥65° C., ≥70° C., ≥75° C., or even ≥80° C.

Full-length wild-type fHbp v3 from strain M1239 has the following amino acid sequence (leader sequence shown in bold font and poly-glycine sequence being underlined):

(SEQ ID NO: 13)
MNRTAFCCLSLTTALILTACSSGGGGSGGGGVAADIGTGLADALTAPLD

HKDKGLKSLTLEDSIPQNGTLTLSAQGAEKTFKAGDKDNSLNTGKLKND

KISRFDFVQKIEVDGQTITLASGEFQIYKQNHSAVVALQIEKINNPDKT

DSLINQRSFLVSGLGGEHTAFNQLPGGKAEYHGKAFSSDDPNGRLHYSI

DFTKKQGYGRIEHLKTLEQNVELAAAELKADEKSHAVILGDTRYGSEEK

GTYHLALFGDRAQEIAGSATVKIGEKVHEIGIAGKQ

The mature lipoprotein lacks the first 19 amino acids of SEQ ID NO: 13:

(SEQ ID NO: 14)
CSSGGGGSGGGGVAADIGTGLADALTAPLDHKDKGLKSLTLEDSIPQNG

TLTLSAQGAEKTFKAGDKDNSLNTGKLKNDKISRFDFVQKIEVDGQTIT

LASGEFQIYKQNHSAVVALQIEKINNPDKTDSLINQRSFLVSGLGGEHT

AFNQLPGGKAEYHGKAFSSDDPNGRLHYSIDFTKKQGYGRIEHLKTLEQ

NVELAAAELKADEKSHAVILGDTRYGSEEKGTYHLALFGDRAQEIAGSA

TVKIGEKVHEIGIAGKQ

The ΔG form of SEQ ID NO: 13 lacks the first 31 amino acids (i.e. lacks the signal sequence and the poly-glycine sequence):

(SEQ ID NO: 15)
VAADIGTGLADALTAPLDHKDKGLKSLTLEDSIPQNGTLTLSAQGAEKT

FKAGDKDNSLNTGKLKNDKISRFDFVQKIEVDGQTITLASGEFQIYKQN

HSAVVALQIEKINNPDKTDSLINQRSFLVSGLGGEHTAFNQLPGGKAEY

HGKAFSSDDPNGRLHYSIDFTKKQGYGRIEHLKTLEQNVELAAAELKAD

EKSHAVILGDTRYGSEEKGTYHLALFGDRAQEIAGSATVKIGEKVHEIG

IAGKQ

In a preferred embodiment, the fusion polypeptide comprises a mutant v3 fHbp polypeptide comprising an amino acid sequence having at least k % sequence identity to SEQ ID NO: 15, with the proviso that the v3 fHbp amino acid sequence includes substitution mutations at residues S32 and L126 of SEQ ID NO: 15. Preferably the substitutions are S32V and L126R.

The value of k may be selected from 80, 85, 86, 87, 88, 89, 90, 91, 92, 93, 94, 95, 96, 97, 98, 99 or 100. It is preferably 80 (i.e. the mutant fHbp v2 amino acid sequence has at least 80% identity to SEQ ID NO: 15) and is more preferably 85, more preferably 90 and more preferably 95.

In some embodiments, the fHbp v3 polypeptide included in the fusion protein is truncated relative to SEQ ID NO: 15. Compared to the wild-type mature sequence, SEQ ID NO: 15 is already truncated at the N-terminus up to and including the poly-glycine sequence (compare SEQ ID NOs: 14 and 15), but SEQ ID NO: 15 can be truncated at the C-terminus and/or further truncated at the N-terminus.

In a preferred embodiment, the v3 fHbp polypeptide included in the fusion protein comprises or consists of the amino acid sequence of SEQ ID NO: 17.

The v3 fHbp polypeptide included in the fusion protein has, under the same experimental conditions, a higher stability than the same polypeptide but without the sequence differences at residues S32 and L126 e.g. higher stability than a wild-type meningococcal polypeptide consisting of SEQ ID NO: 13. The S32V mutation stabilizes the structure by introducing favorable hydrophobic interactions. The L126R mutation abrogates fH binding by introducing clashes with fH and unfavorable charges.

The stability enhancement can be assessed using differential scanning calorimetry (DSC) e.g. as discussed in Johnson (2013) *Arch Biochem Biophys* 531:100-9 and Bruylants et al. (2005) *Current Medicinal Chemistry* 12:2011-20. DSC has previously been used to assess the stability of v3 fHbp (van der Veen et al. (2014) *Infect Immun* PMID 24379280). Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

The increase in stability is evidenced by an at least 5° C., e.g. at least 10° C., 15° C., 20° C., 25° C., 30° C., 35° C. or more, increase in thermal transition midpoint (Tm) of at least one peak as compared to wild-type when assessed by DSC. Wild-type fHbp shows two DSC peaks during unfolding (one for the N-terminal domain and one for the C-terminal domain) and, where a v3 polypeptide included in the fusion protein of the invention includes both such domains, an "increase in stability" refers to an at least 5° C. increase in the $T_m$ of the N-terminal domain. Tm of the N terminal domain can occur at around 60° C. or less with wild-type v3 sequences (Johnson et al. (2012) *PLoS Pathogen* 8:e1002981), whereas C-terminal domains can have a Tm of 80° C. or more. Thus, the mutant fHbp v3 amino acid sequence of the invention preferably has a N-terminal domain with a Tm of at least 65° C. e.g. ≥70° C., ≥75° C., or even ≥80° C.

As described above, in a preferred embodiment the fHbp fusion polypeptide has an amino acid sequence of formula $NH_2$-A-[-X-L]$_3$-B—COOH, wherein each X is a different variant fHbp sequence and L is an optional linker amino acid sequence. In a preferred embodiment, the linker amino acid sequence "L" is a glycine polymer or glycine-serine polymer linker.

Exemplary linkers include, but are not limited to, "GGSG" (SEQ ID NO: 36), "GGSGG" (SEQ ID NO: 37), "GSGSG" (SEQ ID NO: 38), "GSGGG" (SEQ ID NO: 39), "GGGSG" (SEQ ID NO: 40), "GSSSG" (SEQ ID NO: 41) and "GSGGGG" (SEQ ID NO: 42). Other suitable glycine or glycine-serine polymer linkers will be apparent to the skilled person. In a preferred fusion polypeptide according to the invention, the v2 and v3 sequences and the v3 and v1 sequences are connected by the glycine-serine polymer linker "GSGGGG" (SEQ ID NO: 42).

In a preferred embodiment, the fusion polypeptide comprises or consists of one of the following amino acid sequences (glycine-serine linker sequences are underlined and mutated residues are indicated in bold font):

fHbp 23S_1.13_E211A/E232A (SEQ ID NO: 18)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALF

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQTYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLQSLTLDQSVRKNEKLKLAAQGAEKTYGNGDSLNTGKLKNDKVSRFDFIRQI

EVDGKLITLESGEFQVYKQSHSALTALQTEQVQDSEDSGKMVAKRQFRIGDIAGEHTSFDKLPKGGSATYRGT

AFGSDDAGGKLTYTIDFAAKQGHGKIEHLKSPELNVELATAYIKPDEKRHAVISGSVLYNQDAKGSYSLGIFG

GQAQEVAGSAAVETANGIHHIGLAAKQ fHbp 23S_1.13_E211A/S216R (SEQ ID NO: 19)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALF

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

-continued

VELAAAELKADEKSHAVILGDTRYGSEEKGTYHLALFGDRAQEIAGSATVKIGEKVHEIGIAGKQGSGGGGVA

ADIGAGLADALTAPLDHKDKGLQSLTLDQSVRKNEKLKLAAQGAEKTYGNGDSLNTGKLKNDKVSRFDFIRQI

EVDGKLITLESGEFQVYKQSHSALTALQTEQVQDSEDSGKMVAKRQFRIGDIAGEHTSFDKLPKGGSATYRGT

AFGSDDAGGKLTYTIDFAAKQGHGKIEHLKSPELNVELATAYIKPDEKRHAVISGSVLYNQDAKGSYRLGIFG

GQAQEVAGSAEVETANGIHHIGLAAKQ fHbp_23S_1.15_S231R (SEQ ID NO: 20)

VAADIGAGLADALTAPLDHKDKSLQSLTLDQVVRKNEKLKLAAQGAEKTYGNGDSLNTGKLKNDKVSRFDFIR

QIEVDGQLITLESGEFQIYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALF

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLKSLTLEDSISQNGTLTLSAQGAERTFKAGDKDNSLNTGKLKNDKISRFDFI

RQTEVDGQLITLESGEFQVYKQSHSALTALQTEQVQDSEHSGKMVAKRQFRIGDIVGEHTSFGKLPKDVMATY

RGTAFGSDDAGGKLTYTIDFAAKQGHGKIEHLKSPELNVDLAAADIKPDEKHHAVISGSVLYNQAEKGSYRLG

IFGGQAQEVAGSAEVETANGIRHIGLAAKQ fHbp_23S_1.15_E214A/S219R (SEQ ID NO: 21)

VAADIGAGLADALTAPLDHKDKSLQSLTLDQVVRKNEKLKLAAQGAEKTYGNGDSLNTGKLKNDKVSRFDFIR

QIEVDGQLITLESGEFQTYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALF

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLKSLTLEDSISQNGTLTLSAQGAERTFKAGDKDNSLNTGKLKNDKISRFDFI

RQIEVDGQLITLESGEFQVYKQSHSALTALQTEQVQDSEHSGKMVAKRQFRIGDIVGEHTSFGKLPKDVMATY

RGTAFGSDDAGGKLTYTIDFAAKQGHGKIEHLKSPELNVDLAAADIKPDEKHHAVISGSVLYNQAAKGSYRLG

IFGGQAQEVAGSAEVETANGIRHIGLAAKQ fHbp_23S_1.15_E214A/E235A (SEQ ID NO: 22)

VAADIGAGLADALTAPLDHKDKSLQSLTLDQVVRKNEKLKLAAQGAEKTYGNGDSLNTGKLKNDKVSRFDFIR

QIEVDGQLITLESGEFQTYKQDHSAVVALQIEKINNPDKIDSLINQRSFRVSGLGGEHTAFNQLPDGKAEYHG

KAFSSDDAGGKLTYTIDFAAKQGHGKIEHLKTPEQNVELAAAELKADEKSHAVILGDTRYGSEEKGTYHLALF

GDRAQEIAGSATVKIGEKVHEIGIAGKQGSGGGGVAADIGTGLADALTAPLDHKDKGLKSLTLEDVIPQNGTL

TLSAQGAEKTFKAGDKDNSLNTGKLKNDKISRFDFVQKIEVDGQTITLASGEFQIYKQNHSAVVALQIEKINN

PDKTDSLINQRSFRVSGLGGEHTAFNQLPGGKAEYHGKAFSSDDPNGRLHYSIDFTKKQGYGRIEHLKTLEQN

VELAAAELKADEKSHAVILGDTRYGSEEKGTYHLALFGDRAQEIAGSATVKIGEKVHEIGIAGKQGSGGGGVA

ADIGAGLADALTAPLDHKDKGLKSLTLEDSISQNGTLTLSAQGAERTFKAGDKDNSLNTGKLKNDKISRFDFI

-continued

```
RQIEVDGQLITLESGEFQVYKQSHSALTALQTEQVQDSEHSGKMVAKRQFRIGDIVGEHTSFGKLPKDVMATY

RGTAFGSDDAGGKLTYTIDFAAKQGHGKIEHLKSPELNVDLAAADIKPDEKHHAVISGSVLYNQAAKGSYSLG

IFGGQAQEVAGSAAVETANGIRHIGLAAKQ
```

In a preferred embodiment, the fusion polypeptide comprises the amino acid sequence of SEQ ID NO. 19. In an alternative preferred embodiment, the fusion polypeptide comprises the amino acid sequence of SEQ ID NO. 18.

The fusion polypeptide can, after administration to a host animal, preferably a mammal and more preferably a human, elicit antibodies which can recognise wild-type meningococcal fHbp polypeptides, in particular the polypeptides of SEQ ID NO: 31, 32, 10 and/or 13. These antibodies are ideally bactericidal (see below).

As described above, in a preferred embodiment an fHbp fusion polypeptide has an amino acid sequence of formula $NH_2$-A-[-X-L]$_3$-B—COOH, wherein each X is a different variant fHbp sequence and A is an optional N terminal amino acid sequence. In preferred embodiments, fusion proteins described herein further comprise the following N-terminal amino acid sequence, which is advantageous for enabling good expression of the fusion protein:

MGPDSDRLQQRR (SEQ ID NO. 34)

Any of the fusion proteins disclosed herein (e.g. SEQ ID Nos. 18-22, 29 and 30) may be modified to include the amino acid sequence of SEQ ID NO. 34 at the N-terminal of the fusion polypeptide, i.e. the amino acid sequence of SEQ ID NO. 34 is added to the N-terminal of the fHbp v2 component of the fusion polypeptide.

In a preferred embodiment, the serogroup B antigenic component of the immunogenic composition of the invention comprises the complete BEXSERO vaccine product, together with an fHbp fusion polypeptide as defined above. Most preferably, the fHbp fusion polypeptide is fHbp 23S_1.13_E211A/S216R. Preferably, the serogroup B antigenic component is provided in a single fully liquid formulation.

Bactericidal Responses

Preferred v1.13, v1.15 and/or fusion polypeptides described above can elicit antibody responses that are bactericidal against meningococci. Bactericidal antibody responses are conveniently measured in mice and are a standard indicator of vaccine efficacy (e.g. see end-note 14 of Pizza et al. (2000) *Science* 287:1816-1820; also WO2007/028408).

Polypeptides described above can preferably elicit an antibody response which is bactericidal against a *N. meningitidis* serogroup B strain which expresses a v1.13 fHbp sequence.

Preferred polypeptides described above can elicit antibodies in a mouse which are bactericidal against a *N. meningitidis* strain which expresses a v1.13 fHbp sequence in a serum bactericidal assay.

Polypeptides described above can preferably elicit an antibody response which is bactericidal against a *N. meningitidis* serogroup B strain which expresses a v1.15 fHbp sequence.

Preferred polypeptides described above can elicit antibodies in a mouse which are bactericidal against a *N. meningitidis* strain which expresses a v1.15 fHbp sequence in a serum bactericidal assay.

For example, an immunogenic composition comprising these polypeptides can provide a serum bactericidal titer of ≥1:4 using the Goldschneider assay with human complement [Goldschneider et al. (1969) *J. Exp. Med.* 129:1307-26, Santos et al. (2001) *Clinical and Diagnostic Laboratory Immunology* 8:616-23, and Frasch et al. (2009) *Vaccine* 27S:B112-6], and/or providing a serum bactericidal titer of ≥1:128 using baby rabbit complement.

Polypeptides

Polypeptides described above can be prepared by various means e.g. by chemical synthesis (at least in part), by digesting longer polypeptides using proteases, by translation from RNA, by purification from cell culture (e.g. from recombinant expression or from *N. meningitidis* culture), etc. Heterologous expression in an *E. coli* host is a preferred expression route.

Polypeptides are ideally at least 100 amino acids long e.g. 150aa, 175aa, 200aa, 225aa, or longer. They include a mutant fHbp v1, v2 and/or v3 amino acid sequence, and the mutant fHbp v1, v2 or v3 amino acid sequence should similarly be at least 100 amino acids long e.g. 150aa, 175aa, 200aa, 225aa, or longer.

The fHbp is naturally a lipoprotein in *N. meningitidis*. It has also been found to be lipidated when expressed in *E. coli* with its native leader sequence or with heterologous leader sequences. Polypeptides of the invention may have an N-terminus cysteine residue, which may be lipidated e.g. comprising a palmitoyl group, usually forming tripalmitoyl-S-glyceryl-cysteine. In other embodiments the polypeptides are not lipidated.

Polypeptides are preferably prepared in substantially pure or substantially isolated form (i.e. substantially free from other Neisserial or host cell polypeptides). In general, the polypeptides are provided in a non-naturally occurring environment e.g. they are separated from their naturally-occurring environment. In certain embodiments, the polypeptide is present in a composition that is enriched for the polypeptide as compared to a starting material. Thus purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, glycosylated, non-glycosylated, lipidated, disulfide bridges, etc.).

If a polypeptide is produced by translation in a biological host then a start codon is required, which will provide a N-terminus methionine in most hosts. Thus, a polypeptide will, at least at a nascent stage, include a methionine residue upstream of said SEQ ID NO sequence.

Cleavage of nascent sequences means that the mutant fHbp v1, v2 or v3 amino acid sequence might itself provide the polypeptide's N-terminus. In other embodiments, however, a polypeptide can include a N-terminal sequence upstream of the mutant fHbp v1, v2 or v3 amino acid sequence. In some embodiments the polypeptide has a single methionine at the N-terminus immediately followed by the mutant fHbp v1, v2 or v3 amino acid sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. $His_n$ where n=4, 5, 6, 7, 8, 9, 10 or more). Other suitable N-terminal amino acid sequences will be apparent to those skilled in the art.

A polypeptide may also include amino acids downstream of the final amino acid of the mutant fHbp v1, v2 or v3 amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. $His_n$ where n=4, 5, 6, 7, 8, 9, 10 or more), or sequences which enhance polypeptide stability. Other suitable C-terminal amino acid sequences will be apparent to those skilled in the art.

In some embodiments, the invention excludes polypeptides which include a histidine tag (cf. Johnson et al. (2012) *PLoS Pathogen* 8:e1002981, and Pajon et al. (2012) *Infect Immun* 80:2667-77), and in particular a hexahistidine tag at the C-terminus.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention, for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

Polypeptides can occur as single chains or associated chains.

Polypeptides may be attached or immobilised to a solid support.

Polypeptides may comprise a detectable label e.g. a radioactive label, a fluorescent label, or a biotin label. This is particularly useful in immunoassay techniques.

Polypeptides typically consist of an artificial amino acid sequence, namely a sequence which is not present in any naturally-occurring meningococci.

Affinity for factor H can be quantitatively assessed using surface plasmon resonance (e.g. as disclosed in Schneider et al. (2009) *Nature* 458:890-5) with immobilised human fH. Mutations which provide an affinity reduction (i.e. an increase in the dissociation constant, $K_D$) of at least 10-fold, and ideally at least 100-fold, is preferred (when measured under the same experimental conditions relative to the same polypeptide but without the mutation).

Immunogenic Compositions of the Invention

The immunogenic composition of the invention is a pentavalent composition, comprising antigenic components against five different meningococcal serotypes (A, B, C, W135 and Y). Each of these components is as defined above.

In a preferred embodiment, the pentavalent immunogenic composition of the invention comprises the following:

- a serogroup A antigen, which is a synthetic analogue of a serogroup A capsular saccharide, conjugated to CRM 197, as defined above;
- a serogroup C antigen conjugated to CRM 197, as defined above;
- a serogroup W135 antigen conjugated to CRM 197, as defined above;
- a serogroup Y antigen conjugated to CRM 197, as defined above; and
- a combination of serogroup B antigens, comprising the antigens of the licensed vaccine BEXSERO together with an fHBp 231 fusion protein as defined above.

In a preferred embodiment, the pentavalent immunogenic composition of the invention is provided as a fully liquid (aqueous) formulation. For the avoidance of doubt, this mean that each of the components is in a liquid form and none of the components of the immunogenic composition are in solid (lyophilized) form.

According to a further aspect of the invention, there is provided an immunogenic composition comprising as described above; and at least one pharmaceutically acceptable excipient.

Generally, the pharmaceutically acceptable excipient can be any substance that does not itself induce the production of antibodies and is not harmful to the patient receiving the composition, and which can be administered without undue toxicity. Pharmaceutically acceptable carriers and excipient are those used in the art, and can include liquids such as water, saline, glycerol and ethanol. Auxiliary substances, such as wetting or emulsifying agents, pH buffering substances, and the like, can also be present in such vehicles, according to the prior art.

The immunogenic composition may further comprise an adjuvant. The adjuvant may be an aluminium based adjuvant such as aluminium hydroxide or aluminium phosphate.

The immunogenic composition of the invention many be administered in combination with other pharmaceutically active substances or other vaccines. Compositions for administration may include other types of immunogenic compounds such as glycoconjugate, e.g. eliciting an immune response to provide protection against other *N. meningitidis* pathogens.

According to a further aspect of the invention, there is provided a vaccine comprising r an immunogenic composition as described above.

Said immunogenic compositions are useful for immunizing a mammal, preferably a human, against *Neisseria meningitidis* infection.

Immunogenic compositions of the invention are used to immunize a mammal against infection and/or disease caused by *Neisseria meningitidis* serogroups A, B, C, W125 and/or Y, such that recipients of the immunogenic composition mount an immune response which provides protection against infection by and/or disease due to *Neisseria meningitidis* bacteria.

Therefore, immunogenic compositions according to the invention are used in prophylactic methods for immunizing subjects against infection and/or disease caused by *Neisseria meningitidis*. The immunogenic compositions may also be used in therapeutic methods (i.e. to treat *Neisseria meningitidis* infection).

The invention also provides a method for raising an immune response in vivo against *Neisseria meningitidis* infection in a mammal, comprising administering an immunogenic composition of the invention to the mammal. The invention also provides polypeptides of the invention for use in such methods.

The immune response is preferably protective and preferably involves antibodies and/or cell-mediated immunity. Preferably, the immune response is a bactericidal antibody response. The method may raise a booster response. By raising an in vivo immune response, the mammal can be protected against Neisserial disease (in particular meningococcal infection)

The invention also provides a method for protecting a mammal against a Neisserial (e.g. meningococcal) infection, comprising administering to the mammal an immunogenic composition of the invention.

The immunological compositions of the invention are preferably formulated as vaccine products, which are suitable for therapeutic (i.e. to treat an infection) or prophylactic (i.e. to prevent an infection) use. Vaccines are typically prophylactic.

The mammal is preferably a human. The human may be an adult, an adolescent or a child (e.g. a toddler or infant). A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N. meningitidis* (specifically against serogroups A, B, C, W135 and Y).

Protection against *N. meningitidis* can be measured epidemiologically e.g. in a clinical trial, but it is convenient to use an indirect measure to confirm that an immunogenic composition elicits a serum bactericidal antibody (SBA) response in recipients. In the SBA assay, sera from recipients of the composition are incubated with target bacteria (in the present invention, *N. meningitidis*) in the presence of complement (preferably human complement, although baby rabbit complement is often used instead) and killing of the bacteria is assessed at various dilutions of the sera to determine SBA activity. Results observed in the SBA assay can be reinforced by carrying out a competitive SBA assay to provide further indirect evidence of the immunogenic activity of antigen(s) of interest. In the competitive SBA assay, sera from recipients of the immunogenic composition containing the antigen(s) are pre-incubated with said antigen(s), and subsequently incubated with target bacteria in the presence of human complement. Killing of the bacteria is then assessed, and will be reduced or abolished if bactericidal antibodies in the recipients' sera bind to the antigens of interested during the pre-incubation phase and are therefore not available to bind to surface antigen on the bacteria.

It is not necessary that the composition should protect against each and every strain of *N. meningitidis*, or that each and every recipient of the composition must be protected. Such universal protection is not the normal standard in this field. Rather, protection is normally assessed against a panel of reference laboratory strains, often selected on a country-by-country basis and perhaps varying with time, and is measured across a population of recipients.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Immunogenic compositions comprise an immunologically effective amount of immunogen, as well as any other of other specified components, as needed.

By 'immunologically effective amount', it is meant that the administration of that amount to an individual, either in a single dose or as part of a series, is effective for treatment or prevention.

The term "prevention" means that the progression of the disease is reduced and/or eliminated, or that the onset of the disease is eliminated. For example, the immune system of a subject may be primed (e.g. by vaccination) to trigger an immune response and repel infection such that the onset of the disease is eliminated. A vaccinated subject may thus get infected, but is better able to repel the infection than a control subject. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The composition may be administered in conjunction with other immunoregulatory agents.

Vaccine Efficacy

Immunogenic compositions for use in the present invention preferably have a vaccine efficacy against at least one strain of *N. meningitidis* of at least 10% e.g. ≥20%, ≥30%, ≥40%, ≥50%, ≥60%, ≥70%, ≥80%, ≥85%, ≥90%, or more.

Vaccine efficacy is determined by the reduction in relative risk of developing meningococcal disease in subjects who receive a composition according to the invention compared to subjects who do not receive such a composition (e.g. are non-immunized or who receive a placebo or negative control). Thus the incidence of meningococcal disease in a population which has been immunized according to the invention is compared to the incidence in a control population who has not been immunized according to the invention to give relative risk and vaccine efficacy is 100% minus this figure.

Vaccine efficacy is determined for a population rather than for an individual. Thus, it is a useful epidemiologic tool but does not predict individual protection. For instance, an individual subject might be exposed to a very large inoculum of the infecting agent, or might have other risk factors which make them more subject to infection, but this does not negate the validity or utility of the efficacy measure. The size of a population which is immunized according to the invention, and for which vaccine efficacy is measured, is ideally at least 100 and maybe higher e.g. at least 500 subjects. The size of the control group should also be at least 100 e.g. at least 500.

Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Administration by injection is preferred. Intramuscular administration to the thigh or the upper arm is preferred. Injection may be via a needle (e.g. a hypodermic needle), but needle-free injection may alternatively be used.

Preferably, the composition of the invention is packaged in a single hermetically sealed container, preferably a vial or syringe.

Neisserial infections affect various areas of the body and so the compositions may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred.

Most preferably, the immunogenic composition of the invention is provided as a fully liquid formulation, i.e. no antigenic component of the composition of the invention is in a lyophilized form.

The invention may be used to elicit systemic and/or mucosal immunity.

As used herein, a 'dose' of the composition is a volume of the composition suitable for administration to a subject as a single immunisation. Human vaccines are typically administered in a dosage volume of about 0.5 ml, although fractional doses may be administered (e.g., to children). The volume of the dose may further vary depending on the concentration of the antigens in the composition.

The composition may be provided in a 'multidose' kit, i.e., a single container containing sufficient composition for multiple immunisations. Multidoses may include a preservative, or the multidose container may have an aseptic adaptor for removal of individual doses of the composition.

Administration can involve a single dose schedule, but will usually involve a multiple dose schedule. Preferably, a schedule of at least three doses is given. Suitable intervals between priming doses can be routinely determined e.g. between 4-16 weeks, such as one month or two months. For example, BEXSERO® can be administered at ages of 2, 4 & 6 months, or at 2, 3 & 4 months, with a fourth optional dose at 12 months.

The subject who is immunized is a human being, who may be any age e.g. 0-12 months old, 1-5 years old, 5-18 years old, 18-55 years old, or more than 55 years old. Preferably, the subject who is immunized is an adolescent (e.g. 12-18 years old) or an adult (18 years or older).

Optionally, the subject is an adolescent or adult who has been immunized against *N. meningitidis* in childhood (e.g. before 12 years of age), and who receives a booster dose of an immunogenic composition according to the invention.

Non-Antigenic Components

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in Gennaro (2000) *Remington: The Science and Practice of Pharmacy.* 20th edition, ISBN: 0683306472.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [WO03/009869]. Compositions of the invention may be isotonic with respect to humans.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of *Vaccine Design* . . . (1995) eds. Powell & Newman. ISBN: 030644867X. Plenum.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of *Vaccine Design* . . . (1995) eds. Powell & Newman. ISBN: 030644867X. Plenum). The salts can take any suitable form (e.g. gel, crystalline, amorphous, etc.).

General

As used in the present disclosure and claims, the singular forms "a," "an," and "the" include plural forms unless the context clearly dictates otherwise; i.e., "a" means "one or more" unless indicated otherwise.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.). The term "consisting essentially of" limits the scope of a claim to the specified materials or steps "and those that do not materially affect the basic and novel characteristic(s)" of the claimed invention.

Unless specified otherwise, all of the designations "A %-B %," "A-B %," "A % to B %," "A to B %," "A %-B," "A % to B" are given their ordinary and customary meaning. In some embodiments, these designations are synonyms.

The terms "substantially" or "substantial" mean that the condition described or claimed functions in all important aspects as the standard described. Thus, "substantially free" is meant to encompass conditions that function in all important aspects as free conditions, even if the numerical values indicate the presence of some impurities or substances. "Substantial" generally means a value greater than 90%, preferably greater than 95%, most preferably greater than 99%. Where particular values are used in the specification and in the claims, unless otherwise stated, the term "substantially" means with an acceptable error range for the particular value.

The term "about" in relation to a numerical value x is optional and means, for example, x±10%.

Where the disclosure concerns an "epitope", this epitope may be a B-cell epitope and/or a T-cell epitope, but will usually be a B-cell epitope. Such epitopes can be identified empirically (e.g. using PEPSCAN (e.g. see Geysen et al.

(1984) *PNAS USA* 81:3998-4002 and Carter (1994) *Methods Mol Biol* 36:207-23) or similar methods), or they can be predicted (e.g. using the Jameson-Wolf antigenic index (Jameson, B A et al. 1988, *CABIOS* 4(1):181-186), matrix-based approaches (Raddrizzani & Hammer (2000) *Brief Bioinform* 1(2):179-89), MAPITOPE (Bublil et al. (2007) *Proteins* 68(1):294-304), TEPITOPE (De Lalla et al. (1999) *J. Immunol.* 163:1725-29 and Kwok et al. (2001) *Trends Immunol* 22:583-88), neural networks (Brusic et al. (1998) *Bioinformatics* 14(2):121-30), OptiMer & EpiMer (Meister et al. (1995) *Vaccine* 13(6):581-91 and Roberts et al. (1996) *AIDS Res Hum Retroviruses* 12(7):593-610), ADEPT (Maksyutov & Zagrebelnaya (1993) *Comput Appl Biosci* 9(3):291-7), Tsites (Feller & de la Cruz (1991) *Nature* 349(6311):720-1), hydrophilicity (Hopp (1993) *Peptide Research* 6:183-190), or antigenic index (Welling et al. (1985) *FEBS Lett.* 188:215-218)). Epitopes are the parts of an antigen that are recognized by and bind to the antigen binding sites of antibodies or T-cell receptors, and they may also be referred to as "antigenic determinants".

As used herein, references to "percentage sequence identity" between a query amino acid sequence and a subject amino acid sequence are understood to refer to the value of identity that is calculated using a suitable algorithm or software program known in the art to perform pairwise sequence alignment.

A query amino acid sequence may be described by an amino acid sequence identified in one or more claims herein. The query sequence may be 100% identical to the subject sequence, or it may include up to a certain integer number of amino acid alterations (e.g. point mutations, substitutions, deletions, insertions etc.) as compared to the subject sequence, such that the % identity is less than 100%. For example, the query sequence is at least 80, 85, 90, 95, 96, 97, 98, or 99% identical to the subject sequence.

Preferred alignment tools used to perform alignment and calculate percentage (%) sequence identity are local alignment tools, such as the Basic Local Alignment Search Tool (BLAST) algorithms. Software for performing BLAST analyses is publicly available through the National Centre for Biotechnology Information (www.ncbi.nlm.nih.gov). Alignment may be determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489. Other preferred alignment tools are Water (EMBOSS) and Marcher (EMBOSS). Alternatively, preferred alignment tools used to perform alignment and calculate percentage (%) sequence identity are best fit alignment tools, such as GENEPAST, also known as KERR algorithm.

In order to calculate percent identity, the query and subject sequences may be compared and aligned for maximum correspondence over a designated region (e.g. a region of at least about 40, 45, 50, 55, 60, 65 or more amino acids in length, and can be up to the full length of the subject amino acid sequence). Said designated region must include the region of the query sequence comprising any specified point mutations in the amino acid sequence. Alternatively, percentage sequence identity may be calculated over the "full length" of the subject sequence. Any N-terminal or C-terminal amino acid stretches that may be present in the query sequence, such as signal peptides or leader peptide or C-terminal or N-terminal tags, should excluded from the alignment.

The term "fragment" in reference to polypeptide sequences means that the polypeptide is a fraction of a full-length protein. As used herein, a fragment of a mutant polypeptide also comprises the mutation(s). Fragments may possess qualitative biological activity in common with the full-length protein, for example, an "immunogenic fragment" contains or encodes one or more epitopes, such as immunodominant epitopes, that allows the same or similar immune response to be raised to the fragment as is raised to the full length sequence. Polypeptide fragments generally have an amino (N) terminus portion and/or carboxy (C) terminus portion deleted as compared to the native protein, but wherein the remaining amino acid sequence of the fragment is identical to the amino acid sequence of the native protein. Polypeptide fragments may contain, for example: about 8, 10, 12, 14, 16, 18, 20, 22, 24, 26, 28, 30, 32, 24, 26, 28, 40, 45, 50, 55, 60, 70, 80, 90, 100, 150, 200, 240, 241, 242, 243, 244, 245, 246, 247, 248, 249, 250, 251, 252, 253, 254, 255, 256, 257, 258, 259, 260, 261, 262 contiguous amino acids, including all integers in between, of a reference polypeptide sequence, for example between 50 and 260, 50 and 255, 50 and 250, 50 and 200, 50 and 150 contiguous amino acids of a reference polypeptide sequence. The term fragment explicitly excludes full length fHbp polypeptides and mature lipoproteins thereof.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

References herein to "enhanced stability" or "higher stability" or "increased stability" mean that the mutant polypeptides disclosed herein have a higher relative thermostability (in kcal/mol) as compared to a non-mutant (wild-type) polypeptide under the same experimental conditions. The stability enhancement can be assessed using differential scanning calorimetry (DSC), for example as discussed in Bruylants et al. (*Differential Scanning Calorimetry in Life Sciences: Thermodynamics, Stability, Molecular Recognition and Application in Drug Design,* 2005 Curr. Med. Chem. 12: 2011-2020) and Calorimetry Sciences Corporation's "Characterizing Protein stability by DSC" (Life Sciences Application Note, Doc. No. 2021102136 February 2006) or by differential scanning fluorimetry (DSF). An increase in stability may be characterized as an at least about 5° C. increase in thermal transition midpoint ($T_m$), as assessed by DSC or DSF. See, for example, Thomas et al., *Effect of single-point mutations on the stability and immunogenicity of a recombinant ricin A chain subunit vaccine antigen,* 2013 Hum. Vaccin. Immunother. 9(4): 744-752.

An "effective amount" means an amount sufficient to cause the referenced effect or outcome. An "effective amount" can be determined empirically and in a routine manner using known techniques in relation to the stated purpose.

By "immunologically effective amount" or "therapeutically effective amount", it is meant that the administration of that amount to an individual, either in a single dose or as part of a series, is effective for treatment or prevention. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The term "treatment" means any one of more of the following: (i) the prevention of infection or re-infection, as in a traditional vaccine, (ii) the reduction in severity of, or, in the elimination of symptoms, (iii) the delay in recurrence of symptoms, and (iv) the substantial or complete elimination of the pathogen or disorder in question in a subject. Hence, treatment may be affected prophylactically (prior to infection) or therapeutically (following infection).

The term "% w/w" indicates the weight percentage of a given compound, over a different compound or over the whole content of a composition, as indicated.

Analogously, the term "% v/v" indicates the volume percentage of a given compound, over a different compound or over the whole content of a composition, as indicated.

All publications cited herein are incorporated by reference in their entirety.

SEQUENCES

SEQ ID NO: 1 [v1.13 mature polypeptide from strain M982]
CSSGGGGVAADIGAGLADALTAPLDHKDKGLQSLTLDQSVRKNEKLKLAAQGAEKTYGNGDSLNTGKLKNDKVSRFDFIR
QIEVDGKLITLESGEFQVYKQSHSALTALQTEQVQDSEDSGKMVAKRQFRIGDIAGEHTSFDKLPKGGSATYRGTAFGSDD
AGGKLTYTIDFAAKQGHGKIEHLKSPELNVELATAYIKPDEKRHAVISGSVLYNQDEKGSYSLGIFGGQAQEVAGSAEVETAN
GIHHIGLAAKQ SEQ ID NO: 2 [v1.13 ΔG]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDEKGSYSLGIFGGQAQEVAGSAEVETANGIHHIGLA
AKQ SEQ ID NO: 3 [v1.13 ΔG (E211A/E232A)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDAKGSYSLGIFGGQAQEVAGSAAVETANGIHHIGLA
AKQ SEQ ID NO: 4 [v1.13 ΔG (E211A/S216R)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDAKGSYRLGIFGGQAQEVAGSAEVETANGIHHIGLA
AKQ SEQ ID NO: 5 [v1.15 mature polypeptide from strain NM452]
CSSGGGGSGGGGVAADIGAGLADALTAPLDHKDKGLKSLTLEDSISQNGTLTLSAQGAERTFKAGDKDNSLNTGKLKNDKI
SRFDFIRQIEVDGQLITLESGEFQVYKQSHSALTALQTEQVQDSEHSGKMVAKRQFRIGDIVGEHTSFGKLPKDVMATYRGT
AFGSDDAGGKLTYTIDFAAKQGHGKIEHLKSPELNVDLAAADIKPDEKHHAVISGSVLYNQAEKGSYSLGIFGGQAQEVAGS
AEVETANGIRHIGLAAKQ SEQ ID NO: 6 [v1.15 ΔG]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAEKGSYSLGIFGGQAQEVAGSAEVETANGIRHIGL
AAKQ SEQ ID NO: 7 [v1.15 ΔG (S219R)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAEKGSYRLGIFGGQAQEVAGSAEVETANGIRHIG
LAAKQ SEQ ID NO: 8 [v1.15 ΔG (E214A/S219R)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAAKGSYRLGIFGGQAQEVAGSAEVETANGIRHIG
LAAKQ SEQ ID NO: 9 [v1.15 ΔG (E214A/E235A)]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAAKGSYSLGIFGGQAQEVAGSAAVETANGIRHIG
LAAKQ SEQ ID NO: 10 [v2 wt from strain 2996]
MNRTAFCCLSLTAALILTACSSGGGGVAADIGAGLADALTAPLDHKDKSLQSLTLDQSVRKNEKLKLAAQGAEKTYGNGDS
LNTGKLKNDKVSRFDFIRQIEVDGQLITLESGEFQIYKQDHSAVVALQIEKINNPDKIDSLINQRSFLVSGLGGEHTAFNQLPD
GKAEYHGKAFSSDDAGGKLTYTIDFAAKQGHGKIEHLKTPEQNVELAAAELKADEKSHAVILGDTRYGSEEKGTYHLALFGD
RAQEIAGSATVKIGEKVHEIGIAGKQ -continued

SEQUENCES

SEQ ID NO: 11 [v2 mature polypeptide]
CSSGGGGVAADIGAGLADALTAPLDHKDKSLQSLTLDQSVRKNEKLKLAAQGAEKTYGNGDSLNTGKLKNDKVSRFDFIRQ
IEVDGQLITLESGEFQIYKQDHSAVVALQIEKINNPDKIDSLINQRSFLVSGLGGEHTAFNQLPDGKAEYHGKAFSSDDAGGK
LTYTIDFAAKQGHGKIEHLKTPEQNVELAAAELKADEKSHAVILGDTRYGSEEKGTYHLALFGDRAQEIAGSATVKIGEKVHEI
GIAGKQ SEQ ID NO: 12 [v2 ΔG]
VAADIGAGLADALTAPLDHKDKSLQSLTLDQSVRKNEKLKLAAQGAEKTYGNGDSLNTGKLKNDKVSRFDFIRQIEVDGQLI
TLESGEFQIYKQDHSAVVALQIEKINNPDKIDSLINQRSFLVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ SEQ ID NO: 13 [v3 wt from strain M1239]
MNRTAFCCLSLTTALILTACSSGGGGSGGGGVAADIGTGLADALTAPLDHKDKGLKSLTLEDSIPQNGTLTLSAQGAEKTFK
AGDKDNSLNTGKLKNDKISRFDFVQKIEVDGQTITLASGEFQIYKQNHSAVVALQIEKINNPDKTDSLINQRSFLVSGLGGEH
TAFNQLPGGKAEYHGKAFSSDDPNGRLHYSIDFTKKQGYGRIEHLKTLEQNVELAAAELKADEKSHAVILGDTRYGSEEKGT
YHLALFGDRAQEIAGSATVKIGEKVHEIGIAGKQ SEQ ID NO: 14 [v3 mature]
CSSGGGGSGGGGVAADIGTGLADALTAPLDHKDKGLKSLTLEDSIPQNGTLTLSAQGAEKTFKAGDKDNSLNTGKLKNDKI
SRFDFVQKIEVDGQTITLASGEFQIYKQNHSAVVALQIEKINNPDKTDSLINQRSFLVSGLGGEHTAFNQLPGGKAEYHGKAF
SSDDPNGRLHYSIDFTKKQGYGRIEHLKTLEQNVELAAAELKADEKSHAVILGDTRYGSEEKGTYHLALFGDRAQEIAGSATV
KIGEKVHEIGIAGKQ SEQ ID NO: 15 [v3 ΔG]
VAADIGTGLADALTAPLDHKDKGLKSLTLEDSIPQNGTLTLSAQGAEKTFKAGDKDNSLNTGKLKNDKISRFDFVQKIEVDG
QTITLASGEFQIYKQNHSAVVALQIEKINNPDKTDSLINQRSFLVSGLGGEHTAFNQLPGGKAEYHGKAFSSDDPNGRLHYSI
DFTKKQGYGRIEHLKTLEQNVELAAAELKADEKSHAVILGDTRYGSEEKGTYHLALFGDRAQEIAGSATVKIGEKVHEIGIAG
KQ SEQ ID NO: 16 [v2 ΔG S32V/L123R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ SEQ ID NO: 17 [v3 ΔG S32V/L126R]
VAADIGTGLADALTAPLDHKDKGLKSLTLEDVIPQNGTLTLSAQGAEKTFKAGDKDNSLNTGKLKNDKISRFDFVQKIEVDG
QTITLASGEFQIYKQNHSAVVALQIEKINNPDKTDSLINQRSFRVSGLGGEHTAFNQLPGGKAEYHGKAFSSDDPNGRLHYSI
DFTKKQGYGRIEHLKTLEQNVELAAAELKADEKSHAVILGDTRYGSEEKGTYHLALFGDRAQEIAGSATVKIGEKVHEIGIAG
KQ SEQ ID NO: 18 [(23S_1.13_E211A/E232A)]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK
VHEIGIAGKQGSGGGGVAADIGAGLADALTAPLDHKDKGLQSLTLDQSVRKNEKLKLAAQGAEKTYGNGDSLNTGKLKND
KVSRFDFIRQIEVDGKLITLESGEFQVYKQSHSALTALQTEQVQDSEDSGKMVAKRQFRIGDIAGEHTSFDKLPKGGSATYR
GTAFGSDDAGGKLTYTIDFAAKQGHGKIEHLKSPELNVELATAYIKPDEKRHAVISGSVLYNQDAKGSYSLGIFGGQAQEVA
GSAAVETANGIHHIGLAAKQ SEQ ID NO: 19 [23S_1.13_E211A/S216R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK
VHEIGIAGKQGSGGGGVAADIGAGLADALTAPLDHKDKGLQSLTLDQSVRKNEKLKLAAQGAEKTYGNGDSLNTGKLKND
KVSRFDFIRQIEVDGKLITLESGEFQVYKQSHSALTALQTEQVQDSEDSGKMVAKRQFRIGDIAGEHTSFDKLPKGGSATYR
GTAFGSDDAGGKLTYTIDFAAKQGHGKIEHLKSPELNVELATAYIKPDEKRHAVISGSVLYNQDAKGSYRLGIFGGQAQEVA
GSAEVETANGIHHIGLAAKQ SEQ ID NO: 20 [23S_1.15_S219R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK -continued

| SEQUENCES |
|---|

VHEIGIAGKQGSGGGGVAADIGAGLADALTAPLDHKDKGLKSLTLEDSISQNGTLTLSAQGAERTFKAGDKDNSLNTGKLK
NDKISRFDFIRQIEVDGQLITLESGEFQVYKQSHSALTALQTEQVQDSEHSGKMVAKRQFRIGDIVGEHTSFGKLPKDVMAT
YRGTAFGSDDAGGKLTYTIDFAAKQGHGKIEHLKSPELNVDLAAADIKPDEKHHAVISGSVLYNQAEKGSYRLGIFGGQAQE
VAGSAEVETANGIRHIGLAAKQ

SEQ ID NO: 21 [23S_1.15_E214A/S219R]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK
VHEIGIAGKQGSGGGGVAADIGAGLADALTAPLDHKDKGLKSLTLEDSISQNGTLTLSAQGAERTFKAGDKDNSLNTGKLK
NDKISRFDFIRQIEVDGQLITLESGEFQVYKQSHSALTALQTEQVQDSEHSGKMVAKRQFRIGDIVGEHTSFGKLPKDVMAT
YRGTAFGSDDAGGKLTYTIDFAAKQGHGKIEHLKSPELNVDLAAADIKPDEKHHAVISGSVLYNQAAKGSYRLGIFGGQAQE
VAGSAEVETANGIRHIGLAAKQ

SEQ ID NO: 22 [23S_1.15_ E214A/E235A]
VAADIGAGLADALTAPLDHKDKSLQSLTLDQVVRKNEKLKLAAQGAEKTYGNGDSLNTGKLKNDKVSRFDFIRQIEVDGQLI
TLESGEFQIYKQDHSAVVALQIEKINNPDKIDSLINQRSFRVSGLGGEHTAFNQLPDGKAEYHGKAFSSDDAGGKLTYTIDFA
AKQGHGKIEHLKTPEQNVELAAAELKADEKSHAVILGDTRYGSEEKGTYHLALFGDRAQEIAGSATVKIGEKVHEIGIAGKQ
GSGGGGVAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGKAFSSDDP
NGRLHYSIDFTKKQGYGRIEHLKTLEQNVELAAAELKADEKSHAVILGDTRYGSEEKGTYHLALFGDRAQEIAGSATVKIGEK
VHEIGIAGKQGSGGGGVAADIGAGLADALTAPLDHKDKGLKSLTLEDSISQNGTLTLSAQGAERTFKAGDKDNSLNTGKLK
NDKISRFDFIRQIEVDGQLITLESGEFQVYKQSHSALTALQTEQVQDSEHSGKMVAKRQFRIGDIVGEHTSFGKLPKDVMAT
YRGTAFGSDDAGGKLTYTIDFAAKQGHGKIEHLKSPELNVDLAAADIKPDEKHHAVISGSVLYNQAAKGSYSLGIFGGQAQE
VAGSAAVETANGIRHIGLAAKQ

SEQ ID NO: 23 [v1.1 ΔG + His tag]
VAADIGAGLADALTAPLDHKDKGLQSLTLDQSVRKNEKLKLAAQGAEKTYGNGDSLNTGKLKNDKVSRFDFIRQIEVDGQLI
TLESGEFQVYKQSHSALTAFQTEQIQDSEHSGKMVAKRQFRIGDIAGEHTSFDKLPEGGRATYRGTAFGSDDAGGKLTYTID
FAAKQGNGKIEHLKSPELGLAAKQLNVDLAAADIKPDGKRHAVISGSVLYNQAEKGSYSLGIFGGKAQEVAGSAEVKTVNGI
RHLEHHHHHH SEQ ID NO: 24 [v1.13 ΔG + His tag]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDEKGSYSLGIFGGQAQEVAGSAEVETANGIHHIGLA
AKQLEHHHHHH SEQ ID NO: 25 [v1.13 ΔG (E211A)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDAKGSYSLGIFGGQAQEVAGSAEVETANGIHHIGLA
AKQLEHHHHHH SEQ ID NO: 26 [v1.13 ΔG (S216R)]
VAADIGAGLADALTAPLDHKDKGLQSLTLDQSVRKNEKLKLAAQGAEKTYGNGDSLNTGKLKNDKVSRFDFIRQIEVDGKLI
TLESGEFQVYKQSHSALTALQTEQVQDSEDSGKMVAKRQFRIGDIAGEHTSFDKLPKGGSATYRGTAFGSDDAGGKLTYTI
DFAAKQGHGKIEHLKSPELNVELATAYIKPDEKRHAVISGSVLYNQDEKGSYRLGIFGGQAQEVAGSAEVETANGIHHIGLA
AKQLEHHHHHH SEQ ID NO: 27 [v1.15 ΔG + His tag]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAEKGSYSLGIFGGQAQEVAGSAEVETANGIRHIGL
AAKQLEHHHHHH SEQ ID NO: 28 [v1.15 ΔG (E214A) + His tag]
VAADIGAGLADALTAPLDHKDKGLKSLTLEDSISQNGTLTLSAQGAERTFKAGDKDNSLNTGKLKNDKISRFDFIRQIEVDGQ
LITLESGEFQVYKQSHSALTALQTEQVQDSEHSGKMVAKRQFRIGDIVGEHTSFGKLPKDVMATYRGTAFGSDDAGGKLTY
TIDFAAKQGHGKIEHLKSPELNVDLAAADIKPDEKHHAVISGSVLYNQAAKGSYSLGIFGGQAQEVAGSAEVETANGIRHIG
LAAKQLEHHHHHH SEQ ID NO: 29 [fHbp 231 wt fusion polypeptide]
VAADIGAGLADALTAPLDHKDKSLQSLTLDQSVRKNEKLKLAAQGAEKTYGNGDSLNTGKLKNDKVSFDFIRQIEVDGQLIT
LESGEFQIYKQDHSAVVALQIEKINNPDKIDSLINQRSFLVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQGS
GGGGVAADIGTGLADALTAPLDHKDKGLKSLTLEDSIPQNGTLTLSAQGAEKTFKAGDKDNSLNTGKLKNDKISRFDFVQKI
EVDGQTITLASGEFQIYKQNHSAVVALQIEKINNPDKTDSLINQRSFLVSGLGGEHTAFNQLPGGKAEYHGKAFSSDDPNGR
LHYSIDFTKKQGYGRIEHLKTLEQNVELAAAELKADEKSHAVILGDTRYGSEEKGTYHLALFGDRAQEIAGSATVKIGEKVHEI
GIAGKQGSGGGGVAADIGAGLADALTAPLDHKDKGLQSLTLDQSVRKNEKLKLAAQGAEKTYGNGSLNTGKLKNDKVSRF
DFIRQIEVDGQLITLESGEFQVYKQSHSALTAFQTEQIQDSEHSGKMVAKRQFRIGDIAGEHTSFDKLPEGGRATYRGTAFG
SDDAGGKLTYTIDFAAKQGNGKIEHLKSPELNVDLAAAIKPDGKRHAVISGSVLYNQAEKGSYSLGIFGKAQEVAGSAEVKT
VNGIRHIGLAAKQ -continued

SEQUENCES

SEQ ID NO: 30 [fHbp 231S fusion polypeptide]
VAADIGAGLADALTAPLDHKDKSLQSLTLDQVVRKNEKLKLAAQGAEKTYGNGDSLNTGKLKNDKVSFDFIRQIEVDGQLIT
LESGEFQIYKQDHSAVVALQIEKINNPDKIDSLINQRSFRVSGLGGEHTAFNQLPDGKAEYHGKAFSSDDAGGKLTYTIDFAA
KQGHGKIEHLKTPEQNVELAAAELKADEKSHAVILGDTRYGSEEKGTYHLALFGDRAQEIAGSATVKIGEKVHEIGIAGKQGS
GGGGVAADIGTGLADALTAPLDHKDKGLKSLTLEDVIPQNGTLTLSAQGAEKTFKAGDKDNSLNTGKLKNDKISRFDFVQKI
EVDGQTITLASGEFQIYKQNHSAVVALQIEKINNPDKTDSLINQRSFRVSGLGGEHTAFNQLPGGKAEYHGKAFSSDDPNG
RLHYSIDFTKKQGYGRIEHLKTLEQNVELAAAELKADEKSHAVILGDTRYGSEEKGTYHLALFGDRAQEIAGSATVKIGEKVHE
IGIAGKQGSGGGGVAADIGAGLADALTAPLDHKDKGLQSLTLDQSVSKNEKLKLAAQGAEKTYGNGSLNTGKLKNDKVSRF
DFIRQIEVDGQLITLESGEFQVYKQSHSALTAFQTEQIQDSEHSGKMVAKRQFRIGDIAGEHTSFDKLPEGGRATYRGTAFG
SDDAGGKLTYTIDFAAKQGNGKIEHLKSPELNVDLAAAIKPDGKRHAVISGSVLYNQAEKGSYSLGIFGKAQEVAGSAEVKT
VNGIRHIGLAAKQ SEQ ID NO: 31 [v1.13 full-length wt sequence]
MNRTAFCCFSLTAALILTACSSGGGGVAADIGAGLADALTAPLDHKDKGLQSLTLDQSVRKNEKLKLAAQGAEKTYGNGDS
LNTGKLKNDKVSRFDFIRQIEVDGKLITLESGEFQVYKQSHSALTALQTEQVQDSEDSGKMVAKRQFRIGDIAGEHTSFDKLP
KGGSATYRGTAFGSDDAGGKLTYTIDFAAKQGHGKIEHLKSPELNVELATAYIKPDEKRHAVISGSVLYNQDEKGSYSLGIFG
GQAQEVAGSAEVETANGIHHIGLAAKQ SEQ ID NO: 32 [v1.15 full-length wt sequence]
MNRTTFCCLSLTAALILTACSSGGGGSGGGGVAADIGAGLADALTAPLDHKDKGLKSLTLEDSISQNGTLTLSAQGAERTFK
AGDKDNSLNTGKLKNDKISRFDFIRQIEVDGQLITLESGEFQVYKQSHSALTALQTEQVQDSEHSGKMVAKRQFRIGDIVGE
HTSFGKLPKDVMATYRGTAFGSDDAGGKLTYTIDFAAKQGHGKIEHLKSPELNVDLAAADIKPDEKHHAVISGSVLYNQAE
KGSYSLGIFGGQAQEVAGSAEVETANGIRHIGLAAKQ SEQ ID NO: 33 [mature fHbp v1.1]
CSSGGGGVAADIGAGLADALTAPLDHKDKGLQSLTLDQSVRKNEKLKLAAQGAEKTYGNGDSLNTGKLKNDKVSRFDFIQI
EVDGQLITLESGEFQVYKQSHSALTAFQTEQIQDSEHSGKMVAKRQFRIGDIAGEHTSFDKLPEGGRATYRGTAFGSDDAG
GKLTYTIDFAAKQGNGKIEHLKSPELNVDLAAADIKPDGKRHAVISGSVLYNQAEKGSYSLGIFGGKAQEVAGSAEVKTVNGI
RHIGLAAKQ SEQ ID NO: 34 [optional N-terminal amino acid sequence]
MGPDSDRLQQRR SEQ ID NO: 35 [SEQ ID NO: 34 + SEQ ID NO: 19; 23S_1.13_E211A/S216R with additional
N-terminal aminoacid sequence]
MGPDSDRLQQRRVAADIGAGLADALTAPLDHKDKSLQSLTLDQVVRKNEKLKLAAQGAEKTYGNGDSLNTGKLKNDKVS
RFDFIRQIEVDGQLITLESGEFQIYKQDHSAVVALQIEKINNPDKIDSLINQRSFRVSGLGGEHTAFNQLPDGKAEYHGKAFSS
DDAGGKLTYTIDFAAKQGHGKIEHLKTPEQNVELAAAELKADEKSHAVILGDTRYGSEEKGTYHLALFGDRAQEIAGSATVKI
GEKVHEIGIAGKQGSGGGGVAADIGTGLADALTAPLDHKDKGLKSLTLEDVIPQNGTLTLSAQGAEKTFKAGDKDNSLNTG
KLKNDKISRFDFVQKIEVDGQTITLASGEFQIYKQNHSAVVALQIEKINNPDKTDSLINQRSFRVSGLGGEHTAFNQLPGGKA
EYHGKAFSSDDPNGRLHYSIDFTKKQGYGRIEHLKTLEQNVELAAAELKADEKSHAVILGDTRYGSEEKGTYHLALFGDRAQ
EIAGSATVKIGEKVHEIGIAGKQGSGGGGVAADIGAGLADALTAPLDHKDKGLQSLTLDQSVRKNEKLKLAAQGAEKTYGN
GDSLNTGKLKNDKVSRFDFIRQIEVDGKLITLESGEFQVYKQSHSALTALQTEQVQDSEDSGKMVAKRQFRIGDIAGEHTSF
DKLPKGGSATYRGTAFGSDDAGGKLTYTIDFAAKQGHGKIEHLKSPELNVELATAYIKPDEKRHAVISGSVLYNQDAKGSYRL
GIFGGQAQEVAGSAEVETANGIHHIGLAAKQ

MODES FOR CARRYING OUT THE INVENTION

The invention will now be further defined by reference to the following non-limiting examples.

Examples

Synthesis and Characterization of the Conjugated Serogroup A Antigen

General Procedures and Materials.

All chemicals (Acros, Biosolve, Sigma-Aldrich and TCI) were used as received and all reactions were effectuated under an argon atmosphere, at ambient temperature (22° C.), unless stated otherwise. For the TLC analysis were used aluminium sheets (Merck, TLC silica gel 60 F254), sprayed with a solution of $H_2SO_4$ (20%) in EtOH or with a solution of $(NH_4)6Mo_7O_{24}\cdot 4H_2O$ (25 g/L) and $(NH_4)_4Ce(SO_4)_4\cdot 2H_2O$ (10 g/L) in 10% aqueous $H_2SO_4$ or with a solution of $KMnO_4$ (2%) and $K_2CO_3$ (1%) in $H_2O$ and then heated at ≈140° C. For the column chromatography was used 40-63 μm 60 Å silica gel (SD Screening Devices). NMR spectra ($^1H$, $^{13}C$ and $^{31}P$) were recorded with a Bruker AV-400liq or a Bruker AV-500 or a Bruker AV-600. High resolution mass spectra were recorded by direct injection on a mass spectrometer (Thermo Finnigan LTQ Orbitrap) equipped with an electrospray ion source in positive mode (source voltage 3.5 kV, sheath gas flow 10, capillary temperature 250° C.) with resolution R=60000 at m/z 400 (mass range m/z=150-2000) and dioctylphthalate (m/z=391.28428) as a lock mass.

Abbreviations

AcOH=acetic acid
ACN=acetonitrile
DCM=dichloromethane
DMTrCl=4,4'-Diemthoxytrityl chloride
EtOAc=Ethyl acetate
THF=tetrahydrofuran
TBAF=tetrabutylammonium fluoride

Example 1: Preparation of Oligomers of the Invention of Formula (Ia), According to Scheme 1

Acetamido-3,4-di-O-benzyl-2-deoxy-6-O-thexyldimethylsilyl-5a-carba-α-D mannopyranose (13)

Silyl ether 12 may be prepared in accordance with the procedure described in Q. Gao et al. Org. Biomol. Chem., 2012, 10, 6673.

Silyl ether 12 (1.6 g, 2.7 mmol) was dissolved in dry THF (20 mL). The mixture was cooled down to 0° C. A 0.1 M solution in THF of TBAF (4.1 mL, 4.1 mmol) was slowly added. The reaction was heated up to room temperature and stirred for 3 h. To the reaction was added AcOH (0.31 mL). The solution was extracted 3 times with DCM and washed once with brine. The organic layer was dried over $Na_2SO_4$ and concentrated in vacuo. The crude was purified by flash chromatography (EtOAc/Hexane) leading to product 13 (1.1 g, 2.52 mmol) in 92% yield. The spectroscopic data were in agreement with the reported data.

2-Acetamido-3,4-di-O-benzyl-2-deoxy-5a-carba-α-D mannopyranose (14)

Alcohol 13 (1.12 g, 2.5 mmol) was dissolved in MeOH (32 mL). To the mixture was added NaOMe (0.03 g, 0.5 mmol). The reaction was stirred for 3 h at room temperature. Amberlite H+ resin was added until neutral pH was reached. The suspension was filtrated and concentrated in vacuo. $^1$H NMR (400 MHz, $CDCl_3$) δ=1.70-1.85 (m, 2H, H-5a), 1.90 (s, 3H, AcNH), 2.19-2.23 (m, 1H, H-5), 3.60-3.79 (m, 3H, H-6, H-1), 3.83-3.90 (m, 1H, H-2), 3.91-3.99 (m, 1H, H-4), 4.14-4.23 (m, 1H, H-3), 4.33-4.41 (m, 1H, CHH Bn), 4.54-4.72 (m, 3H, CH2 Bn, CHH Bn), 5.79 (m, 1H, NHAc), 7.22-7.42 (m, 10H, Harom). $^{13}$C NMR (100 MHz, $CDCl_3$) δ=23.5 (CH3 AcNH), 30.6 (CH2 C-5a), 39.5 (CH C-5), 53.5 (CH C-3), 64.1 (CH2 C-6), 67.9 (CH C-4), 72.4 (CH2 Bn), 73.8 (CH2 Bn), 75.5 (CH C-1), 79.0 (CH C-4), 127.3-128.9 (CHarom), 171.8 (C═O AcNH). HRMS: [C23H29NO5+H]+ requires 400.21251, found 400.21179.

2-Acetamido-3,4-di-O-benzyl-2-deoxy-6-O-(bis(4-methoxyphenyl) (phenyl))-5-carba-α-D-mannopyranose (10)

Diol 14 (0.9 g, 2.25 mmol) was dissolved in dry DCM (30 mL). To the mixture was added $Et_3N$ (1.9 mL, 13.5 mmol). DMTrCl (1.16 g, 3.38 mmol) was added. The reaction was stirred for 2 hours. To the reaction was added $H_2O$ and was washed once with brine. The organic layer was dried over $Na_2SO_4$ and concentrated in vacuo. The crude was purified by flash chromatography (EtOAc/Hexane) leading to product 10 (1.6 g, 2.04 mmol) in 91% yield. 1H NMR (400 MHz, CD3CN) δ=1.70-1.85 (m, 1H, 5a'-H), 1.91 (s, 3H, AcNH), 2.00-2.21 (m, 2H, 5a-H, 5-H), 3.01-3.19 (m, 1H, 6'-H), 3.27-3.37 (m, 1H, 6-H), 3.51-3.67 (m, 1H, H-4), 3.73 (s, 7H, H-3, 2×OMe), 4.06-4.20 (m, 1H, H-1), 4.22-4.32 (m, 1H, CHH Bn), 4.40-4.62 (m, 3H, CH2 Bn, H-2), 4.65-4.73 (m, 1H, CHH Bn), 6.35-6.44 (m, 1H, NHAc), 6.78-7.47 (m, 23H, Harom). 13C NMR (100 MHz, CD3CN) δ=23.2 (CH3 AcNH), 31.6 (CH2 C-5a), 38.6 (CH C-5), 53.3 (CH C-2), 55.8 (2×CH3 OMe), 64.6 (CH2 C-6), 67.6 (CH C-1), 72.1 (CH2 Bn), 73.8 (CH2 Bn), 77.2 (CH C-4), 79.8 (CH C-3), 86.5 (Cq DMTr), 113.9 (CHarom), 127.3-130.7 (CHarom), 137.2-159.4 (5×Cq DMTr), 171.1 (C═O AcNH). HRMS: [C44H47NO7+Na]+ requires 724.32501, found 724.32483.

1-O—((N,N-Diisopropylamino)-O-2-cyanoethyl-phosphoramidite))-2-Acetamido-3,4-di-O-benzyl-2-deoxy-6-O-(bis(4-methoxyphenyl)(phenyl))-5a-carba-α-D-mannopyranose (9)

Alcohol 10 (1.5 g, 2.14 mmol) was co-evaporated 3 times with ACN, and dissolved in dry DCM (22 mL). To the mixture were added freshly activated MS3 Å and DIPEA (0.6 mL, 3.2 mmol). To the mixture was added 2-cyanoethyl N,N-diisopropyl-chlorophosphoramidite (0.6 mL, 2.6 mmol). The reaction was stirred for 2 hours. To the solution was added $H_2O$, and was washed once with a 1:1 solution of brine/$NaHCO_3$. The organic layer was dried over $Na_2SO_4$ and concentrated in vacuo. The crude was purified by flash chromatography (DCM/Acetone/$Et_3N$) leading to product 9 (1.81 g, 2.0 mmol) in 94% yield (mixture of diastereoisomers). 1H NMR (400 MHz, CD3CN) δ=1.04-1.24 (m, 12H, 4×isopropylamino), 1.70-1.85 (m, 1H, 5a'-H), 1.92 (s, 3H, AcNH), 2.00-2.21 (m, 2H, 5a-H, 5-H), 2.55-2.75 (m, 2H, CH2 cyanoethyl), 2.98-3.10 (m, 1H, 6'-H), 3.27-3.37 (m, 1H, 6-H), 3.47-3.70 (m, 3H, 2×CH isopropylamino, H-4), 3.70-3.88 (m, 9H, H-3, CH2 cyanoethyl, 2×OMe), 4.06-4.20 (m, 1H, H-1), 4.22-4.32 (m, 1H, CHH Bn), 4.40-4.62 (m, 3H, CH2 Bn, H-2), 4.65-4.73 (m, 1H, CHH Bn), 6.35-6.44 (m, 1H, NHAc), 6.78-7.47 (m, 23H, Harom). 13C NMR (100 MHz, CD3CN) δ=20.7 (CH2 cyanoethyl), 22.9 (CH3 AcNH), 24.5-24.7 (2×CH3 isopropylamino), 30.6 (CH2 C-5a), 38.5 (CH C-5), 43.7 (2×CH isopropylamino), 51.7 (CH C-2), 55.5 (2×CH3 OMe), 59.1 (CH2 cyanoethyl), 64.2 (CH2 C-6), 70.5 (CH C-1), 71.5 (CH2 Bn), 74.3 (CH2 Bn), 77.8 (CH C-4), 79.5 (CH C-3), 86.2 (Cq DMTr), 113.6 (CHarom), 127.3-130.7 (CHarom), 136.8-159.2 (5×Cq DMTr), 170 (C═O AcNH).31P NMR (162 MHz, CD3CN) δ=146.9, 147.26.

General Procedure for Phosphoramidite Coupling, Oxidation and Detritylation on a Typical Scale (0.03-0.3 Mmol)

Starting alcohol was co-evaporated 3 times with ACN, and was added freshly activated MS3 Å and DCI (0.25 M solution in ACN, 1.5 eq). The solution was stirred for 15 min. To the mixture was added phosphoramidite reagent (0.1-0.16 M solution in ACN, 1.3-3 eq) and stirred until the total conversion of the starting material (≈2 hours). Subsequently CSO (0.5M solution in ACN, 2 eq) was added to the reaction mixture and stirred for 15 min. The mixture was diluted with EtOAc and washed with a 1:1 solution of brine/$NaHCO_3$. The water layer was extracted 2 times with EtOAc. The organic layer was dried over $Na_2SO_4$ and concentrated in vacuo. The crude was co-evaporated 3 times with ACN and dissolved in DCM (5-10 mL). To the solution was added TCA (0.18M solution in DCM) and stirred for 1 hour. To the reaction mixture was added $H_2O$ and stirred for 15 min. The reaction was washed with a 1:1 solution of brine/$NaHCO_3$. The water layer was extracted with DCM 3 times. The organic layer was dried over $Na_2SO_4$ and concentrated in vacuo. The crude was purified by flash chromatography (DCM/Acetone) or by size exclusion chromatography (sephadex LH-20, MeOH/DCM 1:1).

1-O-((2-Acetamido-3,4-di-O-benzyl-2-deoxy-5a-carba-α-D-mannopyranosyl-1-O-phosphoryl)2-cyanoethyl)-6-hexyl-benzyl-carbamate (15)

Alcohol 10 (0.21 g, 0.3 mmol), was coupled to phosphoramidite 11 (2.5 mL 0.16M in ACN, 0.45 mmol), oxidized, detritylated using the general procedure as described above. The crude was purified by flash chromatography (DCM/Acetone) leading to product 15 (0.216 g, 0.282 mmol) in 94% yield. 1H NMR (400 MHz, CD3CN) δ=1.24-1.40 (m, 4H, 2×CH2 hexylspacer), 1.40-1.51 (m, 2H, CH2 hexylspacer), 1.58-1.70 (m, 2H, CH2 hexylspacer), 1.80-1.92 (m, 4H, 5a'-H, AcNH), 1.96-2.02 (m, 2H, 5a-H, 5-H), 2.72-2.82 (m, 2H, CH2 cyanoethyl), 2.96 (bs, 1H, OH), 3.02-3.12 (m, 2H, CH2 hexylspacer), 3.56-3.74 (m, 3H, H-6, H-4), 3.76-3.84 (m, 1H, H-3), 3.95-4.07 (m, 2H, CH2 hexylspacer), 4.08-4.20 (m, 2H, CH2 cyanoethyl), 4.44-4.63 (m, 5H, H-1, H-2, CH2 Bn, CHH Bn), 4.72-4.80 (m, 1H, CHH Bn), 5.03 (s, 2H, CH2 Bn spacer), 5.70 (bs, 1H, NH), 6.49-6.60 (m, 1H, NHAc), 7.23-7.44 (m, 15H, Harom). 13C NMR (100 MHz, CD3CN) δ=19.9 (CH2 cyanoethyl), 22.8 (CH3 AcNH), 25.4 (CH2 hexylspacer), 26.4 (CH2 hexylspacer), 30.0 (CH2 C-5a), 30.4 (CH2 hexylspacer), 30.5 (CH2 hexylspacer), 40.0 (CH C-5), 41.0 (CH2 hexylspacer), 51.1 (CH C-2), 62.9 (CH2 C-6), 63.0 (CH2 cyanoethyl), 66.3 (CH2 Bn spacer), 68.8 (CH2 hexylspacer), 72.2 (CH2 Bn), 74.0 (CH2 Bn), 75.1 (CH C-1), 76.7 (CH C-4), 79.3 (CH C-3), 128.1-129.1 (CHarom), 138.9-139.7 (3×Cq Bn), 170.8 (C═O AcNH). 31P NMR (162 MHz, CD3CN) δ=−2.40, −2.36. HRMS: [C40H52N3O10P+H]+ requires 766.34707, found 766.34707.

1-O-di-((2-Acetamido-3,4-di-O-benzyl-2-deoxy-5a-carba-α-D-mannopyranosyl-1-O-phosphoryl)2-cyanoethyl)-6-hexyl-benzyl-carbamate (16)

Alcohol 15 (0.186 g, 0.24 mmol), was coupled to phosphoramidite 9 (2.3 mL 0.16 M in ACN, 0.37 mmol), oxidized, detritylated using the general procedure as described above. The crude was purified by size exclusion chromatography (sephadex LH-20, DCM/MeOH 1:1) leading to product 16 (0.255 g, 0.199 mmol) in 82% yield. 1H NMR (400 MHz, CD3CN) δ=1.25-1.40 (m, 4H, 2×CH2 hexylspacer), 1.40-1.51 (m, 2H, CH2 hexylspacer), 1.58-1.71 (m, 2H, CH2 hexylspacer), 1.80-1.92 (m, 8H, 2×5a'-H, 2×AcNH), 1.96-2.02 (m, 4H, 2×5a-H, 2×5-H), 2.70-2.81 (m, 4H, 2×CH2 cyanoethyl), 2.96 (bs, 1H, OH), 3.01-3.12 (m, 2H, CH2 hexylspacer), 3.56-3.87 (m, 6H, 2×H-6, 2×H-4), 3.94-4.28 (m, 8H, 2×H-3, CH2 hexylspacer, 2×CH2 cyanoethyl), 4.29-4.85 (m, 12H, 2×H-1, 2×H-2, 4×CH2 Bn), 5.03 (s, 2H, CH2 Bn spacer), 5.75 (bs, 1H, NH), 6.52-6.62 (m, 1H, NHAc), 6.85-6.99 (m, 1H, NHAc), 7.21-7.41 (m, 25H, Harom). 13C NMR (100 MHz, CD3CN) δ=19.9-20.0 (2×CH2 cyanoethyl), 22.9-23.0 (2×CH3 AcNH), 25.5 (CH2 hexylspacer), 26.5 (CH2 hexylspacer), 29.1-29.2 (2×CH2 C-5a), 30.1 (CH2 hexylspacer), 30.5 (CH2 hexylspacer), 38.1-40.0 (2×CH C-5), 41.1 (CH2 hexylspacer), 50.9-51.4 (2×CH C-2), 62.5-62.6 (2×CH2 C-6), 63.0-63.2 (2×CH2 cyanoethyl), 66.3 (CH2 Bn spacer), 68.9 (CH2 hexylspacer), 72.1-72.3 (4×CH2 Bn), 75.0-75.4 (2×CH C-1), 75.5-76.9 (2×CH C-4), 79.2-79.5 (2×CH C-3), 128.2-129.1 (CHarom), 138.9-139.6 (5×Cq Bn), 170.8 (2×C═O AcNH). 31P NMR (162 MHz, CD3CN) δ=−2.60, −2.58, −2.34, −2.32, −2.22, −2.17. HRMS: [C66H83N5O17P2+H]+ requires 1280.53320, found 1280.53320.

1-O-tri-((2-Acetamido-3,4-di-O-benzyl-2-deoxy-5a-carba-α-D-mannopyranosyl-1-O-phosphoryl)2-cyanoethyl)-6-hexyl-benzyl-carbamate (17)

Alcohol 16 (0.215 g, 0.167 mmol), was coupled to phosphoramidite 9 (1.6 mL 0.16 M in ACN, 0.25 mmol), oxidized, detritylated using the general procedure as described above. The crude was purified by size exclusion chromatography (sephadex LH-20, DCM/MeOH 1:1) leading to product 17 (0.285 g, 0.158 mmol) in 95% yield. 1H NMR (400 MHz, CD3CN) δ=1.25-1.40 (m, 4H, 2×CH2 hexylspacer), 1.40-1.51 (m, 2H, CH2 hexylspacer), 1.58-1.71 (m, 2H, CH2 hexylspacer), 1.80-1.92 (m, 12H, 3×5a'-H, 3×AcNH), 1.96-2.30 (m, 6H, 3×5a-H, 3×5-H), 2.68-2.83 (m, 6H, 3×CH2 cyanoethyl), 2.93 (bs, 1H, OH), 3.00-3.11 (m, 2H, CH2 hexylspacer), 3.59-3.89 (m, 9H, 3×H-6, 3×H-4), 3.96-4.22 (m, 11H, 3×H-3, CH2 hexylspacer, 3×CH2 cyanoethyl), 4.31-4.86 (m, 18H, 3×H-1, 3×H-2, 6×CH2 Bn), 5.03 (s, 2H, CH2 Bn spacer), 5.78 (bs, 1H, NH), 6.55-6.65 (m, 1H, NHAc), 6.9-7.15 (m, 2H, 2×NHAc), 7.19-7.40 (m, 35H, Harom). 13C NMR (100 MHz, CD3CN) δ=20.0-20.1 (3×CH2 cyanoethyl), 22.9-23.0 (3×CH3 AcNH), 25.5 (CH2 hexylspacer), 26.5 (CH2 hexylspacer), 28.9-29.2 (3×CH2 C-5a), 30.1 (CH2 hexylspacer), 30.5 (CH2 hexylspacer), 38.0-40.0 (3×CH C-5), 41.1 (CH2 hexylspacer), 50.8-51.4 (3×CH C-2), 62.5-63.0 (3×CH2 C-6), 63.0-63.3 (3×CH2 cyanoethyl), 66.3 (CH2 Bn spacer), 68.4 (CH2 hexylspacer), 72.1-74.1 (6×CH2 Bn), 75.2-75.5 (3×CH C-1), 75.5-76.1 (3×CH C-4), 79.3-79.5 (3×CH C-3), 128.2-129.1 (CHarom), 138.9-139.7 (7×Cq Bn), 170.9-171.2 (3×C═O AcNH). 31P NMR (162 MHz, CD3CN) δ=−2.82, −2.77, −2.62, −2.58, −2.36, −2.33, −2.24, −2.20, −2.16. HRMS: [C92H114N7O24P3+H]+ requires 1795.72333, found 1795.22333.

1-O-tetra-((2-Acetamido-3,4-di-O-benzyl-2-deoxy-5a-carba-α-D-mannopyranosyl-1-O-phosphoryl)2-cyanoethyl)-6-hexyl-benzyl-carbamate (18)

Alcohol 17 (0.267 g, 0.148 mmol), was coupled to phosphoramidite 9 (1.4 mL 0.16 M in ACN, 0.22 mmol), oxidized, detritylated using the general procedure as described above. The crude was purified by size exclusion chromatography (sephadex LH-20, DCM/MeOH 1:1) leading to product 18 (0.299 g, 0.129 mmol) in 87% yield. 1H NMR (400 MHz, (CD3)2CO) δ=1.31-1.47 (m, 4H, 2×CH2 hexylspacer), 1.47-1.57 (m, 2H, CH2 hexylspacer), 1.62-1.75 (m, 2H, CH2 hexylspacer), 1.85-2.02 (m, 16H, 4×5a'-H, 4×AcNH), 2.07-2.17 (m, 8H, 4×5a-H, 4×5-H), 2.82-3.00 (m, 8H, 4×CH2 cyanoethyl), 3.08-3.18 (m, 2H, CH2 hexylspacer), 3.66-4.01 (m, 12H, 4×H-6, 4×H-4), 4.04-4.36 (m, 14H, 4×H-3, CH2 hexylspacer, 4×CH2 cyanoethyl), 4.40-4.94 (m, 24H, 4×H-1, 4×H-2, 8×CH2 Bn), 5.05 (s, 2H, CH2 Bn spacer), 6.39 (bs, 1H, NH), 7.17-7.42 (m, 45H, Harom), 7.42-7.80 (m, 4H, NHAc). 13C NMR (100 MHz, (CD3)2CO) δ=20.0-20.1 (4×CH2 cyanoethyl), 23.1-23.2 (4×CH3 AcNH), 25.8 (CH2 hexylspacer), 26.8 (CH2 hexylspacer), 29.2-29.8 (4×CH2 C-5a), 30.8 (CH2 hexylspacer), 30.8 (CH2 hexylspacer), 38.3-40.3 (4×CH C-5), 41.4 (CH2 hexylspacer), 51.2-51.5 (4×CH C-2), 62.6-63.4 (4×CH2 C-6), 63.4-63.6 (4×CH2 cyanoethyl), 66.2 (CH2 Bn spacer), 68.8 (CH2 hexylspacer), 72.0-75.0 (8×CH2 Bn), 75.6-75.8 (4×CH C-1), 76.5-77.2 (4×CH C-4), 79.7-79.8 (4×CH C-3), 128.1-129.1 (CHarom), 139.3-140.1 (9×Cq Bn), 170.7-171.2 (4×C═O AcNH). 31P NMR (162 MHz, CD3)2CO) δ=−2.84, −2.77, −2.68, −2.47, −2.42, −2.37, −2.30, −1.96, −1.91, −1.89. HRMS: [C118H145N9O31P4+2H]++ requires 1155.45892, founded 1155.45892.

1-O-penta-((2-Acetamido-3,4-di-O-benzyl-2-deoxy-5a-carba-α-D-mannopyranosyl-1-O-phosphoryl)2-cyanoethyl)-6-hexyl-benzyl-carbamate (19)

Alcohol 18 (0.277 g, 0.120 mmol), was coupled to phosphoramidite 9 (1.1 mL 0.16 M in ACN, 0.18 mmol), oxidized, detritylated using the general procedure as described above. The crude was purified by size exclusion chromatography (sephadex LH-20, DCM/MeOH 1:1) leading to product 19 (0.31 g, 0.110 mmol) in 92% yield. 1H NMR (400 MHz, (CD3)2CO) δ=1.31-1.46 (m, 4H, 2×CH2 hexylspacer), 1.46-1.58 (m, 2H, CH2 hexylspacer), 1.62-1.75 (m, 2H, CH2 hexylspacer), 1.84-2.02 (m, 20H, 5×5a'-H, 5×AcNH), 2.07-2.19 (m, 10H, 5×5a-H, 5×5-H), 2.82-2.97 (m, 10H, 5×CH2 cyanoethyl), 3.08-3.18 (m, 2H, CH2 hexylspacer), 3.67-4.02 (m, 15H, 5×H-6, 5×H-4), 4.04-4.36 (m, 17H, 5×H-3, CH2 hexylspacer, 5×CH2 cyanoethyl), 4.38-4.95 (m, 30H, 5×H-1, 5×H-2, 10×CH2 Bn), 5.05 (s, 2H, CH2 Bn spacer), 6.43 (bs, 1H, NH), 7.16-7.41 (m, 55H, Harom), 7.42-7.86 (m, 5H, NHAc). 13C NMR (100 MHz, (CD3)2CO) δ=19.8-20.0 (5×CH2 cyanoethyl), 23.0-23.1 (5×CH3 AcNH), 25.7 (CH2 hexylspacer), 26.7 (CH2 hexylspacer), 29.2-30.0 (5×CH2 C-5a), 30.7 (CH2 hexylspacer), 30.7 (CH2 hexylspacer), 38.2-40.2 (5×CH C-5), 41.2 (CH2 hexylspacer), 51.0-51.4 (5×CH C-2), 62.5-63.2 (5×CH2 C-6), 63.3-63.5 (5×CH2 cyanoethyl), 66.1 (CH2 Bn spacer), 68.7 (CH2 hexylspacer), 72.0-75.0 (10×CH2 Bn), 75.6-75.8 (5×CH C-1), 76.5-77.2 (5×CH C-4), 79.7-79.8 (5×CH C-3), 128.0-129.0 (CHarom), 139.2-140.0 (11×Cq Bn), 170.7-171.2 (5×C═O AcNH). 31P NMR (162 MHz, CD3)2CO) δ=−2.84, −2.77, −2.68, −2.47, −2.42, −2.37, −2.30, −1.96, −1.88, −1.89, −1.86, −1.84, −1.79. HRMS: [C144H176N11O38P5+2H]++ requires 1412.55219, found 1412.55219.

1-O-hexa-((2-Acetamido-3,4-di-O-benzyl-2-deoxy-5a-carba-α-D-mannopyranosyl-1-O-phosphoryl)2-cyanoethyl)-6-hexyl-benzyl-carbamate (20)

Alcohol 19 (0.280 g, 0.099 mmol), was coupled to phosphoramidite 9 (1.24 mL 0.16 M in ACN, 0.20 mmol), oxidized, detritylated using the general procedure as described above. The crude was purified by size exclusion chromatography (sephadex LH-20, DCM/MeOH 1:1) leading to product 20 (0.29 g, 0.087 mmol) in 88% yield. 1H NMR (500 MHz, (CD3)2CO) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 24H, 6×5a'-H, 6×AcNH), 2.07-2.30 (m, 12H, 6×5a-H, 6×5-H), 2.82-2.97 (m, 12H, 6×CH2 cyanoethyl), 3.09-3.18 (m, 2H, CH2 hexylspacer), 3.67-4.04 (m, 18H, 6×H-6, 6×H-4), 4.04-4.38 (m, 20H, 6×H-3, CH2 hexylspacer, 6×CH2 cyanoethyl), 4.38-5.00 (m, 36H, 6×H-1, 6×H-2, 12×CH2 Bn), 5.05 (s, 2H, CH2 Bn spacer), 6.42 (bs, 1H, NH), 7.16-7.41 (m, 65H, Harom), 7.42-7.89 (m, 6H, NHAc). 13C NMR (100 MHz, (CD3)2CO) δ=19.9-20.0 (6×CH2 cyanoethyl), 23.0-23.1 (6×CH3 AcNH), 25.7 (CH2 hexylspacer), 26.8 (CH2 hexylspacer), 29.2-30.2 (6×CH2 C-5a), 30.4 (CH2 hexylspacer), 30.7 (CH2 hexylspacer), 38.2-40.2 (6×CH C-5), 41.3 (CH2 hexylspacer), 51.0-51.4 (6×CH C-2), 62.5-63.4 (6×CH2 C-6), 63.4-63.5 (6×CH2 cyanoethyl), 66.2 (CH2 Bn spacer), 68.7 (CH2 hexylspacer), 72.2-75.6 (12×CH2 Bn), 75.6-75.8 (6×CH C-1), 76.5-77.2 (6×CH C-4), 79.7-79.8 (6×CH C-3), 128.1-129.1 (CHarom), 139.2-140.0 (13×Cq Bn), 170.7-171.2 (6×C═O AcNH). 31P NMR (162 MHz, CD3)2CO) δ=−2.84, −2.77, −2.68, −2.45, −2.42, −2.37, −2.31, −1.94, −1.81, −1.78. HRMS: [C170H207N13O45P6+NH4]+ requires 3356.312, found 3357.010.

In order to prepare the oligomer where n=6, the general deprotection procedure described below may be performed after the above step.

1-O-epta-((2-Acetamido-3,4-di-O-benzyl-2-deoxy-5a-carba-α-D-mannopyranosyl-1-O-phosphoryl)2-cyanoethyl)-6-hexyl-benzyl-carbamate (21)

Alcohol 20 (0.140 g, 0.042 mmol), was coupled to phosphoramidite 9 (0.8 mL 0.1 M in ACN, 0.84 mmol), oxidized, detritylated using the general procedure as described above. The crude was purified by size exclusion chromatography (sephadex LH-20, DCM/MeOH 1:1) leading to product 21 (0.139 g, 0.036 mmol) in 86% yield. 1H NMR (500 MHz, (CD3)2CO) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 28H, 7×5a'-H, 7×AcNH), 2.07-2.30 (m, 14H, 7×5a-H, 7×5-H), 2.82-2.97 (m, 14H, 7×CH2 cyanoethyl), 3.09-3.18 (m, 2H, CH2 hexylspacer), 3.67-4.04 (m, 21H, 7×H-6, 7×H-4), 4.04-4.38 (m, 23H, 7×H-3, CH2 hexylspacer, 7×CH2 cyanoethyl), 4.38-5.00 (m, 42H, 7×H-1, 7×H-2, 14×CH2 Bn), 5.05 (s, 2H, CH2 Bn spacer), 6.42 (bs, 1H, NH), 7.16-7.41 (m, 75H, Harom), 7.42-7.89 (m, 7H, NHAc). 13C NMR (125 MHz, (CD3)2CO) δ=19.9-20.0 (7×CH2 cyanoethyl), 23.0-23.1 (7×CH3 AcNH), 25.7 (CH2 hexylspacer), 26.8 (CH2 hexylspacer), 29.2-30.2 (7×CH2 C-5a), 30.4 (CH2 hexylspacer), 30.7 (CH2 hexylspacer), 38.2-40.2 (7×CH C-5), 41.3 (CH2 hexylspacer), 51.0-51.4 (7×CH C-2), 62.5-63.4 (7×CH2 C-6), 63.4-63.5 (7×CH2 cyanoethyl), 66.2 (CH2 Bn spacer), 68.7 (CH2 hexylspacer), 72.2-75.6 (14×CH2 Bn), 75.6-75.8 (7×CH C-1), 76.5-77.2 (7×CH C-4), 79.7-79.8 (7×CH C-3), 128.1-129.1 (CHarom), 139.2-140.0 (15×Cq Bn), 170.7-171.2 (7×C═O AcNH). 31P NMR (202 MHz, CD3)2CO) δ=−2.84, −2.77, −2.68, −2.45, −2.42, −2.37, −2.31, −1.94, −1.81, −1.78. HRMS: [C196H238N15O52P7+2H]++ requires 1926, 73908, founded 1926, 73908.

1-O-octa-((2-Acetamido-3,4-di-O-benzyl-2-deoxy-5a-carba-α-D-mannopyranosyl-1-O-phosphoryl)2-cyanoethyl)-6-hexyl-benzyl-carbamate (22) n=8

Alcohol 22 (0.105 g, 0.027 mmol), was coupled to phosphoramidite 9 (0.7 mL 0.1 M in ACN, 0.68 mmol), oxidized, detritylated using the general procedure as described above. The crude was purified by size exclusion chromatography (sephadex LH-20, DCM/MeOH 1:1) leading to product 22 (0.103 g, 0.023 mmol) in 87% yield. 1H NMR (500 MHz, (CD3)2CO) δ=1.31-1.46 (m, 4H, 2×CH2 hexylspacer), 1.46-1.57 (m, 2H, CH2 hexylspacer), 1.63-1.74 (m, 2H, CH2 hexylspacer), 1.84-2.02 (m, 32H, 8×5a'-H, 8×AcNH), 2.07-2.30 (m, 16H, 8×5a-H, 8×5-H), 2.82-2.97 (m, 16H, 8×CH2 cyanoethyl), 3.09-3.18 (m, 2H, CH2 hexylspacer), 3.67-4.04 (m, 24H, 8×H-6, 8×H-4), 4.04-4.38 (m, 26H, 8×H-3, CH2 hexylspacer, 8×CH2 cyanoethyl), 4.38-5.00 (m, 48H, 8×H-1, 8×H-2, 16×CH2 Bn), 5.05 (s, 2H, CH2 Bn spacer), 6.42 (bs, 1H, NH), 7.16-7.41 (m, 85H, Harom), 7.42-7.89 (m, 8H, NHAc). 13C NMR (125 MHz, (CD3)2CO) δ=19.9-20.0 (8×CH2 cyanoethyl), 23.0-23.1 (8×CH3 AcNH), 25.7 (CH2 hexylspacer), 26.8 (CH2 hexylspacer), 29.2-30.2 (8×CH2 C-5a), 30.4 (CH2 hexylspacer), 30.7 (CH2 hexylspacer), 38.2-40.2 (8×CH C-5), 41.3 (CH2 hexylspacer), 51.0-51.4 (8×CH C-2), 62.5-63.4 (8×CH2 C-6), 63.4-63.5 (8×CH2 cyanoethyl), 66.2 (CH2 Bn spacer), 68.7 (CH2 hexylspacer), 72.2-75.6 (16×CH2 Bn), 75.6-75.8 (8×CH C-1), 76.5-77.2 (8×CH C-4), 79.7-79.8 (8×CH C-3), 128.1-129.1 (CHarom), 139.2-140.0 (17×Cq Bn), 170.7-171.2 (8×C═O AcNH). 31P NMR (202 MHz, CD3)2CO) δ=−2.84, −2.77, −2.68, −2.45, −2.42, −2.37, −2.31, −1.94, −1.81, −1.78. HRMS: [C222H269N17O59P8+2H]++ requires 2184.33410, found 2184.33410.

General Procedure for Deprotection on a Typical Scale (5-40 μMol)

Starting alcohol was dissolved in NH3 (aqueous solution 30-33%, 1 mL per 10 μmol) and dioxane (until it completely dissolved). The reaction mixture was stirred for 2 hours. The mixture was concentrated in vacuo. 1H NMR and 31P NMR analysis showed a total conversion to the semi-protected intermediate. The crude was dissolved in MilliQ H2O and eluted through a column containing Dowex Na+ cation-exchange resin (type: 50WX4-200, stored on a 0.5 M NaOH in H2O, flushed with MilliQ H2O and MeOH before use). The crude was dissolved in MilliQ H2O (2 mL per 10 µmol). To the reaction mixture was added 4-5 drops of glacial AcOH. The mixture was purged with Ar. To the solution was added a scup of Pd black. The reaction mixture was purged with H2 for a few seconds and stirred under H2 atmosphere for 3 days. To the mixture was added celite. The solution was filtrated and concentrated in vacuo. The crude was purified by size-exclusion chromatography (Toyopearl HW-40). The pure compound was dissolved in MilliQ H2O, eluted through a column containing Dowex Na+ cation-exchange resin (type: 50WX4-200, stored on a 0.5 M NaOH in H2O, flushed with MilliQ H2O and MeOH before use) and lyophilized.

1-O-octa-(2-Acetamido-2-deoxy-5a-carba-α-D-mannopyranosyl-1-O-phosphoryl)-6-hexyl-amine (8) n=8

Alcohol 22 (23.2 µmol) was deprotected using the general procedure described above. The pure oligomer 8 was obtained in 44% yield (25.9 mg, 10.2 µmol). $^1$H NMR (500 MHz, $D_2O$) δ=1.33-1.43 (m, 4H, 2×$CH_2$ hexylspacer), 1.57-1.69 (m, 4H, 2×$CH_2$ hexylspacer), 1.73-2.08 (m, 48H, 8×5a'-H, 8×5a-H, 8×5-H, 8×AcNH), 2.92-3.00 (m, 2H, $CH_2$ hexylspacer), 3.48-3.68 (m, 8H, 8×H-4), 3.68-3.76 (m, 2H, $CH_2$ hexylspacer), 3.81-4.22 (m, 24H, 8×H-3, 8×H-6), 4.25-4.36 (m, 8H, 8×H-1), 4.37-4.53 (m, 8H, 8×H-2). $^{13}$C NMR (126 MHz, $D_2O$) δ=21.9 (8×$CH_3$ AcNH), 24.4 ($CH_2$ hexylspacer), 25.1 ($CH_2$ hexylspacer), 26.6 ($CH_2$ hexylspacer), 28.0 (8×$CH_2$ C-5a), 29.5 ($CH_2$ hexylspacer), 38.6 (8×CH C-5), 39.4 ($CH_2$ hexylspacer), 53.5 (8×CH C-2), 61.9 (8×$CH_2$ C-6), 66.2 ($CH_2$ hexylspacer), 70.1 (8×CH C-1), 70.4 (8×CH C-4), 71.9 (8×CH C-3), 174.7 (8×C═O AcNH). 31P NMR (202 MHz, $D_2O$) δ=0.25, 0.37, 0.41, 0.44, 0.48. HRMS: $[C_{78}H_{145}N_9O_{57}P_8+H]^{++}$ requires 1183.83071, founded 1183.83071.

Production of Randomly Acetylated Carba Oligomers According to the Invention

1. Amine Protection as Boc Derivative

The dried carba-analogues DP6 (n=6), DP7 (n=7) and DP8 (n=8) were solubilized in $H_2O$:dioxane 1:1 v/v, then $NaHCO_3$ (2.95 eq) and $(Boc)_2O$ (1.13 eq) were added at 4° C. The reactions were then kept under magnetic stirring at room temperature overnight, then the products were purified by Sephadex G10 column (Eluent: $H_2O$) and fractions containing the compounds were dried.

2. Random O-Acetylation

The dried Boc protected carba-analogues from step 1 were resuspended in acetonitrile, then acetic anhydride (3.6 eq for each —OH group in the molecule) and imidazole (1.8 eq) were added. The reactions were kept at 40° C. and the acetylation reaction time was extended until the target acetylation % (~75%) was reached (monitoring by $^1$H-NMR). Then the crude acetylated compounds were dried.

For the avoidance of doubt, "random O-acetylation" is intended to mean that there is no ultimate control over which and how many of $R^x$ and $R^y$ are —C(O)$CH_3$. However, using NMR techniques, it is possible to determine the total % O-acetylation in the oligomer.

The oligomer is also indicated herein as Ac-carbaMenA with the corresponding degree of polymerization (DP) of the oligomer, e.g., Ac-CarbaMenA DP8.

3. Boc Deprotection

The dried crude O-acetylated carba-analogues from step 2 were solubilized in $CH_2Cl_2$:TFA 4:1 v/v and the reactions were kept under magnetic stirring at room temperature for 1 h. Then the crude reactions were dried, resolubilized in $H_2O$ and purified by Sephadex G10 column (Eluent: $H_2O$).

NMR Protocol for % Acetylation Determination

The samples were dried under vacuum, reconstituted in 0.6 mL $D_2O$ and transferred to 5 mm NMR tubes. The proton NMR spectra were collected by a standard monodimensional pulseprogram at 400 MHz and 25° C. The acquisition and processing has been conducted by TopSpin Bruker software.

The determination of % O-acetylation in carba-analogues has been done by integrating the peaks of $H_3$+$H_4$ O—Ac (i.e. H of acetate groups) at 5-5.4 ppm and the triplet of the $CH_2$ next to the $NH_2$ of the linker at ~3 ppm, to which is given the value 2. Looking at FIG. 1, by assuming that, if the O-Acetylation is 100%, the integration value of $H_3$+$H_4$ O—Ac must be 12 for DP6 (14 for DP7 and 16 for DP8), the following proportion can be applied:

12:100=9.04:X where X=% Acetylation

Figure 2:
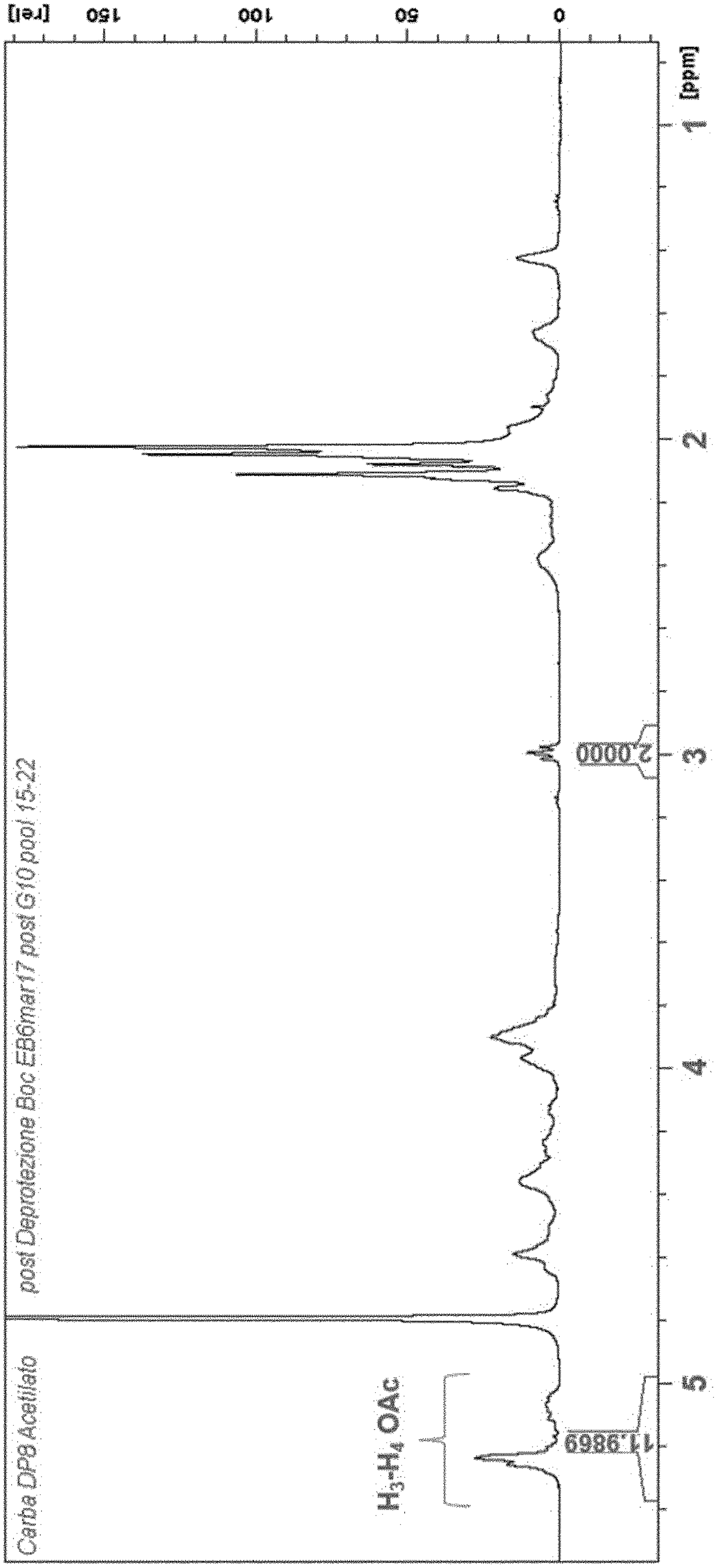
FIG. 2 is a $^1$H-NMR of the final randomly O-acetylated carba-analogue DP8 (i.e. Formula (Ia) where n=8) with integrals for acetylation % determination.

The final products were characterized by $^1$H-NMR to confirm the identity structure and to determine the O-acetylation % of the synthetic sugars (FIG. 2 and Table 1).

FIG. 2 depicts the 1H NMR of the final randomly acetylated carba-analogue, with integrals for % acetylation determination, where n=8.

TABLE 1

| Carba-analogue | Random O-Acetylation degree % (by $^1$H-NMR) |
|---|---|
| DP 6 | 75 |
| DP 7 | 78 |
| DP 8 | 75 |

Figure 3:
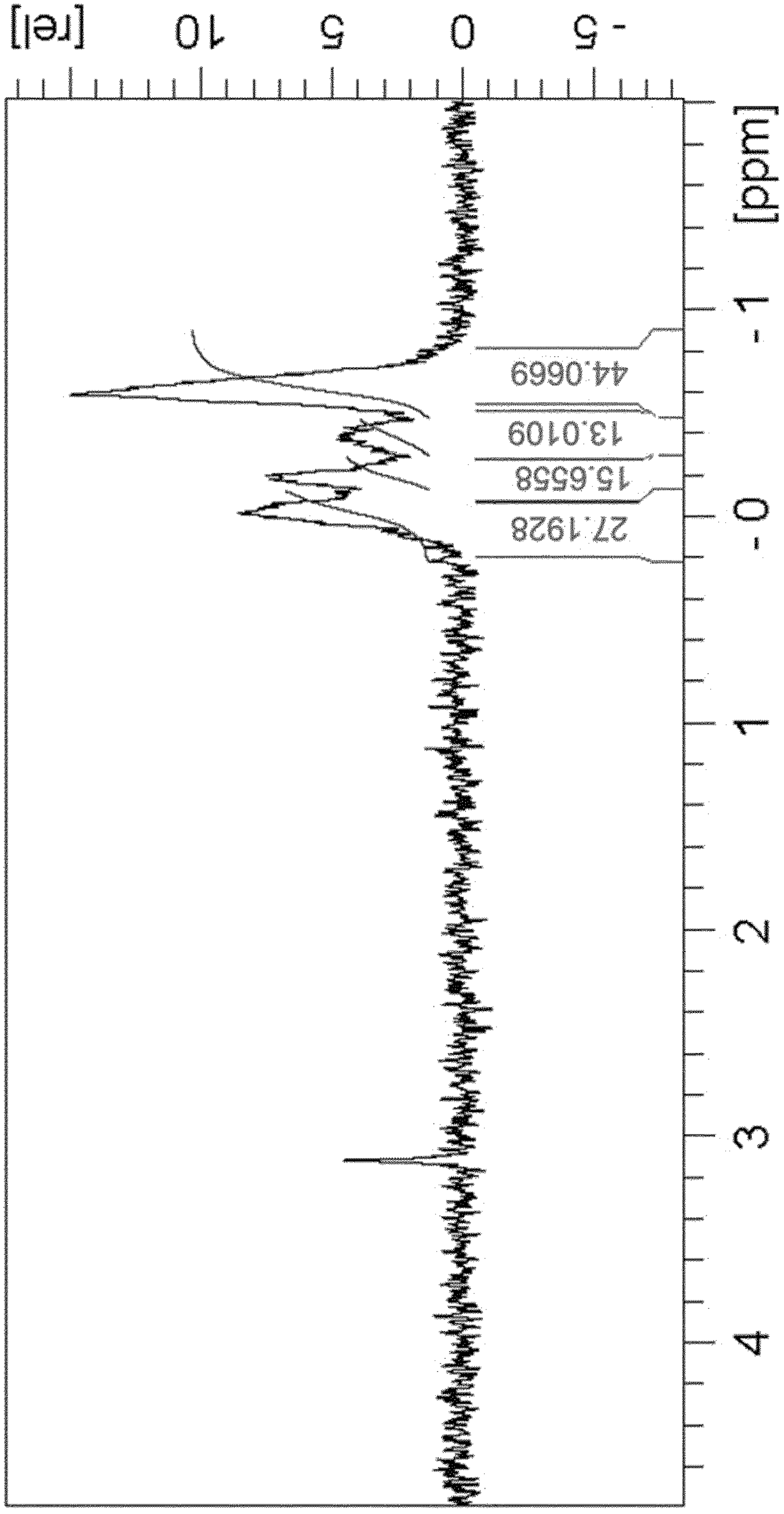
FIG. 3 is a $^{31}$P NMR spectrum of the final randomly O-acetylated carba-analogue DP8 (Formula Ia). The spectrum shows concomitant acetylation occurring to an extent of 44% at position C3+C4, and acetylation at either C3 or C4 to an extent of 28%. 27% of the molecule is non acetylated.

For the same randomly acetylated carba-analogue of Formula (Ia) with n=8 the distribution of the acetyl groups between 3 and 4 positions was determined by $^{31}$P NMR spectroscopy (101 MHz, $D_2O$). The spectrum recorded is depicted in FIG. 3: it shows concomitant acetylation occurring to an extent of 44% at positions C3 and C4 (i.e. $R^x$ and $R^y$ in a same repeat unit of the oligomer are both —C(O)$CH_3$), and acetylation at either C3 or C4 (i.e. $R^x$ is —C(O)$CH_3$ and $R^y$ is H or $R^x$ is H and $R^y$ is —C(O)$CH_3$ in a same repeat unit) to an extent of 28%; and 27% of the repeat units are non-acetylated.

Example 2: Production of Selectively Acetylated Carba Monomer Building Block in Accordance with Scheme 2 (e.g. Where $R^x$ is H and $R^y$ is —C(O)$CH_3$)

D-Glucal (23)

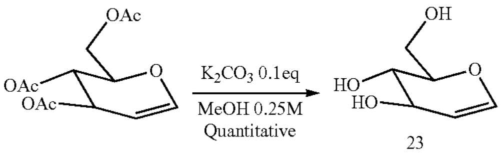 [SMILES: CC(=O)OCC1OC=CC(OC(C)=O)C1OC(C)=O ; OCC1OC=CC(O)C1O]

23

To a mixture of 3,4,6-tri-O-acetyl-D-glucal (10.0 g, 36.7 mmol) was added $K_2CO_3$ (508 mg, 3.67 mmol) in $MeOH_{dry}$ (150 mL) and then stirred under $N_2$ at room temperature. After 1 hour the reaction was completed and quenched with acetic acid to reach a pH of 7. The solvent was evaporated under reduced pressure and the crude product of D-glucal, a transparent oil, was directly involved in the next step.

4,6-O-(4-Methoxybenzylidene)-D-glucal (24)

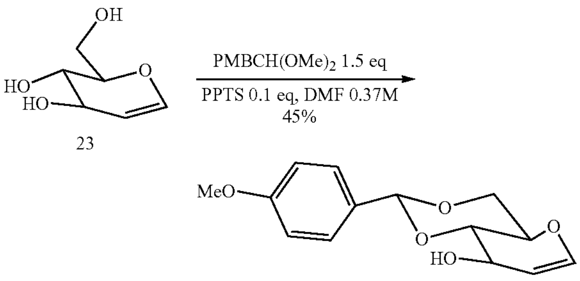

23

24

To the crude compound 23 in dry DMF (100 mL) were added anisaldehyde dimethyl acetal (9.40 mL, 55.1 mmol) and then pyridine p-toluenesulfonate (922 mg, 3.67 mmol) under $N_2$. The reaction was carried at 25-30° C. under vacuum (180 mbar) for 2.5-3 hours, on a rotavapor. The DMF was then evaporated under reduced pressure and the crude product was extracted by 100 mL of DCM. The organic layer was washed successively by 50 mL $NH_4Cl$, 50 mL of distilled water and 50 mL of a brine solution. Finally the gathered aqueous layers was extracted by 50 mL DCM. The mixture was then dried over $Na_2SO_4$ and evaporated under reduced pressure to obtain 4,6-O-(4-Methoxybenzylidene)-D-glucal as a white powder with a yield of 45%.

δ $^1H$ (400 MHz; CDCl3)

7.43 (2H, td, J 8.6, J 4.7, 8-H), 6.90 (2H, dt, J 8.8, J 4.9, 9-H), 6.33 (1H, ddd, J 6.1, J 1.6, J 0.4, 1-H), 5.55 (1H, s, 7-H), 4.76 (1H, dd, J 6.1, J 2.0, 2-H), 4.49 (1H, br d, J 7.3, 3-H), 4.35 (1H, dd, J 10.3, J 5.0, 5-H), 3.93-3.87 (1H, m, 6-H), 3.83-3.79 (1H, m, 6-H), 3.80 (3H, s, —OMe), 3.77-3.75 (1H, m, 4-H), 2.47 (1H, s, —OH).

δ $^{13}C$ (100 MHz; CDCl3)

159.4 (11-C), 143.3 (1-C), 128.6 (8-C), 126.7 (9-C), 112.8 (10-C), 102.7 (2-C), 100.9 (7-C), 79.8 (4-C), 68.9 (5-C), 67.6 (6-C), 65.7 (3-C), 54.4 (OMe).

3-O-Benzyloxy-4,6-O-(4-Methoxybenzylidene)-D-glucal (25)

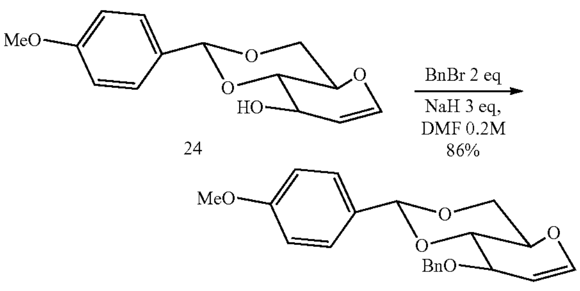

24

25

To a solution of 24 (16.05 g, 60.7 mmol) in DMF (350 mL) at 0° C. was added portionwise Sodium Hydride 60% in mineral oil (7.29 g, 182 mmol)-NaH can be previously washed off its mineral oil with n-Hexane dry 3 times. After 30 minutes stirring at the same temperature, the ice bath was removed. Benzyl Bromide was added (14.4 mL, 121 mmol) and the reaction was stirred overnight, while the temperature was warming up to room temperature. The mixture was then quenched by methanol (20 mL) and the DMF was evaporated under reduced pressure. The organic phase was extracted by 100 mL of EtOAc and then the organic layer was washed with $NH_4Cl$, $NaHCO_3$ and brine (50 mL each). The organic layer was dried over $Na_2SO_4$ and the solvent was evaporated under reduced pressure. The residue was purified by flash column chromatography on silica gel (EtOAc/Hexane=3:7) to afford 3-O-Benzyloxy-4,6-O-(4-Methoxybenzylidene)-D-glucal (18.43 g, 86%) as a white powder.

δ $^1H$ (400 MHz; CDCl3)

7.42 (2H, dt, J 8.5, J 4.6, 8-H), 7.37-7.23 (7H, m, $H_{arom}$), 6.90 (2H, dt, J 8.9, J 4.9, 9-H), 6.34 (1H, dd, J 6.2, J 1.4, 1-H), 5.58 (1H, s, 7-H), 4.81 (1H, dd, J 6.17, J 2.06, 2-H), 4.79 (1H, d, J 12.1, 10-H $CH_2$ Ph), 4.70 (1H, d, J 12.1, 10-H $CH_2$ Ph), 4.36-4.32 (2H, m, 3-H, 6a-H), 4.00 (1H, dd, J 9.8, J 7.4, 6b-H), 3.88 (1H, td, J 10.1, J 4.7, 5-H), 3.81 (1H, t, J 10.1, 4-H), 3.80 (3H, s, —OMe).

δ $^{13}C$ (100 MHz; CDCl3)

160.2 (11-C), 144.5 (1-C), 138.6 (13-C), 129.9 (8-C), 129.9-127.2 ($C_{arom}$ 9, 14, 15, 16-C), 113.7 (10-C), 102.4 (2-C), 101.3 (7-C), 80.1 (5-C), 73.2 (4-C), 72.1 (6-C), 68.8 (3-C), 68.4 (12-C), 55.4 (—OMe).

3-O-Benzyloxy-4-O-(4-Methoxybenzyloxy)-D-glucal (26)

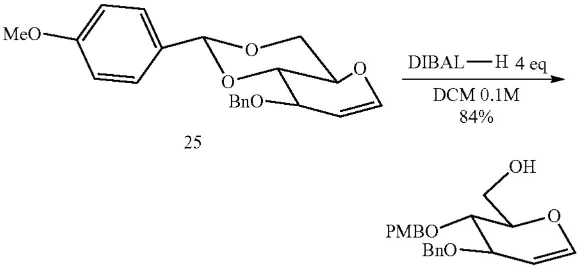

25

26

The glucal 25 (780 mg, 2.20 mmol) was dissolved in DCM (20 mL), cooled at 0° C. and stirred for 20 minutes at RT. DIBAL-H 1 M in hexane (11.0 mL, 11.0 mmol) was then added dropwise at 0° C. The mixture was stirred for 2 h at 0° C. The reaction was quenched by a solution of potassium sodium tartrate tetrahydrate commonly named Rochelle salt in distilled water (1.5 g tartrate in 7.5 mL water) for 20 minutes. The mixture was then extracted by DCM (30 mL) and the organic layer was washed by distilled water twice and brine (40 mL each). The aqueous layers were finally extracted with DCM (20 mL). The organic phases were grouped and dried on $Na_2SO_4$. The solvent was evaporated under reduced pressure. The residue was purified by flash chromatography on silica gel (EtOAc/Hexane=1:3) to afford 3-O-Benzyloxy-4-O-(4-Methoxybenzyloxy)-D-glucal as a white solid yielding 84%

δ $^1H$ (400 MHz; CDCl3)

7.34-7.20 (7H, m, $H_{arom}$), 6.83 (2H, dt, J 8.7, J 4.8, 9-H), 6.34 (1H, dd, J 6.1, J 1.2, 1-H), 4.82 (1H, dd, J 6.1, J 2.6, 2-H), 4.75 (1H, d, J 11.1, 10-H $CH_2$ Ph), 4.63 (1H, d, J 11.1, 10-H $CH_2$ Ph), 4.61 (1H, d, J 11.8, 7-H $CH_2$ Ph(4-OMe)), 4.52 (1H, d, J 11.8, 7-H $CH_2$ Ph(4-OMe)), 4.19 (1H, ddd, J 6.3, J 2.4, J 2.3, 3-H), 3.87 (1H, dt, J 8.8, J 4.2, 5-H), 3.81-3.79 (2H, m, 6-H), 3.77 (1H, dd, J 8.7, J 6.3, 4-H), 3.71 (3H, s, —OMe), 2.65 (1H, s, —OH).

δ $^{13}C$ (100 MHz; CDCl3)

159.2 (11-C), 144.4 (1-C), 138.1 (13-C), 130.1 (8-C), 129.7-127.6 ($C_{arom}$ 9, 14, 15, 16-C), 113.7 (10-C), 100.1 (2-C), 77.5 (5-C), 75.6 (3-C), 74.1 (4-C), 73.3 (12-C), 70.4 (7-C), 61.4 (6-C), 55.1 (—OMe).

1,5-Anhydro-3-O-benzyloxy-4-O-(4-methoxybenzyloxy)-2,6,7-trideoxy-D-arabino-hept-1,6-dienitol (28)

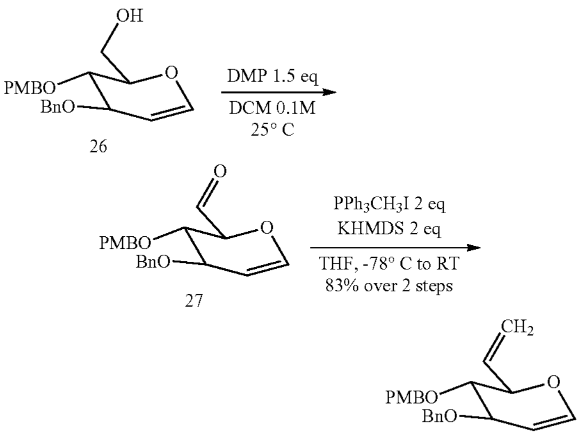

26 27 28

To a solution of the previous alcohol 26 (650 mg, 1.82 mmol) in DCM dry (6.1 mL) was added DMP (926 mg, 2.18 mmol). The mixture was then stirred at room temperature (25° C.) for 1 hour.

Meanwhile, the ylide was prepared with fresh $PPh_3CH_3I$ (1.48 g, 3.65 mmol) in THF dry (12.0 mL) at −78° C. and stirred for 25 minutes. KHMDS (7.3 mL, 3.65 mmol, 0.5M in Toluene) was then added dropwise at −78° C. The mixture was sequentially stirred at −78° C. for 20 min, at 0° C. for 50 min and finally at −78° C. for 30 min to form the ylide.

Besides the oxidation reaction was quenched by a solution of $Na_2S2O_3$ (30 mL) and $NaHCO_3$ (30 mL) for 10 min. Then the aldehyde was worked up with DCM (3*40 mL), dried over $Na_2SO_4$ and the DCM was evaporated under reduced pressure.

The aldehyde in THF dry (11.0 mL) was then added dropwise to the ylide at −78° C. The reaction was stirred overnight. The mixture was worked up with $NH_4Cl$ (20 mL) and DCM (50 mL). Then the organic layer was again extracted with DCM (2*30 mL), washed by NaCl (80 mL) and dried over $Na_2SO_4$. The residue was purified by flash chromatography (nHexane/EtOAc=7:3) to afford the alkene as a yellow oil with a yield of 83% over 2 steps.

δ $^1H$ (400 MHz; CDCl3)

7.37-7.27 (4H, m, $H_{arom}$), 7.24 (2H, dt, J 8.6, J 5.5, 9-H), 6.86 (2H, td, J 8.7, J 5.5, 10-H), 6.41 (1H, dd, J 6.1, J 1.3, 1-H), 6.04 (1H, ddd, J 17.2, J 10.6, J 6.6, 6-H), 5.43 (1H, dt, J 2.9, J 17.3, 7b-H), 5.31 (1H, dt, J 2.6, J 10.6, 7a-H), 4.88 (1H, dd, J 6.2, J 2.7, 2-H), 4.70 (1H, d, J 10.9, 11-H, $CH_2$ Ph), 4.64 (1H, d, J 11.7, 8-H, $CH_2$ Ph(4-OMe)), 4.62 (1H, d, J 10.9, 11-H $CH_2$ Ph), 4.58 (1H, d, J 11.7, 8-H $CH_2$ Ph(4-OMe)), 4.31 (1H, dd, J 7.1, J 8.0, 5-H), 4.19 (1H, ddd, J 6.2, J 2.5, J 1.5, 3-H), 3.79 (3H, s, —OMe), 3.59 (1H, dd, J 8.6, J 6.2, 4-H).

δ $^{13}C$ (100 MHz; CDCl3)

159.4 (12-C), 144.6 (1-C), 138.5 (14-C), 134.5 (6-C), 130.3 (9-C), 129.8-127.8 ($C_{arom}$ 10, 15, 16, 17-C), 118.4 (7-C), 113.9 (11-C), 100.5 (2-C), 78.2 (5-C), 78.0 (4-C), 75.5 (3-C), 73.6 (8-C), 70.8 (13-C), 55.4 (—OMe).

(3R,4R,5R)-4-O-Benzyloxy-3-O-(4-methoxybenzyloxy)-5-(hydroxymethyl)cyclohexene (29)

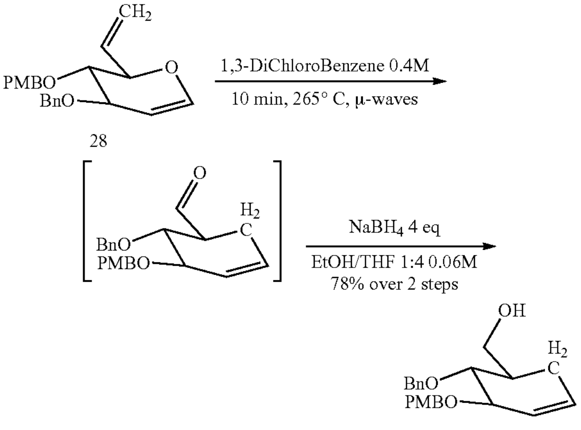

28 29

The alkene 28 (200 mg, 0.57 mmol) was dissolved in m-DCB (1.43 mL, 0.4M) at RT. The Claisen rearrangement was then carried out under micro-waves at 265° C. for 10 min. After consumption of the yellow solution of reactive aldehyde was immediately poured in a mixture of $NaBH_4$ (86 mg, 2.27 mmol) in THF/EtOH (10 mL, 4:1) and stirred for 1 h at RT (monospot on the TLC, orange solution). The reaction was quenched with distilled water (10 mL). The aqueous phase was increased by 10 mL of distilled water and extracted with DCM (3*20 mL). Finally, the organic layers were dried over $Na_2SO_4$. The residue was purified by flash chromatography (nHexane/EtOAc=8:2) to afford the alcohol 7 as a colorless oil with a yield of 78% over 2 steps.

δ $^1H$ (400 MHz; CDCl3)

7.28-7.16 (7H, m, $H_{arom}$), 6.79 (2H, br d, J 8.3, 14-H), 5.67-5.64 (1H, m, 1-H), 5.64-5.59 (1H, m, 2-H), 4.88 (1H, d, J 11.3, 8-H $CH_2$ Ph), 4.64 (1H, d, J 11.3, 8-H $CH_2$ Ph), 4.56 (1H, d, J 11.2, 12-H $CH_2$ Ph(4-OMe)), 4.48 (1H, d, J 11.7, 12-H $CH_2$ Ph(4-OMe)), 4.12 (1H, br d, 4-H), 3.71 (3H, s, —OMe), 3.57-3.47 (3H, m, 3-H, 6-H), 2.35 (1H, s, —OH), 2.07-2.00 (1H, m, 7-H), 1.97-1.88 (1H, m, 5-H), 1.82-1.75 (1H, m, 7-H). δ $^{13}C$ (100 MHz; CDCl3)

δ $^{13}C$ (100 MHz; CDCl3)

159.4 (17-C), 138.5 (9-C), 132.1 (14-C), 130.5-128.0 ($C_{arom}$ 10, 11, 12, 15-C), 127.7 (1-C), 126.1 (2-C), 114.0 (16-C), 82.3 (3-C), 80.9 (4-C), 74.4 (8-C), 71.1 (13-C), 65.9 (6-C), 55.4 (—OMe), 40.7 (5-C), 28.1 (7-C).

4-O-Benzyl-3-O-(4-methoxybenzyloxy)-6-O-thexyldimethylsilyl-5-methylcyclohexene (30)

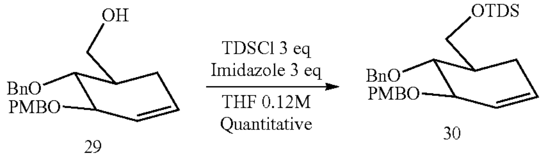

29 30

The alcohol 29 (715 mg, 2.02 mmol) was dissolved in dry THF (17 mL) at RT. Imidazole (125 mg, 1.83 mmol) was added and the mixture was stirred at RT for 5 min and then at 0° C. for 10 min. ThexylDimethylSilylChloride (1.19 mL, 6.05 mmol) was then added dropwise to pay attention to the formation of a white precipitate. Thus the ice bath was removed at the first precipitation and TDSCl remaining was added slowly to the mixture, left warming up to RT and stirring overnight. The reaction was monitored by TLC (Pent/AcOEt 3:1). The organic phase was extracted by EtOAc and then washed with distilled water (5 times). The residue was purified by flash chromatography (nHex/AcOEt 95:5) to allow the formation of compound 30 as a yellow oil with a quantitative yield.

δ $^1$H (400 MHz; CDCl3)

7.37-7.16 (7H, m, $H_{arom}$), 6.88-6.84 (2H, m, 14-H), 5.75 (1H, ddq, J 9.0, J 4.3, J 2.4, 1-H), 5.64 (1H, br d, 2-H), 4.91 (1H, d, J 11.0, 8-H $CH_2$ Ph), 4.68 (1H, d, J 11.0, 8-H $CH_2$ Ph), 4.64 (1H, d, J 11.3, 12-H $CH_2$ Ph(4-OMe)), 4.60 (1H, d, J 11.3, 12-H $CH_2$ Ph(4-OMe)), 4.16 (1H, ddq, J 7.1, J 3.6, J 1.8, 3-H), 3.86 (1H, dd, J 9.8, J 4.8, 6-H), 3.79 (3H, s, —OMe), 3.64 (1H, dd, J 10.0, J 6.6, 4-H), 3.63-3.58 (1H, m, 6-H), 2.28-2.16 (1H, m, 7-H), 2.10 (1H, dt, J 18.4, J 5.3, 7-H), 1.91 (1H, ttd, J 10.5, J 5.1, J 2.7, 5-H), 1.64 (1H, hept, J 6.9, 17-H), 0.90 (6H, d, J 6.9, 18-H), 0.87 (6H, s, 16-H), 0.13 (6H, s, 15-H).

δ $^{13}$C (100 MHz; CDCl3)

159.3 (14-C), 139.3 (9-C), 133.8 (17-C), 131.0-128.0 (Carom 10, 11, 12, 15-C), 127.6 (1-C), 126.3 (2-C), 113.9 (16-C), 81.5 (3-C), 79.7 (4-C), 74.7 (8-C), 71.5 (13-C), 62.6 (6-C), 55.4 (—OMe), 41.4 (5-C), 34.3 (21-C), 28.7 (7-C), 25.3 (19-C), 20.5-20.3 (20-C), 18.8-18.7 (22-C), -3.27--3.46 (18-C).

4-O-Benzyl-3-O-(4-methoxybenzyloxy)-6-O-thexyldimethylsilyl-5a-carba-α-D-glucopyranose (31)

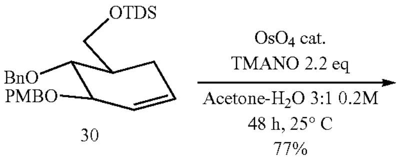

30

31

Compound 30 (230 mg, 0.46 mmol) was dissolved in a mixture of acetone (1.69 mL) and water (562 μL). A solution of $OsO_4$ (537 μL based on a preparation of 250 mg $OsO_4$ in 4.5 mL $H_2O$ and 18 mL acetone) and TMANO (116 mg, 1.02 mmol) were added at RT. The reaction was carried out at 25° C. for 48 h. A saturated aqueous solution of $Na_2S_2O_3$ (2 mL) was added and the mixture was stirred at RT to reduce the $OsO_4$. The organic phase was extracted by $CHCl_3$ (15 mL), washed by brine (10 mL) and finally dried over $Na_2SO_4$. The crude product was purified by flash chromatography (nHex/AcOEt, 8.2) to afford the formation of the diol 31 as a colourless oil with a yield of 77%.

δ $^1$H (400 MHz; CDCl3)

7.37-7.15 (7H, m, $H_{arom}$), 6.87 (2H, br d, J 8.7, 14-H), 4.90 (1H, d, J 12, 8-H $CH_2$ Ph), 4.88 (1H, d, J 8, 12-H $CH_2$ Ph(4-OMe)), 4.69 (1H, d, J 10.9, 8-H $CH_2$ Ph), 4.61 (1H, d, J 11.1, 12-H $CH_2$ Ph(4-OMe)), 4.05 (1H, br d, J 2.7, 1-H), 3.96 (1H, dd, J 10.0, J 3.3, 6-H), 3.78 (3H, s, —OMe), 3.71 (1H, t, J 9.4, 3-H), 3.48 (2H, t, J 10.0, 6-H, 4-H), 3.43 (1H, dd, J 2.3, J 9.4, 2-H), 2.64 (1H, s, —OH), 2.58 (1H, s, —OH), 2.09-2.03 (1H, m, 5-H), 1.77 (1H, dt, J 14.5, J 3.6, 7-H), 1.62 (1H, hept, J 6.9, 17-H), 1.59-1.52 (1H, m, 7-H), 0.88 (6H, d, J 6.9, 18-H), 0.85 (6H, d, d 1.2, 16-H), 0.07 (6H, s, 15-H).

δ $^{13}$C (100 MHz; CDCl3)

159.5 (14-C), 138.9 (9-C), 130.9 (17-C), 129.7-127.7 ($C_{arom}$ 10, 11, 12, 15-C), 114.2 (16-C), 83.4 (3-C), 81.0 (4-C), 75.1 (13-C), 74.9 (8-C), 74.6 (2-C), 68.5 (1-C), 62.1 (6-C), 55.3 (—OMe), 38.9 (5-C), 34.3 (21-C), 30.4 (7-C), 25.2 (19-C), 20.5-20.4 (20-C), 18.8-18.7 (22-C), -3.35--3.56 (18-C).

1-O-Acetyl-4-O-benzyl-3-O-(4-methoxybenzyloxy)-6-O-thexyldimethylsilyl-5a-carba-α-D-glucopyranose (32)

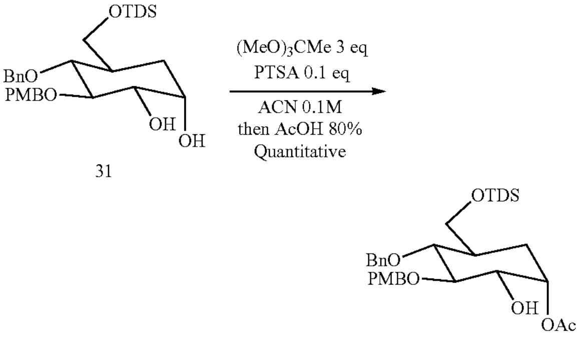

31

32

Compound 31 (155 mg, 0.29 mmol) was dissolved in acetonitrile (2.9 mL) at room temperature, under nitrogen. Trimethyl orthoacetate (115 μL, 0.88 mmol) and PTSA (5 mg, 0.03 mmol) were successively added to the mixture which was then stirred for 60 min at room temperature under nitrogen. After completion of the reaction, a solution of AcOH 80% (2.32 mL AcOH+0.58 mL $H_2O$) was added. The following reaction of acetylation was fully ended in 60 min. The organic phase was extracted with DCM (5 mL) then washed by water (5 mL) and $NaHCO_3$ (5 mL) and finally dried over $Na_2SO_4$. The residue was purified by flash chromatography (nHex/AcOEt) to afford the compound 32 selectively acetylated on the pseudo anomeric position as an uncolored oil in a quantitative yield.

δ $^1$H (400 MHz; CDCl3)

7.39-7.13 (7H, m, $H_{arom}$), 6.87 (2H, dt, J 8.7, J 5.0, 14-H), 5.26 (1H, dd, J 5.7, J 3.0, 1-H), 4.91 (1H, d, J 10.6, 8-H $CH_2$ Ph), 4.90 (1H, d, J 10.9, 12-H $CH_2$ Ph(4-OMe)), 4.70 (1H, d, J 10.0, 8-H $CH_2$ Ph), 4.68 (1H, d, J 10.5, 12-H $CH_2$ Ph(4-OMe)), 3.95 (1H, dd, J 10.0, J 3.5, 6-H), 3.80 (3H, s, —OMe), 3.75 (1H, t, J 9.3, 3-H), 3.58 (1H, br d, J 9.6, 2-H), 3.53 (1H, dd, J 9.1, J 10.1, 4-H), 3.50 (1H, dd, J 9.8, J 2.4, 6-H), 2.28 (1H, s, —OH), 2.08 (3H, s, —OAc), 1.95-1.88 (1H, m, 5-H), 1.85 (1H, dt, J 14.8, J 7.6, 7-H), 1.61 (1H, dt, J 13.8, J 6.9, 7-H), 1.61 (1H, hept, J 6.9, 17-H), 0.88 (6H, d, J 6.8, 18-H), 0.84 (6H, d, J 1.7, 16-H), 0.07 (6H, d, J 4.4, 15-H).

δ $^{13}$C (100 MHz; CDCl3)

170.9 (C(O), —OAc), 159.5 (14-C), 138.7 (9-C), 130.8 (17-C), 129.8-127.9 ($C_{arom}$ 10, 11, 12, 15-C), 114.8 (16-C), 84.0 (3-C), 80.5 (4-C), 75.4 (13-C), 75.3 (8-C), 73.4 (2-C), 71.8 (1-C), 61.8 (6-C), 55.4 (—OMe), 39.6 (5-C), 34.3 (21-C), 28.8 (7-C), 25.3 (19-C), 21.4 ($CH_3$, —OAc), 20.5-20.4 (20-C), 18.8-18.7 (22-C), -3.28--3.53 (18-C).

1-O-Acetyl-2-azido-4-O-benzyloxy-3-O-(4-methoxybenzyloxy)-6-O-thexyldimethylsilyl-5a-carba-α-D-mannopyranose

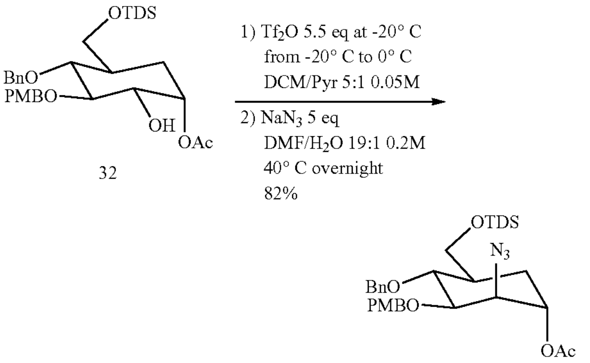

32

Compound 32 (220 mg, 0.38 mmol) was dissolved in a mixture of DCM/Pyridine (5:1, 0.05M) and stirred for 10 min at −10° C. under nitrogen. Triflate anhydride (355 μL, 2.11 mmols) was added dropwise at −10° C. The mixture was sequentially stirred for 30 min to slowly reach 0° C. and another 30 min at 0° C. After completion of the reaction, the organic phase was washed with $NaHCO_3$ and brine. The organic layer was dried over $Na_2SO_4$ and the crude afforded was directly involved in the next step after coevaporation with toluene (3 times). Next, the dry crude was dissolved in DMF/$H_2O$ (19:1, 0.2M) at 40° C. Sodium azide (125 mg, 1.92 mmols) and 15-crown-5 (15.2 μL, 0.08 mmol) were added at room temperature and the reaction was processed overnight at 40° C. After the complete disappearance of the triflate intermediate, the solvent was evaporated and the residue was finally purified by flash chromatography (nHex/EtOAc) to allow the formation of the title compound azide with a yield of 82% as an uncolored oil.

δ $^1$H (400 MHz; CDCl3)

7.38-7.14 (7H, m, Harom), 6.86 (2H, dt, J 8.6, J 4.9, 14-H), 4.98-4.94 (1H, m, 1-H), 4.88 (1H, d, J 10.7, 8-H $CH_2$ Ph), 4.66 (1H, d, J 19.1, 12-H $CH_2$ Ph(4-OMe)), 4.63 (1H, d, J 19.5, 12-H $CH_2$ Ph(4-OMe)), 4.59 (1H, d, J 10.9, 8-H $CH_2$ Ph), 3.87-3.84 (1H, m, 2-H), 3.84 (1H, dd, J 6.3, J 2.7, 6-H), 3.80 (3H, s, —OMe), 3.82-3.75 (2H, m, 4-H, 3-H), 3.52 (1H, dd, J 9.9, J 2.1, 6-H), 2.00 (3H, s, —OAc), 1.91-1.82 (2H, m, 5-H, 7-H), 1.65-1.57 (2H, m, 7-H, 17-H), 0.89 (6H, d, J 6.9, 18-H), 0.85 (6H, d, J 1.2, 16-H), 0.07 (6H, d, J 4.1, 15-H).

δ $^{13}$C (100 MHz; CDCl3)

169.8 (C(O), —OAc), 159.6 (14-C), 138.9 (9-C), 130.2 (17-C), 129.8-127.8 ($C_{arom}$ 10, 11, 12, 15-C), 114.0 (16-C), 81.1 (4-C), 77.0 (3-C), 75.4 (8-C), 72.9 (13-C), 70.6 (1-C), 62.2 (6-C), 61.4 (2-C), 55.4 (—OMe), 39.8 (5-C), 34.4 (21-C), 27.1 (7-C), 25.3 (19-C), 21.2 ($CH_3$, —OAc), 20.6-20.5 (20-C), 18.8-18.7 (22-C), -3.35--3.52 (18-C).

1-O-Acetyl-2-acetamide-4-O-benzyloxy-3-O-(4-methoxybenzyloxy)-6-O-thexyldimethylsilyl-5a-carba-α-D-mannopyranose (33)

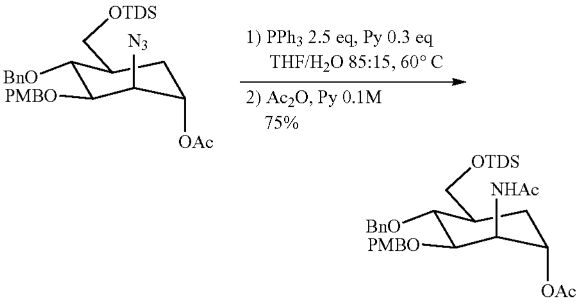

33

To a mixture of the azide as shown (334 mg, 0.56 mmol), $PPh_3$ (366 mg, 1.40 mmols) and a catalytic amount of pyridine (13.6 μL, 0.17 mmol) was added in THF/$H_2O$ (85:15, 0.14M) and stirred at 60° C. for 24 h. After disappearance of the starting material, the generated amine was dried off the solvent and then dissolved in Pyridine (5.6 mL). Acetic anhydride (1.06 mL, 11.2 mmols) was added and the solution was again stirred 24 h. The crude material was purified by flash chromatography (nHex/AcOEt), providing the acetamide 33 as a yellow oil in 75% yield.

δ $^1$H (400 MHz; CDCl3)

7.39-7.28 (5H, m, $H_{arom}$), 7.19 (2H, dt, J 9.4, J 4.6, 13-H), 6.86 (2H, dt, J 9.4, J 4.8, 14-H), 5.59 (1H, d, J 8.1, NHAc), 5.12 (1H, td, J 7.2, J 3.9, 1-H), 4.71 (1H, d, J 11.3, 8-H $CH_2$ Ph), 4.56 (1H, d, J 11.3, 8-H $CH_2$ Ph), 4.50 (1H, d, J 11.2, 12-H $CH_2$ Ph(4-OMe)), 4.42 (1H, td, J 7.7, J 4.1, 2-H), 4.36 (1H, d, J 11.2, 12-H $CH_2$ Ph(4-OMe)), 3.84 (1H, dd, J 2.4, J 4.0, 3-H), 3.85-3.82 (1H, m, 6-H), 3.80 (3H, s, —OMe), 3.72 (1H, t, J 6.3, 4-H), 3.60 (1H, dd, J 9.9, J 5.5, 6-H), 2.09-2.02 (1H, m, 5-H), 2.01 (3H, s, —OAc), 1.90 (3H, s, —NHAc), 1.82 (2H, tdd, J 14.2, J 7.4, J 4.6, 7-H), 1.66-1.57 (1H, hept, J 6.9, 17-H), 0.89 (6H, d, J 6.9, 18-H), 0.84 (6H, s, 16-H), 0.08 (6H, d, J 6.2, 15-H).

δ $^{13}$C (100 MHz; CDCl3)

170.7 (C(O), —NHAc), 170.1 (C(O), —OAc), 159.6 (14-C), 138.6 (9-C), 130.0 (15-C), 129.9 (17-C), 128.6-127.8 ($C_{arom}$ 10, 11, 12-C), 114.1 (16-C), 78.7 (3-C), 74.4 (4-C), 73.6 (8-C), 71.9 (13-C), 69.6 (1-C), 62.5 (6-C), 55.4 (—OMe), 50.6 (2-C), 39.9 (5-C), 34.4 (21-C), 27.1 (7-C), 25.2 (19-C), 23.5 (CH3, —NHAc), 21.3 (CH3, —OAc), 20.5 (20-C), 18.8 (22-C), -3.37--3.48 (18-C).

1-O-terbutylsilyl-2-acetamide-4-O-benzyl-2-deoxy-3-O-(4-methoxybenzyloxy)-6-O-thexyldimethylsilyl-5a-carba-α-D-mannopyranose (35)

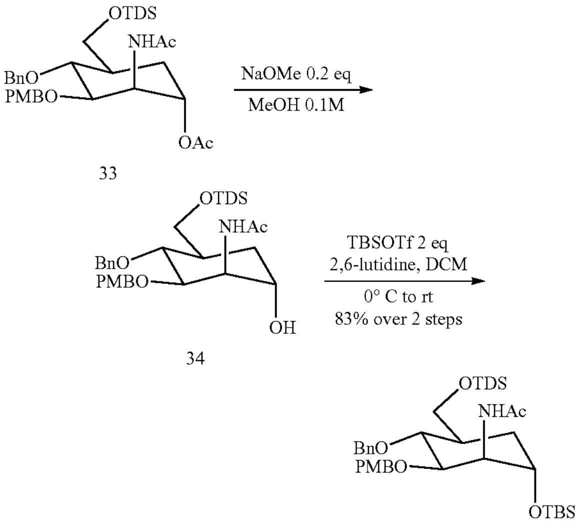

33 34 35

Compound 33 (582 mg, 0.95 mmol) was dissolved in MeOH (9.5 mL). To the mixture was added NaOMe (11 mg, 0.2 mmol). The reaction was stirred for 3 h at RT. Amberlite $H^+$ ion exchange resin was added until neutral pH was reached. The suspension was filtered and concentrated in vacuo. The crude was coevaporated 3 times with Toluene.

Under a flow of $N_2$ gas, the flask was charged with a solution of 34 (0.95 mmol) in DCM (4 mL). At 0° C., added was 2,6-lutidine (2.37 mmol) followed by TBSOTf (437 µL, 1.9 mmols) in a dropwise fashion. The mixture was stirred allowing to warm up to room temperature. After its completion, the reaction was cooled to RT, quenched with MeOH and the mixture was diluted with chloroform. The mixture was washed with 10% aq. $CuSO_4$ solution (2×), $H_2O$ and brine, dried over $Na_2SO_4$, filtered and concentrated in vacuo. Purification by column chromatography (nHex/EtOAc) furnished the title compound 35 as an orange oil in 83% yield over 2 steps.

J. D. C. Codée et al., J. Org. Chem, 2017, 82, 2, 848-868.

δ $^{1}$H (400 MHz; CDCl3)

7.41-7.24 (5H, m, $H_{arom}$), 7.19 (2H, dt, J 9.5, J 4.6, 13-H), 6.86 (2H, dt, J 9.4, J 4.8, 14-H), 5.57 (1H, d, J 5.7, NHAc), 4.93 (1H, d, J 10.6, 8-H $CH_2$ Ph), 4.58 (1H, d, J 10.5, 8-H $CH_2$ Ph), 4.56 (1H, d, J 11.1, 12-H $CH_2$ Ph(4-OMe)), 4.48 (1H, d, J 11.1, 12-H $CH_2$ Ph(4-OMe)), 4.27 (1H, dd, J 5.2, J 2.3, 2-H), 4.25-4.21 (1H, m, 1-H), 4.03 (1H, dd, J 9.6, J 4.5, 3-H), 3.97 (1H, dd, J 9.7, J 3.6, 6-H), 3.81 (3H, s, —OMe), 3.54 (1H, t, J 9.9, 4-H), 3.48 (1H, dd, J 9.7, J 2.2, 6-H), 2.09-2.02 (1H, m, 5-H), 2.01 (3H, s, —NHAc), 1.78-1.69 (1H, m, 7-H), 1.69-1.59 (1H, m, 17-H), 1.52-1.45 (1H, m, 7-H), 0.93 (6H, d, J 6.9, 18-H), 0.87 (6H, s, 16-H), 0.86 (6H, s, 20-H), 0.84 (6H, s, 16-H), 0.12 (6H, d, J 12.0, 19-H), 0.09 (6H, d, J 9.4, 15-H).

δ $^{13}$C (100 MHz; CDCl3)

170.7 (C(O), —NHAc), 159.5 (14-C), 139.1 (9-C), 130.2 (17-C), 130.0 (15-C), 128.6-127.7 ($C_{arom}$ 10, 11, 12-C), 114.0 (16-C), 78.5 (3-C), 77.6 (4-C), 75.5 (8-C), 71.4 (13-C), 67.7 (2-C), 62.6 (6-C), 55.4 (—OMe), 53.4 (1-C), 38.6 (5-C), 34.6 (21-C), 30.4 (7-C), 25.9 (25-C), 25.2 (19-C), 23.6 ($CH_3$—NHAc), 20.7-20.6 (20-C), 18.9-18.8 (22-C), 18.0 (24-C), −3.37–−3.58 (18-C), −4.82–−4.92 (23-C).

1-O-tertbutylsylil-2-acetamide-4-O-benzyloxy-3-O-(4-methoxybenzyoxy)-6-O-thexyldimethylsilyl-5a-carba-α-D-mannopyranose

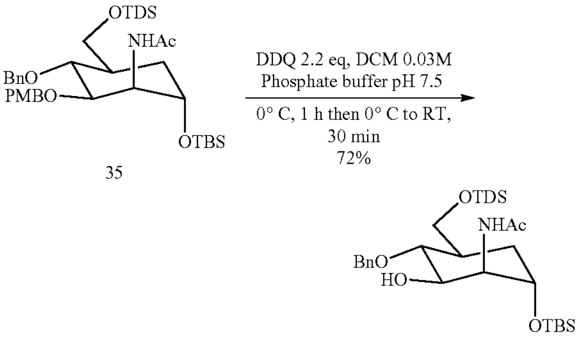

35

To a cooled (0° C.) solution of 14 (71 mg, 0.10 mmol) in DCM (3.4 mL) a freshly prepared phosphate buffer (362 µL, pH 7.5, 10 mM) was added. Freshly prepared DDQ (50.0 mg, 0.22 mmol) was added over 1 h in small portions, after which the mixture was allowed to warm up to RT and was stirred for 30 min. The mixture was diluted with $NaHCO_3$ and the aqueous layer was extracted with DCM twice. The combined organic layers were dried over $Na_2SO_4$ and concentrated in vacuo. Purification by column chromatography (nHex/EtOAc) afforded the compound 15 as an orange solid yielding 72%.

Dan Van Der Es, Thesis, 2016, Universiteit Leiden, pp 160.

δ $^{1}$H (400 MHz; CDCl3)

7.41-7.27 (5H, m, $H_{arom}$), 5.52 (1H, d, J 5.4, NHAc), 4.73 (2H, s, 8-H $CH_2$ Ph), 4.26 (1H, br d, J 2.7, 1-H), 4.16 (1H, dt, J 9.0, J 3.8, 3-H), 4.06 (1H, dd, J 9.0, J 4.5, 2-H), 3.94 (1H, dd, J 9.9, J 3.7, 6-H), 3.53 (1H, dd, J 10.0, J 2.1, 6-H), 3.46 (1H, t, J 9.5, 4-H), 2.73 (1H, s, —OH), 2.10-2.03 (1H, m, 5-H), 2.00 (3H, s, —NHAc), 1.81-1.69 (1H, m, 7-H), 1.69-1.59 (1H, m, 14-H), 1.51 (1H, dt, J 13.7, J 3.2, 7-H), 0.93 (6H, d, J 6.9, 15-H), 0.88 (6H, s, 17-H), 0.87 (6H, s, 13-H), 0.14-0.04 (12H, m, 16-H, 12-H).

δ $^{13}$C (100 MHz; CDCl3)

170.1 (C(O), —NHAc), 138.8 (9-C), 128.7-127.7 ($C_{arom}$ 10, 11, 12-C), 79.6 (4-C), 74.8 (8-C), 70.7 (3-C), 67.6 (1-C), 62.9 (6-C), 56.5 (2-C), 38.5 (5-C), 34.6 (16-C), 31.2 (7-C), 25.9 (20-C), 25.3 (14-C), 23.6 (CH3, —NHAc), 20.7-20.6 (15-C), 18.9-18.8 (17-C), 18.0 (19-C), −3.37–−3.53 (13-C), −4.80–−4.90 (18-C).

1-O-tertbutylsylil-2-acetamide-4-O-benzyloxy-6-O-thexyldimethylsilyl-5a-carba-α-D-mannopyranose (36)

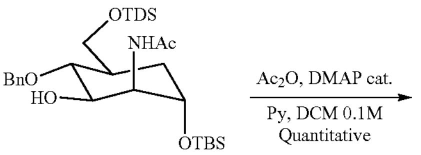

-continued

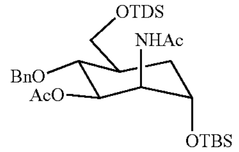

36

Alcohol as shown (180 mg, 0.32 mmol) was dissolved in dry DCM (3.2 mL) at RT under nitrogen. Pyridine (257 µL, 3.18 mmols), acetic anhydride (601 µL, 6.36 mmols) and a catalytic amount of DMAP (7.8 mg, 0.06 mmol) were successively added and the mixture was stirred until the reaction was over. The solution was quenched with MeOH and then concentrated under reduced pressure. Purification by flash chromatography (nHex/EtOAc) allowed the formation of compound 36 as a yellow oil in a quantitative yield.

δ $^{1}H$ (400 MHz; CDCl3)

7.37-7.13 (5H, m, $H_{arom}$), 5.44 (1H, dd, J 10.3, J 4.5, 3-H), 5.27 (1H, d, J 7.4, NHAc), 4.70 (2H, d, J 10.9, 8-H $CH_2$ Ph), 4.61 (1H, d, J 10.9, 8-H $CH_2$ Ph), 4.31 (1H, dt, J 7.3, J 3.8, 2-H), 4.10 (1H, br d, J 2.7, 1-H), 3.97 (1H, dd, J 9.8, J 3.2, 6-H), 3.61 (1H, t, J 10.3, 4-H), 3.46 (1H, dd, J 9.8, J 2.0, 6-H), 2.18-2.11 (1H, m, 5-H), 2.00 (3H, s, —NHAc), 1.98 (3H, s, —OAc), 1.79-1.70 (1H, m, 7-H), 1.70-1.61 (1H, m, 14-H), 1.52 (1H, dt, J 14.3, J 2.8, 7-H), 0.95 (6H, d, J 6.9, 15-H), 0.90 (6H, s, 17-H), 0.88 (6H, s, 13-H), 0.13 (6H, d, J 15.1, 16-H), 0.09 (6H, d, J 14.8, 12-H).

δ $^{13}C$ (100 MHz; CDCl3)

170.0 (C(O), —NHAc), 169.8 (C(O), —OAc), 138.7 (9-C), 128.6-127.6 ($C_{arom}$ 10, 11, 12-C), 76.2 (4-C), 75.1 (8-C), 73.2 (3-C), 68.1 (1-C), 62.3 (6-C), 54.0 (2-C), 38.7 (5-C), 34.6 (16-C), 30.6 (7-C), 25.8 (20-C), 25.3 (14-C), 23.6 (CH3, —NHAc), 21.2 (CH3, —OAc), 20.7-20.6 (15-C), 19.0-18.9 (17-C), 18.1 (19-C), -3.41--3.62 (13-C), -4.90--4.99 (18-C).

2-acetamide-4-O-benzyloxy-5a-carba-α-D-mannopyranose (37)

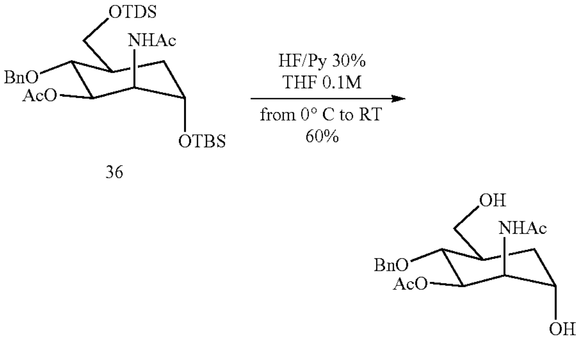

36

37

Compound 36 (120 mg, 0.20 mmol) was dissolved in dry THF (2.0 mL) at 0° C. A solution of HF/Py 30% (420 µL) was added dropwise and the reaction was left stirring overnight, slowly warming up from 0° C. to RT. The mixture was then quenched with $NaHCO_3$ (3 mL). The organic layer was extracted with EtOAc twice, washed with brine and dried over $Na_2SO_4$. The crude compound 37 afforded was filtrated on silica to provide a white solid in 60% yield.

δ $^{1}H$ (400 MHz; $CD_3OD$)

7.37-7.26 (5H, m, $H_{arom}$), 5.33 (1H, dd, J 8.4, J 4.4, 3-H), 4.72 (2H, d, J 11.4, 8-H $CH_2$ Ph), 4.66 (1H, d, J 11.4, 8-H $CH_2$ Ph), 4.45 (1H, t, J 4.8, 2-H), 4.10 (1H, br d, J 2.7, 1-H), 3.87 (1H, q, J 4.5, 1-H), 3.78-3.73 (2H, m, 4-H, 6-H), 3.68 (1H, dd, J 10.6, J 4.2, 6-H), 2.17-2.09 (1H, m, 5-H), 2.04 (1H, s, —OH), 2.03 (1H, s —OH), 2.02 (3H, s, —NHAc), 1.98 (3H, s, —OAc), 1.83 (2H, dd, J 7.8, J 3.8, 7-H).

δ $^{13}C$ (100 MHz; CDCl3)

173.6 (C(O), —NHAc), 172.0 (C(O), —OAc), 140.0 (9-C), 129.3-128.6 (Carom 10, 11, 12-C), 77.2 (4-C), 74.9 (8-C), 74.7 (3-C), 68.2 (1-C), 63.1 (6-C), 54.0 (2-C), 40.7 (5-C), 30.9 (7-C), 22.5 (CH3, —NHAc), 21.1 (CH3, —OAc).

2-acetamide-4-O-benzyloxy-6-O-dimethoxytrityl-5a-carba-α-D-mannopyranose (38)

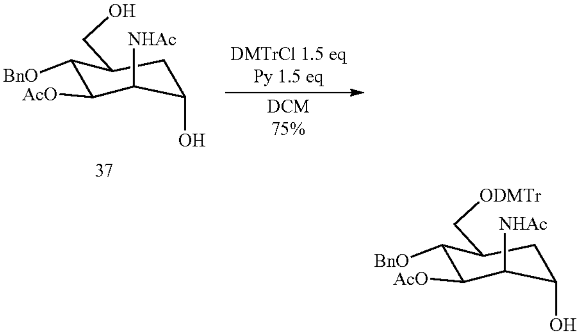

37

38

Compound 37 (15 mg, 42.7 µmol) was dissolved in dry DCM under nitrogen at RT. Pyridine dry (5.2 µL, 64.0 µmol) and DMTrCl (217 mg, 64.0 µmol) were successively added and the mixture was then stirred 3 h at RT. To the reaction was then added $H_2O$. The organic layer was washed once with brine and dried over $Na_2SO_4$ and concentrated in vacuo. Purification by flash chromatography (nHex/AcOEt, 0.1% TEA) furnished compound 38 as a white solid in 74% yield.

δ $^{1}H$ (400 MHz; $CD_3OD$)

7.40-7.05 (14H, m, $H_{arom}$), 6.79 (4H, dd, J 8.9, J 1.7, 13-H), 5.24 (1H, dd, J 7.9, J 4.3, 3-H), 4.53 (1H, d, J 11.3, 8-H $CH_2$ Ph), 4.38 (1H, t, J 4.8, 2-H), 4.31 (1H, d, J 11.3, 8-H $CH_2$ Ph), 3.79 (1H, q, J 5.2, 1-H), 3.72 (3H, s, —OMe), 3.72 (3H, s, —OMe), 3.61 (1H, t, J 8.1, 4-H), 3.34-3.26 (1H, m, 6-H), 3.05 (1H, t, J 8.3, 6-H), 2.34-2.24 (1H, m, 5-H), 2.08-1.98 (1H, m, 7-H), 1.95 (3H, s, —NHAc), 1.86 (3H, s, —OAc), 1.85-1.79 (1H, m, 7-H).

δ $^{13}C$ (100 MHz; $CD_3OD$)

173.6 (C(O), —NHAc), 172.0 (C(O), —OAc), 160.0 (17-C), 146.7 (9-C), 137.6 (14-C), 137.5 (14-C), 137.3 (9-C), 131.4 (18-C), 129.9-126.3 (Carom 10, 11, 12, 15, 19, 20, 21-C), 114.0 (16-C), 87.2 (13-C), 77.3 (4-C), 74.5 (3-C), 74.4 (8-C), 68.0 (1-C), 65.0 (6-C), 55.7 (—OMe), 54.1 (2-C), 39.2 (5-C), 31.9 (7-C), 22.5 (CH3, —NHAc), 21.1 (CH3, —OAc).

Example 3 (Reference Example): Preparation of Oligomer Conjugate without Acetylation—CRM-MenA DP6 (No OAC) and CRM-MenA DP8 (No OAc)

The starting oligomers (DP6 and DP8) were vacuum dried, solubilized in 1:9 $H_2O$:DMSO solution to a final amino group concentration of 40 mmol/mL, and reacted with a 12-fold molar excess of di-N-hydroxysuccinimidyl adipate linker (SIDEA), in the presence of 5-fold molar excess triethylamine as compared with amino groups. The reaction was kept under gentle stirring at room temperature for 3 h. The activated oligosaccharides were purified by precipitation with 4 volumes of ethyl acetate followed by ten washes of the pellet with 1 mL of the same solvent. Finally, the pellet was dried under vacuum, and the content of introduced N-hydroxysuccinimide ester groups was determined.

Conjugates have been prepared in 50 mM NaH2PO4 pH 7 using an active ester (AE):protein molar ratio of 40:1, carried over night at room temperature with gentle stirring. The conjugates were purified by tangential flow filtration (Vivaspin) using a cut-off of 30 kDa and using PBS pH 7.2 as buffer. Conjugates were characterized by SDS-page, by micro BCA (Smith, P. K., et al. (1985) Measurement of protein using bicinchoninic acid. Anal Biochem 150:76-85) for total protein content and by MALDI analysis for total saccharide content. As shown in Table 2 below, a saccharide/protein molar ratio of 16.9 and 10.4 was determined by MALDI TOF MS for the two conjugates from carba DP6 and DP8, respectively.

TABLE 2

| Conjugate | Saccharide/Protein w/w (mg/mL) | Saccharide/Protein mol/mol |
|---|---|---|
| (avDP15) MenA-$CRM_{197}$ | 0.53 | 6.3 |
| Carba DP6-$CRM_{197}$ | 0.63 | 16.9 |
| Carba DP8-$CRM_{197}$ | 0.50 | 10.5 |

Sodium Dodecyl Sulfate-Polyacrilammide gel electrophoresis (SDS-Page). SDS-Page has been performed on pre-casted 3-8% polyacrylamide gels (NuPAGE® Invitrogen). The electrophoretic runs have been performed in Tris-Acetate SDS running buffer (NuPAGE® Invitrogen) loading 5 μg of protein for each sample, using the electrophoretic chamber with a voltage of 150V for about 40 minutes. Samples were prepared by adding 3 μl of NuPAGE® LDS sample buffer. After electrophoretic running, the gel has been washed in $H_2O$ for 3 times and then dye with comassie.

Example 4: Preparation of Oligomer Conjugate of the Invention According to Formula (IIa)

The randomly O-acetylated carba-analogues were activated with di-N-hydroxysuccinimidyl adipate linker (SIDEA) and the % of activation obtained for the oligosaccharides was estimated to be 56% for DP6OAc, 79% for DP7OAc and 84% for DP8OAc.

Figure 4:
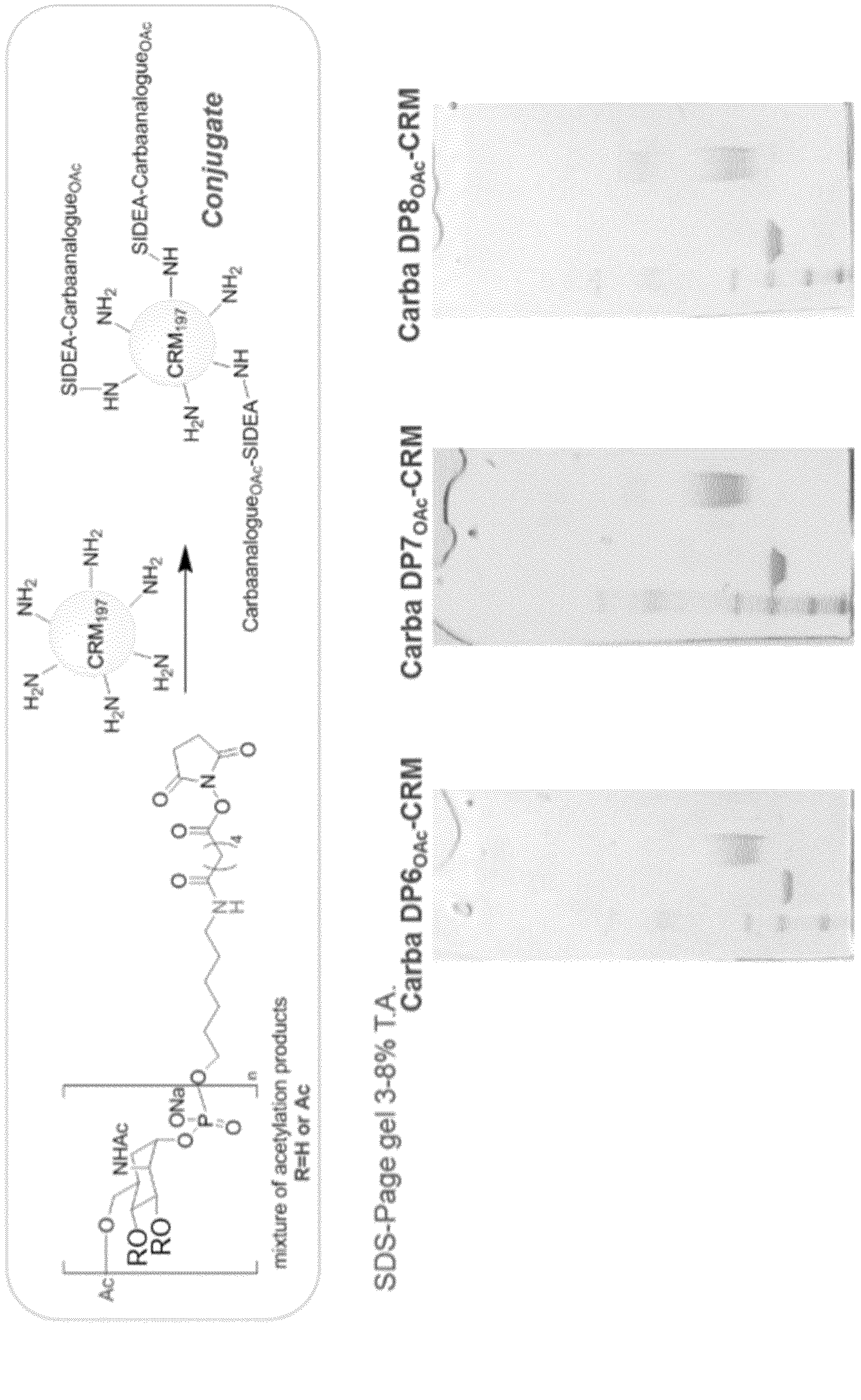
FIG. 4 depicts a conjugation scheme of an oligomer according to the invention with $CRM_{197}$ and SDS-page characterization of the crude reaction.

The activated oligosaccharides (i.e. the activated O-acetylated carba-analogues) were lyophilized to be ready for the conjugation step. Conjugates were obtained by applying the chemistry reported in FIG. 4 and in the same figure there is shown the SDS-page characterization, where the smear of the conjugates can be observed.

Purified glycoconjugates (i.e. those including the O-acetylated carba-analogues) were characterized in terms of protein content by MicroBCA (Smith, P. K., et al. (1985) Measurement of protein using bicinchoninic acid. Anal Biochem 150:76-85) and saccharide content by HPAEC-PAD, as shown in Table 3.

TABLE 3

| | sacc/prot w/w | Saccharide/Protein mol/mol |
|---|---|---|
| Carba DP6 OAc - $CRM_{197}$ | 0.25 | 6.6 |
| Carba DP7 OAc - $CRM_{197}$ | 0.27 | 6.2 |
| Carba DP8 OAc - $CRM_{197}$ | 0.13 | 2.5 |

Example 5: In Vitro Selection of Oligomer Length

An important prerequisite for the immunogenicity of the carba-analogues is their ability to mimic the natural MenA CPS. To investigate this property in vitro, binding of oligomers with the different length to a bactericidal anti-MenA mAb (JW-A1) in comparison to CPS and a medium length oligomer with avDP ~15 was tested as described in Giuntini, S. et al., *PLoS One,* 2012, 7, e34272; Tsang, R. S. et al., *Clin. Diagn. Lab. Immunol.,* 2005, 12, 152-156; and Reyes, F. et al., *Biologicals,* 2013, 41, 275-278.

Figure 5A:
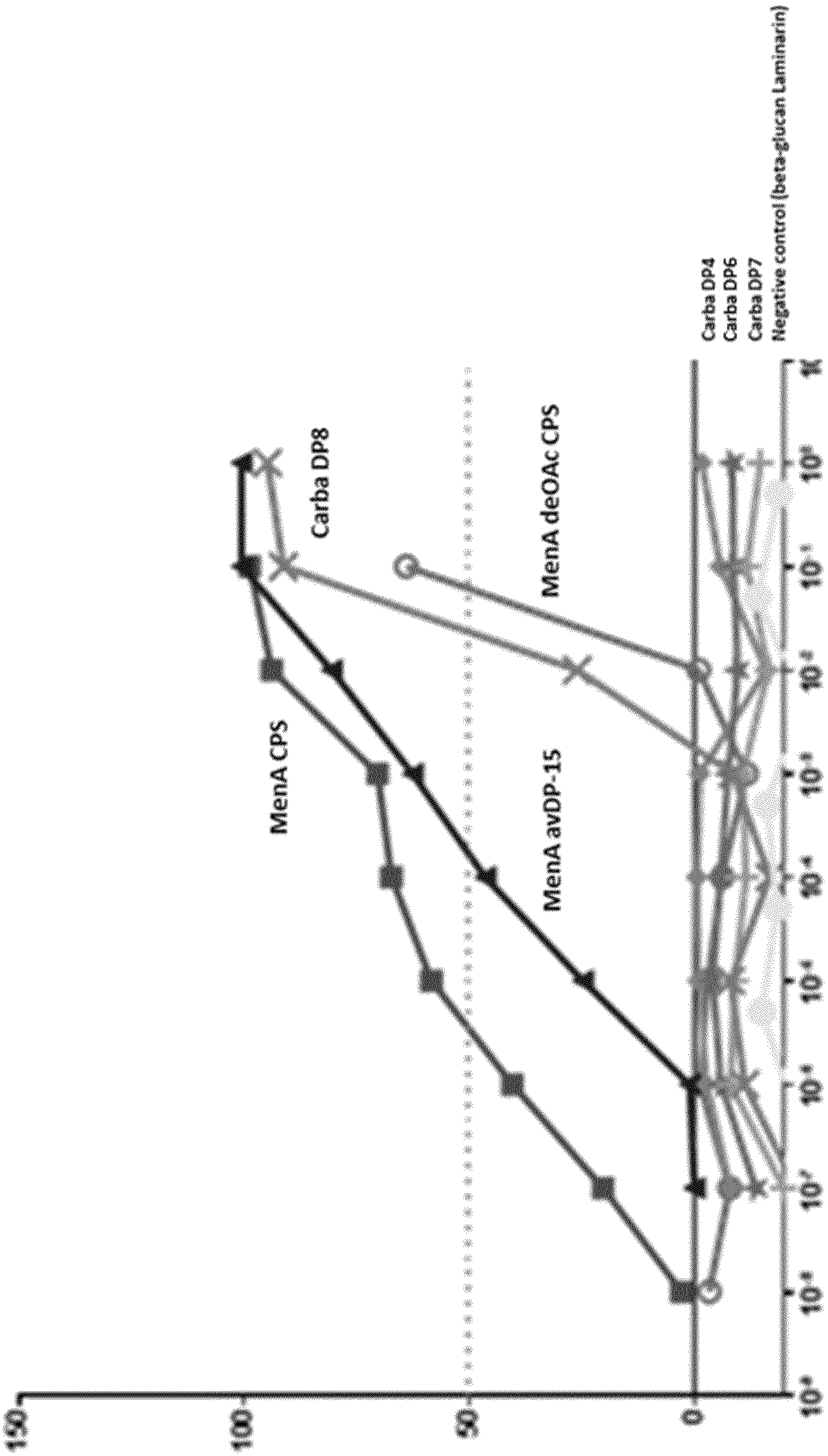
FIG. 5 shows inhibition of the binding of anti-MenA antibodies to CPS. Competitive ELISA with anti-MenA mAb (FIG. 5A), anti-MenA polyclonal serum (FIG. 5B) using different length non-acetylated carbaMenA oligomers as inhibitors and CPS as coating.
(FIG. 5C) Competitive SPR of binding between anti-MenA mAb and immobilized biotylinated CPS. MenA CPS and deOAc CPS were the positive controls and the beta-glucan Laminarin was the negative control in A and B. MenA CPS and fragments thereof were used as positive controls and anti-MenC mAb was flown on the chip as negative control in C.

Remarkably, as shown in FIG. 5A, while DPs from 4 to 7 did not recognize the mAb, binding was observed with DP8, although with 4 orders of magnitude higher $IC_{50}$ compared to the native CPS. De-O-acetylation of MenA CPS led to diminished recognition, signifying the specificity of the mAb for acetylated epitopes.

Figure 5B:
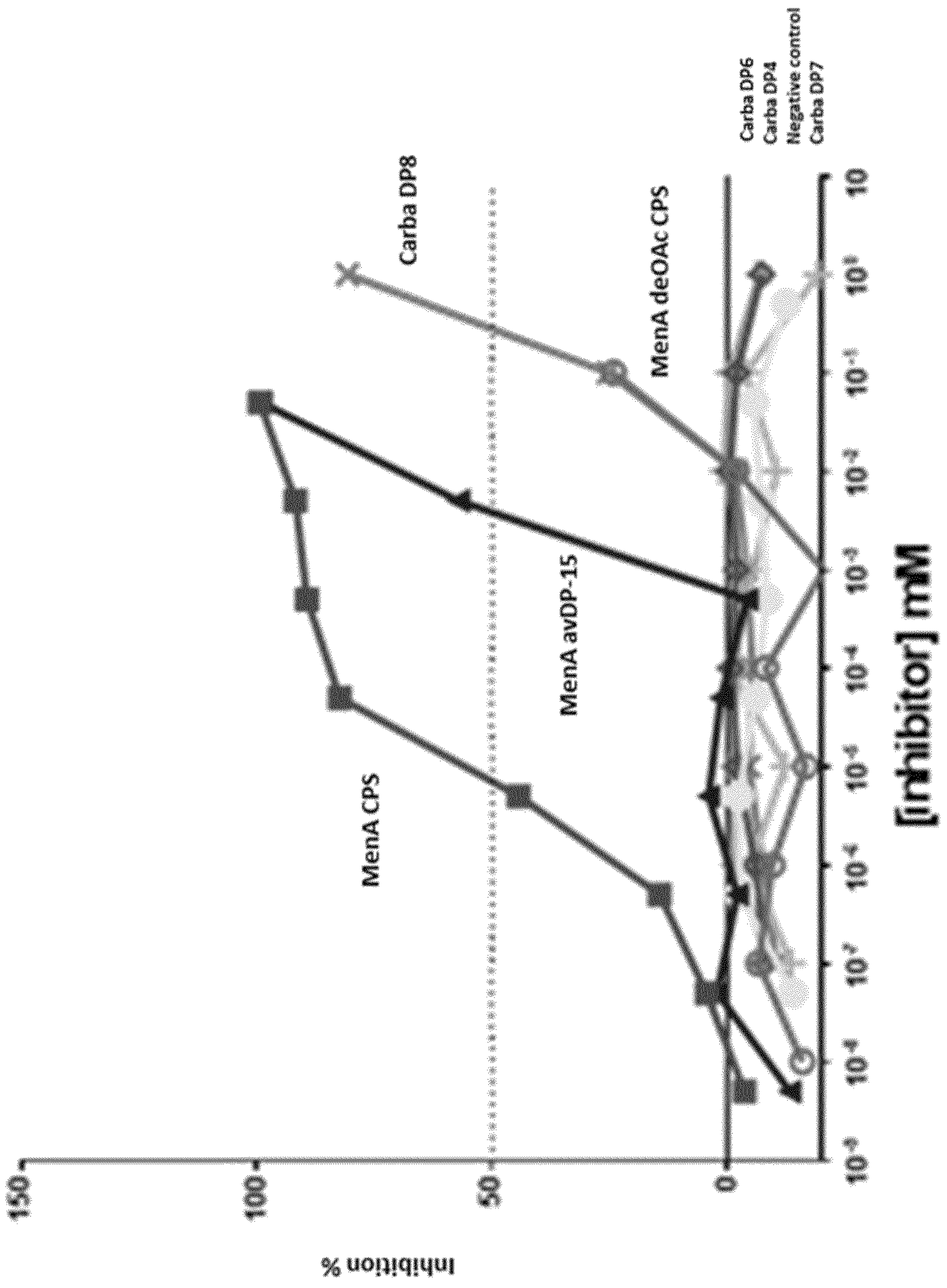
Figure 5C:
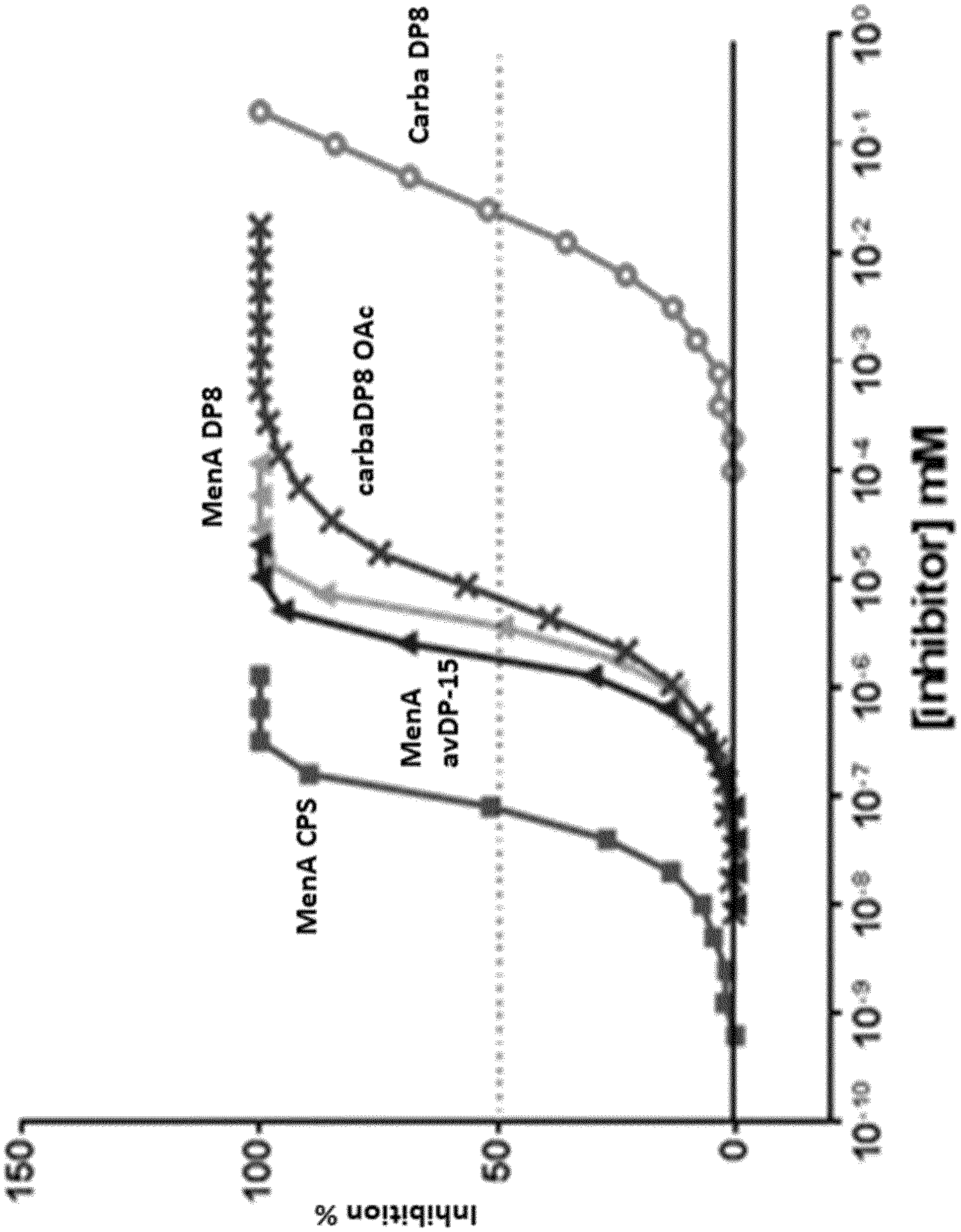

A similar behavior was observed when the inhibitors were assayed with an anti-MenA polyclonal serum generated by immunization of mice with a MenA-$CRM_{197}$ conjugate (FIG. 5B), when the carba DP8 performed as inhibitor comparably to the deOAc CPS.

This corroborated the propensity of carba DP8 to anti-MenA antibody binding. The different fragments were then tested against an anti-deOAc MenA serum. In this case the deOAc CPS ($IC_{50}$=1.86×$10^{-6}$) inhibited similarly to the Ac counterpart, indicating the specificity of the serum for the CPS backbone independently of the acetylation pattern. Most importantly, recognition was observed for all the carba DP4-8 analogues, demonstrating that they all resembled de-acetylated MenA CPS portions.

Of note, the binding affinity of carba DP8 ($IC_{50}$=1.59×$10^{-2}$ mM) was one order of magnitude higher than DP7 ($IC_{50}$=1.84×$10^{-1}$ mM). Based on these results DP8 and DP6 were selected for conjugation to carrier protein to compare the capacity of the two oligomers to elicit antibodies in mice, the first clearly binding to anti-MenA antibodies and the latter showing no recognition.

Example 6: Conjugation of carbaMenA DP6 and DP8 to $CRM_{197}$

CarbaMenA DP6 and DP8 compounds were coupled to $CRM_{197}$ using a conjugation procedure previously reported by Adamo et al., (*ACS Chem. Biol.,* 2012, 7, 1420-1428) and Adamo et al., (*J. Carbohydr. Chem.,* 2011, 30, 249-280), taking advantage of the di-N-hydroxysuccinimidyl adipate linker. Conjugates produced by this method are known not to elicit anti-linker antibodies (Adamo et al., *Chem. Sci.,* 2014, 5, 4302-4311). After treatment of the amines of the DP6 and DP8 compounds with the spacer in DMSO containing triethylamine, the obtained activated oligomer was purified by co-precipitation with acetone and used for conjugation. Overnight incubation with $CRM_{197}$ at a 100:1 glycan/protein molar ratio (corresponding to 0.40-50 active ester:protein, as determined by NHS quantification) in buffered pH 7.2 solution, gave the desired neo-glycoconjugate, as assessed by SDS page gel electrophoresis, which was purified by dialysis against a 30 kDa MW cutoff membrane. A saccharide/protein molar ratio of 16.9 and 10.4 was determined by MALDI TOF MS for the two conjugates from carba DP6 and DP8, respectively.

Immunogenicity of the carbaMenA $CRM_{197}$ Conjugates.

To test the immunogenicity of the conjugated carbaMenA DP6 and DP8, groups of eight BALB/c female mice were immunized with the neoglycoconjugates, according to the methodology described in more detail below. Conjugates prepared as previously described from sized MenA polysaccharide with avDP8.5 and ~15 were used as controls.

Mice received three subcutaneously (s.c.) doses (2 μg on saccharide base), two weeks apart. The neo-glycoconjugate induced an immune response at week 3, as observed by assaying the sera elicited by the conjugate against the same product coated on ELISA plates. At the serum dilutions tested no anti-$CRM_{197}$ antibodies were detectable. Each of the conjugates gave antibodies recognizing the conjugated antigen and the specificity of this recognition was confirmed by competitive ELISA. The binding of the anti-carbaMenA DP8 serum was inhibited by the unconjugated octamer to a greater extent than its conjugated form, due to the multivalent exposition of the antigen. Furthermore, this binding was inhibited for ~25% by the deOAc CPS and almost equally by the naturally acetylated counterpart, anticipating the potential of the raised antibodies in recognizing the capsule structure.

To determine the capacity of the elicited antibodies to cross-react with the backbone CPS structure deprived of the acetyl substituents, the sera were assayed against the non-acetylated CPS conjugated to Human Serum Albumin (HSA). The carbaMenA conjugates clearly showed an anti-deOAc CPS immune response, but IgG titers were inferior to those elicited by the conjugated avDP8.5 and ~15 used as controls ($p \leq 0.003$, FIG. 6B). The response of the two carba-analogues conjugates was not statistical different, however the number of responder mice to the DP8 conjugate was higher than for the DP6 conjugate.

When the ELISA was conducted using the acetylated CPS as coating reagent, the difference between the anti-native MenA IgG titers elicited by the carbaMenA DP6 and DP8 neoglycoconjugates and the controls was even more evident ($p<0.0001$, FIG. 6A).

The functionality of the elicited antibodies was next assessed on pooled sera by measuring the complement mediate lysis of bacteria expressing the acetylated CPS, as reported in Gao, Q et al., *CS Chem. Biol.,* 2013, 8, 2561-2567; and Adamo, R. et al., *Glycoconj. J.,* 2014, 31, 637-647. This assay is considered predictive of protection in humans for meningococcal vaccines.

It revealed poor bactericidal activity for the pooled serum from responder mice raised using the carbaMenA DP6 and DP8 conjugates (1024 vs 512, respectively). When the Serum Bactericidal Activity (SBA) was measured using human complement, the carba DP8-$CRM_{197}$ showed a titer of 128, significantly lower that the SBA of serum generated by the benchmark vaccine, based on the natural MenA CPS avDP~15. These results (seen in FIG. 6A) are in line with the observation reported in literature that antibodies elicited by a conjugate of the deOAc MenA CPS are scarcely functional (Berry, D. S et al., *Infect. Immun.,* 2002, 70, 3707-3713).

Taken together, this data revealed that the carbaMenA DP8 is an effective, stable mimic of the MenA CPS, capable of binding anti-MenA CPS antibodies. The carbaMenA DP8 conjugate induced antibodies able to activate human complement deposition, while the carbaMenA DP6 did not, highlighting the DP8 molecule as lead antigen. The carbaMenA DP8 neoglycoconjugate vaccine, however, elicited only low levels of bactericidal anti-MenA antibodies. Considering that the MenA CPS is variably O-acetylated at position 3 and 4, the inventors therefore sought to further increase the resemblance to the natural polysaccharide and increase the generation of protective antibodies by randomly O-acetylating the carbaMenA DP8 lead molecule.

Example 7: Optimization of the Glycomimetic Vaccine Candidate

To introduce acetyl esters on carbaMenA DP8, the inventors first installed a temporary Boc protecting group on the amine group of the linker. The resulting compound was next carefully acetylated by treatment with $Ac_2O$/imidazole to reach an acetylation level of 75%, similarly to the natural CPS. Boc-deprotection then provided the conjugation-ready Ac-carbaMenA DP8. NMR analysis revealed the acetyls to reside on either the C-3 or C-4 positions, with also concomitant acetylation at C-3/4 up to an extent of 44%. To test this compound as a potential antigen, the inventors first evaluated binding with the anti-MenA CPS mAb, in a competitive Surface Plasmon Resonance (SPR) experiment. This SPR was optimized to increase the sensitivity of the assay compared to the previously done standard ELISA.

Figures 6C, 6D:
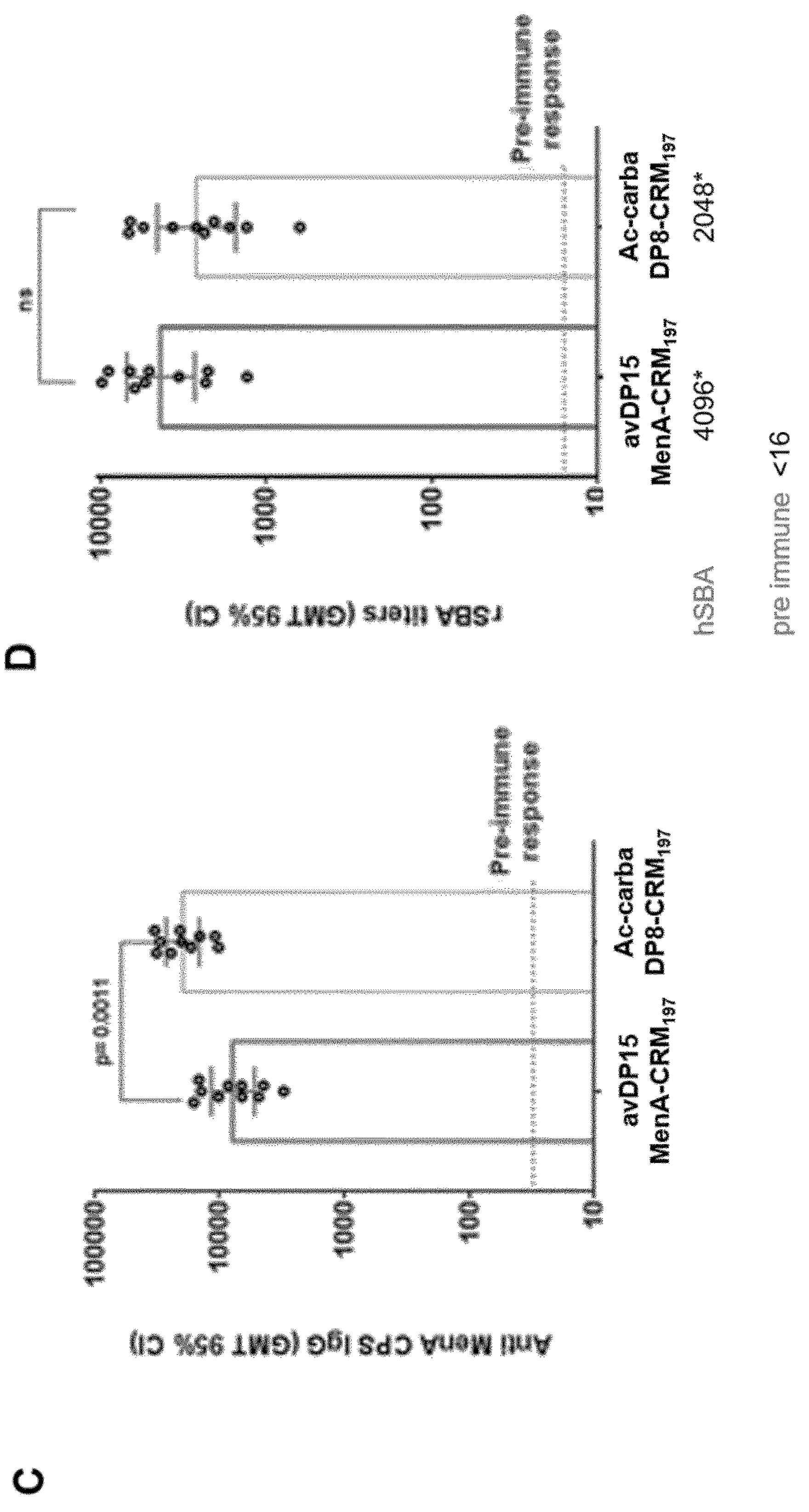

Ac-carbaMenA DP8 was conjugated to $CRM_{197}$ through the two-step procedure used for the non-acetylated oligomers, involving reaction with the di-N-hydroxysuccinimidyl adipate spacer and incubation with $CRM_{197}$. The purified neo-glycoconjugate was used in an immunization study with ten BALB/c female mice, using the avDP~15 $CRM_{197}$ conjugate as comparator. After three s.c. injections (2 μg on saccharide base), the sera were collected and analyzed for the content of bactericidal IgGs. As shown in FIG. 6C, Ac-carbaDP8-$CRM_{197}$ exhibited a 4-log higher capacity as inhibitor, compared to its non-acetylated counterpart carbaDP8-$CRM_{197}$ (shown in FIG. 6A), and binding to the mAb was almost comparable to the natural avDP8 and avDP~15 oligomers.

Remarkably, the Ac-carbaMenA DP8-$CRM_{197}$ conjugate induced higher levels of anti-MenA CPS antibodies compared to the control. SBA titers analyzed in individual mice also showed that the synthetic antigen was able to induce rabbit complement mediated bactericidal killing of MenA bacteria statistically non-inferior to the vaccine benchmark (FIG. 6D). Analysis in pooled sera confirmed that the human complement mediated bactericidal activity was also comparable between Ac-carbaMenA DP8 and the natural avDP~15, revealing Ac-carbaMenA DP8 as a true and potent mimic of the MenA CPS, that can be used in the generation of a stabilized neoglycoconjugate vaccine.

Example 8: Immunological Evaluation of Randomly O-Acetylated carbaMenA DP6 and DP8 Analogues To test the immunogenicity of the conjugated carba DP6 and DP8 analogues with and without random acetylation, groups of eight BALB/c female mice were immunized with the neoglycoconjugates. Conjugated sized MenA polysaccharide was used as control. Mice were immunized with three subcutaneously (s.c.) doses (2 μg on saccharide base) two weeks apart. Anti-MenA CPS response was evaluated and data showed no response for the conjugates obtained with carbaMenA sugar antigen without O-Acetylation, with both the sugar chain length 6 (n=6) and 8 (n=8). Conversely, carbaMenA conjugates obtained after random O-acetylation of the oligomer induced a significantly higher response against the native MenA CPS compared with the non-acetylated vaccine (Table 4). In comparison, the response induced by the O-acetylated vaccines was lower than the benchmark MenA-CRM197 conjugate, but only 2-fold lower for DP8 that gave the better response between those tested.

The vaccine formulation used for the carba MenA conjugates was as follows:

324.96 μl of $AlPO_4$ (4.43 mg/ml containing 2 mg/ml NaCl) was added to the conjugate of interest. The volume was brought to 1.2 ml at a concentration of 1.2 mg/ml of $AlPO_4$ by addition of PBS buffer at pH 7.2. The solution was finally diluted 1:1 v/v with PBS to a volume of 2.4 ml at a final concentration of 0.6 mg/ml of $AlPO_4$. 200 μl/mouse of the formulation were injected. This procedure was used also for formulation of MenA-$CRM_{197}$ from a stock solution.

The ELISA response after two and three doses is reported in Table 4. As can be seen, Groups 2 and 3 are those according to the invention. For Group 2, an oligomer conjugate having n=6 and random acetylation as described above was used. For Group 3, an oligomer conjugate having n=8 and random acetylation as described above was used. The level of acetylation of Groups 2 and 3 conjugates was around 75%.

TABLE 4

| | Group 1 MenA-$CRM_{197}$ Native Post 2/Post 3 | Group 2 carbaMenA DP6OAc-$CRM_{197}$ (random OAc) Post 2/Post 3 | Group 3 carbaMenA DP8OAc-$CRM_{197}$ (random OAc) Post 2/Post 3 | Group 4 carbaMenA DP6-$CRM_{197}$ (no OAc) Post 2/Post 3 | Group 5 carbaMenA DP8-$CRM_{197}$ (no OAc) Post 2/Post 3 |
|---|---|---|---|---|---|
| GMTs | 1670/6202 | 174/1317 | 400/5480 | 2/2 | 2/100 |
| | 272/3200 | 400/3200 | 1396/4635 | 2/2 | 2/2 |
| | 1165/5434 | 800/5266 | 381/1350 | 2/100 | 2/2 |
| | 3200/12800 | 275/1600 | 186/1063 | 2/2 | 2/2 |
| | 400/6400 | 687/800 | 800/5398 | 2/2 | 13/100 |
| | 3200/11275 | 80/1600 | 670/3200 | 2/2 | 50/100 |
| | 3200/11708 | 200/1600 | 400/1428 | 2/2 | 2/2 |
| | 2526/12232 | 742/4351 | 168/1600 | 2/2 | 2/2 |
| | 800/4472 | 270/2397 | 800/2932 | 2/2 | 2/2 |
| | 1222/192 | 274/2990 | 400/1009 | 2/2 | 2/2 |
| | 1328/5114 | 314/2165 | 463/2306 | 2/3 | 3/6 |

Figure 8A:
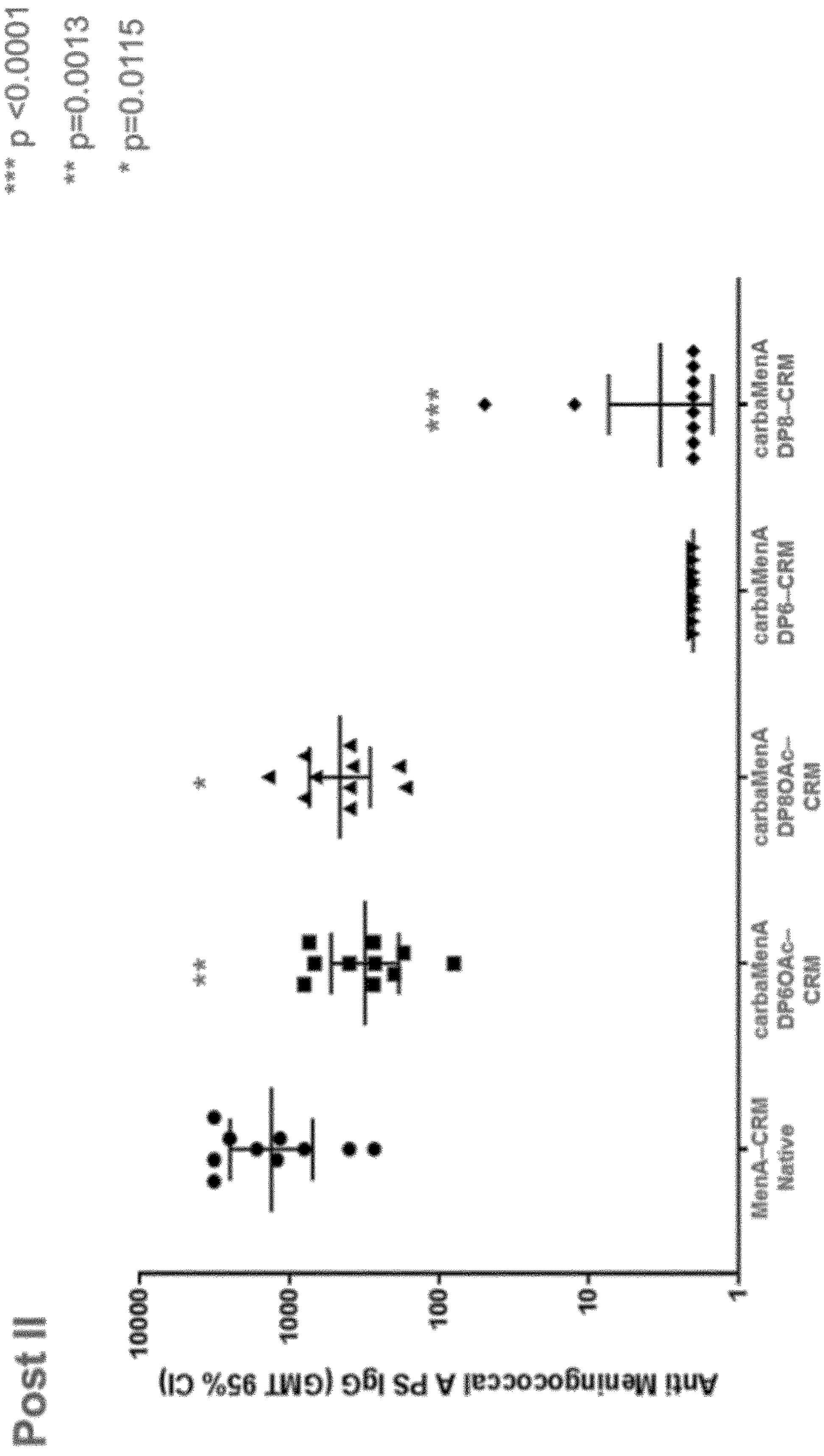
FIGS. 8A and 8B are ELISA titers post two and three doses of vaccines. The p values refer to the comparison between the benchmark MenA-$CRM_{197}$ native and the other groups of vaccination.
Figure 8B:
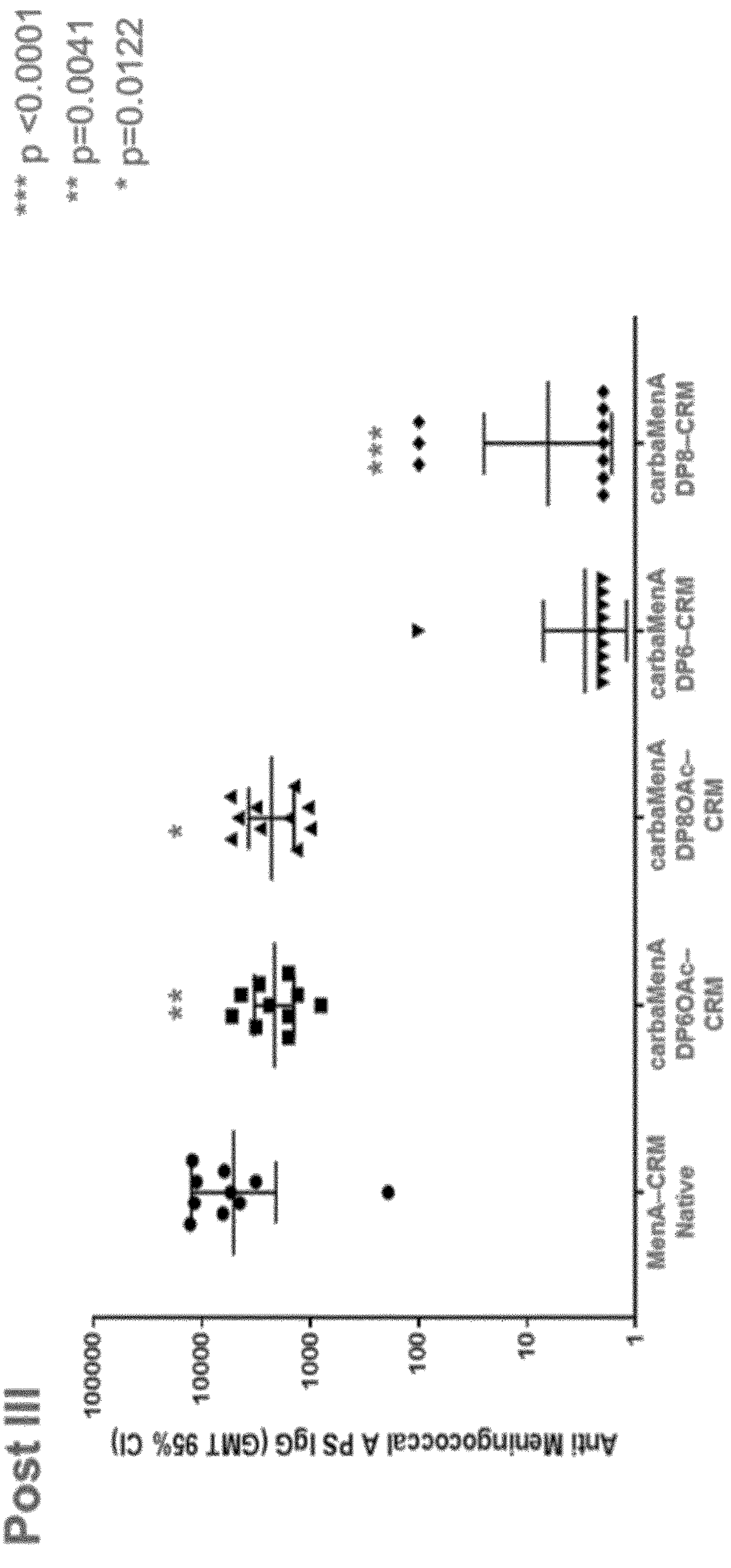

FIG. 8A and FIG. 8B provide ELISA titers post two and three doses. The p values refer to the comparison between the benchmark native MenA-CRM197 and the other groups.

A second immunological study was carried out as described in the following, by comparing the above said randomly O-acetylated carbaMenA DP8 analogue of this invention with a carbaMenA DP8 selectively O-acetylated only at position 3 with a percentage of O-acetylation of about 70%, and with the MenA vaccine as a positive control, all conjugated to $CRM_{197}$.

Figure 7:
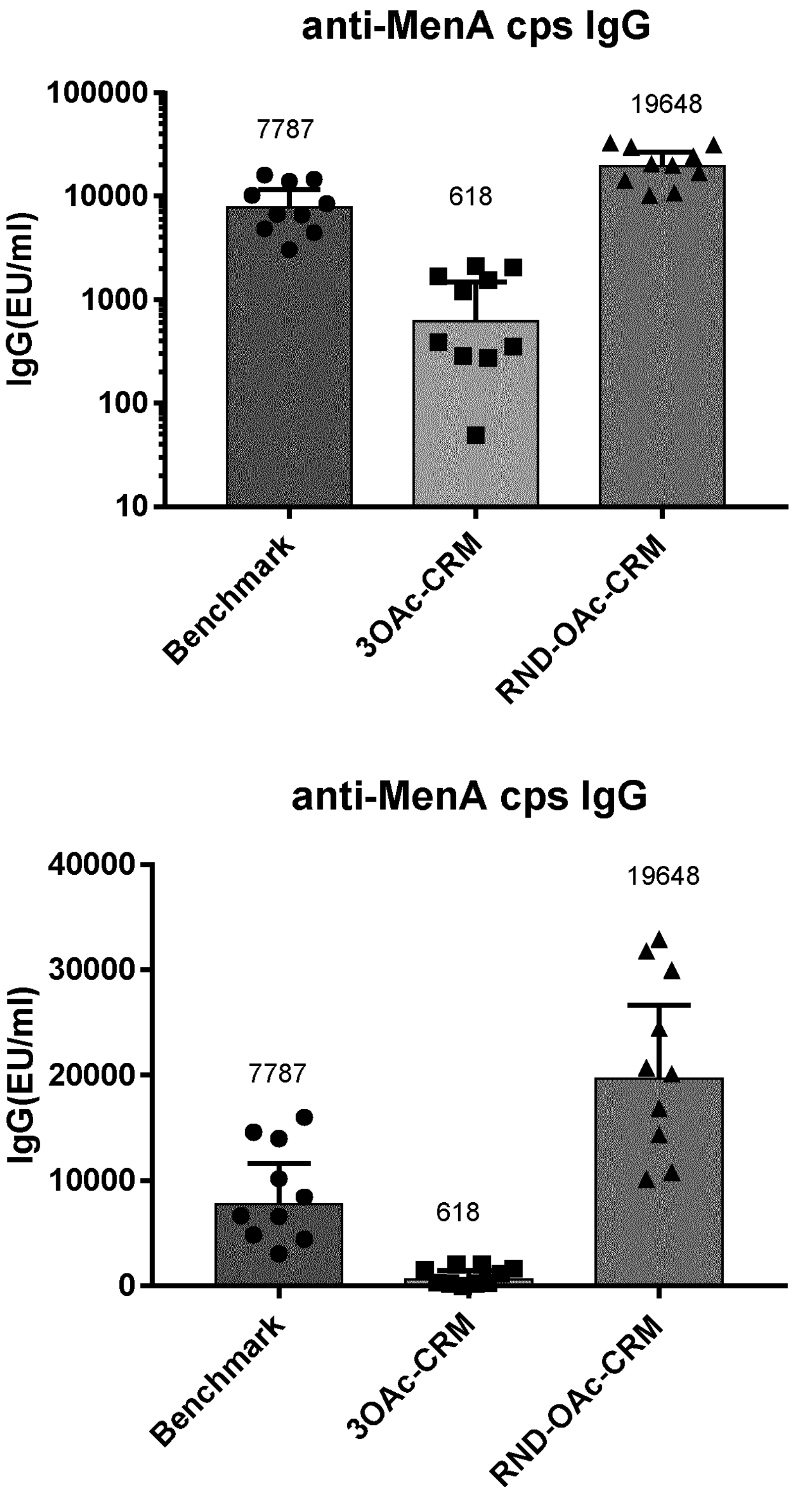
FIG. 7 shows ELISA titers measured post three doses of vaccine: anti-MenA polysaccharide IgG antibodies have been evaluated with $CRM_{197}$ conjugates of randomly O-acetylated carbaMenA analogue DP8 in comparison with $CRM_{197}$ conjugates of selectively 3-O-acetylated carbaMenA DP8 and with native MenA-$CRM_{197}$ vaccine as the benchmark (i.e. positive control).

Three groups of ten Balb/C mice were immunized with the above said conjugates. Mice were immunized with three subcutaneously (s.c.) doses (2 μg on saccharide base; 200 μl/mouse of the formulation) two weeks apart. The vaccine formulation used for the carba MenA conjugates was the same as reported above for the first immunological study. Anti-MenA CPS response was evaluated, and the data (summarized in Table 5) showed a total IgG response after the third immunization about 10 times lower for the 3 O-acetylated carbaMenA DP8 than the MenA vaccine benchmark. Conversely, the randomly O-acetylated carbaMenA DP8 conjugate of the invention induced a significantly higher response against the native MenA CPS compared with the 3 O-acetylated conjugate, and substantially equivalent to that of the MenA vaccine benchmark (see FIG. 7).

TABLE 5

| | Group 1 MenA $CRM_{197}$ native | Group 2 DP8 carbaMenA $CRM_{197}$ (3-OAc) | Group 3 DP8 carbaMenA $CRM_{197}$ (random OAc) |
|---|---|---|---|
| ELISA GMT (min; max) | 7787 (3056; 16016) | 618 (50; 2086) | 19648 (10158; 32933) |
| SBA GMT (min; max) | 4350 (1310; 9892) | 63 (8; 526) | 2644 (6788; 630) |

Figure 9:
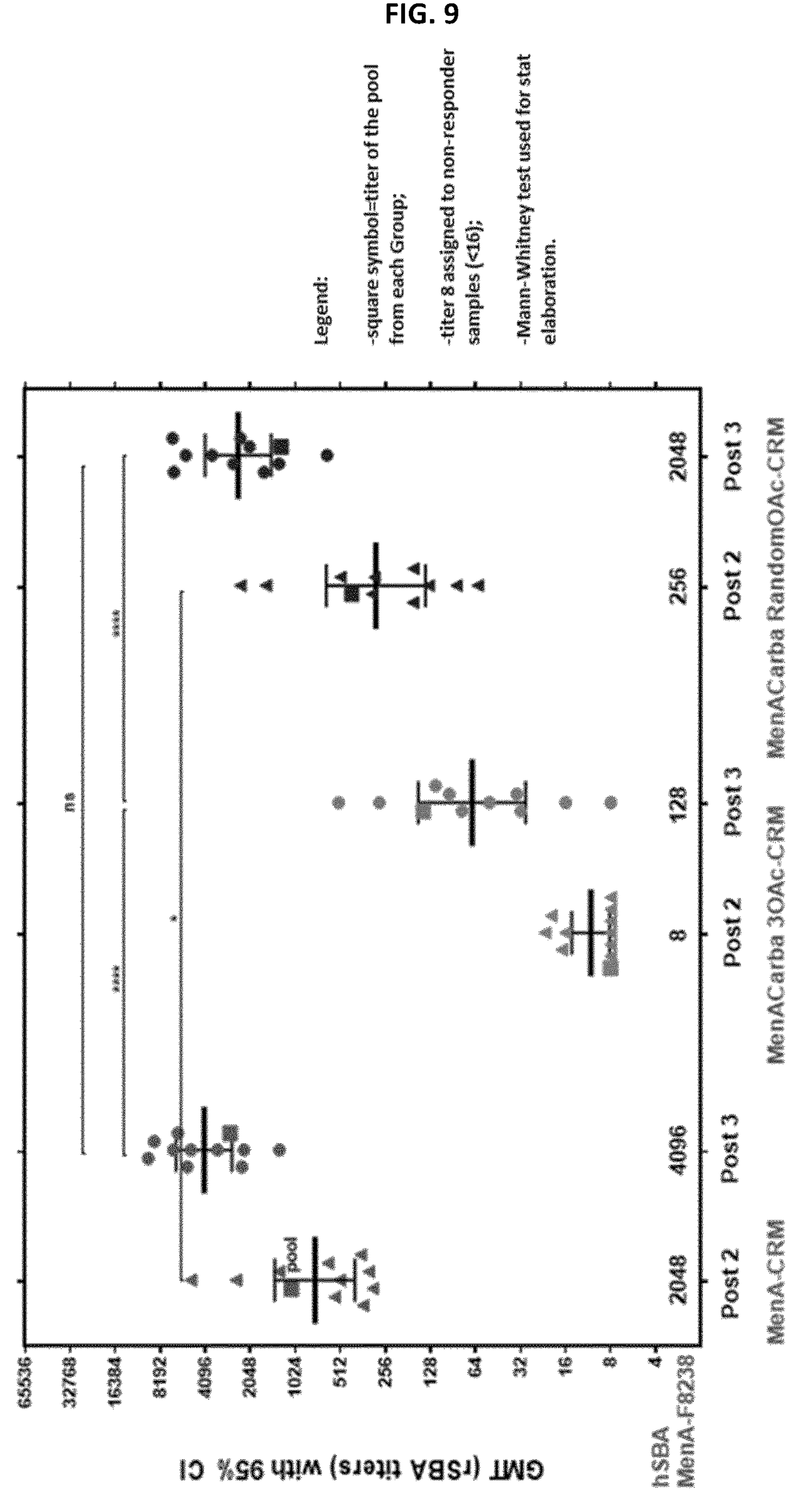
FIG. 9 shows SBA titers post three doses of vaccine: human complement mediated bactericidal titers were measured on sera elicited with the $CRM_{197}$ conjugate of randomly O-acetylated carbaMenA analogue DP8 in comparison with $CRM_{197}$ conjugates of selectively 3-O-acetylated carbaMenA DP8 and with native MenA-$CRM_{197}$ vaccine as the benchmark (i.e. positive control).

FIG. 9 shows human complement mediated serum bactericidal titers elicited by $CRM_{197}$-conjugates of selectively 3-O-acetylated carbaMenA DP8 and the randomly acetylated carbaMenA DP8 of the invention, after three doses. MenA-$CRM_{197}$ vaccine was the positive control.

The SBA titers induced by the randomly O-acetylated CarbaMenA-$CRM_{197}$ conjugate were statistically comparable to the MenA vaccine benchmark after three doses, while the 3 O-acetylated CarbaMenA-$CRM_{197}$ conjugate induced far lower SBA titers in sera compared to the vaccine benchmark, as measured with both baby rabbit complement and human complement.

Figure 10:
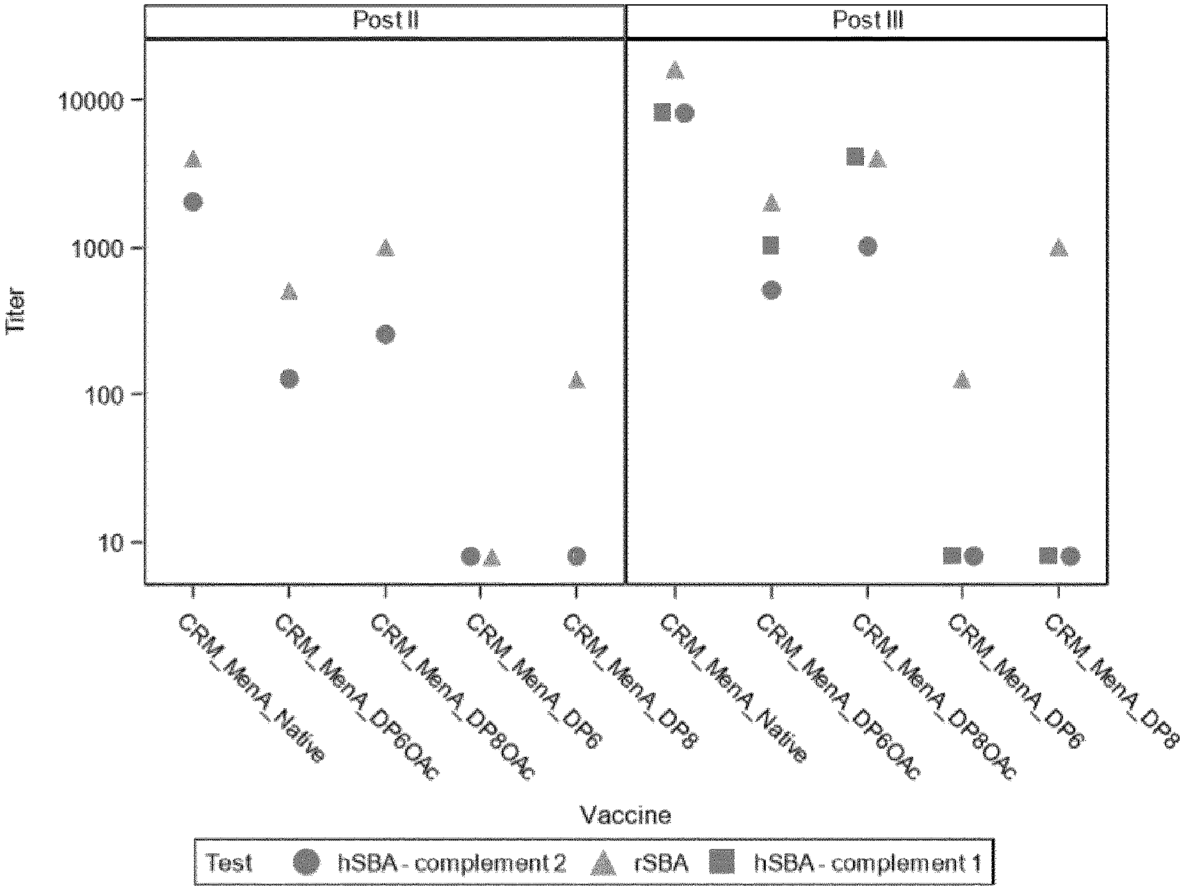
FIG. 10 shows SBA titers post two and three doses of a vaccine according to the invention (DP8-OAc), and also for a vaccine not according to the invention (DP6-OAc), obtained with rabbit (rSBA) and human complement (hSBA).

The results reported in FIG. 10 and Table 6 show the ability of the anti-MenA antibody to be bactericidal against the MenA strain. In particular, the native MenA-CRM197 vaccine and the vaccines obtained with two O-acetylated synthetic carba-analogues (Group 2 (DP6) and Group 3 (DP8)), were able to maintain a significant bactericidal activity also when tested with human complement. The DP8 O-acetylated synthetic carba-analogue according to the invention (Group 3) shows better bactericidal activity than the DP6 O-acetylated synthetic carba-analogue (Group 2). FIG. 10 depicts SBA titers post two and three doses obtained with rabbit (rSBA) and human (hSBA) complement.

TABLE 6

| | Group 1 MenA-CRM Native | Group 2 carbaMenA DP6OAc-CRM (random OAc) | Group 3 carbaMenA DP8OAc-CRM (random OAc) | Group 4 carbaMenA DP6-CRM (no OAc) | Group 5 carbaMenA DP8-CRM (no OAc) |
|---|---|---|---|---|---|
| Post 2 | | | | | |
| rSBA | 4096 | 512 | 1024 | <16 | 128 |
| hSBA (human complement donor 2) | 2048 | 128 | 256 | <16 | <16 |
| Post 3 | | | | | |
| rSBA | 16384 | 2048 | 4096 | 128 | 1024 |
| hSBA (human complement donor 1) | 8192 | 1024 | 4096 | <16 | <16 |
| hSBA (human complement donor 2) | 8192 | 512 | 1024 | <16 | <16 |

CONCLUSIONS

Based on data obtained, it can be concluded that carba MenA oligomers of the invention can be used for the development of more stable versions of MenA vaccines and the OAc moiety in combination with the oligomer length are key to elicit a functional immune response against MenA strains.

Methods

Preparation of neoglycoconjugates The amino-oligosaccharides were vacuum dried, solubilized in 1:9 $H_2O$:DMSO solution to a final amino group concentration of 40 mmol $mL^{-1}$, and reacted with a 12-fold molar excess of di-N-hydroxysuccinimidyl adipate linker (SIDEA), in presence of 5-fold molar excess triethylamine as compared with amino groups. The reaction was kept under gentle stirring at room temperature for 3 h. The activated oligosaccharides were purified by precipitation with 4 volumes of ethyl acetate followed by ten washes of the pellet with 1 mL of the same solvent. Finally, the pellet was dried under vacuum, and the content of introduced N-hydroxysuccinimide ester groups was determined.

Conjugates have been prepared in 50 mM $NaH_2PO_4$ pH 7 using an active ester (AE):protein molar ratio of 40:1, carried over night at room temperature with gentle stirring. The conjugates were purified by tangential flow filtration (Vivaspin) using a cutoff of 30 kDa and using PBS pH 7.2 as buffer. Conjugates were characterized by micro BCA (Smith, P. K., et al. (1985) Measurement of protein using bicinchoninic acid. Anal Biochem 150:76-85) for total protein content and by MALDI analysis for total saccharide content.

Mice Immunization and ELISA Analysis:

All mice were housed under specific pathogen-free conditions. Antigens formulations have been prepared under sterile conditions. Groups of 10 BALB/c mice were immunized on days 1, 14 and 28; bleedings were performed on day 0 (pre immune), day 27 (post 2) and day 42 (post 3). Vaccines were administered in saccharide dose and the dosage of 2 μg/mice per dose in terms of saccharide. Adjuvant $AlPO_4$ was used at the dose of 0.12 mg of $Al^{3+}$. The antibody response induced by the glycoconjugates has been measured by ELISA. The pre-immune serum was used as negative control in this analysis. Plates have been coated with HSA-deOAc or MenA CPS by adding 100 μL/well of a 5 μg $mL^{-1}$ polysaccharide solution in PBS buffer at pH 8.2 followed by incubation overnight at 4° C.[46]. HSA-deOAc MenA CPS, $CRM_{197}$ conjugates and $CRM_{197}$ were coated at the protein concentration of 2 μg $mL^{-1}$ in pH 7.2 PBS buffer. Coating solutions were removed from the plates by washing tree times with PBS buffer with 0.05% of Tween 20 (Sigma) (TPBS). A blocking step has been then performed by adding 100 μl/well of BSA solution at 3% in TPBS and incubating the plates 1 h at 37° C. Blocking solution has been removed from the plates by washing three times with TPBS. 200 μL/well of pre-diluted serum (1:25 for pre immune negative control, 1:200/1:500 for a reference serum and from 1:25/1:200 for test sera) was added in the first well of each column of the plate, while on the other wells 100 μl of TPBS has been dispensed. Eight two-fold serial dilutions along each column were then performed by transferring from well to well 100 μL of sera solutions. After primary antibody dilution, plates have been incubated for 2 h at 37° C. Three washes with TPBS, 100 μL/well TPBS solutions of secondary antibody alkaline phosphates conjugates (anti mouse IgG 1:10000, Sigma-Aldrich) were then added, and the plates incubated 1 h at 37° C. After three more washes with TPBS, 100 μL/well of a 1 mg $mL^{-1}$ of p-NPP (Sigma) in a 0.5 M di-ethanolamine buffer pH 9.6 was added. Finally, plates were incubated for 30 min at room temperature and read at 405 nm using the plate reader Spectramax 190. Sera titers were expressed as the reciprocal of sera dilution corresponding to a cut-off OD=1.

Each immunization group has been represented as the geometrical mean (GMT) with 95% Cl of the single mouse titers. The statistical and graphical analysis has been done by GraphPad Prism 7 software.

In Vitro Bactericidal Assay:

Functional antibodies induced by vaccine immunization were analyzed by measuring the complement-mediated lysis of *N. meningitidis* with an in vitro bactericidal assay (Jackson, L. A et al., *Clin. Infect. Dis.,* 2009, 49, el-10). A commercial lot of baby rabbit complement (Peel Freeze Biological, cod. 31061) was used as source of active complement for rSBA, while plasma was used as complement source of hSBA.

*N. meningitidis* strain was grown overnight on chocolate agar plates at 37° C. in 5% $CO_2$. Colonies were inoculated in Mueller-Hinton broth, containing 0.25% glucose to reach an OD600 of 0.05-0.08 and incubated at 37° C. with shaking. When bacterial suspensions reached OD600 of 0.25-0.27, bacteria were diluted in the assay buffer (DPBS with 1% BSA and 0.1% glucose) at the working dilution (ca. $10^4$ CFU $mL^{-1}$). The total volume in each well was 50 μL with 25 μL of serial two-fold dilutions of the test serum, 12.5 μL of bacteria at the working dilution and 12.5 μL of complement source. The tested sera were pooled and heat-inactivated for 30 minutes at 56° C. Negative controls included bacteria incubated, separately, with the complement serum without the test serum and with test sera and the heat-inactivated complement. Immediately after the addition of the baby rabbit complement, negative controls were plated on Mueller-Hinton agar plates, using the tilt method (time 0). The microtiter plate was incubated for 1 hour at 37° C., then each sample was spotted in duplicate on Mueller-Hinton agar plates while the controls were plated using the tilt method (time 1). Agar plates were incubated overnight at 37° C. and the colonies corresponding to time 0 and time 1 (surviving bacteria) were counted. The serum bactericidal titre was defined as the serum dilution resulting in 50% decrease in colony forming units (CFU) per mL, after 60 min incubation of bacteria in the reaction mixture, compared to control CFU per mL at time 0. Typically, bacteria incubated without the test either pooled or individual murine serum in the presence of complement (negative control) showed a 150 to 200% increase in CFU $mL^{-1}$, during the 60 min incubation time. The reference strain for meningococcal serotype A was F8238 (Mak, P. A., Santos, G. F., Masterman, K. A., Janes, J., Wacknov, B., Vienken, K., Giuliani, M., Herman, A. E., Cooke, M., Mbow, M. L., Donnelly, J., *Clin. Vacc. Immunol.,* 2011, 18, 1252-1260).

Statistical Methods

Non-parametric t test was performed on data obtained from ELISA, Mann-Whitney was conducted applying GraphPad software comparing the rank between two groups of interest (i.e. $CRM_{197}$-MenA avDP15 and $CRM_{197}$-MenA DP6OAc or DP8OAc). ELISA data were reported as geometric mean with 95% of Cl. In addition, an Analysis Of Variance (ANOVA) model was fitted on the log 10 antibody titers including group (all of them except 4 and 5), time and group by time interaction as fixed effects. A heterogeneous variance model was used since identical variances were not assumed between the groups. For each endpoint, this model was used to estimate the group geometric means and their 95% CIs as well as the geometric mean ratios (O-Acetylated formulations vs Benchmark) and 95% CIs. Differently, for SBA data, as there is a single observation for each group at each time point (pools of sera), only a graphical analysis was performed.

Protocol for Quantification of Hydrolyzed MenA and carbaMenA Oligomer in Final Conjugates HPAEC-PAD was used to quantify the amount of monomer released over time from the MenA and carbaMenA conjugates of the invention. Titers reported were obtained by hydrolyzing the samples with HCl at final concentration 6M at 110° C. for 2 hours in dry oven. After incubation samples were dried in a Speedvac system and then re-dissolved with water and filtered 0.45 μm. Quantification was performed by using a standard curve built in the range 0.5-5.0 μg/mL with CarbaMenA DP7, quantified by NMR, and treated as samples. The analysis was performed on a ICS5000 system (Dionex-Themo Fisher) equipped with a CarboPac PA1 column with guard. Elution was made with a gradient of sodium acetate in presence of 100 mM sodium hydroxide at 1.0 mL/min and peak detected in pulse integrated amperometry by using the quadruple wave form for carbohydrates. Results were elaborated with Chromeleon™ 7.2 Chromatography Data System (CDS) Software.

Example 9: Comparison of ABCWY Combo Vaccine Vs carbaMenA-BCWY Combo Vaccine

In order to study the MenACarba (Random OAc) response in combination with MenBCWY antigens four groups of Balb/C mice were immunized with the vaccine formulations indicated in Table 7 below. Mice were immunized with three subcutaneous (s.c.) doses (2 μg on saccharide base; 200 μl/mouse of the formulation) two weeks apart (days 1, 14 and 28), with blood draws at days 0, 27 and 42.

The vaccine formulation used for the carba MenA conjugates was the same as reported above for the first immunological study.

*$B_{NG}$ indicates that the Men B antigen component of the composition was comprised of the BEXSERO vaccine antigens, together with an additional fHbp fusion protein, corresponding to the 231.13 fusion protein identified above as SEQ ID NO: 35.

TABLE 7

| Group | Antigen | Adjuvant |
|---|---|---|
| 1 (8 mice) | MenAB$_{NG}$ * CWY | AlumOH |
| 2 (8 mice) | MenA (benchmark) | AlumOH |
| 3 (4 mice) | MenAcarba(RandomOAc) + MenB$_{NG}$ * CWY | AlumOH |
| 4 (4 mice) | MenAcarba(RandomOAc) | AlumOH |

Groups 1 and 2 were administered vaccine formulations comprising solid (lyophilized) MenA components. Groups 3 and 4 were administered fully liquid formulations. For clarity, MenAcarba corresponds to carbaMenA.

Figure 11:
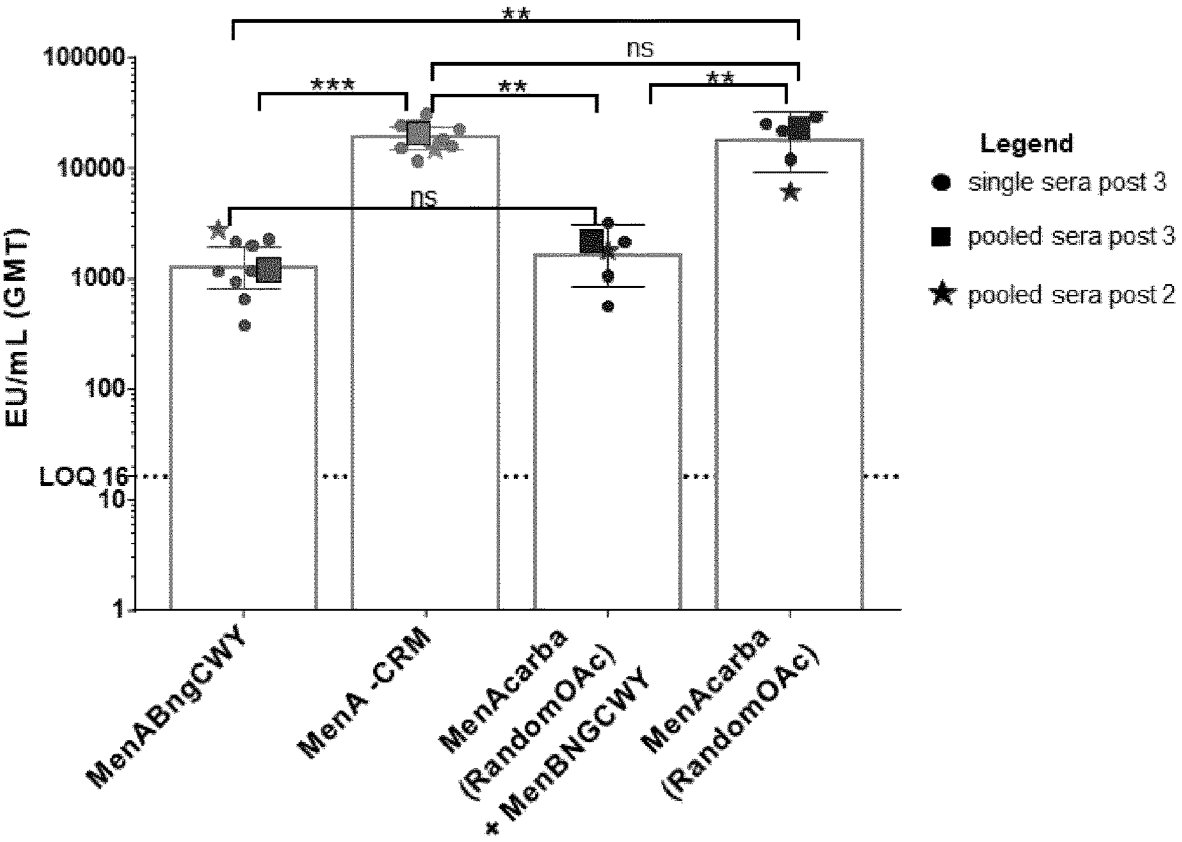
FIG. 11 shows total IgG titers on single and pooled sera measured by HT-ELISA for benchmark MenABCWY and MenA formulations having a solid (lyophilized) MenA component versus corresponding fully liquid formulations comprising randomly acetylated carbaMenA antigens.

The total IgG was measured by HT-ELISA on single and pooled sera post-3, and on pooled sera post-2. As shown in FIG. 11, IgG titers induced by carbaMenA are comparable to MenA in combination with BCWY antigens.

Importantly, data shown in the first column of FIG. 11 (MenAB$_{NG}$CWY) relates to lyophilized Men A component mixed with liquid BCWY components, whereas the data for MenAcarba (RandomOAc)+MenB$_{NG}$CWY is a fully liquid formulation (no lyophilized MenA component).

Figure 12:
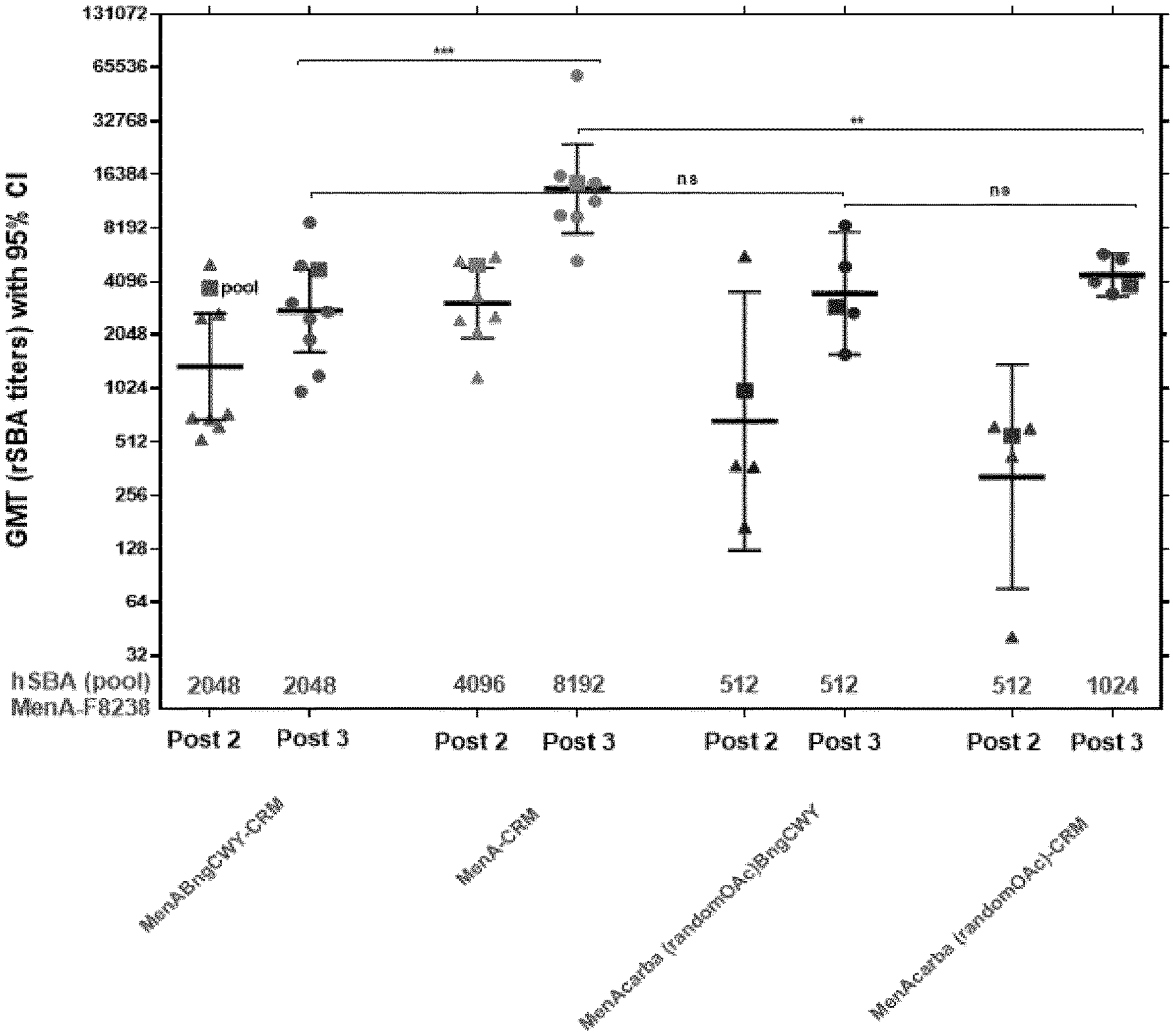
FIG. 12 shows functional antibody responses measured by rSBA and SBA for benchmark MenABCWY and MenA formulations having a solid (lyophilized) MenA component versus corresponding fully liquid formulations comprising randomly acetylated carbaMenA antigens.

Functional antibody responses were measured by both rSBA and hSBA and, as shown in FIG. 12, antibody functionality induced by carbaMenA combined with B$_{NG}$CWY is comparable to the benchmark combination AB$_{NG}$CWY.

Therefore, immunogenic compositions according to the present invention have the advantage of being effective in a fully liquid formulation, without comprising on the immunological efficacy of the benchmark pentavalent composition, which incorporates a lyophilized MenA components requiring reconstitution with the BCWY components prior to administration.

Example 10: Comparison of ABCWY Combo Vaccine Vs carbaMenA-BCWY Combo Vaccine in Rats Methods Preparation of Neoglycoconjugates To introduce acetyl esters on carbaMenA DP8 and DP10, the inventors first installed a temporary Boc protecting group on the amine group of the linker. The resulting compound was next carefully acetylated by treatment with $Ac_2O$/imidazole to reach an acetylation level of 75%, similarly to the natural CPS. Boc-deprotection then provided the conjugation-ready Ac-carbaMenA DP10 and Ac-carbaMenA DP10.

The amino-oligosaccharides were vacuum dried, solubilized in 1:9 $H_2O$:DMSO solution to a final amino group concentration of 40 mmol $mL^{-1}$, and reacted with a 12-fold molar excess of di-N-hydroxysuccinimidyl adipate linker (SIDEA), in presence of 5-fold molar excess triethylamine as compared with amino groups. The reaction was kept under gentle stirring at room temperature for 3 h. The activated oligosaccharides were purified by precipitation with 4 volumes of ethyl acetate followed by ten washes of the pellet with 1 mL of the same solvent. Finally, the pellet was dried under vacuum, and the content of introduced N-hydroxysuccinimide ester groups was determined.

Conjugates have been prepared in 100 mM $NaH_2PO_4$ pH 7 using an active ester (AE):protein molar ratio reported in the table below (Table 8):

TABLE 8

| Glycoconjugate | mol NHS/ mol protein |
|---|---|
| $CRM_{197}$-Carba DP8 low | 13:1 |
| $CRM_{197}$-Carba DP8 high | 30:1 |
| $CRM_{197}$-Carba DP10 low | 12:1 |
| $CRM_{197}$-Carba DP10 high | 28:1 |

Figure 13:
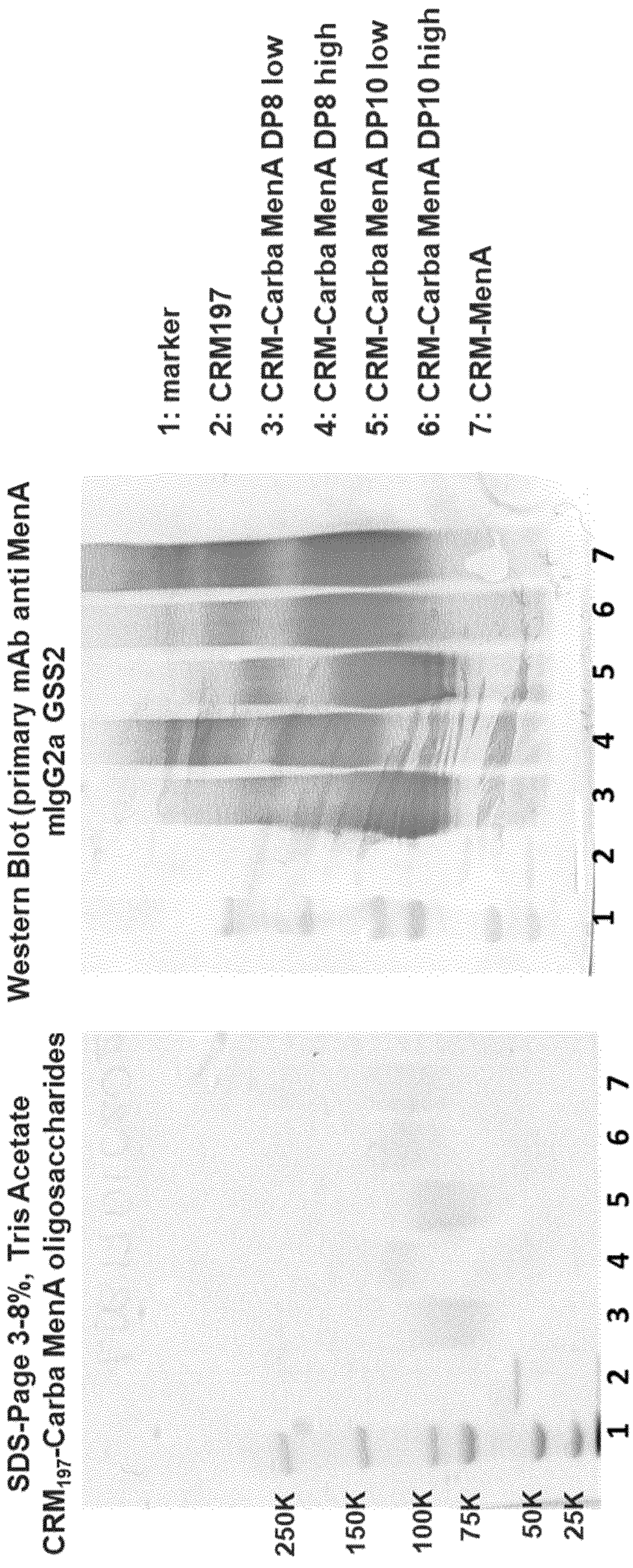
FIG. 13 shows the SDS-page and Western Blot characterization of carbaMenA DP8 and DP10 conjugates.

The reactions have been carried over night at room temperature with gentle stirring. The conjugates were purified by tangential flow filtration (Vivaspin) using a cutoff of 30 kDa and using 10 mM $NaH_2PO_4$ pH 7.2 as buffer. Conjugates were characterized by micro BCA (Smith, P. K., et al. (1985). Measurement of protein using bicinchoninic acid. Anal Biochem 150:76-85) for total protein content, by HPAEC-PAD analysis for total saccharide content (Table 9), by SDS-Page and Western Blot (FIG. 13).

TABLE 9

| Glycoconjugate | Saccharide content (ug/mL) | Protein content (mg/mL) | Saccharide/ protein ratio (w/w) | Saccharide/ protein ratio (mol/mol) |
|---|---|---|---|---|
| $CRM_{197}$-Carba DP8 low | 167.1 | 0.741 | 0.23 | 4.4 |
| $CRM_{197}$-Carba DP8 high | 241.6 | 0.470 | 0.51 | 9.9 |
| $CRM_{197}$-Carba DP10 low | 153.1 | 0.502 | 0.30 | 4.7 |
| $CRM_{197}$-Carba DP10 high | 78.3 | 0.175 | 0.45 | 7.0 |

Rats Immunization:

All rats were housed under specific pathogen-free conditions. Antigens formulations have been prepared under sterile conditions. Groups of CD(SD) Sprague-Dawley 10 rats were immunized on days 1, 22 and 36; bleedings were performed on day 0 (pre immune) and day 49 (post 3). Vaccines were administered intramuscularly (IM) at a dosage of ⅕ of, i.e. a 1:5 dilution (1:5 dil) of, ACWY-7B human dose (⅕ HD). Adjuvant AlOH was used at the dose of 3 mg/ml.

TABLE 10

| Groups | Antigen | Doses | Adjuvant | Route | Volume doses |
|---|---|---|---|---|---|
| 1 | Men ACWY_7B fHbp1X dil 1:5 | 2 μg (saccharide) | Alum Hydroxide 3 mg/ml | IM | 200 μl |
| 2 | MenCWY_7B CarbaMenA dil 1:5 | 2 μg (saccharide) | Alum Hydroxide 3 mg/ml | IM | 200 μl |
| 3 | CarbaMenA DP10-CRM dil 1:5 | 2 μg (saccharide) | Alum Hydroxide 3 mg/ml | IM | 200 μl |
| 4 | MenA-CRM dil 1:5 | 2 μg (saccharide) | Alum Hydroxide 3 mg/ml | IM | 200 μl |

MenACWY RAT ELISA (Conventional HT-ELISA):

Plate were coated with a solution 5 μg/ml in PBS 1×pH 8.2 of each polysaccharide (A, C, W135, Y) and incubated O.N. at +2-8° C. After washing (PBS1× Tween20) plate were blocked by addition of 200 μl of Smartblock (Candor Bioscience) and incubated 2 hrs at RT. After washing plates were sealed with Liquid Plate Sealer (Candor Bioscience) and incubated 2 hrs at RT. Plates were finally aspirated and stored in the fridge at 2-8° C.

Samples were diluted in a solution of PBS 1×BSA 1% pH 7.4 from a starting dilution 1:100 (MenA and MenY), 1:500 (MenC) and 1:200 MenW135 and then along further five two-fold serial dilutions.

Plates were then incubated for 90 min at 30° C., then washed as described before and 100 μl of a solution of secondary antibody (anti-RAT total IgG Alkaline Phosphatase conjugate) was added. Plates were then incubated for 60 min at 30° C.

After washing plates were added 100 μl of substrate (para-Nitrophenyl Phosphate) and read at 405 nm after 30' incubation at 30° C.

Bexsero+NG RAT ELISA (Conventional HT-ELISA):

Plates were coated with a solution 0.15 μM in PBS 1× of recombinant proteins (287-953, 936-741, 961c, 741-231.16) and 2 μg/ml in Tris 100 mM pH 9.0 for OMV-NZ and incubated O.N. at +2-8° C. After washing (PBS1× Tween20) plates were blocked by addition of 200 μl of Smartblock (Candor Bioscience) and incubated 2 hrs at RT. After washing plates were sealed with Liquid Plate Sealer (Candor Bioscience) and incubated 2 hrs at RT. Plates were finally aspirated and stored in the fridge at 2-8° C.

Samples were diluted in a solution of PBS 1×BSA 1% pH 7.4 from a starting dilution 1:1000 (936-741), 1:500 (287-953, 961c and OMV-NZ) and 1:1000 (741-231.13) and then along further five two-fold serial dilutions.

Plates were then incubated for 90 min at 37° C., then washed as described before and 100 μl of a solution of secondary antibody (anti-RAT total IgG Alkaline Phosphatase conjugate) was added. Plates were then incubated for 60 min at 37° C.

After washing plates were added 100 μl of substrate (para-Nitrophenyl Phosphate) and read at 405 nm after 25-30' incubation at 37° C.

Figure 14A:
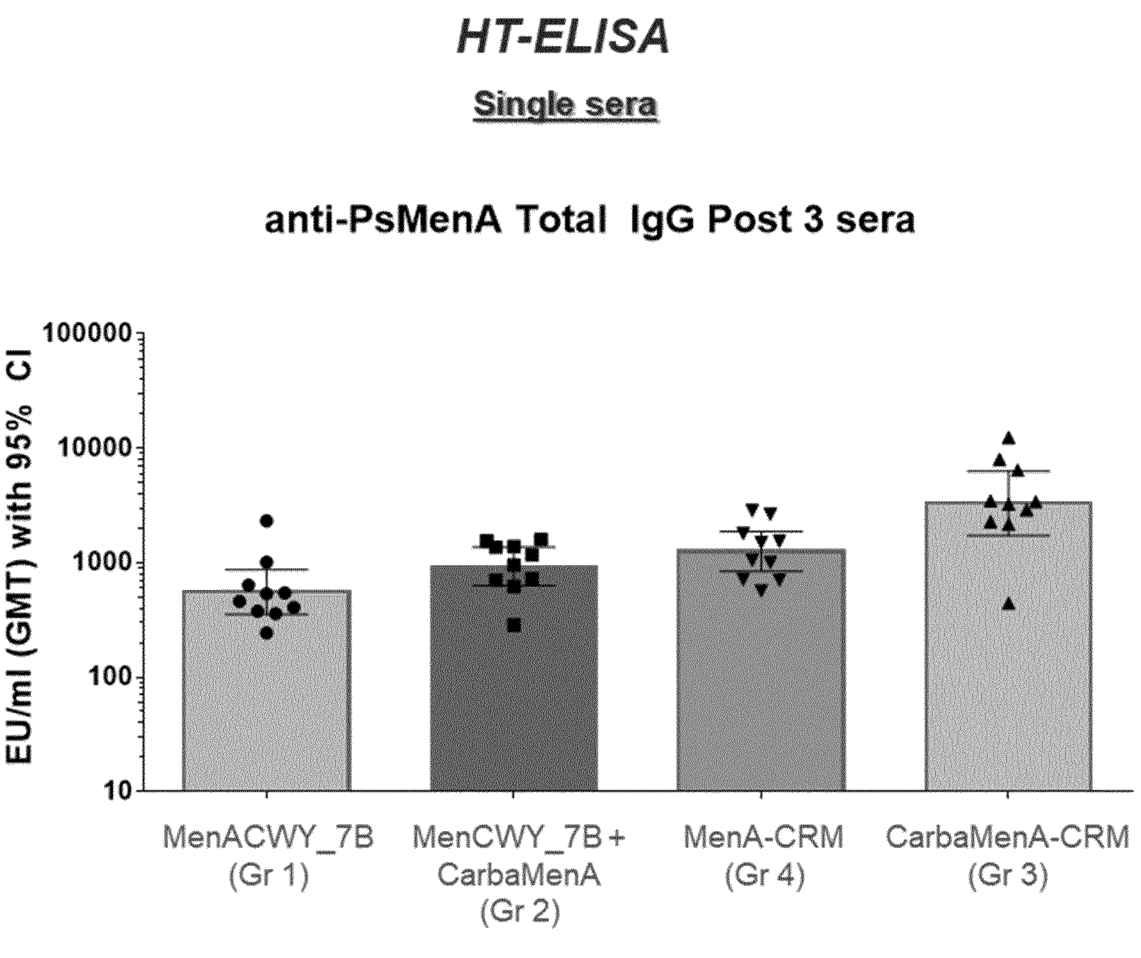
FIG. 14A shows anti-MenA polysaccharide IgG antibodies, FIG. 14B anti-MenC, anti-MenW and anti-MenY polysaccharides IgG antibodies.

The total IgG was measured by HT-ELISA on single sera post-3. As show in FIG. 14A, IgG titers against Men A PS are comparable in rat sera immunized with ABNGCWY or carbaMenA combined with BNGCWY, and higher in rats immunized with CarbaMenA than in those immunized with MenA-CRM.

Figure 14B:
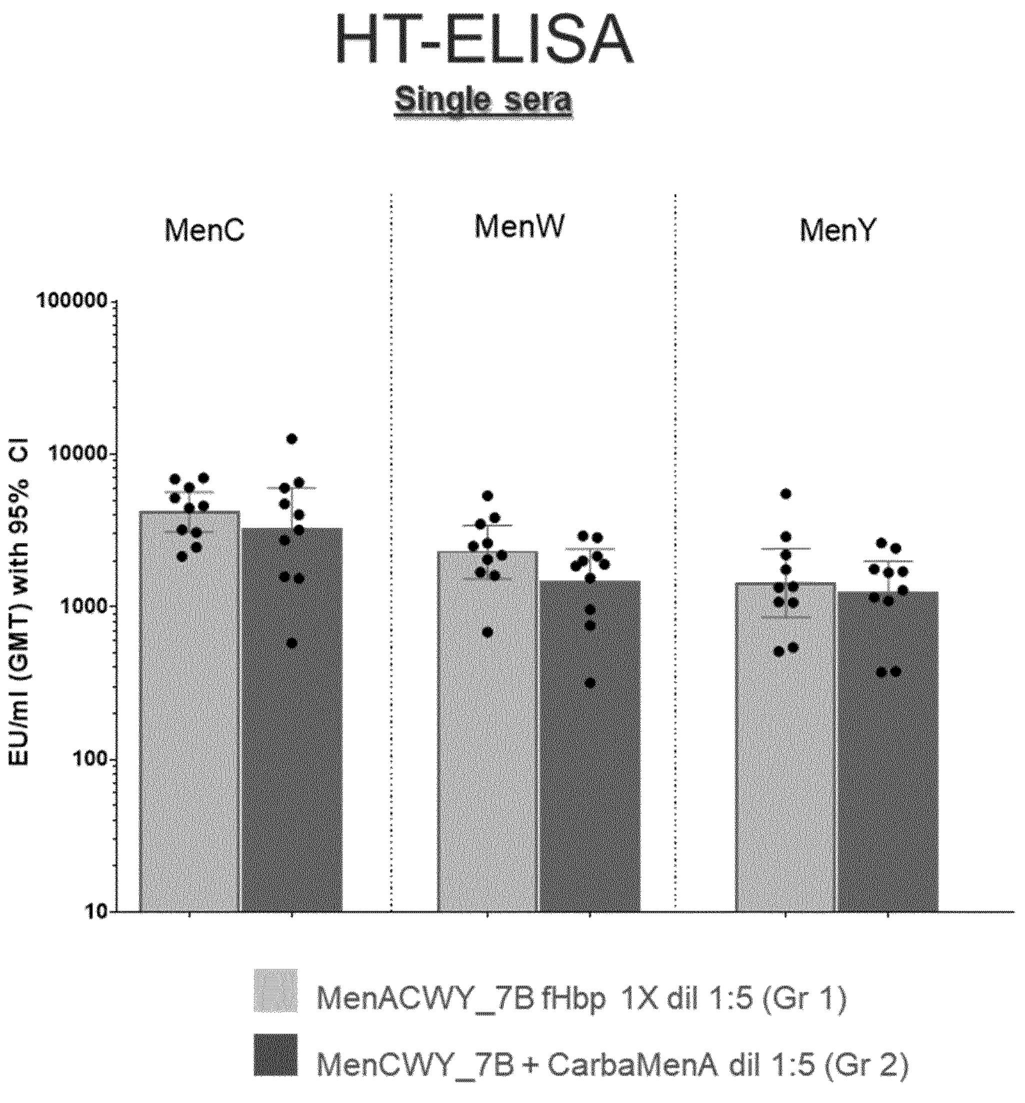
FIG. 14 shows ELISA titers measured after three doses of vaccine with randomly O-acetylated carbaMenA analogue DP10 combined with BNGCWY in comparison with ABNGCWY vaccine as benchmark (i.e. positive control).
FIG. 14C shows anti-NadA, anti-FHbp var.1.1, anti-NHBA, anti-231.13NB and anti-OMV proteins IgG antibodies, wherein for each antigen the ABNGCWY vaccine benchmark is shown in the left bar and the randomly O-acetylated carbaMenA analogue DP10 combined with BNGCWY is shown in the right bar.

In FIG. 14B it is shown that comparable IgG titers were obtained against Men CWY PS measured in rat sera immunized with ABNGCWY or carbaMenA combined with BNGCWY.

Figure 14C:
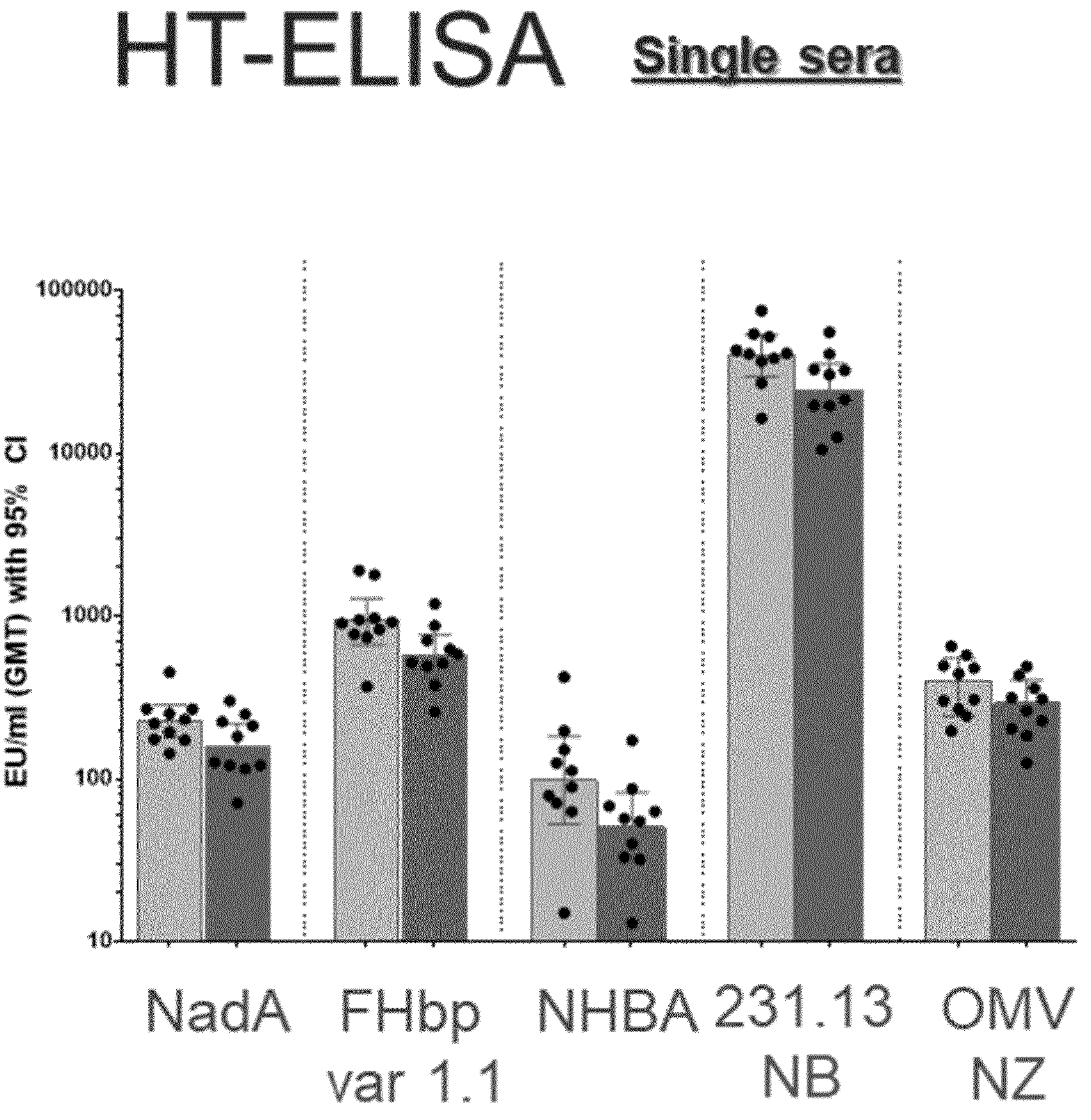

In FIG. 14C it is shown that comparable IgG titers were obtained against Bexsero Antigen and 231.13_NB fusion protein measured in rat sera immunized with ABNGCWY or carbaMenA combined with BNGCWY.

Carba-MenA formulation induced anti-PS MenA IgG titers superior to the MenA-CRM group. No significant results were noted for the comparison MenCWY_7B-Carba MenA with the standard pentavalent formulation.

In Vitro Bactericidal Assay:

At Day 1, meningococcal bacteria were streaked for isolation from a mother culture on chocolate agar polyvitex plates (BIOMERIEUX 43101) and incubated 16 (±2) hours at 37° C. with 5% $CO_2$. At Day 2, bacteria were collected from the agar plates and re-suspended in Mueller Hinton Medium to an optical density (OD600) of 0.05 and grown at 37% with 5% $CO_2$ with shaking at 135 rpm until OD of 0.25 (corresponding to 109 CFU/ml), before use in the assay.

Bacteria were then diluted to 105 CFU/ml in reaction buffer (Dulbecco's saline phosphate buffer, 0.1% glucose and 1% Bovine Serum Albumin) containing 5 U/mL Heparin, 10 mM MgCl2 and 1.5 mM CaCl2).

The SBA was run in 96 well microplates in a final volume of 40 µl per well by mixing 2-fold serially diluted test sera in 20 µl of working buffer, 10 µl of bacteria (⅗x104 CFU/ml) and 10 µl of active plasma complement (plasma is stocked at −80° C. and thawed just before use). Human plasma obtained from volunteer donors under informed consent was selected for use as complement source with a particular meningococcal strain only if it did not significantly reduce the number of colony-forming units of that strain when added to the assay at a concentration of 50%.

The bactericidal assay contains two internal controls:

1) Complement Dependent Control to evaluate the bacterial killing by complement alone in the absence of antibodies; these reactions include only bacteria and active complement.
2) Complement Independent Control to evaluate the killing by serum alone in presence of heat inactivated complement; these reactions contain bacteria, serum sample and heat inactivated complement.

The reaction mixtures were incubated at 37° C. for 60 minutes (T60) with 5% $CO_2$.

At T60, 100 µl of melted TSB/0.7% agar medium was added in each well and was allowed to solidify for 10 minutes. A second layer of 50 µl of melted agar medium was added in each well and was allowed to solidify for additional 10 minutes. Plates were then incubated with cover overnight at 37° C. After an overnight at 37 C° with 5% $CO_2$, microplates were loaded into the AxioLab system (MicroTechniX BVBA) and images of each well were acquired and automatically saved in a fileshare of raw and analysed pictures. Images analysis was performed by AxioVision Rel. 4.8 4.8.2 and colonies counting was automatically obtained. Bactericidal titer (hSBA titer) was determined as the reciprocal serum dilution that resulted in at least a 50% reduction in colony forming units (CFU) relative to the number of CFU present in the control reaction without serum. For statistical analysis interpolated SBA titers have been used.

Figure 15A:
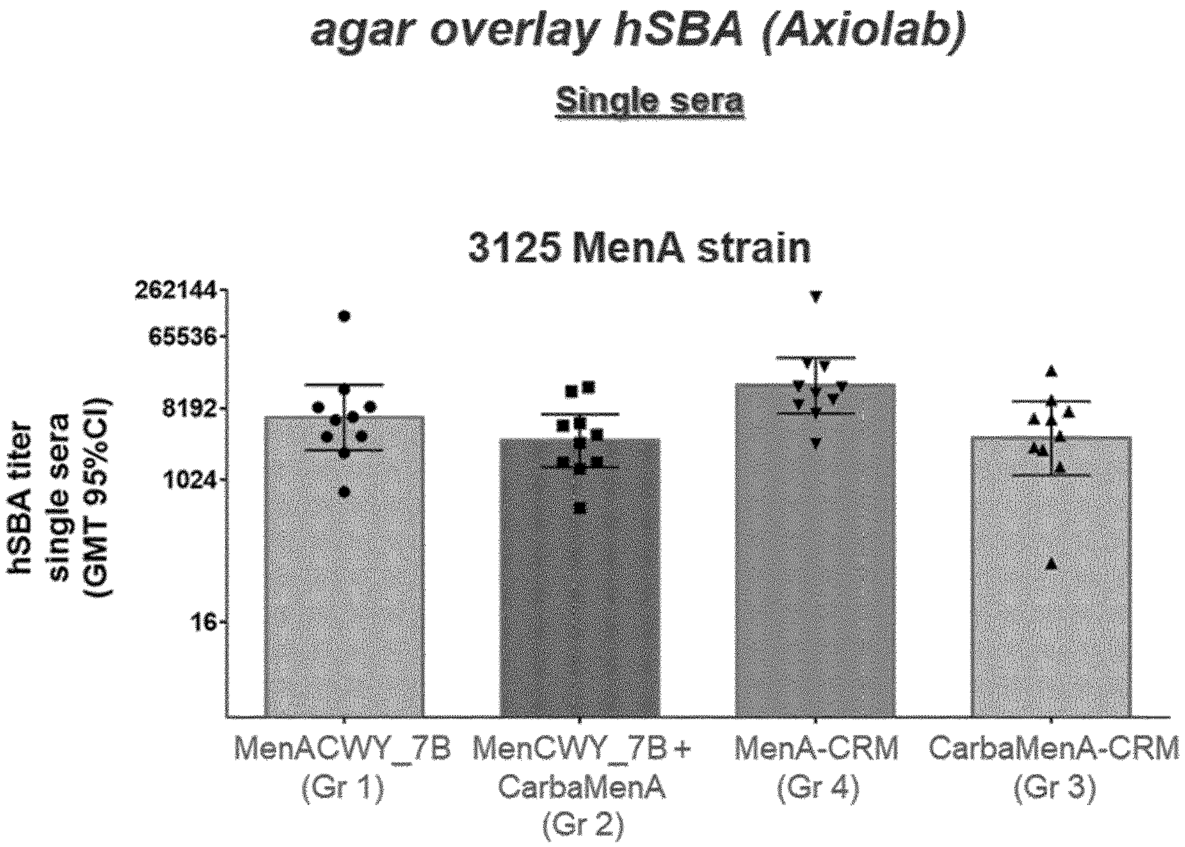
FIG. 15A shows human complement mediated bactericidal titers measured on sera elicited with randomly O-acetylated carbaMenA analogue DP10 combined with BNGCWY in comparison with ABNGCWY vaccine as the benchmark (i.e. positive control) by using 3125 and F8238 MenA strains.
Figure 15A:
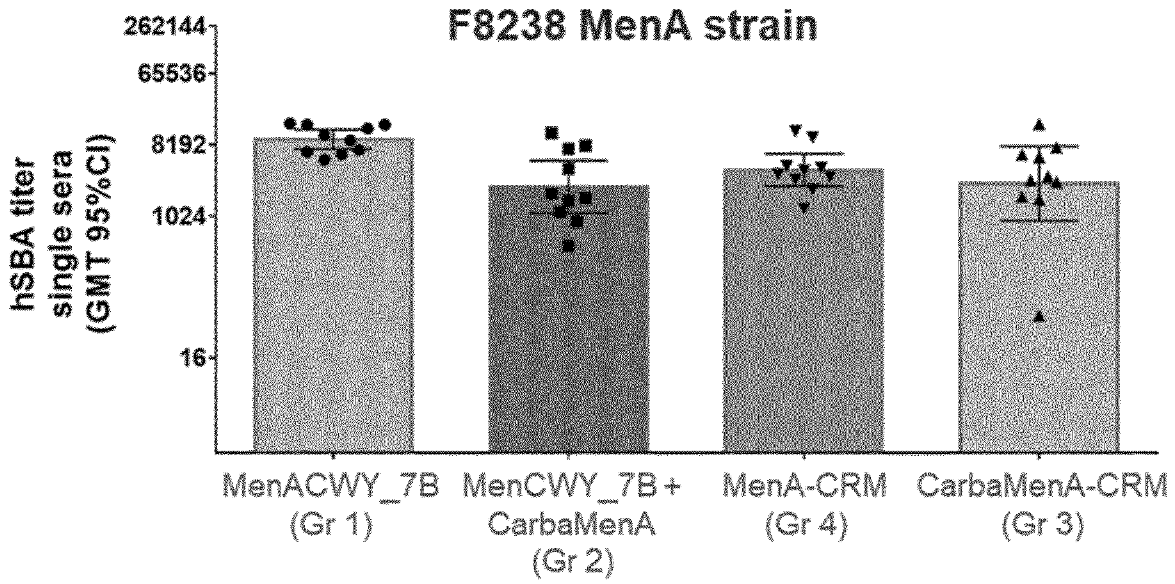
Figure 15B:
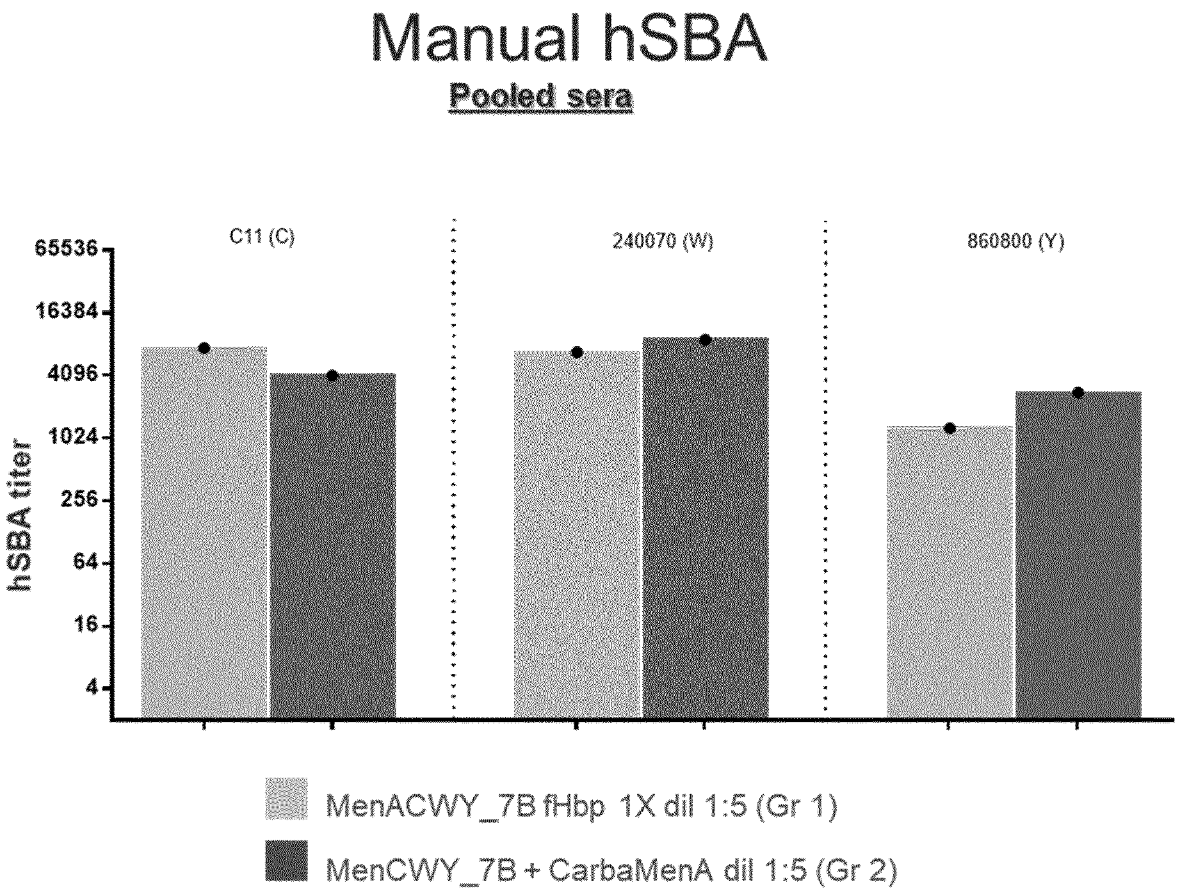
FIG. 15B shows human complement mediated bactericidal titers measured on sera elicited with randomly O-acetylated carbaMenA analogue DP10 combined with BNGCWY in comparison with ABNGCWY vaccine as the benchmark (i.e. positive control) by using C11 (form MenC), 240070 (for MenW) and 860800 (for MenY) strains.
Figure 15C:
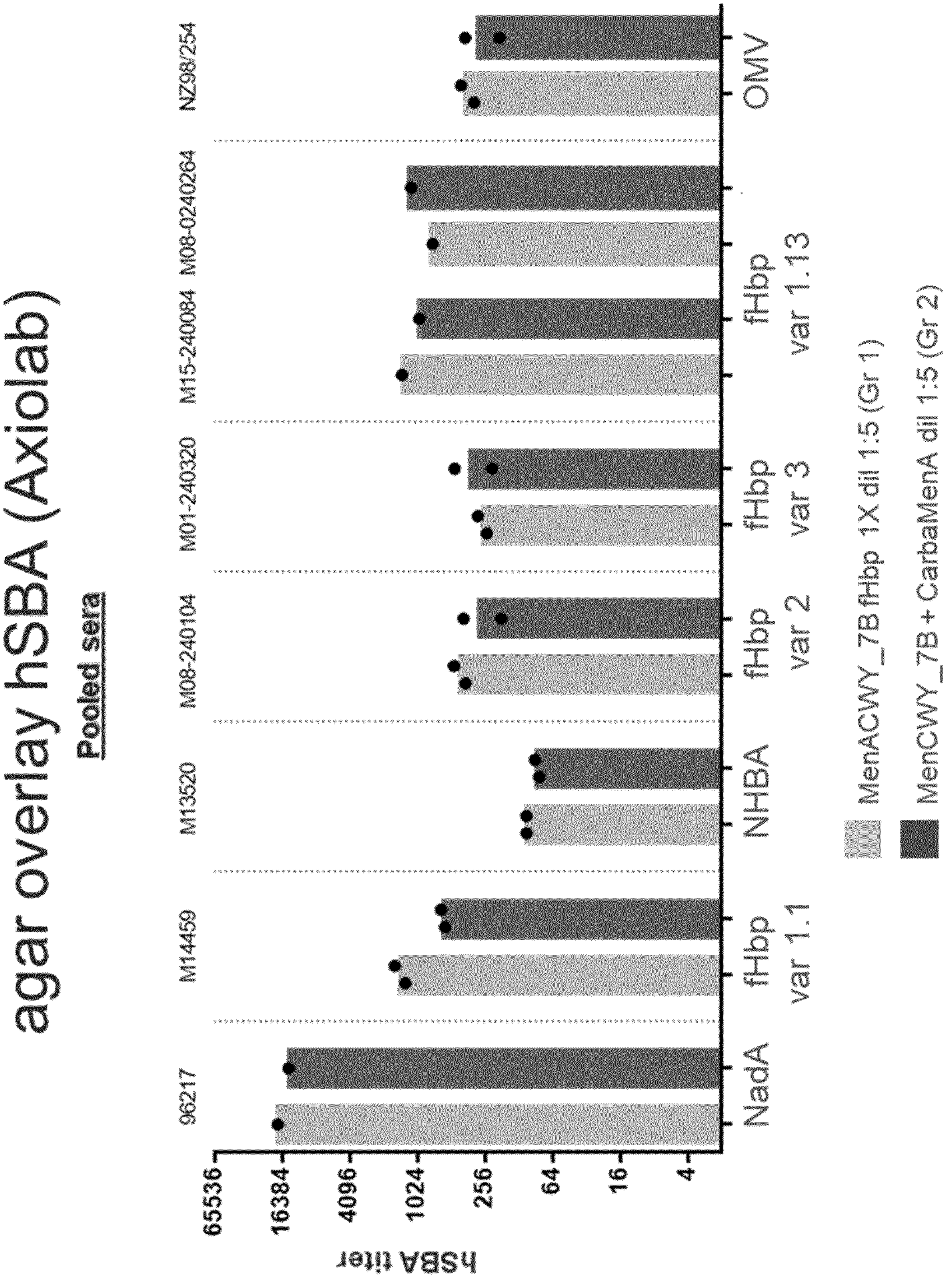
FIG. 15C shows human complement mediated bactericidal titers measured on sera elicited with randomly O-acetylated carbaMenA analogue DP10 combined with BNGCWY in comparison with ABNGCWY vaccine as the benchmark (i.e. positive control) by using 96217 (for NadA), M14459 (for fHbp var1.1), M13530 (for NHBA), M08-240104 (for fHbp var2), M01-240320 (for fHbp var3), M15-240084 and M08-0240264 (for fHbp var1.13) and NZ98/254 strains.

Functional antibody responses were measured by hSBA and, as shown in FIG. 15A, FIG. 15B, FIG. 15C, antibody functionality induced by carbaMenA combined with BNGCWY is comparable to the benchmark combination ABNGCWY, furthermore comparable hSBA titers were also induced by the other CWY antigens and proteins. by Bexsero (FIG. 15B and FIG. 15C).

Carba-MenA formulations showed inferior hSBA titers against MenA 3125 strain when compared to MenA-CRM. No differences were detected between MenACWY_7B fHbp 1× and MenCWY_7B-CarbaMenA formulations.

MenACWY-7B fHbp 1× formulation showed superior hSBA titers against MenA F8238 strain when compared to MenCWY_7B-CarbaMenA formulation. No differences were noted between MenA-CRM and the Carba MenA formulation.

Embodiments of the invention are further described in the subsequent numbered paragraphs:

1. An aqueous immunogenic composition which, after administration to a subject, is able to induce an immune response that is bactericidal against serogroups A, B, C, W135 and Y of *Neisseria meningitidis*, wherein the composition comprises:
   i. a conjugated serogroup A antigen;
   ii. a conjugated serogroup C antigen;
   iii. a conjugated serogroup W135 antigen;
   iv. a conjugated serogroup Y antigen; and
   v. one or more polypeptide antigens from serogroup B, wherein (ii), (iii) and (iv) are capsular saccharide antigens, and wherein (i) is a synthetic analogue of a serogroup A capsular saccharide.
2. The composition of paragraph 1, wherein the conjugated serogroup A antigen is an oligomer conjugate and comprises an oligomer of Formula (Ia) or (Ib):

(Ia)

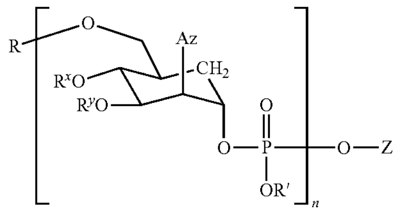

or (Ib)

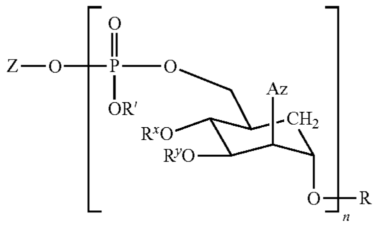

wherein n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N($R^1$)$_2$ and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, optionally substituted phenyl, —C(O)Y, or a linear or branched $C_1$-$C_6$-alkyl-X, wherein Y is H, a linear or branched $C_1$-$C_6$-alkyl or a protecting group, and wherein X is —$NH_2$, —$N_3$, —C≡CH, —CH═$CH_2$, —SH or —S—C≡N.

3. The composition of paragraph 1 or 2, wherein the conjugated serogroup A antigen is a conjugate of Formula (IIa) or (IIb), preferably of formula (IIa):

(IIa)

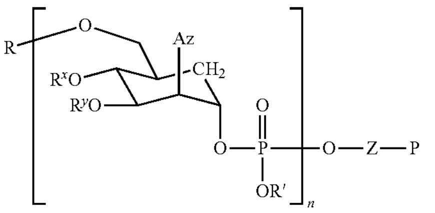

or (IIb)

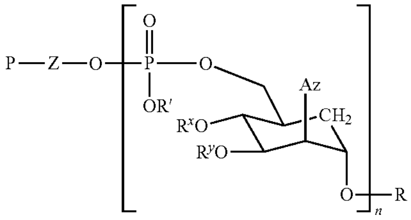

Wherein in the oligomer n is ≥6;

R is H or —P(O)(OR")$_2$, wherein R" is H or a pharmaceutically acceptable phosphate counterion;

R' is H or a pharmaceutically acceptable phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit;

Az is an aza substituent selected from the group consisting of —NH(CO)$R^1$, —N($R^1$)2 and —$N_3$, wherein $R^1$ is independently selected from the group consisting of H, a linear or branched $C_1$-$C_6$-alkyl and a linear or branched $C_1$-$C_6$-haloalkyl;

Z is (i) a functional linker or a bond; and

P is a protein.

4. The composition of paragraph 2 or 3, wherein in the oligomer $R^x$ is —C(O)$CH_3$ in at least one repeat unit.

5. The composition of any one of paragraphs 2 to 4, wherein in the oligomer n is 6 to 30.

6. The composition of any one of paragraphs 2 to 4, wherein in the oligomer n is 8 to 20.

7. The composition of any one of paragraphs 2 to 4, wherein in the oligomer n is 8 to 15.

8. The composition of any one of paragraphs 2 to 4, wherein in the oligomer n is 8 or 10.

9. The composition according to any one of paragraphs 2 to 8, wherein in the oligomer Az is —NHC(O)$CH_3$.

10. The composition according to any one of paragraphs 2 to 9, wherein in the oligomer both of $R^x$ and $R^y$ are —C(O)$CH_3$ in at least one same repeat unit.

11. The composition according to any one of paragraphs 2 to 10, wherein in the oligomer $R^x$ is H and $R^y$ is —C(O)$CH_3$ in at least one same repeat unit.

12. The composition according to any one of paragraphs 2 to 11, wherein in the oligomer $R^x$ is —C(O)$CH_3$ and $R^y$ is H in at least one same repeat unit.

13. The composition according to any one of paragraphs 2 to 12, wherein in the oligomer $R^x$ and $R^y$ are both —C(O)$CH_3$ in at least one same repeat unit.

14. The composition according to any one of paragraphs 2 to 13, wherein in the oligomer $R^x$ is H and $R^y$ is —C(O)$CH_3$ in at least one same repeat unit and $R^x$ is —C(O)$CH_3$ and $R^y$ is H in at least one same repeat unit.

15. The composition according to any one of paragraphs 2 to 14, wherein in the oligomer $R^x$ is H and $R^y$ is —C(O)$CH_3$ in at least one same repeat unit, $R^x$ is —C(O)$CH_3$ and $R^y$ is H in at least one same repeat unit and $R^x$ and $R^y$ are both —C(O)$CH_3$ in at least one same repeat unit 16. The composition according to any one of paragraphs 2 to 15, wherein both of $R^x$ and $R^y$ are —C(O)$CH_3$ in 40 to 50% of the repeat units of the oligomer.

17. The composition according to paragraph 16, wherein in 10 to 20% of the remaining repeat units of the oligomer one of $R^x$ or $R^y$ is —C(O)$CH_3$, the rest of the repeat units in the oligomer having $R^x$=$R^t$=H.

18. The composition according to any one of paragraphs 2 to 17, wherein about 50 to 90% of $R^x$ and $R^y$ in the oligomer is —C(O)$CH_3$.

19. The composition according to any one of paragraphs 2 to 18, wherein $R^x$ in each repeat unit is H and at least 80% of $R^y$ in the oligomer is —C(O)$CH_3$.

20. The composition according to any one of paragraphs 2 to 19, wherein P is an inactivated bacterial toxin selected from diphtheria toxoid (DT), tetanus toxoid (TT), $CRM_{197}$, *E. coli* ST and *Pseudomonas aeruginosa* exotoxin (rEPA), or P is a polyamino acid such as poly(lysine:glutamic acid) or P is hepatitis B virus core protein or SPR96-2021.

21. The composition of any one of paragraphs 2 to 20, wherein P is $CRM_{197}$.

22. The composition of any one of paragraphs 2 to 21, wherein Z is a linker having the following formula:

$$*—(CH_2)_p—NH(CO)—(CH_2)_p—(X—(CH_2)_p)_p—C(O)—*$$

wherein * represents the point of attachment, and wherein p is independently selected from 1 to 10; and X is selected from —O—, —S— and —NH—.

23. The composition of any one of paragraphs 2 to 21, wherein Z is a linker having the following formula:

$$*—(CH_2)_m—NHC(O)—(CH_2)_m—C(O)—*$$

wherein m is independently selected from 1 to 10.

24. The composition according to any one of paragraphs 2 to 23, wherein the oligomer conjugate has the following structure:

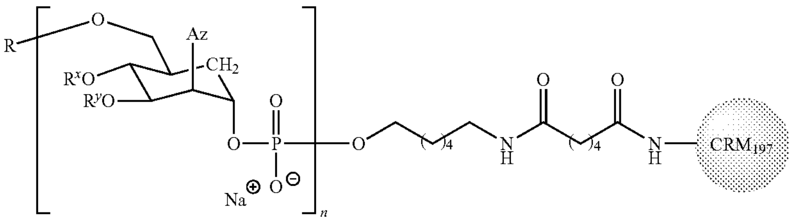

wherein n, Az, R, $R^x$ and $R^y$ are as defined in any one of paragraphs 2 to 19.

25. The composition according to any one of the preceding paragraphs, wherein the conjugated serogroup C, W135 and Y antigens are conjugated to a carrier protein selected from diptheria toxoid, tetanus toxoid, *H. influenzae* protein D and $CRM_{197}$.
26. The composition according to paragraph 25, wherein the serogroup C, W135 and Y antigens are conjugated to $CRM_{197}$.
27. The composition according to any one of the preceding paragraphs, wherein the one or more polypeptide antigens from serogroup B includes one or more of a meningococcal NHBA antigen, a meningococcal NadA antigen, a meningococcal fHbp antigen, and meningococcal outer membrane vesicles (OMVs).
28. The composition according to paragraph 27, comprising a mutant v1.13 meningococcal fHbp polypeptide comprising an amino acid sequence having at least 80% sequence identity to SEQ ID NO: 2 wherein the amino acid sequence includes a substitution mutation at one or more of residues S216, E211 or E232 of SEQ ID NO: 2.
29. The composition according to paragraph 28, wherein the amino acid sequence differs from SEQ ID NO: 2 by at least one or more of the substitutions S216R, E211A and E232A.
30. The composition according to paragraph 29, wherein the amino acid sequence comprises substitutions at multiple residues selected from the following:
    (i) E211A and S216R, and
    (ii) E211A and E232A.
31. The composition according to any of paragraphs 28 to 30, wherein the v1.13 meningococcal fHbp polypeptide has the amino acid sequence of SEQ ID NO: 3 or SEQ ID NO: 4.
32. The composition according to paragraph 27, comprising a fusion polypeptide comprising v1, v2 and v3 meningococcal fHbp polypeptides in the order v2-v3-v1 from N- to C-terminus, and wherein the v1 fHbp polypeptide is a mutant v1.13 fHbp polypeptide as defined in any of paragraphs 28 to 31.
33. The composition according to paragraph 32, wherein:
    (a) the v2 fHbp polypeptide is a mutant v2 fHbp polypeptide comprising an amino acid sequence having at least 80% sequence identity to SEQ ID NO: 12, wherein the v2 fHbp amino acid sequence includes a substitution mutation at residues S32 and L123 of SEQ ID NO:12, and wherein the substitutions are S32V and L123R; and
    (b) the v3 fHbp polypeptide is a mutant v3 fHbp polypeptide comprising an amino acid sequence having at least 80% sequence identity to SEQ ID NO: 15 wherein the v3 fHbp amino acid sequence includes a substitution mutation at residues S32 and L126 of SEQ ID NO: 15, and wherein the substitutions are S32V and L126R.
34. The composition according to paragraph 33, wherein:
    (a) the v2 fHbp polypeptide comprises or consists of the amino acid sequence of SEQ ID NO: 16; and/or
    (b) the v3 fHbp polypeptide comprises or consists of the amino acid sequence of SEQ ID NO: 17.
35. The composition according to any of paragraphs 32 to 34, wherein the v2 and v3 fHbp amino acid sequences and the v3 and v1 fHbp amino acid sequences are connected by a glycine-serine linker, and preferably wherein the v2 sequence has an N-terminal leader sequence corresponding to SEQ ID NO: 18.
36. The composition according to any of paragraphs 32 to 35, wherein the fHbp fusion polypeptide comprises the amino acid sequence of any of SEQ ID NOS: 19-23.
37. The composition according to paragraph 36, wherein the fHbp fusion polypeptide additionally comprises the optional N-terminal amino acid sequence of SEQ ID NO: 34.
38. The composition according to paragraph 36, wherein the fHbp fusion polypeptide has the sequence of SEQ ID NO. 35.
39. The composition according to any of paragraphs 28 to 36, wherein the composition further comprises a meningococcal NHBA antigen, a meningococcal NadA antigen, a meningococcal fHbp antigen, and meningococcal outer membrane vesicles (OMVs).
40. The composition according to any of the preceding paragraphs, further comprising an adjuvant.
41. The composition according to paragraph 40, wherein the adjuvant is aluminium hydroxide.
42. The composition according to any of the preceding paragraphs, wherein the composition comprises BEXSERO.
43. The composition according to any of the preceding paragraphs, packaged in a single hermetically sealed container, preferably a vial or syringe.
44. A method for raising an immune response in a mammal, comprising administering an immunogenic composition according to any of paragraphs 1 to 43, optionally wherein the mammal is a human.
45. A method for the treatment or prevention of infection and/or disease caused by *N. meningitidis* in a mammal in need thereof comprising administering said mammal an immunologically effective amount of the composition according to any of paragraphs 1 to 43, optionally wherein the mammal is a human.

46. The immunogenic composition according to any of paragraphs 1 to 43 for use in medicine.
47. The immunogenic composition according to any of paragraphs 1 to 43 for use as a vaccine.
48. The immunogenic composition according to any of paragraphs 1 to 43 for use in a method of raising an immune response in a mammal, optionally wherein the mammal is a human.
49. The composition according to any of paragraphs 1 to 43, for use in immunizing a mammal against *N. meningitidis* infection, optionally wherein the mammal is a human.
50. Use of a composition as defined in any of paragraphs 1-43 in the manufacture of a medicament for use in the treatment or prevention of infection and/or disease caused by *N. meningitidis*.

The invention claimed is:

1. An aqueous immunogenic composition which, after administration to a subject, induces an immune response that is bactericidal against serogroups A, B, C, W135 and Y of *Neisseria meningitidis*, wherein the composition comprises:

i. a conjugated serogroup A antigen;

ii. a conjugated serogroup C antigen;

iii. a conjugated serogroup W135 antigen;

iv. a conjugated serogroup Y antigen; and v. one or more polypeptide antigens from serogroup B, wherein (ii), (iii) and (iv) are capsular saccharide antigens, and wherein (i) is a synthetic analogue of a serogroup A capsular saccharide, wherein the conjugated serogroup A antigen is an oligomer conjugate and comprises an oligomer of Formula (Ia) or (Ib):

(Ia)

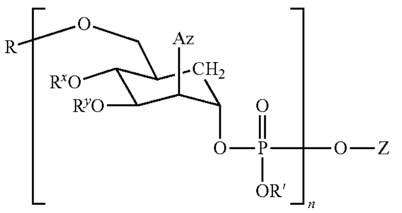

or

-continued (Ib)

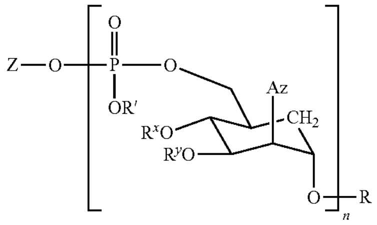

wherein n is ≥6;

R is H or —P(O)(OR")$_2$, wherein R" is H or a phosphate counterion;

R' is H or a phosphate counterion;

$R^x$ is H or —C(O)$CH_3$ and may be the same or different in each repeat unit;

$R^y$ is H or —C(O)$CH_3$ and may be the same or different in each repeat unit;

wherein at least one of $R^x$ or $R^y$ is —C(O)$CH_3$ in at least one repeat unit; and wherein both of $R^x$ and $R^y$ are —C(O)$CH_3$ in at least one same repeat unit;

Az is an aza substituent selected from the group consisting of —NH(CO)$R^1$, —N($R^1$)2 and —$N_3$, wherein $R^1$ is independently selected from the group consisting of H, a linear or branched $C_1$-$C_6$-alkyl and a linear or branched $C_1$-$C_6$-haloalkyl;

Z is (i) a protecting group, (ii) a functional linker for conjugation to a protein, or (iii) a linear or branched $C_1$-$C_6$ alkyl, wherein Y is H, a linear or branched $C_1$-$C_6$-alkyl or a protecting group, and wherein X is $—NH_2$, $—N_3$, —C≡CH, —CH=$CH_2$, —SH or —S—C≡N.

2. The composition of claim 1, wherein the conjugated serogroup A antigen is a conjugate of Formula (IIa) or (IIb):

(IIa)

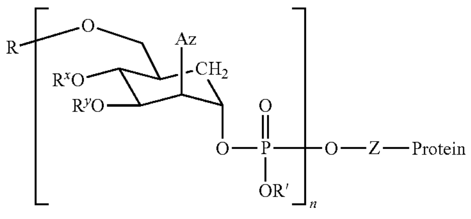

or

-continued (IIb)

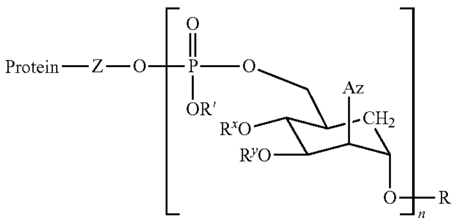

wherein in the oligomer n, R, R', $R^x$, $R^y$, Az are as defined in claim 1;

Z is a functional linker or a bond.

3. The composition of claim 1, wherein n is 6 to 30, 8 to 20, 8 to 15, 8 or 10.

4. The composition according to claim 1, wherein (i) $R^x$ is H and $R^y$ is $—C(O)CH_3$ in at least one same repeat unit and $R^x$ is $—C(O)CH_3$ and $R^y$ is H in at least one same repeat unit, (ii) $R^x$ is H and $R^y$ is $—C(O)CH_3$ in at least one same repeat unit, $R^x$ is $—C(O)CH_3$ and $R^y$ is H in at least one same repeat unit and $R^x$ and $R^y$ are both $—C(O)CH_3$ in at least one same repeat unit, (iii) both of $R^x$ and $R^y$ are $—C(O)CH_3$ in 40 to 50% of the repeat units of the oligomer, (iv) about 50 to 90% of $R^x$ and $R^y$ in the oligomer is $—C(O)CH_3$, and/or (v) about 60 to 80% of $R^x$ and $R^y$ in the oligomer is $—C(O)CH_3$.

5. The composition according to claim 2, wherein the Protein in a conjugate of formulae (IIa) or (IIb) is an inactivated bacterial toxin selected from diphtheria toxoid (DT), tetanus toxoid (TT), $CRM_{197}$, *E. coli* ST and *Pseudomonas aeruginosa* exotoxin (rEPA), or the Protein is a polyamino acid or the Protein is hepatitis B virus core protein or SPR96-2021.

6. The composition of claim 1, wherein Z is a linker having the following formula:

$$*—(CH_2)_p—NH(CO)—(CH_2)_p—(X—(CH_2)_p)_p—C(O)—*$$

wherein * represents the point of attachment, and wherein p is independently selected from 1 to 10; and X is selected from —O—, —S— and —NH— or wherein Z is a linker having the following formula:

$$*—(CH_2)_m—NHC(O)—(CH_2)_m—C(O)—*$$

wherein m is independently selected from 1 to 10.

7. The composition according to claim 1, wherein the oligomer conjugate has the following structure:

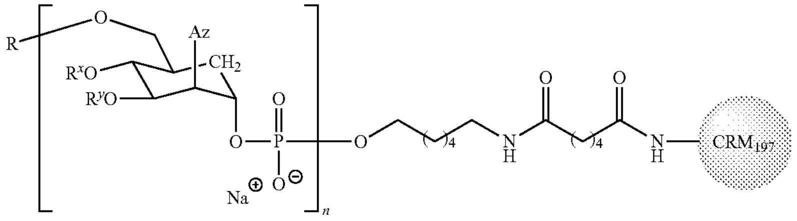

wherein n, Az, R, $R^x$ and $R^y$ are as defined in claim 1.

8. The composition according to claim 1, wherein the conjugated serogroup C, W135 and Y antigens are conjugated to a carrier protein selected from diphtheria toxoid, tetanus toxoid, *H. influenzae* protein D and $CRM_{197}$.

9. The composition according to claim 1, wherein the one or more polypeptide antigens from serogroup B includes one or more of a meningococcal NHBA antigen, a meningococcal NadA antigen, a meningococcal fHbp antigen, and meningococcal outer membrane vesicles (OMVs).

10. The composition according to claim 9, wherein the meningococcal fHbp antigen comprises a mutant v1.13 meningococcal fHbp polypeptide comprising an amino acid sequence having at least 80% sequence identity to SEQ ID NO: 2, wherein the amino acid sequence comprises substitutions at residues E211A and S216R.

11. The composition according to claim 1, comprising a fusion polypeptide comprising v1, v2 and v3 meningococcal fHbp polypeptides in the order v2-v3-v1 from N- to C-terminus, wherein:

(a) the v2 fHbp polypeptide is a mutant v2 meningococcal fHbp polypeptide comprising an amino acid sequence having at least 80% sequence identity to SEQ ID NO: 12, wherein the v2 fHbp amino acid sequence includes substitution mutations at residues S32 and L123 of SEQ ID NO: 12, and wherein the substitutions are S32V and L123R; and (b) the v3 fHbp polypeptide is a mutant v3 meningococcal fHbp polypeptide comprising an amino acid sequence having at least 80% sequence identity to SEQ ID NO: 15, wherein the v3 fHbp amino acid sequence includes substitution mutations at residues S32 and L126 of SEQ ID NO: 15, and wherein the substitutions are S32V and L126R; and (c) the v1 fHbp polypeptide is a mutant v1.13 meningococcal fHbp polypeptide comprising an amino acid sequence having at least 80% sequence identity to SEQ ID NO: 2, wherein the v1 fHbp amino acid sequence includes substitution mutations at residues E211 and S216 of SEQ ID NO: 2, and wherein the substitutions are E211A and S216R.

12. The composition according to claim 11, wherein the fHbp fusion polypeptide comprises the amino acid sequence of SEQ ID NO: 19.

13. The composition according to claim 10, wherein the composition further comprises a meningococcal NHBA antigen, a meningococcal NadA antigen, a meningococcal fHbp antigen, and meningococcal outer membrane vesicles (OMVs).

14. The composition according to claim 1, further comprising an adjuvant.

15. The composition according to claim 1, packaged in a single hermetically sealed container.

16. A vaccine comprising the immunogenic composition according to claim 1.

17. A method of immunizing a mammal against *N. meningitidis* infection with the immunogenic composition of claim 1.

18. The composition according to claim 11, wherein the composition further comprises a meningococcal NHBA antigen, a meningococcal NadA antigen, and meningococcal outer membrane vesicles (OMVs).

19. The composition according to claim 5, wherein the polyamino acid is poly(lysine:glutamic acid).

* * * * *